US011162122B2

(12) United States Patent
Louis et al.

(10) Patent No.: US 11,162,122 B2
(45) Date of Patent: Nov. 2, 2021

(54) METHIONINE-PRODUCING YEAST

(71) Applicant: ADISSEO FRANCE S.A.S., Antony (FR)

(72) Inventors: Dominique Louis, Forges les Bains (FR); Karine Jaillardon, Saint Michel sur Orge (FR); Dominique Thomas, Gif sur Yvette (FR)

(73) Assignee: ADISSEO FRANCE S.A.S., Antony (FR)

( * ) Notice: Subject to any disclaimer, the term of this patent is extended or adjusted under 35 U.S.C. 154(b) by 0 days.

(21) Appl. No.: 16/630,540

(22) PCT Filed: Jul. 10, 2018

(86) PCT No.: PCT/EP2018/068714
§ 371 (c)(1),
(2) Date: Jan. 13, 2020

(87) PCT Pub. No.: WO2019/011942
PCT Pub. Date: Jan. 17, 2019

(65) Prior Publication Data
US 2020/0224230 A1    Jul. 16, 2020

(30) Foreign Application Priority Data
Jul. 11, 2017 (EP) .................... 17305906

(51) Int. Cl.
*C12P 13/12* (2006.01)
*C12N 9/04* (2006.01)
*C12N 9/06* (2006.01)
*C12N 9/10* (2006.01)
*C12N 9/12* (2006.01)

(52) U.S. Cl.
CPC ............ *C12P 13/12* (2013.01); *C12N 9/0006* (2013.01); *C12N 9/0016* (2013.01); *C12N 9/1007* (2013.01); *C12N 9/1029* (2013.01); *C12N 9/1085* (2013.01); *C12N 9/1096* (2013.01); *C12N 9/1205* (2013.01); *C12Y 101/01003* (2013.01); *C12Y 101/01145* (2013.01); *C12Y 104/01002* (2013.01); *C12Y 201/01013* (2013.01); *C12Y 203/01031* (2013.01); *C12Y 205/01048* (2013.01); *C12Y 206/01042* (2013.01); *C12Y 206/01057* (2013.01); *C12Y 207/01039* (2013.01)

(58) Field of Classification Search
CPC .... C12Y 101/01003; C12Y 206/01057; C12Y 205/01048; C12Y 207/01039; C12Y 101/01145; C12Y 206/01042; C12Y 104/01002; C12Y 201/01013; C12Y 203/01031; C12P 13/12; C12N 9/1007; C12N 9/0008; C12N 9/1029; C12N 9/0006; C12N 9/1217; C12N 9/1096; C12N 9/1205; C12N 9/1085; C12N 9/0016; C12N 15/52
See application file for complete search history.

(56) References Cited

U.S. PATENT DOCUMENTS

| | | | |
|---|---|---|---|
| 4,439,525 | A | 3/1984 | Shay et al. |
| 2007/0122888 | A1 | 5/2007 | Boy et al. |
| 2009/0298135 | A1 | 12/2009 | Maier et al. |
| 2012/0190084 | A1 | 7/2012 | Schneider et al. |
| 2013/0183727 | A1 | 7/2013 | Dischert et al. |

FOREIGN PATENT DOCUMENTS

| | | | | |
|---|---|---|---|---|
| DE | WO 2016/184663 A1 | * | 11/2016 | ............ C12N 15/52 |
| WO | 02/18613 A1 | | 3/2002 | |
| WO | 2004/076659 A2 | | 9/2004 | |
| WO | 2006/134277 A1 | | 12/2006 | |
| WO | 2007/012078 A1 | | 1/2007 | |
| WO | 2007/077041 A1 | | 7/2007 | |
| WO | 2009/043372 A1 | | 4/2009 | |
| WO | 2012/090021 A1 | | 7/2012 | |
| WO | 2013/001055 A1 | | 1/2013 | |
| WO | 2013/190343 A1 | | 12/2013 | |
| WO | 2014/064244 A2 | | 5/2014 | |

OTHER PUBLICATIONS

Berger et al., Methionine Regeneration and Aminotransferases in Bacillus subtilis, Bacillus cereus, and Bacillus anthracis. J. Bacteriol., 2003, vol. 185(8): 2418-2431. (Year: 2003).*
Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Martzen et al., A Biochemical Genomics Approach for Identifying Genes by the Activity of Their Products. Science, 1999, vol. 286: 1153-1155. (Year: 1999).*
Seffernick et al., Melamine deaminase and Atrazine chlorohydrolase: 98 percent identical but functionally different. J. Bacteriol., 2001, vol. 183 (8): 2405-2410. (Year: 2001).*
Suk Lee Me., Tools, strategies, and applications of synthetic biology in *Saccharomyces cerevisiae*. Doctoral Thesis, Univ. of California, Berkeley, 2015, 109 pages (Year: 2015).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*

(Continued)

*Primary Examiner* — Ganapathirama Raghu
(74) *Attorney, Agent, or Firm* — Oliff PLC

(57) ABSTRACT

A method of the bio-production of methionine and/or of its derivatives thereof from a reduced source of sulfur, such as MeSH or MeSNa including genetically modified yeasts, having an increased ability to produce methionine and/or its derivatives thereof, as compared to the parent yeasts.

24 Claims, 1 Drawing Sheet
Specification includes a Sequence Listing.

(56) References Cited

OTHER PUBLICATIONS

Yanjun Li et al., Current status on metabolic engineering for the production of L-aspartate family amino acids and derivatives. Bioresource Technol., 2017, vol. 245: 1588-1602; available online May 24, 2017. (Year: 2017).*
Lee et al.; "Systems metabolic engineering of *Escherichia coli* for L-threonine production;" Molecular Systems Biology; 2007; pp. 1-8; vol. 3, No. 149.
Van Der Werf et al.; "Environmental and physiological factors affecting the succinate product ratio during carbohydrate fermentation by *Actinobacillus* sp. 130Z;" Arch Microbiol; 1997; pp. 332-342; vol. 167.
Ravid et al.; "Degradation signal diversity in the ubiquitin-proteasome system;" Nat Rev Mol Cell Biol.; 2008; pp. 679-690; vol. 9, No. 9.
Sagers et al.; "Acetate Formation in Clostridium Acidi-Urici Acetokinase;" J. Bacteriol; 1961; pp. 233-238; vol. 82.
Velculescu et al.; "Characterization of the Yeast Transcriptome;" Cell; 1997; pp. 243-251; vol. 88.
Wang et al; "Consequences of a Modified Putative Substrate-Activation Site on Catalysis by Yeast Pyruvate Decarboxylase;" Biochemistry; 2001; pp. 1755-1763; vol. 40.
Yagi et al.; "Aspartate: 2-Oxoglutarate Aminotransferase from Bakers' Yeast: Crystallization and Characterization;" J. Biochem. 1982; pp. 35-43; vol. 92.
Yamanishi et al; "A Genome-Wide Activity Assessment of Terminator Regions in *Saccharomyces cerevisiae* Provides a "Terminatome" Toolbox;" ACS Synthetic Biology; 2013; pp. 337-347; vol. 2, No. 6.
Yu et al.; "Pac-Man for biotechnology: co-opting degrons for targeted protein degradation to control and alter cell function;" Currentl Opinion in Biotechnology; 2015; pp. 199-204; vol. 36.
Bachmair et al.; "In Vivo Half-Life of a Protein Is a Function of Its Amino-Terminal Residue;" Science; 1986; pp. 179-186; vol. 234.
Bazaes et al; "Comparative Kinetic Effects of Mn (II), Mg (II) and the ATP/ADP Ratio on Phosphoenolpyruvate Carboxykinases from Anaerobiospirillum succiniciproducens and *Saccharomyces cerevisiae*;" The Protein Journal; 2007; pp. 265-269; vol. 26, No. 4.
Cho et al; "A degron created by SMN2 exon 7 skipping a principal contributor to spinal muscular atrophy severity;" Genes & Development; 2010; pp. 438-442; vol. 24.
DiCarlo et al.; Genome engineering *Saccharomyces cerevisiae* using CRISPR-Cas systems; Nucleic Acids Research; 2013; pp. 4336-4343 vol. 41, No. 7.
Faehnle et al; A New Branch in the Family: Structure of Asparatate-β-semialdehyde Dehydrogenase from Methanococcus Jannaschii; J. Mol. Biol.; 2005; pp. 1055-1068; vol. 353.
Fischer et al.; "Catalytic properties of a bacterial acylating acetaldehyde dehydrogenase: Evidence for several active oligomeric states and coenzyme A activation upon binding;" Chemico-Biological Interactions; 2013; pp. 70-77; vol. 202.
Fortmann et al.; "A regulated, ubiquitin-independent degron in IκBα;" J Mol Biol. 2015; pp. 2748-2756; vol. 427, No. 17.
Ganzhorn et al.; "Kinetic Characterization of Yeast Alcohol Dehydrogenases;" The Journal of Biological Chemistry; 1987; pp. 3754-3761; vol. 262, No. 8.
Gerrard Wheeler et al.; "Identification of domains involved in the allosteric regulation of cytosolic *Arabidopsis thaliana* NADP-malic enzymes;" FEBS Journal; 2009; pp. 5665-5677; vol. 276.
He et al.; "Crystal structure of *Saccharomyces cerevisiae* 6-phosphogluconate dehydrogenase Gnd I;" BMC Structural Biology; 2007; pp. 1-9; vol. 7, No. 38.
Hochstrasser; "Ubiquitin-Dependent Protein Degradation;" Annu. Rev. Genet.; 1996; pp. 405-439; vol. 30.
Stadtman et al.; "Feed-back Inhibition and Repression of Aspartokinase Activity in *Escherichia coli* and *Saccharomyces cerevisiae*;" The Journal of Biological Chemistry; 1961; pp. 2033-2038; vol. 236, No. 7.

Keren et al.; "Promoters maintain their relative activity levels under different growth conditions;" Molecular Systems Biology; 2013; pp. 1-17; vol. 9, No. 701.
Koller et al.; "The CUP I promoter of *Saccharomyces cerevisiae* is inducible by copper in Pichia pastoris;" Yeast; 2000; pp. 651-656; vol. 16.
Kuby et al.; Glucose 6-Phosphate Dehydrogenase (Cystalline) from Brewers' Yeast; Dehydrogenases and Oxidases; 1966; pp. 116-125.
Peng et al.; "Coupling gene regulatory patterns to bioprocess conditions to optimize synthetic metabolic modules for improved sesquiterpene production in yeast;" Biotechnol Biofuels; 2017; pp. 1-16; vol. 10, No. 43.
Park et al.; "Characteristics of methionine production by an engineered Corynebacterium glutamicum strain;" Metab Eng.; 2007; pp. 327-336; vol. 9, No. 4.
Lopez De Felipe et al.; Purification and characterisation of the water forming NADH-oxidase from Lactococcus lactis; International Dairy Journal; 2001; pp. 37-44; vol. 11.
Loizeau et al.; "Regulation of One-Carbon Metabolism in *Arabidopsis*: The N-Terminal Regulatory Domain of Cystathionine γ-Synthase Is Cleaved in Response to Folate Starvation;" Plant Physiology; 2007; pp. 491-503; vol. 145.
Onoue et al.; "S-Adenosyl-L-methionine Induces Compaction of Nascent Peptide Chain inside the Ribosomal Exit Tunnel upon Translatio Arrest in the *Arabidopsis* CGS1 Gene;" The Journal of Biological Chemistry; 2011; pp. 14903-14912; vol. 286, No. 17.
Gibbs et al.; "The eukaryotic N-end rule pathway: conserved mechanisms and diverse functions;" Trends in Cell Biology; 2014; pp. 1-9; vol. 1059.
Halász et al.; Study of the Sulphur Metabolism of Methionine-Rich Yeasts; Periodica Polytechnica Ser. Chem. Eng.; 1996; pp. 53-76; vol. 40, No. 1-2.
Becker et al.; "Systems and synthetic metabolic engineering for amino acid production—the heartbeat of industrial strain development;" Current Opinion in Biotechnology; 2012; pp. 718-726; vol. 23.
Cahyanto et al.; "Regulation of aspartokinase, aspartate semialdehyde dehydrogenase, dihydrodipicolinate synthase and dihydrodipicolinate reductase in Lactobacillus plantarum;" Microbiology; 2006; pp. 105-112; vol. 152.
Ravanel et al.; Methionine Biosynthesis in Higher Plants. I. Purification and Characterzation of Cystathionine g-Synthase from Spinach Chloroplasts; Archives of Biochemistry and Biophysics; 1995; pp. 572-584; vol. 316, No. 1.
Susan-Resiga et al.; "Proton Donor in Yeast Pyruvate Kinase: Chemical and Kinetic Properties of the Active Site Thr 298 to Cys Mutant;" Biochemistry; 2004; p. 15230-15245; vol. 43.
Yamagata; "Partial Purification and Some Properties of Homoserine O-Acetyltransferase of a Methionine Auxotroph of *Saccharomyces cerevisiae*;" Journal of Bacteriology; 1987; pp. 3458-3463; vol. 169, No. 8.
Castaño-Cerezo et al.; An insight into the role of phosphotransacetylase (pta) and the acetate/acetyl-CoA node in *Escherichia coli*; Microbial Cell Factories; 2009; pp. 1-19; vol. 8, No. 54.
Mannhaupt et al.; "Yeast homoserine kinase: Characteristics of the corresponding gene, THR1, and the purified enzyme, and evolutionary relationships with other enzymes of threonine metabolism;" Eur. J. Biochem.; 1990; pp. 115-122; vol. 191.
Jouhten et al.; "Yeast metabolic chassis designs for diverse biotechnological products;" Scientific Reports; 2016; pp. 1-9, vol. 6.
Willke; "Methionine production—a critical review;" Appl Microbiol Biotechnol; 2014; pp. 1-21; vol. 98, No. 22.
Thomas et al.; "Structure of the HOM2 gene of *Saccharomyces cerevisiae* and regulation of its expression;" Mol Gen Genet.; 1989; pp. 149-154; vol. 217.
Aug. 10, 2018 Search Report issued in International Patent Application No. PCT/EP2018/068714.
Aug. 10, 2018 Written Opinion of the International Searching Authority issued in International Patent Application No. PCT/EP2018/068714.

(56) References Cited

OTHER PUBLICATIONS

Noor et al.; "Allosteric NADP-glutamate dehydrogenase from aspergilli: purification, characterization and implications for metabolic regulation at the carbon-nitrogen interface;" Microbiology; 2005; pp. 1409-1419; vol. 151.

* cited by examiner

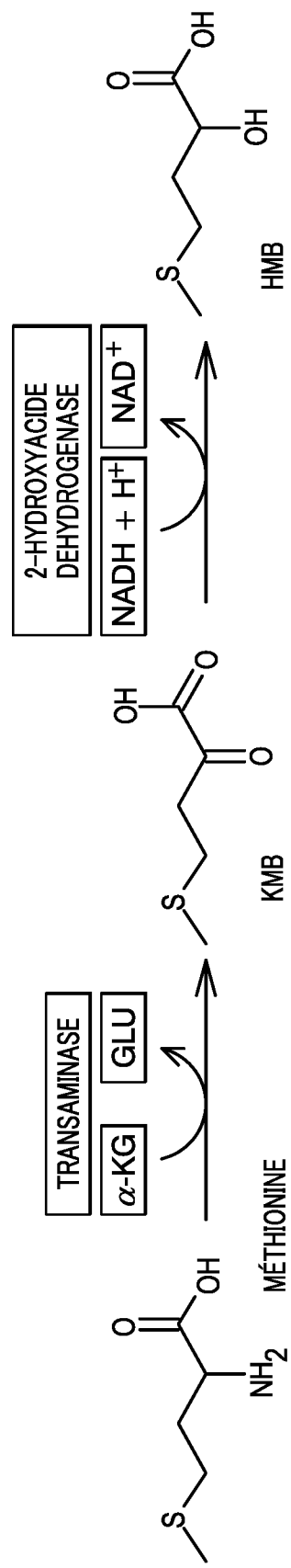

METHIONINE-PRODUCING YEAST

FIELD OF THE INVENTION

The present invention relates to the field of bio-production of methionine and/or of its derivatives thereof, and in particular of bio-production of methionine and/or of its derivatives thereof from a reduced source of sulfur, such as MeSH or MeSNa.

BACKGROUND OF THE INVENTION

Methionine is one of the two sulfur-containing proteinogenic amino acids and is essential in the metabolism of numerous living organisms, including non-human and human mammals. Methionine is mainly present in structural proteins such as collagen or keratin in skin, hair feathers and nails, respectively. The highest methionine content of about 5% can be found in albumins, especially egg albumin.

Most plants, fungi and bacteria can synthesize methionine from carbohydrates, organic or inorganic nitrogen and sulfur sources. However, animals, including humans, depend on externally provided methionine sources. In organic farming, especially poultry and pig breeding, the supply with methionine has become a problem, since methionine is regarded as the first and third limiting amino acid in poultry and piglet feed, respectively. Most of the produced methionine is used for animal feed in livestock production. Today, methionine is mainly produced by chemical synthesis from methyl mercaptan, acrolein and hydrogen cyanide. Chemically produced methionine can be used for most applications. However, against the background of decreasing fossil resources and the stronger environmental constraints (e.g. hazardous intermediates and waste), alternative and more sustainable processes based on natural resources are gaining more and more interest. Further, there is a general search for cost-saving sources of methionine for a plurality of industrial applications.

Methionine may be produced by non-synthetic processes by enzymatic conversion or fermentation starting from precursor compounds, such as 5-monosubstituted hydantoin derivatives, O-succinyl-L-homoserine or O-acetylhomoserine. However, because the precursors are often chemically synthesized or have to be produced in a first step by fermentation, there is no real industrial or financial advantage over the processes of chemical synthesis. Illustrative embodiments of processes for producing and purifying methionine by fermentation methods are disclosed in the US patent applications no. US 2012/0190084 and no. US 2007/0122888.

Production of methionine by fermentation from natural sources may solve many of the above-mentioned problems. There are numerous bacteria and yeasts which are able to overproduce amino acids under adequate conditions. However, because of the very complex regulation of the L-methionine syntheses, only a few strains are able to produce relevant amounts of methionine. Thus, the main drawback of producing methionine by a fermentation process is the very complex biosynthesis of methionine with manifold feedback inhibition (Becker et al., 2012, Current opinion in Biotechnology, Vol. 23(5): 718-726). An additional issue is the sulfur source, which is usually provided as inorganic sulfate and has therefore been strongly reduced, before it can be transferred to methionine. In all cases, candidate methionine producer organisms have to undergo numerous rounds of mutation and selection before being retained as relevant producers. Illustrative embodiments of candidate methionine-producing microorganisms selected after spontaneous mutation or chemically-induced mutagenesis are disclosed in the U.S. Pat. No. 4,439,525 as well as in Halasz et al. (1996, Periodica Polytechnica Ser. Chem. Engl., Vol. 40(1-2): 53-78).

The production of essential amino acids such as methionine through the biosynthetic pathways of bacteria and yeasts requires an important amount of reducing power in the form of NADPH. However, the main pathway for the metabolisation of glucose in these microorganisms, and in particular in yeasts, is glycolysis followed by fermentation which only produces NADH. Maintaining an appropriate NADPH/NADH balance within the microorganism, albeit complex, is therefore essential to optimize bio-production of methionine while obtaining a viable recombinant microorganism.

The major known bacterial amino acid producer is *C. glutanicum*, a gram-positive, facultative anaerobic, non-pathogenic soil bacterium. *C. glutanicum* is used for the large-scale industrial production of the flavor enhancer L-glutamate as well as of the food additive L-lysine. Various attempts have been performed for producing methionine by fermentation of *C. glutanicum*, especially by providing reduced sulfur in the bacterial growth medium.

According to other improvement strategies, an increase in methionine production by fermentation has been explored through genetic engineering of candidate microorganisms, mainly the bacterial organisms *E. coli* and *C. glutamicum*. Illustrating embodiments are disclosed in the PCT patent applications no. WO 02/18613, no. WO 2007/077041, no. WO 2009/043372, no. WO 2012/090021, no. WO 2013/001055, no. WO 2013/190343, in the US patent applications no. US 2009/0298135 and no. US 2013/0183727, as well as in Park et al. (2007, Metab Eng, Vol. 9(4): 327-336).

There is still a need in the art for further methionine production methods.

SUMMARY OF THE INVENTION

The present invention accordingly relates to a methionine-producing and/or methionine derivatives-producing recombinant yeast, in the genome of which:

(A) at least one nucleic acid encoding an aspartate semi-aldehyde dehydrogenase and/or at least one nucleic acid encoding an aspartate semi-aldehyde dehydrogenase that can use as coenzyme both NAD and NADP is overexpressed and/or is under the control of an inducible or repressible promoter;

(B) at least one nucleic acid encoding an aspartokinase is under the control of an inducible or repressible promoter; and (C) (i) a) at least one nucleic acid encoding an homoserine-O-acetyltransferase MET2 is overexpressed and/or is under the control of an inducible or repressible promoter;

and/or at least one nucleic acid encoding an homoserine-O-acetyltransferase METX is overexpressed and/or is under the control of an inducible or repressible promoter, and b) at least one nucleic acid encoding a methionine synthase is overexpressed and/or is under the control of an inducible or repressible promoter;

and/or (ii) a) at least one nucleic acid encoding an homoserine kinase is overexpressed and/or is under the control of an inducible or repressible promoter, and b) at least one nucleic acid encoding a cystathionine gamma-synthase 1 that has an improved O-phospho-L- homoserine (OHPS) dependent methionine synthase activity is overexpressed and/or is under the control of an inducible or repressible promoter.

As illustrated in the enclosed examples, the recombinant yeasts of the invention have an increased methionine and/or methionine derivatives production.

Said advantageous property can be further increased by also recombining the yeast with additional modifications described here-after.

A methionine-producing and/or methionine derivatives-producing recombinant yeast can consequently advantageously be used in a method for producing methionine and/or at least one of its derivatives as described here-after or be used for the production of methionine and/or of its derivatives thereof.

The invention further relates to a method for producing methionine and/or at least one of its derivatives, said method comprising the steps of:

(a) culturing a recombinant yeast according to the invention in a culture medium, said culture medium preferably comprising MeSH, MeSNa and/or MeSMe; and (b) recovering the methionine and/or at least one of its derivatives from said culture medium.

In a particular embodiment, the culture medium comprises at least a carbon source, preferably a carbon source selected from the group consisting of glucose and sucrose.

A further object of the present invention is the use of a recombinant yeast according to the invention for the production of methionine and/or of its derivatives thereof, in particular for the production of methionine and/or of 2-hydroxy-4-(methylthio) butanoic acid (HMB) and/or of 2-keto-4-methylthiobutyric acid (KMB), preferably for the production of methionine and/or of 2-hydroxy-4-(methylthio) butanoic acid (HMB).

Derivatives of methionine are compounds that are obtained after modification of the methionine. Accordingly, in the present invention, in order to obtain a derivative of methionine, it is first necessary to produce methionine and then, through at least one additional step, to transform methionine in one of its derivatives, in particular one of its derivatives mentioned in the present text.

BRIEF DESCRIPTION OF DRAWINGS

The FIGURE is an illustration of how 2-hydroxy-4-(methylthio) butanoic acid (HMB) and 2-keto-4-methylthiobutyric acid (KMB) can be obtained from methionine.

DETAILED DESCRIPTION OF THE INVENTION

The inventors have conceived genetically modified microorganisms, and especially genetically modified yeasts, having an increased ability to produce methionine and/or its derivatives thereof, as compared to the parent microorganisms, and especially as compared to the parent yeasts.

These genetically modified microorganisms, including these genetically modified yeasts, are described throughout the present specification.

Definitions

The term "microorganism", as used herein, refers to a yeast which is not modified artificially. The microorganism may be "donor" if it provides genetic element to be integrated in the microorganism "acceptor" which will express this foreign genetic element or if it used as tool for genetic constructions or protein expressions. The microorganism of the invention is chosen among yeast which expresses genes for the biosynthesis of methionine.

The term "recombinant microorganism" or "genetically modified microorganism" or "recombinant yeast" or "genetically modified yeast", as used herein, refers to a yeast genetically modified or genetically engineered. It means, according to the usual meaning of these terms, that the microorganism of the invention is not found in nature and is modified either by introduction or by deletion or by modification of genetic elements from equivalent microorganism found in nature. It can also be modified by forcing the development and evolution of new metabolic pathways by combining directed mutagenesis and evolution under specific selection pressure (see for instance WO 2004/076659).

A microorganism may be modified to express exogenous genes if these genes are introduced into the microorganism with all the elements allowing their expression in the host microorganism. A microorganism may be modified to modulate the expression level of an endogenous gene. The modification or "transformation" of microorganism, like yeast, with exogenous DNA is a routine task for those skilled in the art. In particular, a genetic modification of a microorganism according to the invention, more particularly the genetic modification(s) herein defined, may be carried out by using CRISPR-Cas systems, as described in DiCarlo et al. (Nucl. Acids Res., vol. 41, No. 7, 2013: 4336-4343).

The term "endogenous gene" means that the gene was present in the microorganism before any genetic modification, in the wild-type strain. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, in the down-regulation and/or attenuation of the activity of the endogenous gene product. Another way to enhance expression of endogenous genes is to introduce one or more supplementary copies of the gene onto the chromosome or a plasmid.

The term "exogenous gene" means that the gene was introduced into a microorganism, by means well known by the man skilled in the art, whereas this gene is not naturally occurring in the wild-type microorganism. Microorganism can express exogenous genes if these genes are introduced into the microorganism with all the elements allowing their expression in the host microorganism. Transforming microorganisms with exogenous DNA is a routine task for the man skilled in the art. Exogenous genes may be integrated into the host chromosome, or be expressed extra-chromosomally from plasmids or vectors. A variety of plasmids, which differ with respect to their origin of replication and their copy number in the cell, are all known in the art. The sequence of exogenous genes may be adapted for its expression in the host microorganism. Indeed, the man skilled in the art knows the notion of codon usage bias and how to adapt nucleic sequences for a particular codon usage bias without modifying the deduced protein.

The term "heterologous gene" means that the gene is derived from a species of microorganism different from the recipient microorganism that expresses it. It refers to a gene which is not naturally occurring in the microorganism.

In the present application, all genes are referenced with their common names and with references to their nucleotide sequences and, the case arising, to their amino acid sequences. Using the references given in accession number for known genes, those skilled in the art are able to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerated probes to clone the corresponding gene in another organism.

The man skilled in the art knows different means to modulate, and in particular up-regulate or down-regulate, the expression of endogenous genes. For example, a way to enhance expression of endogenous genes is to introduce one or more supplementary copies of the gene onto the chromosome or a plasmid.

Another way is to replace the endogenous promoter of a gene with a stronger promoter. These promoters may be homologous or heterologous. Promoters particularly interesting in the present invention are described in more detail elsewhere in the present specification.

The nucleic acid expression construct may further comprise 5' and/or 3' recognition sequences and/or selection markers.

The term "overexpression" means that the expression of a gene or of an enzyme is increased as compared to the non-modified microorganism. Increasing the expression of an enzyme is obtained by increasing the expression of a gene encoding said enzyme. Increasing the expression of a gene may be carried out by all techniques known by the one skilled in the art. In this regard, it may be notably cited the implementation of a strong promoter upstream the nucleic acid intended to be overexpressed or the introduction of a plurality of copies of the said nucleic acid between a promoter, especially a strong promoter, and a terminator.

The term "underexpression" means that the expression of a gene or of an enzyme is decreased as compared to the non-modified microorganism. Decreasing the expression of an enzyme is obtained by decreasing the expression of a gene encoding said enzyme. Decreasing the expression of a gene may be carried out by all techniques known by the one skilled in the art. In this regard, it may be notably cited the implementation of a weak promoter upstream the nucleic acid intended to be underexpressed. It may be also cited the implementation of a nucleic acid encoding a variant of the said enzyme that is less active than the parent enzyme or a variant of the said enzyme that is more rapidly degraded in the cell than the parent enzyme. Variants of a parent enzyme that is more rapidly degraded that the said parent enzyme encompass degron-tagged enzymes. It may also be cited the decrease of the expression of a transcription activator of the gene of interest.

The term "inducible promoter" is used to qualify a promoter whose activity is induced, i.e. increased:
in the presence of one or more particular metabolite(s). The higher the metabolite concentration in the medium, the stronger the promoter activity; or
in the presence of a low concentration, or in the absence, of one or more metabolite(s). These metabolites are different from those whose increasing presence induces the activity of the promoter. The lower the metabolite concentration in the medium, the stronger the promoter activity.

The term "repressible promoter" is used to qualify a promoter whose activity is repressed, i.e. reduced:
in the presence of one or more particular metabolite(s). The higher the metabolite concentration in the medium, the weaker the promoter activity; or
in the presence of a low concentration, or in the absence, of one or more metabolite(s). These metabolites are different from those whose increasing presence represses the activity of the promoter. The lower the metabolite concentration in the medium, the weaker the promoter activity.

A used herein, a "degron-tagged" enzyme means an enzyme comprising an added protein-degradation signal amino acid sequence that serves as a destruction signal that will cause the said enzyme to be the subject of a degradation, which may be either (i) a ubiquitin-independent degradation or (ii) an ubiquitin-dependent degradation. The said added protein-degradation signal, that is also termed "degron" in the art, encompasses an amino acid sequence that serves as a destruction signal, the said amino acid sequence consisting of a transferrable degradation signal causing a targeted protein degradation. Degrons encompass "N-degrons", which are transferrable N-terminal amino acids that cause the target protein degradation following the well known N-end rule (Bachmair et al., 1986, Science, Vol. 234 (4773): 179-186). The unstable nature of the N-degron is attributed to its first amino acids, which are prone to acetylation or arginylation modifications and ultimately lead to ubiquitination and degradation. Generally, a degron requires at least two components to ensure targeted protein degradation: (i) a target degradation recognition tag, such as a poly-ubiquitin tag and (ii) an unstructured amino acid sequence in close proximity to the degradation recognition tag. For degron-tagging a protein, and especially herein for degron-tagging an enzyme, the one skilled in the art may refer to Yu et al. (2015, Current Opinion in Biotechnology, Vol. 36: 199-204), Cho et al. (2010, Genes & Development, Vol. 24: 438-442), or to Fortmann et al. (2015, J Mol Biol, Vol. 427 (17): 2748-2756), Ravid et al. (2008, Nat Rev Mol Cell Biol, Vol. 9(9): 679-690) and Hochstrasser (1996, Annu Rev Genet, Vol. 30: 405-439).

The "activity" of an enzyme is used interchangeably with the term "function" and designates, in the context of the invention, the capacity of an enzyme to catalyze a desired reaction.

The terms "reduced activity" or "attenuated activity" of an enzyme mean either a reduced specific catalytic activity of the protein obtained by mutation in the amino acids sequence and/or decreased concentrations of the protein in the cell obtained by mutation of the nucleotide sequence or by deletion of the cognate corresponding gene or also by degron-tagging of the protein.

The term "enhanced activity" of an enzyme designates either an increased specific catalytic activity of the enzyme, and/or an increased quantity/availability of the enzyme in the cell, obtained for example by overexpression of the gene encoding the enzyme.

The terms "encoding" or "coding" refer to the process by which a polynucleotide, through the mechanisms of transcription and translation, produces an amino-acid sequence.

The gene(s) encoding the enzyme(s) considered in the present invention can be exogenous or endogenous.

"Attenuation" of genes means that genes are expressed at an inferior rate than in the non modified microorganism. The attenuation may be achieved by means and methods known to the man skilled in the art and contains gene deletion obtained by homologous recombination, gene attenuation by insertion of an external element into the gene or gene expression under a weak promoter. The man skilled in the art knows a variety of promoters which exhibit different strengths and which promoter to use for a weak genetic expression.

The methods implemented in the present invention preferably require the use of one or more chromosomal integration constructs for the stable introduction of a heterologous nucleotide sequence into a specific location on a chromosome or for the functional disruption of one or more target genes in a genetically modified microbial cell. In some embodiments, disruption of the target gene prevents the expression of the related functional protein. In some embodiments, disruption of the target gene results in the expression of a non-functional protein from the disrupted gene.

Parameters of chromosomal integration constructs that may be varied in the practice of the present invention include, but are not limited to, the lengths of the homologous sequences; the nucleotide sequence of the homologous sequences; the length of the integrating sequence; the nucleotide sequence of the integrating sequence; and the nucleotide sequence of the target locus. In some embodiments, an effective range for the length of each homologous sequence is 20 to 5,000 base pairs, preferentially 50 to 100 base pairs. In particular embodiments, the length of each homologous sequence is about 50 base pairs. For more information on the length of homology required for gene targeting, see D. Burke et al., Methods in yeast Genetics—A cold spring harbor laboratory course Manual (2000).

In some embodiments, (a) disrupted gene(s) in which the above-mentioned DNA construct(s) is/are intended to be inserted may advantageously comprises one or more selectable markers useful for the selection of transformed microbial cells. Preferably, said selectable marker(s) are comprised in the DNA construct(s) according to the present invention.

In some embodiments, the selectable marker is an antibiotic resistance marker. Illustrative examples of antibiotic resistance markers include, but are not limited to the, NAT1, AUR1-C, HPH, DSDA, KAN<R>, and SH BLE gene products. The NAT 1 gene product from *S. noursei* confers resistance to nourseothricin; the AUR1-C gene product from *Saccharomyces cerevisiae* confers resistance to Auerobasidin A (AbA); the HPH gene product of *Klebsiella pneumonia* confers resistance to Hygromycin B; the DSDA gene product of *E. coli* allows cells to grow on plates with D-serine as the sole nitrogen source; the KAN<R> gene of the Tn903 transposon confers resistance to G418; and the SH BLE gene product from *Streptoalloteichus hindustanus* confers resistance to Zeocin (bleomycin).

In some embodiments, the antibiotic resistance marker is deleted after the genetically modified microbial cell of the invention is isolated. The man skilled in the art is able to choose suitable marker in specific genetic context.

In some embodiments, the selectable marker rescues an auxotrophy (e.g., a nutritional auxotrophy) in the genetically modified microbial cell. In such embodiments, a parent microbial cell comprises a functional disruption in one or more gene products that function in an amino acid or nucleotide biosynthetic pathway, such as, for example, the HIS3, LEU2, LYS1, LYS2, MET 15, TRP1, ADE2, and URA3 gene products in yeast, which renders the parent microbial cell incapable of growing in media without supplementation with one or more nutrients (auxotrophic phenotype). The auxotrophic phenotype can then be rescued by transforming the parent microbial cell with a chromosomal integration encoding a functional copy of the disrupted gene product (NB: the functional copy of the gene can originate from close species, such as *Kluveromyces, Candida* etc.), and the genetically modified microbial cell generated can be selected for based on the loss of the auxotrophic phenotype of the parent microbial cell.

For each of the nucleic acid sequences comprising a promoter sequence, a coding sequence (e.g. an enzyme coding sequence), or a terminator sequence, reference sequences are described herein. The present description also encompasses nucleic acid sequences having specific percentages of nucleic acid identity, with a reference nucleic acid sequence.

For each or the amino acid sequences of interest, reference sequences are described herein. The present description also encompasses amino acid sequences (e.g. enzyme amino acid sequences), having specific percentages of amino acid identity, with a reference amino acid sequence.

For obvious reasons, in all the present description, a specific nucleic acid sequence or a specific amino acid sequence which complies with, respectively, the considered nucleotide or amino acid identity, should further lead to obtaining a protein (or enzyme) which displays the desired biological activity. As used herein, the "percentage of identity" between two nucleic acid sequences or between two amino acid sequences is determined by comparing both optimally aligned sequences through a comparison window.

The portion of the nucleotide or amino-acid sequence in the comparison window may thus include additions or deletions (for example "gaps") as compared to the reference sequence (which does not include these additions or these deletions) so as to obtain an optimal alignment between both sequences.

The identity percentage is calculated by determining the number of positions at which an identical nucleic base, or an identical amino-acid residue, can be noted for both compared sequences, then by dividing the number of positions at which identity can be observed between both nucleic bases, or between both amino-acid residues, by the total number of positions in the comparison window, then by multiplying the result by hundred to obtain the percentage of nucleotide identity between the two sequences or the percentage of amino acid identity between the two sequences.

The comparison of the sequence optimal alignment may be performed by a computer using known algorithms.

Most preferably, the sequence identity percentage is determined using the CLUSTAL W software (version 1.82) the parameters being set as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAP DISTANCES="hide".

The "fermentation" or "culture" is generally conducted in fermenters with an appropriate culture medium adapted to the microorganism being cultivated, containing at least one simple carbon source, and if necessary co-substrates.

Microorganisms disclosed herein may be grown in fermentation media for the production of a product from oxaloacetate. For maximal production of methionine, the microorganism strains used as production hosts preferably have a high rate of carbohydrate utilization. These characteristics may be conferred by mutagenesis and selection, genetic engineering, or may be natural. Fermentation media, or "culture medium", for the present cells may contain at least about 10 g/L of glucose. Additional carbon substrates may include but are not limited to monosaccharides such as fructose, mannose, xylose and arabinose; oligosaccharides such as lactose maltose, galactose, or sucrose; polysaccharides such as starch or cellulose or mixtures thereof and unpurified mixtures from renewable feedstocks such as cheese whey permeate cornsteep liquor, sugar beet molasses, and barley malt. Other carbon substrates may include glycerol.

Hence, it is contemplated that the source of carbon utilized in the present invention may encompass a wide variety of carbon containing substrates and will only be limited by the choice of organism.

Although it is contemplated that all of the above-mentioned carbon substrates and mixtures thereof are suitable in the present invention, preferred carbon substrates are glucose, fructose, and sucrose, or mixtures of these with C5 sugars such as xylose and/or arabinose for microorganisms modified to use C5 sugars, and more particularly glucose.

A preferred carbon substrate is glucose.

In addition to an appropriate carbon source, fermentation media may contain suitable minerals, salts, cofactors, buffers and other components, known to those skilled in the art, suitable for the growth of the cultures and promotion of the enzymatic pathway necessary for the production of the desired product.

Besides, additional genetic modifications suitable for the growth of recombinant microorganisms according to the invention may be considered.

The terms "Aerobic conditions" refers to concentrations of oxygen in the culture medium that are sufficient for an aerobic or facultative anaerobic microorganism to use di-oxygene as a terminal electron acceptor.

"Microaerobic condition" refers to a culture medium in which the concentration of oxygen is less than that in air, i.e. oxygen concentration up to 6% 02.

An "appropriate culture medium" designates a medium (e.g. a sterile, liquid medium) comprising nutrients essential or beneficial to the maintenance and/or growth of the cell such as carbon sources or carbon substrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids, vitamins, growth promoters, and the like. The term "carbon source" or "carbon substrate" or "source of carbon" according to the present invention denotes any source of carbon that can be used by those skilled in the art to support the normal growth of a microorganism, including hexoses (such as glucose, galactose or lactose), pentoses, monosaccharides, oligosaccharides, disaccharides (such as sucrose, cellobiose or maltose), molasses, starch or its derivatives, cellulose, hemicelluloses and combinations thereof.

According to the present invention, a "derivative of methionine" is a compound that can be obtained from methionine after modification by enzymes naturally and/or artificially present in the microorganism producing the methionine according to the invention, in particular in the yeast producing the methionine according to the invention.

Examples of such derivatives of methionine can for example be the 2-hydroxy-4-(methylthio) butanoic acid (HMB) or the 2-keto-4-methylthiobutyric acid (KMB).

General Features of Genetic Modifications Introduced According to the Invention

Genes are over expressed by two kinds of non mutually exclusive modifications:

Placing them under the control of a strong promoter; and/or

Inserting a plurality of copies of the considered gene.

All the genome modifications are inserted in yeast according to known genetic engineering techniques:

The successive genes included in a gene construct that is introduced in the yeast genome according to the invention are of the following structure:

$Prom_1$-$ORF_1$-$term_1$-$ORF_2$-$gene_2$-$term_2$- . . . / . . . -$Prom_n$-$ORF_n$-$term_n$, wherein:

Prom1 is a sequence regulating the expression of the coding sequence ORF1,

ORF1 is a nucleic acid sequence encoding a desired protein PROT1, and especially a desired enzyme PROT1, Term1 is a transcription terminator sequence that mediates transcriptional termination by providing signals in the newly synthesized mRNA that trigger processes which release the mRNA from the transcriptional complex, and "1", "2", . . . / . . . "n" may or may not describe the same ORF (Open Reading Frame), promoter or terminator. The order of the genes does not matter. "n" is an integer usually ranging from 5 and 20. These constructs are inserted in one of the yeast chromosome at a controlled location. In some embodiments, the insertion site is not essential for the functionality of the inserted construct, nor for the viability of the resulting genetically modified yeast.

When the yeast is for example *Saccharomyces cerevisiae*, genes introduced in the yeast genome and originating from other organisms than *Saccharomyces cerevisiae* are generally "transcoded" (generally codon-optimized"), meaning the these genes are synthesized with an optimal codon usage for expression *S. cerevisiae*. The nucleotide sequence (and not the protein sequence) of some genes from *S. cerevisiae* has also been modified ("transcoded") to minimize recombination with an endogenous copy of the said gene.

Genes may be deleted through standard procedures used in yeast genetic engineering. In some embodiments, the genes targeted for deletion may be interrupted by insertion of one of the above described gene constructs, or alternatively the genes targeted for deletion are replaced by a short stretch of nucleotide.

Down regulating gene expression may be obtained by disrupting the endogenous copy of the gene and replacing it with a copy of the ORF under the control of a weak promoter. A list and sequences of weak promoters is described elsewhere in the present specification.

A gene may be rendered "inducible or repressible" by deleting the endogenous copy of the gene (if necessary) and placing a new copy of the ORF under the control of an inducible or repressible promoter. An inducible or repressible promoter is a promoter which activity is modulated and controlled, i.e. increased or decreased, upon a change in the environmental conditions or external stimuli. Induction or repression may be artificially controlled, which encompasses induction or repression by abiotic factors such as chemical compounds not found naturally in the organism of interest, light, oxygen levels, heat or cold. A list and sequence of inducible or repressible promoters is described elsewhere in the present specification.

As already specified elsewhere herein, a protein may be underexpressed by destabilization by using "the degron" technology which is described in Yu et al. 2015, (Current Opinion in Biotechnology, Vol. 36: 199-204). In brief, this technology consists in introducing in the protein sequence a modification that targets it for degradation. It can consist only in the two first amino acids following the principle known as the N-end rule, or a larger sequence targeting the whole protein to the ubiquitin-preoteasome degradation pathway.

Recombinant Yeast According to the Invention

The inventors have conceived recombinant microorganisms, and especially recombinant yeasts, having an increased ability of producing methionine and/or its derivatives thereof.

The present invention relates to recombinant yeasts having an increased methionine and/or methionine derivatives production, and wherein the increased methionine and/or methionine derivatives production is obtained through a plurality of alterations that have been introduced in the genome thereof, by genetic engineering methods.

This invention pertains to a methionine-producing and/or methionine derivatives-producing recombinant yeast, in the genome of which:

(A) at least one nucleic acid encoding an aspartate semi-aldehyde dehydrogenase HOM2 and/or at least one nucleic acid encoding an aspartate semi-aldehyde dehydrogenase HOM2 that can use as coenzyme both NAD and NADP is overexpressed and/or is under the control of an inducible or repressible promoter;

(B) at least one nucleic acid encoding an aspartokinase HOM3 is under the control of an inducible or repressible promoter; and (C) (i) a) at least one nucleic acid encoding an homoserine-O-acetyltransferase MET2 is overexpressed and/or is under the control of an inducible or repressible promoter;

and/or at least one nucleic acid encoding an homoserine-O-acetyltransferase METX is overexpressed and/or is under the control of an inducible or repressible promoter, and b) at least one nucleic acid encoding a methionine synthase MET17 is overexpressed and/or is under the control of an inducible or repressible promoter;

and/or (ii) a) at least one nucleic acid encoding an homoserine kinase THR1 is overexpressed and/or is under the control of an inducible or repressible promoter, and b) at least one nucleic acid encoding a cystathionine gamma-synthase 1 CGS1 that has an improved O-phospho-L-homoserine (OHPS) dependent methionine synthase activity is overexpressed and/or is under the control of an inducible or repressible promoter.

The inventors have found that an increased production of methionine and/or of methionine derivatives by yeast cells may be reached by introducing in the genome of these yeast cells a plurality of genetic alterations. As it is fully described herein, the said plurality of genetic alterations encompass an overexpression of certain genes, a controlled expression of certain other genes, as well as repression or deletion of further other genes.

The increased methionine and/or methionine derivatives production by yeast cells has been reached by the inventors by optimizing the metabolism of oxaloacetate, so as to direct the subsequent artificially modified metabolic pathway mainly towards methionine and/or methionine derivatives production whereas in the same time maintaining an optimal viability of the resulting genetically modified yeast cells.

After a lengthy research time period, the present inventors have determined that a high methionine and/or methionine derivatives production by yeast cells is obtained by increasing the conversion of oxaloacetate into the successive intermediate metabolites phospho-aspartyl, aspartyl-semialdehyde and homoserine, and additionally enhancing the conversion of homoserine into methionine, while, notably, maintaining a redox status allowing a good viability of the resulting recombinant yeast cells. This last point is essential and represented a significant challenge for the inventors throughout their research work.

The proposed solution according to the invention unexpectedly allows maintaining a viable NADH/NADPH equilibrium in the yeast cells throughout the methionine-production pathway through the consumption of less reducing power, the consumption of reducing power in the form of NADH rather than NADPH, and/or the production of NADH instead of NADPH.

As disclosed in detail in the present specification, the resulting recombinant yeast cells are genetically modified so as (I) to effect an over expression and/or a controlled expression of an aspartate semialdehyde dehydrogenase-encoding gene (HOM2), and (II) to effect a controlled expression of an aspartokinase-encoding gene (HOM3).

Further, in some embodiments of a recombinant yeast according to the invention, the said yeast comprises further genetic modifications for an optimal use of the intermediate metabolite aspartyl-semialdehyde for methionine and/or methionine derivatives production, the said further genetic modifications comprising an over expression of (i) a homoserine O-acetyltransferase-encoding gene (MET2; METX) and of (ii) a methionine synthase (MET17).

In some embodiments of a recombinant yeast according to the invention, the said yeast comprises alternative further genetic modifications for an optimal use of the intermediate metabolite aspartyl-semialdehyde for methionine and/or methionine derivatives production, the said further genetic modifications comprising (i) an over expression of an homoserine kinase-encoding gene (THR1) and (ii) an over expression of a cystathionine gamma-synthase 1 (CGS1) that has an improved O-phospho-L-homoserine (OHPS) dependent methionine synthase activity.

Thus, the present invention relates to a methionine-producing and/or methionine derivatives-producing recombinant yeast, the genome of which has been altered so as to:

(A) overexpress an aspartate-semialdehyde dehydrogenase and/or put it under the control of an inducible or repressible promoter, (B) control the expression of an aspartokinase, and (C) increase production of methionine from aspartyl-semialdehyde by:

(i) overexpressing and/or put under the control of an inducible or repressible promoter (a) a homoserine-O-acetyltransferase and (b) a methionine synthase, and/or (ii) (a) overexpressing and/or put under the control of an inducible or repressible promoter a homoserine kinase and (b) a cystathionine gamma-synthase 1 that has an improved O-phospho-L-homoserine (OHPS) dependent methionine synthase activity.

A recombinant yeast according to the invention produces methionine and/or methionine derivatives with a higher yield than the parent yeast which does not contain the genetic modifications described above. Further, a recombinant yeast according to the invention produces methionine and/or methionine derivatives without a requirement for sulfate but instead produces methionine and/or methionine derivatives by using a source of reduced sulfur, such as methanethiol (MeSH), sodium methanethiolate (MeSNa) or dimethylthioether (MeSMe). Using sulfur under its reduced form (SH) instead of, for example, sulfates (SO4) advantageously allows reducing the consumption of NADPH. Moreover, using MeSH, MeSNa or MeSMe, in particular MeSH, to synthesize methionine has the double avantage of not only being a source of reduced sulfur, but also of being an important source of methyl. This advantageously allows obtaining methionine directly from acetyl-homoserine (or from phosphohomoserine) and does not necessitate to go through the production of neither cystationine nor homocysteine.

Moreover, a recombinant yeast according to the invention has been genetically engineered so as to promote the expression of enzymes utilizing NADH rather than NADPH, such as an appropriate glutamate dehydrogenase or an appropriate aspartate semialdehyde dehydrogenase.

In some embodiments of a recombinant yeast according to the invention, the aspartate-semialdehyde dehydrogenase (HOM2) that are over expressed consist of the S. cerevisiae endogenous gene that is placed under the control of strong promoters and/or of inducible or repressible promoters.

In some embodiments, the aspartate-semialdehyde dehydrogenase is preferably encoded by the S. cerevisiae HOM2 gene.

In some embodiments, the aspartate-semialdehyde dehydrogenase is most preferably encoded by a variant of the S. cerevisiae HOM2 gene, which gene codes for a mutated HOM2 protein that uses both NAD and NADP, as it is shown in the examples herein. Such gene variant is for example illustrated in the examples and is called HOM2-1. It corresponds to the S. cerevisiae HOM2 gene mutated as discussed here-under.

The nature of the mutations aiming several amino acid residues in the aspartate-semialdehyde dehydrogenase variant in order to relaxe the high selectivity of HOM2 for NADP as coenzyme and enhance the affinity of the enzyme for NAD are known to the man skilled in the art and can for example be found in Faehnle, C. R. et al., Journal of Molecular Biology 1055-1068 (2005). In particular, the mutation S39 to E39 corresponding to the replacement of the nucleotides TCT in position 115 to 117 of the nucleotide sequence by the nucleotides GAG can be mentioned.

According to the nomenclature of the amino acids well known to the man skilled in the art, S represents a Serine and E represents a Glutamic acid.

In some embodiments, the aspartokinase (HOM3) is most preferably encoded by the S. cerevisiae HOM3 gene, as it is shown in the examples herein.

Further, the controlled expression of the aspartokinase expression is achieved by placing the aspartokinase-encoding nucleic acid under the control of an inducible or repressible promoter. Illustrative inducible or repressible promoters that may be used for obtaining a recombinant methionine-producing and/or methionine derivatives-producing yeast according to the invention are described elsewhere in the present specification.

Illustratively, in the embodiments wherein the said inducible or repressible promoter is pCUP1-1 promoter originating from S. cerevisiae, the expression of the aspartokinase may be induced by adding copper to the culture medium. The one skilled in the art may notably refer to Koller et al. (2000, Yeast, Vol. 16: 651-656).

Embodiment "(C)-(i)" of a Recombinant Yeast

As already specified previously herein, according to embodiment "(C)-(i)" of a recombinant yeast of the invention, there is (a) an over expression of a homoserine-O-acetyltransferase (MET2 and/or METX) and (b) an overexpression of a methionine synthase (MET17).

In some embodiments, the homoserine-O-acetyltransferase is most preferably encoded by the S. cerevisiae MET2-gene, as disclosed in the examples herein.

In some embodiments, the methionine synthase is most preferably encoded by the S. cerevisiae MET17-gene, as disclosed in the examples herein.

Embodiment "(C)-(ii)" of a Recombinant Yeast

As already specified previously herein, according to embodiment "(C)-(ii)" of a recombinant yeast of the invention, there is (a) an overexpression of a homoserine kinase (THR1) and (b) the insertion of an exogenous nucleic acid encoding a cystathionine gamma-synthase 1 (CGS1) that has an improved O-phospho-L-homoserine (OHPS) dependent methionine synthase activity.

In some embodiments, the homoserine kinase is most preferably encoded by the S. cerevisiae THR1-gene, as disclosed in the examples herein.

In some embodiments, the cystathionine gamma-synthase 1 is most preferably encoded by the Arabidopsis thaliana CGS1-gene, as discussed here-after and as disclosed in the examples herein.

Features of the genetic modifications introduced for obtaining a recombinant yeast according to the invention are further detailed below.

In a particular embodiment, a recombinant yeast of the invention can comprise the modifications according to embodiment "(C)-(i)" and to embodiment "(C)-(ii)".

Aspartate-Semialdehyde Dehydrogenase-Encoding Gene Over Expression and/or Controlled Expression In preferred embodiments of a recombinant yeast according to the invention, over expression of an aspartate-semialdehyde dehydrogenase-encoding gene is obtained by inserting, at selected location(s) of the yeast genome, one or more copies of an expression cassette comprising an aspartate-semialdehyde dehydrogenase coding sequence. Aspartate-semialdehyde dehydrogenase and an aspartate-semialdehyde dehydrogenase-encoding gene that are encompassed by the invention are detailed elsewhere in the present specification.

In some of these embodiments, the said one or more copies of an expression cassette comprising an aspartate-semialdehyde dehydrogenase coding sequence comprise(s) regulatory sequences allowing a strong expression of the aspartate-semialdehyde dehydrogenase, such as a strong promoter that is functional in yeast cells.

In addition to or as an alternative to these embodiments of a recombinant yeast according to the invention, at least one aspartate-semialdehyde dehydrogenase-encoding gene can be under the control of an inducible or repressible promoter that is functional in yeast cells.

Without wishing to be bound by any particular theory, the inventors believe that over expression of an aspartate-semialdehyde dehydrogenase may enhance the conversion of the intermediate metabolite aspartyl phosphate (Aspartyl-P) into aspartyl-semialdehyde. The same applies when at least one aspartate-semialdehyde dehydrogenase coding sequence is under the control of an inducible or repressible promoter.

In some embodiments, the aspartate-semialdehyde dehydrogenase may be an enzyme variant that uses both NADH or NADPH for catalyzing the conversion of aspartyl phosphate (Aspartyl-P) into aspartyl-semialdehyde.

In some preferred embodiments, the said aspartate-semialdehyde dehydrogenase-encoding gene is the HOM2 gene from *Saccharomyces cerevisiae*, or alternatively a variant of HOM2 utilizing both NADH and NADPH as shown in the examples herein and discussed previously.

In preferred embodiments, the said aspartate semi-aldehyde dehydrogenase-encoding gene is placed under the control of the strong promoter pADH1, of the strong promoter pTEF1, the inducible or repressible promoter pCUP1-1 or the inducible or repressible promoter pACU8.

Illustratively, the HOM2 gene may be inserted within the HOM3 gene and/or within the PYK2 gene and/or within the MUP3 gene and/or within the SAM1 gene and/or whitin the SAM2 gene, as it is shown in the examples herein.

Controlled Expression of an Aspartokinase-Encoding Gene

Aspartokinase and an aspartokinase-encoding gene that are encompassed by the invention are detailed elsewhere in the present specification.

Without wishing to be bound by any particular theory, the inventors believe that with a controlled expression of an aspartokinase-encoding gene, a controlled level of conversion of aspartate into aspartyl phosphate (Aspartyl-P) is obtained that shall contribute to the high level of viability of a recombinant yeast according to the invention.

In some embodiments of a recombinant yeast according to the invention, a controlled expression of an aspartokinase-encoding gene is obtained by inserting, at selected location(s) of the yeast genome, one or more copies of an expression cassette comprising an aspartokinase coding sequence that is placed under the control of an inducible regulatory element, such as an inducible or repressible promoter.

In some embodiments, a controlled expression of an aspartokinase-encoding gene is obtained by inserting, at the location of the natural yeast aspartokinase open reading frame, an inducible regulatory sequence, such as an inducible or repressible promoter, that replaces the endogenous promoter initially present in the yeast genome at this genome location.

In some preferred embodiments, the said aspartokinase-encoding gene is the HOM3 gene from *Saccharomyces cerevisiae*, as shown in the examples herein. In preferred embodiments, the said aspartokinase-encoding gene is placed under the control of the inducible or repressible promoter pCUP-1-1, of the inducible or repressible promoter pSAM4 or of the inducible or repressible promoter pACU3p.

Illustratively, the HOM3 gene may be inserted within the TRP1 gene and/or within the HOM3 gene and/or within the MUP3 gene and/or within the SAM3 gene, as it is shown in the examples herein.

First Embodiments of a Modified Pathway for Conversion of Homoserine into Methionine According to these embodiments of a recombinant yeast according to the invention, the said yeast comprises further genetic modifications for an optimal use of the intermediate metabolite aspartyl-semialdehyde for methionine production, the said further genetic modifications comprising an over expression of (i) a homoserine 0-acetyltransferase-encoding gene (MET2 or METX) and of (ii) a methionine synthase (MET17, also named MET25 or MET15), and/or a controlled expression of these genes.

Accordingly, in a particular embodiment, a genome of a recombinant yeast according to the invention is such that:

a) at least one nucleic acid encoding an homoserine-O-acetyltransferase MET2 is overexpressed and/or under the control of an inducible or repressible promoter, and/or at least one nucleic acid encoding an homoserine-O-acetyltransferase METX is overexpressed and/or under the control of an inducible or repressible promoter, and b) at least one nucleic acid encoding an O-acetyl homoserine-O-acetyl serine sulfhydrylase MET17 is overexpressed and/or under the control of an inducible or repressible promoter.

Homoserine-O-Acetyltransferase-Encoding Gene Over Expression and/or Controlled Expression In preferred embodiments of a recombinant yeast according to the invention, over expression of a homoserine-O-acetyltransferase-encoding gene is obtained by inserting, at selected location(s) of the yeast genome, one or more copies of an expression cassette comprising a homoserine-O-acetyltransferase coding sequence. Homoserine-O-acetyltransferase and a homoserine-O-acetyltransferase-encoding gene that are encompassed by the invention are detailed elsewhere in the present specification.

In some of these embodiments, the said one or more copies of an expression cassette comprising a homoserine-O-acetyltransferase coding sequence comprise regulatory sequences allowing a strong expression of the homoserine-O-acetyltransferase, such as a strong promoter that is functional in yeast cells.

In addition to or as an alternative to these embodiments of a recombinant yeast according to the invention, at least one homoserine-O-acetyltransferase-encoding gene can be under the control of an inducible or repressible promoter that is functional in yeast cells.

Without wishing to be bound by any particular theory, the inventors believe that over expression of a homoserine-O-acetyltransferase increases the level of conversion of the intermediate metabolite homoserine into O-acetylhomoserine, in the presence of acetyl-CoA. The same applies when at least one homoserine-O-acetyltransferase coding sequence is under the control of an inducible or repressible promoter.

In preferred embodiments, the said homoserine-O-acetyltransferase-encoding gene is the gene from *Saccharomyces cerevisiae*, as shown in the examples herein.

In preferred embodiments, the said homoserine-O-acetyltransferase-encoding gene is the METX gene from *Corynebacterium glutamicum*, as shown in the examples herein.

In a particularly preferred embodiment, a recombinant yeast according to the invention comprises at least one homoserine-O-acetyltransferase-encoding gene which is the gene from *Saccharomyces cerevisiae* and at least one homoserine-O-acetyltransferase-encoding gene which is the METX gene from *Corynebacterium glutamicum*.

In preferred embodiments, the said homoserine-O-acetyltransferase-encoding gene is, independently for each copy of said gene if multiple copies are present, placed under the control of a strong promoter such as pPDC1, pTDH3, pADH1, pCCW12, pENO2 or pTEF3, or a strong inducible or repressible promoter such as pCUP1, pCUP1-1 or pSAM4.

Illustratively, the homoserine-O-acetyltransferase MET2/METX gene may be inserted within the HOM3 gene and/or within the MAE1 gene and/or within the MUP3 gene and/or within the URA3 gene and/or within the LYP1 gene, as it is shown in the examples herein.

Methionine Synthase-Encoding Gene Over Expression or Controlled Expression

In preferred embodiments of a recombinant yeast according to the invention, over expression of a methionine synthase-encoding gene is obtained by inserting, at selected location(s) of the yeast genome, one or more copies of an expression cassette comprising a methionine synthase coding sequence. Methionine synthase and a methionine synthase-encoding gene that are encompassed by the invention are detailed elsewhere in the present specification.

In some of these embodiments, the said one or more copies of an expression cassette comprising a methionine synthase coding sequence comprise regulatory sequences allowing a strong expression of the methionine synthase, such as a strong promoter that is functional in yeast cells.

In addition to or as an alternative to these embodiments of a recombinant yeast according to the invention, at least one methionine synthase-encoding gene can be under the control of an inducible or repressible promoter that is functional in yeast cells.

Without wishing to be bound by any particular theory, the inventors believe that an over expression of a methionine synthase increases the conversion of the intermediate metabolite O-acetylhomoserine into methionine. The same applies when at least one methionine synthase coding sequence is under the control of an inducible or repressible promoter.

In preferred embodiments, the said methionine synthase-encoding gene is the gene from *Saccharomyces cerevisiae*, as shown in the examples herein. MET17 may also be termed MET25 or MET15 in the art, as well as in some locations of the present specification.

In preferred embodiments, the said methionine synthase-encoding gene is the gene from *Ruegeria pomeroyi*.

In preferred embodiments, the said methionine synthase-encoding gene is placed under the control of the strong promoters pTEF3, pCUP1, pCUP1-1 or pENO2.

Illustratively, the methionine synthase gene may be inserted within the URA3 gene, within the HOM3 gene and/or within the MAE1 gene and/or within the MUP3 gene and/or within the GNP1 gene and/or within the LYP1 gene, as it is shown in the examples herein.

Second Embodiments of a Modified Pathway for Conversion of Homoserine into Methionine According to these embodiments of a recombinant yeast according to the invention, the said yeast comprise alternative or complementary, further genetic modifications for an optimal use of the intermediate metabolite aspartyl-semialdehyde for methionine production, the said further genetic modifications comprising (i) an over expression of an homoserine kinase-encoding gene (THR1) and (ii) an over expression of a cystathionine gamma-synthase 1 (CGS1), and/or a controlled expression of these genes.

Accordingly, in a particular embodiment, a genome of a recombinant yeast according to the invention is such that at least one nucleic acid encoding a homoserine kinase THR1 is, independently, under the control of an inducible or repressible promoter and/or is in a destabilized form.

Homoserine Kinase-Encoding Gene Over Expression or Controlled Expression

In preferred embodiments of a recombinant yeast according to the invention, over expression of a homoserine kinase-encoding gene is obtained by inserting, at selected location(s) of the yeast genome, one or more copies of an expression cassette comprising a homoserine kinase coding sequence. Homoserine kinase and a homoserine kinase-encoding gene that are encompassed by the invention are detailed elsewhere in the present specification.

In some of these embodiments, the said one or more copies of an expression cassette comprising a homoserine kinase-coding sequence comprise regulatory sequences allowing a strong expression of the homoserine kinase, such as a strong promoter that is functional in yeast cells.

In addition to or as an alternative to these embodiments of a recombinant yeast according to the invention, at least one homoserine kinase-encoding gene can be under the control of an inducible or repressible promoter that is functional in yeast cells.

Without wishing to be bound by any particular theory, the inventors believe that an over expression of a homoserine kinase increases the conversion of the intermediate metabolite into phospho-homoserine. The same applies when at least one homoserine kinase coding sequence is under the control of an inducible or repressible promoter.

In preferred embodiments, the said homoserine kinase-encoding gene is the gene from *Saccharomyces cerevisiae*, as shown in the examples herein.

In preferred embodiments, the said homoserine kinase-encoding gene is placed under the control of the strong promoter pTDH3 or the inducible or repressible promoter pACU6.

Illustratively, the homoserine kinase gene may be inserted within the SAM3 gene, as it is shown in the examples herein.

Cystathionine Gamma Synthase 1-Encoding Gene Over Expression or Controlled Expression In preferred embodiments of a recombinant yeast according to the invention, over expression of a cystathionine gamma synthase 1-encoding gene is obtained by inserting, at selected location(s) of the yeast genome, one or more copies of an expression cassette comprising a cystathionine gamma synthase 1 coding sequence. Cystathionine gamma synthase 1 and a cystathionine gamma synthase 1-encoding gene that are encompassed by the invention are detailed elsewhere in the present specification.

As indicated previously, this cystathionine gamma synthase 1 of the invention has an improved O-phospho-L-homoserine (OHPS) dependent methionine synthase activity.

In some of these embodiments, the said one or more copies of an expression cassette comprising a cystathionine gamma synthase 1 coding sequence comprise regulatory sequences allowing a strong expression of the cystathionine gamma synthase 1, such as a strong promoter that is functional in yeast cells.

In addition to or as an alternative to these embodiments of a recombinant yeast according to the invention, at least one cystathionine gamma synthase 1-encoding gene can be under the control of an inducible or repressible promoter that is functional in yeast cells.

Without wishing to be bound by any particular theory, the inventors believe that an over expression of a cystathionine gamma synthase 1 increases the conversion of the intermediate metabolite phospho-homoserine into methionine. The same applies when at least one cystathionine gamma synthase 1 coding sequence is under the control of an inducible or repressible promoter.

In preferred embodiments, the said cystathionine gamma synthase 1-encoding gene is the gene from *Arabidopsis thaliana*, as shown in the examples herein.

In a preferred embodiment, the cystathionine gamma synthase 1 comprises a mutation that relieves the translational repression exerted by S-adenosylmethionine on CGS1 (Onoue et al. Journal of Biological Chemistry 286 (2011), 14903-149 1). Such mutated CGS1 is in particular as disclosed in the application WO 2014064244.

In preferred embodiments, the said cystathionine gamma synthase 1-encoding gene is placed under the control of the strong promoter pCCW12 or the strong inducible or repressible promoter pCUP1-1.

Illustratively, the cystathionine gamma synthase 1 gene may be inserted within the SAM3 gene, as it is shown in the examples herein.

A description of the genes encoding (i) an aspartate semialdehyde dehydrogenase, (ii) an aspartokinase, (iii) a homoserine O-acetyl transferase, (iv) a methionine synthase, (v) a homoserine kinase, and (vi) a cystathionine gamma synthase 1, is found hereunder.

Aspartate-Semialdehyde Dehydrogenase (HOM2)

The aspartate-semialdehyde dehydrogenase is a protein which is known in the art to catalyze the NADPH-dependent formation of L-aspartate-semialdehyde by the reductive dephosphorylation of L-aspartyl-4-phosphate. The aspartate-semialdehyde dehydrogenase encoded by the genome of *Saccharomyces cerevisiae* may be termed HOM2.

A method implemented to measure the activity level of aspartate-semialdehyde dehydrogenase belongs to the general knowledge of the one skilled in the art.

Preferred aspartate semialdehyde-dehydrogenase in the present specification is an enzyme having an EC number 1.2.1.11.

According to a preferred embodiment, the nucleic acid(s) encoding an aspartate-semialdehyde dehydrogenase may be nucleic acid(s) originating from organisms preferably selected in a group comprising prokaryotic organisms and eukaryotic organisms. In some embodiments, the nucleic acid(s) encoding an aspartate-semialdehyde dehydrogenase may be nucleic acid(s) originating from archaebacteria. In some preferred embodiments, the nucleic acid(s) encoding an aspartate-semialdehyde dehydrogenase may be nucleic acid(s) originating from yeast, and especially from *Saccharomyces cerevisiae*.

According to other preferred embodiment, the nucleic acid encoding an aspartate-semialdehyde dehydrogenase may be a variant or a mutant of the aspartate-semialdehyde dehydrogenase from *Saccharomyces cerevisiae*, wherein the said variant enzyme or the said mutant enzyme uses both NADH or NADPH for catalyzing reactions. Such variant or mutant enzymes are known in the art and are previously discussed in the present text.

According to a yet preferred embodiment, the nucleic acid(s) encoding an aspartate-semialdehyde dehydrogenase may be nucleic acid(s) selected from the group consisting of sequences having at least 27%, advantageously at least 65%, preferably at least 80%, nucleic acid identity with a nucleic acid selected in a group consisting of the reference nucleic acid sequences of SEQ ID NO: 1 and SEQ ID NO. 2, and also a biological activity of the same nature. The nucleic acids of SEQ ID NO: 1 and SEQ ID NO. 2 encode an aspartate-semialdehyde dehydrogenase originating from *Saccharomyces*, that may also be collectively termed HOM2 herein.

A biological activity of the same nature regarding this sequence is the capacity to code for an enzyme that catalyzes the NADPH-dependent formation of L-aspartate-semialdehyde by the reductive dephosphorylation of L-aspartyl-4-phosphate.

As described herein, a nucleic acid sequence having at least 27% nucleotide identity with a reference nucleic acid sequence encompasses nucleic acid sequences having at least 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequences, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequences, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the aspartate-semialdehyde dehydrogenase from *Saccharomyces cerevisiae*, the one skilled in the art may refer to the accession number NP010442 in the UniProt database, or to SEQ ID NO. 3 described herein.

According to another particular embodiment, the nucleic acid(s) encoding an aspartate-semialdehyde dehydrogenase may be nucleic acid(s) encoding an amino acid sequence selected from the group consisting of sequences having at least 27%, advantageously at least 65%, preferably at least 80%, amino acid identity with the amino acid sequence of SEQ ID NO: 3, and also a biological activity of the same nature. Illustratively, the aspartate-semialdehyde dehydrogenase originating from *Lactobacillus wasatchensis* has 27% amino acid identity with the aspartate-semialdehyde dehydrogenase of SEQ ID NO. 3.

A biological activity of the same nature regarding this sequence is as described previously, i.e. the capacity to catalyze the NADPH-dependent formation of L-aspartate-semialdehyde by the reductive dephosphorylation of L-aspartyl-4-phosphate.

As described herein, an amino acid sequence having at least 27% amino acid identity with a reference nucleic acid sequence encompasses amino acid sequences having at least 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the aspartate-semialdehyde dehydrogenase in the present invention is regulated by at least one promoter and at least one terminator, such as herein after defined more in details, which are present in 5' and 3' position respectively of the nucleic acid sequence encoding the said aspartate-semialdehyde dehydrogenase.

As it is specified elsewhere in the present description, the aspartate-semialdehyde dehydrogenase is overexpressed and/or under the control of an inducible or repressible promoter in a recombinant yeast according to the invention.

In some embodiments, overexpression of the aspartate-semialdehyde dehydrogenase may result from the control of the corresponding gene by a strong promoter within the said recombinant yeast.

In some other embodiments, overexpression of the aspartate-semialdehyde dehydrogenase may result from the presence of a plurality of copies of an aspartate-semialdehyde dehydrogenase-encoding sequence within the genome of the said recombinant yeast.

In still further embodiments, overexpression of the aspartate-semialdehyde dehydrogenase may result from both (i) the control of the corresponding gene by a strong promoter within the said recombinant yeast and (ii) the presence of a plurality of copies of an aspartate-semialdehyde dehydrogenase-encoding sequence within the genome the said recombinant yeast.

Aspartokinase (HOM3)

The aspartokinase enzyme is a protein which is described in the art for catalyzing the conversion of L-aspartate in the presence of ATP into 4-phospho-L-aspartate. The aspartokinase encoded by the genome of *Saccharomyces cerevisiae* may be termed HOM3.

A method implemented to measure the activity level of aspartokinase belongs to the general knowledge of the one skilled in the art.

In this regard, the one skilled in the art may advantageously refer to the method described by Stadtman et al. (1961, J Biol Chem, Vol. 236 (7): 2033-2038).

Preferred aspartokinase in the present specification is an enzyme having an EC number of no. EC 2.7.2.4.

According to a preferred embodiment, the nucleic acid(s) encoding an aspartokinase may be nucleic acid(s) originating from organisms preferably selected in a group comprising prokaryotic organisms and eukaryotic organisms. In some embodiments, the nucleic acid(s) encoding an aspartokinase may be nucleic acid(s) originating from archaebacteria. In some embodiments, the nucleic acid(s) encoding an aspartokinase may be nucleic acid(s) originating from organisms preferably selected from *Bacillus subtilis*, and yeasts. In some other preferred embodiments, the nucleic acid(s) encoding an aspartokinase may be nucleic acid(s) originating from a yeast, and especially from *Saccharomyces cerevisiae*.

According to a yet preferred embodiment, the nucleic acid(s) encoding an aspartokinase may be nucleic acid(s) selected from the group consisting of sequences having at least 25%, advantageously at least 65%, preferably at least 80%, nucleic acid identity with a nucleic acid of SEQ ID NO: 4, and also a biological activity of the same nature. The nucleic acid of SEQ ID NO: 4 encodes an aspartokinase originating from *Saccharomyces*, that may also be termed HOM3.

A biological activity of the same nature regarding this sequence is the capacity to code for an enzyme that catalyzes the conversion of L-aspartate in the presence of ATP into 4-phospho-L-aspartate.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the aspartokinase from *Saccharomyces cerevisiae*, the one skilled in the art may refer to the accession number NP010972 in the UniProt database, or to SEQ ID NO: 5 described herein.

According to another particular embodiment, the nucleic acid(s) encoding aspartokinase may be nucleic acid(s) encoding an amino acid sequence selected from the group consisting of sequences having at least 25%, advantageously at least 65%, preferably at least 80%, amino acid identity with the amino acid sequence of SEQ ID NO: 5, and also a biological activity of the same nature. Illustratively, the aspartokinase originating from *Aquamarina atlantica* has 25% amino acid identity with the aspartokinase of SEQ ID NO. 5.

A biological activity of the same nature regarding this sequence is as described previously, i.e. the capacity to catalyze the conversion of L-aspartate in the presence of ATP into 4-phospho-L-aspartate.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the aspartokinase in the present invention is regulated by at least one promoter and at least one terminator, such as herein after defined more in details, which are present in 5' and 3' position respectively of the nucleic acid sequence encoding the said aspartokinase.

As it is specified elsewhere in the present description, the strong aspartokinase expression shall be controlled in a recombinant yeast according to the invention.

In preferred embodiments, the controlled strong expression of the aspartokinase is performed by placing the aspartokinase-encoding nucleic acid sequence under the control of an appropriate inducible or repressible promoter, preferably a strong inducible or repressible promoter.

Homoserine O-Acetyltransferase (MET2; METX)

The homoserine O-acetyltransferase enzyme is a protein which is described in the art for catalyzing the reaction between Acetyl-CoA and L-homoserine into CoA and O-acetyl-L-homoserine. The homoserine O-acetyltransferase encoded by the genome of *Saccharomyces cerevisiae* may be termed MET2.

A method implemented to measure the activity level of homoserine O-acetyltransferase belongs to the general knowledge of the one skilled in the art.

In this regard, the one skilled in the art may advantageously refer to the method described by Shuzo Yamagata (1987, The Journal of Bacteriology, Vol. 169(8): 3458-3463.

Preferred homoserine O-acetyltransferase in the present specification is an enzyme having an EC number of no. EC 2.3.1.31.

According to a preferred embodiment, the nucleic acid(s) encoding a homoserine O-acetyltransferase may be nucleic acid(s) originating from organisms preferably selected in a group comprising prokaryotic organisms and eukaryotic organisms. In some embodiments, the nucleic acid(s) encoding a homoserine 0-acetyltransferase may be nucleic acid(s) originating from archaebacteria. In some embodiments, the nucleic acid(s) encoding a homoserine O-acetyltransferase may be nucleic acid(s) originating from organisms preferably selected from *Corynebacterium glutamicum*, and yeasts. In some other preferred embodiments, the nucleic acid(s) encoding a homoserine O-acetyltransferase may be nucleic acid(s) originating from yeast, and especially from *Saccharomyces cerevisiae*.

In a particular embodiment, the nucleic acid encoding an homoserine-O-acetyltransferase METX are nucleic acid from a bacterium, in particular from a bacterium selected, independently, from the group consisting of *Corynebacterium glutamicum, Escherichia coli, Haemophilus influenza, Streptomyces lavendulae, Leptospira interrogans, Streptococcus pneumonia* and *Mycobacterium tuberculosis*.

According to a yet preferred embodiment, the nucleic acid(s) encoding a homoserine O-acetyltransferase may be nucleic acid(s) selected from the group consisting of sequences having at least 27%, advantageously at least 65%, preferably at least 80%, nucleic acid identity with a nucleic acid of SEQ ID NO: 6, and also a biological activity of the same nature. The nucleic acid of SEQ ID NO: 6 encodes a homoserine 0-acetyltransferase originating from *Saccharomyces cerevisiae*, that may also be termed MET2. The homoserine O-acetyltransferase originating from *Corynebacterium glutamicum* is usually termed METX.

A biological activity of the same nature regarding this sequence is the capacity to code for an enzyme that catalyzes the reaction between Acetyl-CoA and L-homoserine into CoA and O-acetyl-L-homoserine.

As described herein, a nucleic acid sequence having at least 27% nucleotide identity with a reference nucleic acid sequence encompasses nucleic acid sequences having at least 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the the homoserine O-acetyltransferase from *Saccharomyces cerevisiae*, the one skilled in the art may refer to the accession number NP014122 in the UniProt database, or to SEQ ID NO. 7 described herein.

According to another particular embodiment, the nucleic acid(s) encoding a homoserine O-acetyltransferase may be nucleic acid(s) encoding an amino acid sequence selected from the group consisting of sequences having at least 27%, advantageously at least 65%, preferably at least 80%, amino acid identity with the amino acid sequence of SEQ ID NO: 7, and also a biological activity of the same nature. Illustratively, the homoserine O-acetyltransferase originating from *Aquamarina atlantica* has 27% amino acid identity with the homoserine O-acetyl transferase of SEQ ID NO. 7.

A biological activity of the same nature regarding this sequence is as described previously, i.e. the capacity to catalyze the reaction between Acetyl-CoA and L-homoserine into CoA and O-acetyl-L-homoserine.

As described herein, an amino acid sequence having at least 27% amino acid identity with a reference nucleic acid sequence encompasses amino acid sequences having at least 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of a homoserine 0-acetyltransferase in the present invention is regulated by at least one promoter and at least one terminator, such as herein after defined more in details, which are present in 5' and 3' position respectively of the nucleic acid sequence encoding the said homoserine 0-acetyltransferase.

As it is specified elsewhere in the present description, in some embodiments of the invention, the homoserine O-acetyltransferase is overexpressed and/or under the control of an inducible or repressible promoter in a recombinant yeast according to the invention.

In some embodiments, overexpression of the homoserine O-acetyltransferase may result from the control of the corresponding gene by a strong promoter within the said recombinant yeast.

In some other embodiments, overexpression of the homoserine O-acetyltransferase may result from the presence of a plurality of copies of a homoserine O-acetyltransferase-encoding sequence within the genome the said recombinant yeast.

In still further embodiments, overexpression of the homoserine O-acetyltransferase may result from both (i) the control of the corresponding gene by a strong promoter within the said recombinant yeast and (ii) the presence of a plurality of copies of a homoserine O-acetyltransferase-encoding sequence within the genome the said recombinant yeast.

Methionine Synthase (MET17)

The methionine synthase is a protein which is described in the art for catalyzing the conversion of O-acetyl-L-homoserine (OAH) in the presence of methanthiol into methionine and acetate. The methionine synthase is also described in the art for catalyzing the conversion of OAH into homocysteine or the conversion of O-acetylserine (OAS) into cysteine. The methionine synthase encoded by the genome of *Saccharomyces cerevisiae* may be termed MET17. The methionine synthase encoded by the genome of *Saccharomyces cerevisiae* may also be termed MET25 or MET15 in the art.

A method implemented to measure the activity level of methionine synthase belongs to the general knowledge of the one skilled in the art.

In this regard, the one skilled in the art may advantageously refer to the method described by Ravanel (1995, Archives of Biochemistry and Biophysics, Vol. 316: 572-584).

Preferred methionine synthase in the present specification is an enzyme having an EC number of no. 2.5.1.49.

According to a preferred embodiment, the nucleic acid(s) encoding a methionine synthase may be nucleic acid(s) originating from organisms preferably selected in a group comprising prokaryotic organisms and eukaryotic organisms. In some embodiments, the nucleic acid(s) encoding a methionine synthase may be nucleic acid(s) originating from archaebacteria. In some embodiments, the nucleic acid(s) encoding a methionine synthase may be nucleic acid(s) originating from organisms preferably selected from yeast, and especially from *Saccharomyces cerevisiae*.

According to a yet preferred embodiment, the nucleic acid(s) encoding a methionine synthase may be nucleic acid(s) selected from the group consisting of sequences having at least 47%, advantageously at least 65%, preferably at least 80%, nucleic acid identity with a nucleic acid of SEQ ID NO: 8, and also a biological activity of the same nature. The nucleic acid of SEQ ID NO: 8 encodes a methionine synthase originating from *Saccharomyces cerevisiae*, that may also be termed MET17.

A biological activity of the same nature regarding this sequence is the capacity to code for an enzyme that catalyzes the conversion of O-acetyl-L-homoserine (OAH) into methionine and acetate in the presence of methanthiol.

As described herein, a nucleic acid sequence having at least 47% nucleotide identity with a reference nucleic acid sequence encompasses nucleic acid sequences having at least 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the methionine synthase from *Saccharomyces cerevisiae*, the one skilled in the art may refer to the accession number NP013406 in the UniProt database, or to SEQ ID NO. 9 described herein.

According to another particular embodiment, the nucleic acid(s) encoding methionine synthase may be nucleic acid(s) encoding an amino acid sequence selected from the group consisting of sequences having at least 47%, advantageously at least 65%, preferably at least 80%, amino acid identity with the amino acid sequence of SEQ ID NO: 9. Illustratively, the methionine synthase originating from *Lactococcus plantarum* has 47% amino acid identity with the methionine synthase of SEQ ID NO: 9.

A biological activity of the same nature regarding this sequence is as described previously, i.e. the capacity to catalyze the conversion of O-acetyl-L-homoserine (OAH) into methionine and acetate in the presence of methanthiol.

As described herein, an amino acid sequence having at least 47% amino acid identity with a reference nucleic acid sequence encompasses amino acid sequences having at least 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the methionine synthase in the present invention is regulated by at least one promoter and at least one terminator, such as herein after defined more in details, which are present in 5' and 3' position respectively of the nucleic acid sequence encoding the said methionine synthase.

As it is specified elsewhere in the present description, in some embodiments of the invention, the methionine synthase is overexpressed and/or under the control of an inducible or repressible promoter in a recombinant yeast according to the invention.

In some embodiments, overexpression of the methionine synthase may result from the control of the corresponding gene by a strong promoter within the said recombinant yeast.

In some other embodiments, overexpression of the methionine synthase may result from the presence of a plurality of copies of a methionine synthase encoding sequence within the genome the said recombinant yeast.

Homoserine Kinase (THR1)

Homoserine kinase enzyme is a protein which is described in the art for catalyzing the ATP-dependent phosphorylation of L-homoserine to L-homoserine phosphate. Homoserine kinase encoded by the genome of *Saccharomyces cerevisiae* may be termed THR1.

A method implemented to measure the activity level of homoserine kinase belongs to the general knowledge of the one skilled in the art.

In this regard, the one skilled in the art may advantageously refer to the method described by Mannhaupt and Feldmann (1990, Eur J Biochem, Vol. 191: 115-122).

Preferred homoserine kinase in the present specification is an enzyme having an EC number of no. EC 2.7.1.39.

According to a preferred embodiment, the nucleic acid(s) encoding a homoserine kinase may be nucleic acid(s) originating from organisms preferably selected in a group comprising prokaryotic organisms and eukaryotic organisms. In some embodiments, the nucleic acid(s) encoding a homoserine kinase may be nucleic acid(s) originating from archaebacteria. In some other preferred embodiments, the nucleic acid(s) encoding a homoserine kinase may be nucleic acid(s) originating from yeast, and especially from *Saccharomyces cerevisiae*.

According to a yet preferred embodiment, the nucleic acid(s) encoding a homoserine kinase may be nucleic acid(s) selected from the group consisting of sequences having at least 25%, advantageously at least 65%, preferably at least 80%, nucleic acid identity with a nucleic acid of SEQ ID NO: 10, and also a biological activity of the same nature. The nucleic acid of SEQ ID NO: 10 encodes a homoserine kinase originating from *Saccharomyces*, that may also be termed THR1.

A biological activity of the same nature regarding this sequence is the capacity to code for an enzyme that catalyzes the ATP-dependent phosphorylation of L-homoserine to L-homoserine phosphate.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the homoserine kinase from *Saccharomyces cerevisiae*, the one skilled in the art may refer to the accession number NP011890 in the UniProt database, or to SEQ ID NO. 11 described herein.

According to another particular embodiment, the nucleic acid(s) encoding homoserine kinase may be nucleic acid(s) encoding an amino acid sequence selected from the group consisting of sequences having at least 25%, advantageously at least 65%, preferably at least 80%, amino acid identity with the amino acid sequence of SEQ ID NO: 11, and also a biological activity of the same nature. Illustratively, the homoserine kinase originating from *Aquamarina atlantica* has 25% amino acid identity with the homoserine kinase of SEQ ID NO. 11.

A biological activity of the same nature regarding this sequence is as described previously, i.e. the capacity to catalyze the ATP-dependent phosphorylation of L-homoserine to L-homoserine phosphate.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the homoserine kinase in the present invention is regulated by at least one promoter and at least one terminator, such as herein after defined more in details, which are present in 5' and 3' position respectively of the nucleic acid sequence encoding the said homoserine kinase.

As it is specified elsewhere in the present description, in some embodiments of the invention, the homoserine kinase is overexpressed and/or under the control of an inducible or repressible promoter in a recombinant yeast according to the invention.

In some embodiments, overexpression of the homoserine kinase may result from the control of the corresponding gene by a strong promoter within the said recombinant yeast.

In some other embodiments, overexpression of the homoserine kinase may result from the presence of a plurality of copies of a homoserine kinase-encoding sequence within the genome the said recombinant yeast.

In still further embodiments, overexpression of the homoserine kinase may result from both (i) the control of the corresponding gene by a strong promoter within the said recombinant yeast and (ii) the presence of a plurality of copies of a homoserine kinase-encoding sequence within the genome the said recombinant yeast.

Cystathionine Gamma Synthase 1 (CGS1)

The cystathionine gamma synthase 1 enzyme is a protein which is described in the art for catalyzing the formation of L-cystathionine from homoserine esters and L-cysteine, via a gamma-replacement reaction. The cystathionine gamma synthase 1 encoded by the genome of *Arabidopsis thaliana* may be termed CGS1.

A method implemented to measure the activity level of cystathionine gamma synthase 1 belongs to the general knowledge of the one skilled in the art.

In this regard, the one skilled in the art may advantageously refer to the method described by Loizeau et al. (2007, Plant Physiology, Vol. 145: 491-503).

Preferred cystathionine gamma synthase 1 in the present specification is an enzyme having an EC number of no. EC 2.5.1.48.

According to a preferred embodiment, the nucleic acid(s) encoding a cystathionine gamma synthase 1 may be nucleic acid(s) originating from organisms preferably selected in a group comprising prokaryotic organisms and eukaryotic organisms. In some preferred embodiments, the nucleic acid(s) encoding a cystathionine gamma synthase 1 may be nucleic acid(s) originating from a plant, and especially from *Arabidopsis thaliana*.

According to a yet preferred embodiment, the nucleic acid(s) encoding a cystathionine gamma synthase 1 may be nucleic acid(s) selected from the group consisting of sequences having at least 40%, advantageously at least 65%, preferably at least 80%, nucleic acid identity with a nucleic acid having the accession number NM 110977.3 in the UniProt database, in particular having a nucleic acid of SEQ ID NO: 12 which encodes a cystathionine gamma synthase 1 originating from *Arabidobsis thaliana*, that may also be termed CGS1, and also a biological activity of the same nature.

In a particular embodiment, the nucleic acid encoding a cystathionine gamma-synthase 1 CGS1 mutated are nucleic acid belonging to a microorganism selected, independently, from the group consisting of plant cystathionine gamma synthase 1 and is preferably the cystathionine gamma synthase 1 from *Arabidopsis thaliana*.

A biological activity of the same nature regarding this sequence is the capacity to code for an enzyme that catalyzes the formation of L-cystathionine from homoserine esters and L-cysteine, via a gamma-replacement reaction.

As described herein, a nucleic acid sequence having at least 40% nucleotide identity with a reference nucleic acid sequence encompasses nucleic acid sequences having at least 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence having the nucleic acid of SEQ ID NO: 12, and in particular having 100% nucleotide identity with the nucleic acid sequence of SEQ ID NO: 12, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence having the nucleic acid of SEQ ID NO: 12, and in particular having 100% nucleotide identity with the nucleic acid sequence of SEQ ID NO: 12, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence having the nucleic acid of SEQ ID NO: 12, and in particular having 100% nucleotide identity with the nucleic acid sequence of SEQ ID NO: 12, and also a biological activity of the same nature.

For the amino acid sequence of the cystathionine gamma synthase 1 from *Arabidopsis thaliana*, the one skilled in the art may refer to the accession number NP186761 in the UniProt database, or to SEQ ID NO. 13 described herein.

According to another particular embodiment, the nucleic acid(s) encoding cystathionine gamma synthase 1 may be nucleic acid(s) encoding an amino acid sequence selected from the group consisting of sequences having at least 40%, advantageously at least 65%, preferably at least 80%, amino acid identity with the amino acid sequence of SEQ ID NO: 13 or with the amino acid sequence having the accession number NP186761 in the UniProt database, and also a biological activity of the same nature.

A biological activity of the same nature regarding this sequence is as described previously, i.e. the capacity to catalyze the formation of L-cystathionine from homoserine esters and L-cysteine, via a gamma-replacement reaction.

As described herein, an amino acid sequence having at least 40% amino acid identity with a reference nucleic acid sequence encompasses amino acid sequences having at least 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence SEQ ID NO: 13 or with the amino acid sequence having the accession number NP186761 in the UniProt database, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence SEQ ID NO: 13 or with the amino acid sequence having the accession number NP186761 in the UniProt database, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence SEQ ID NO: 13 or with the amino acid sequence having the accession number NP186761 in the UniProt database, and also a biological activity of the same nature.

According to a preferred embodiment, the cystathionine gamma synthase 1 used in a recombinant yeast of the present application can be selected among the mutants of CGS1 disclosed in the application WO2014064244, and is in particular a O-phospho-L-homoserine (OHPS) dependent methionine synthase according to this document.

According to this particular embodiment, the cystathionine gamma synthase 1 regarding the present invention can be:

(i) OHPS dependent methionine synthases which are derived from a cystathionine gamma synthase 1 having the amino acid sequence shown in SEQ ID NO: 13 by substitution or deletion of at least one amino acid residue in SEQ ID NO: 13 selected from the group consisting of:

(a) proline 10;
(b) asparagine 11;
(c) glutamine 15;
(d) isoleucine 27;
(e) alanine 30;
(f) leucine 45;
(g) serine 47;
(h) valine 60;
(i) alanine 68;
(j) phenylalanine 150;
(k) threonine 178;
(l) aspartate 183;
(m) isoleucine 185;
(n) threonine 220;
(o) methionine 232;
(P) valine 245;
(q) alanine 257;
(r) asparagine 259;
(s) phenylalanine 261; (t) phenylalanine 275;
(u) isoleucine 287;
(v) histidine 289;
(w) tyrosine 324;
(x) glycine 326;
(y) proline 356;
(z) threonine 371;
(aa) valine 396;
(bb) proline 405;
(cc) aspartate 431;
(dd) isoleucine 436;
(ee) isoleucine 457;
(ff) aspartate 459;
(gg) proline 470;
(hh) glutamate 472;
(ii) alanine 506;
(jj) isoleucine 507.
or (ii) OHPS dependent methionine synthases which are derived from a cystathionine gamma synthase 1, the amino acid sequence of which shows at least 60% sequence identity to the amino acid sequence shown in SEQ ID NO: 13, by substitution or deletion of at least one amino acid residue corresponding to any one of (a) to (jj) listed above in SEQ ID NO: 13. Preferably, the sequence identity is at least 70%, even more preferably at least 80% and most preferably at least 90%.

According to one embodiment, the OHPS dependent methionine synthase of the present invention has an amino acid sequence in which:

(i) the amino acid residue at position 10 in the amino acid sequence shown in SEQ ID NO: 13 or at a position corresponding to this position, is substituted with leucine; and/or (ii) the amino acid residue at position 11 in the amino acid sequence shown in SEQ ID NO: 13 or at a position corresponding to this position, is substituted with aspartate; and/or (iii) the amino acid residue at position 15 in the amino acid sequence shown in SEQ ID NO: 13 or at a position corresponding to this position, is substituted with arginine; and/or (iv) the amino acid residue at position 27 in the amino acid sequence shown in SEQ ID NO: 13 or at a position corresponding to this position, is substituted with serine; and/or (v) the amino acid residue at position 30 in the amino acid sequence shown in SEQ ID NO: 13 or at a position corresponding to this position, is substituted with threonine; and/or (vi) the amino acid residue at position 45 in the amino acid sequence shown in SEQ ID NO: 13 or at a position corresponding to this position, is substituted with serine; and/or (vii) the amino acid residue at position 47 in the amino acid sequence shown in SEQ ID NO: 13 or at a position corresponding to this position, is substituted with threonine; and/or (viii) the amino acid residue at position 60 in the amino acid sequence shown in SEQ ID NO: 13 or at a position corresponding to this position, is substituted with aspartate; and/or (ix) the amino acid residue at position 68 in the amino acid sequence shown in SEQ ID NO: 13 at a position corresponding to this position, is substituted with threonine; and/or (x) the amino acid residue at position 150 in the amino acid sequence shown in SEQ ID NO: 13 or at a position corresponding to this position, is substituted with leucine; and/or (xi) the amino acid residue at position 178 in the amino acid sequence shown in SEQ ID NO: 13 or at a position corresponding to this position, is substituted with isoleucine; and/or (xii) the amino acid residue at position 183 in the amino acid sequence shown in SEQ ID NO: 13 or at a position corresponding to this position, is substituted with glutamate; and/or (xiii) the amino acid residue at position 185 in the amino acid sequence shown in SEQ ID NO: 13 at a position corresponding to this position, is substituted with valine; and/or (xiv) the amino acid residue at position 220 in the amino acid sequence shown in SEQ ID NO: 13 or at a position corresponding to this position, is substituted with serine; and/or (xv) the amino acid residue at position 232 in the amino acid sequence shown in SEQ ID NO: 13 or at a position corresponding to this position, is substituted with leucine; and/or (xvi) the amino acid residue at position 245 in the amino acid sequence shown in SEQ ID NO: 13 or at a position corresponding to this position, is substituted with alanine; and/or (xvii) the amino acid residue at position 257 in the amino acid sequence shown in SEQ ID NO: 13 or at a position corresponding to this position, is substituted with threonine; and/or (xviii) the amino acid residue at position 259 in the amino acid sequence shown in SEQ ID NO: 13 or at a position corresponding to this position, is substituted with aspartate or serine; and/or (xiv) the amino acid residue at position 261 in the amino acid sequence shown in SEQ ID NO: 13 or at a position corresponding to this position, is substituted with serine; and/or (xx) the amino acid residue at position 275 in the amino acid sequence shown in SEQ ID NO: 13 or at a position corresponding to this position, is substituted with leucine; and/or (xxi) the amino acid residue at position 287 in the amino acid sequence shown in SEQ ID NO: 13 or at a position corresponding to this position, is substituted with valine or phenylalanine; and/or (xxii) the amino acid residue at position 289 in the amino acid sequence shown in SEQ ID NO: 13 or at a position corresponding to this position, is substituted with tyrosine or arginine; and/or (xxiii) the amino acid residue at position 324 in the amino acid sequence shown in SEQ ID NO: 13 or at a position corresponding to this position, is substituted with phenylalanine; and/or (xxiv) the amino acid residue at position 326 in the amino acid sequence shown in SEQ ID NO: 13 or at a position corresponding to this position, is substituted with serine; and/or (xxv) the amino acid residue at position 356 in the amino acid sequence shown in SEQ ID NO: 13 or at a position corresponding to this position, is substituted with threonine; and/or (xxvi) the amino acid residue at position 371 in the amino acid sequence shown in SEQ ID NO: 13 or at a position corresponding to this position, is substituted with alanine; and/or (xxvii) the amino acid residue at position 396 in the amino acid sequence shown in SEQ ID NO: 13 or at a position corresponding to this position, is substituted with alanine; and/or (xxviii) the amino acid residue at position 405 in the amino acid sequence shown in SEQ ID NO: 13 or at a position corresponding to this position, is substituted with serine; and/or (xxix) the amino acid residue at position 431 in the amino acid sequence shown in SEQ ID NO: 13 or at a position corresponding to this position, is substituted with glycine; and/or (xxx) the amino acid residue at position 436 in the amino acid sequence shown in SEQ ID NO: 13 or at a position corresponding to this position, is substituted with threonine; and/or (xxxi) the amino acid residue at position 457 in the amino acid sequence shown in SEQ ID NO: 13 or at a position corresponding to this position, is substituted with leucine; and/or (xxxii) the amino acid residue at position 459 in the amino acid sequence shown in SEQ ID NO: 13 or at a position corresponding to this position, is substituted with asparagine; and/or (xxxiii) the amino acid residue at position 470 in the amino acid sequence shown in SEQ ID NO: 13 or at a position corresponding to this position, is substituted with serine; and/or (xxxiv) the amino acid residue at position 472 in the amino acid sequence shown in SEQ ID NO: 13 or at a position corresponding to this position, is substituted with glycine; and/or (xxxv) the amino acid residue at position 506 in the amino acid sequence shown in SEQ ID NO: 13 or at a position corresponding to this position, is substituted with glycine; and/or (xxxvi) the amino acid residue at position 507 in the amino acid sequence shown in SEQ ID NO: 13 or at a position corresponding to this position, is substituted with valine.

In one embodiment, the positions in which substitutions and/or deletions occur are the following:

In one embodiment, the positions in which substitutions and/or deletions occur are the following: positions 10, 27, 60, 324 and 457.

In one embodiment, the positions in which substitutions and/or deletions occur are the following: positions 32, 287, 289 and 356.

In one embodiment, the positions in which substitutions and/or deletions occur are the following: positions 10, 232, 245, 259, 356, 431 and 436.

In one embodiment, the positions in which substitutions and/or deletions occur are the following: positions 11, 15, 30, 45, 47, 68, 178, 356, 371 and 459.

In one embodiment, the positions in which substitutions and/or deletions occur are the following: positions 32 and 356.

In one embodiment, the positions in which substitutions and/or deletions occur are the following: positions 32, 60, 324 and 457.

In one embodiment, the positions in which substitutions and/or deletions occur are the following: positions 32, 287, 289 and 356. In one embodiment, the positions in which substitutions and/or deletions occur are the following: positions 32, 232, 245, 259, 356, 431 and 436.

In one embodiment, the positions in which substitutions and/or deletions occur are the following: positions 32, 45, 47, 68, 178, 356, 371 and 459.

In one embodiment, the positions in which substitutions and/or deletions occur are the following: positions 232, 245, 259, 356, 431 and 436.

In one embodiment, the positions in which substitutions and/or deletions occur are the following: positions 178, 356, 371 and 459.

In one embodiment, the positions in which substitutions and/or deletions occur are the following: positions 150, 257, 259, 261, 275, 289, 356 and 506.

In one embodiment, the positions in which substitutions and/or deletions occur are the following: positions 185, 356 and 405.

In one embodiment, the positions in which substitutions and/or deletions occur are the following: positions 275, 356, 396 and 472.

In one embodiment, the positions in which substitutions and/or deletions occur are the following: positions 275, 326, 356 and 396.

In one embodiment, the positions in which substitutions and/or deletions occur are the following: positions 220, 275, 356 and 396.

In one embodiment, the positions in which substitutions and/or deletions occur are the following: positions 83, 275, 356, 396 and 507.

In one embodiment, the positions in which substitutions and/or deletions occur are the following: positions 275, 287, 356, 396 and 507.

In one embodiment, the positions in which substitutions and/or deletions occur are the following: positions 275, 356, 396 and 470.

In one embodiment, the positions in which substitutions and/or deletions occur are the following: positions 275, 356 and 507.

In one embodiment, the positions in which substitutions and/or deletions occur are the following: positions 275, 356 and 396.

In one embodiment, the positions in which substitutions and/or deletions occur are the following: positions 275, 287 and 356.

As above-mentioned, the expression level of the cystathionine gamma synthase 1 in the present invention is regulated by at least one promoter and at least one terminator, such as herein after defined more in details, which are present in 5' and 3' position respectively of the nucleic acid sequence encoding the said cystathionine gamma synthase 1.

As it is specified elsewhere in the present description, in some embodiments of the invention, the cystathionine gamma synthase 1 is overexpressed and/or under the control of an inducible or repressible promoter in a recombinant yeast according to the invention.

In some embodiments, overexpression of the cystathionine gamma synthase 1 may result from the control of the corresponding gene by a strong promoter within the said recombinant yeast.

In some other embodiments, overexpression of the cystathionine gamma synthase 1 may result from the presence of a plurality of copies of a cystathionine gamma synthase 1-encoding sequence within the genome the said recombinant yeast.

In still further embodiments, overexpression of the cystathionine gamma synthase 1 may result from both (i) the control of the corresponding gene by a strong promoter within the said recombinant yeast and (ii) the presence of a plurality of copies of a cystathionine gamma synthase 1-encoding sequence within the genome the said recombinant yeast.

According to a preferred embodiment, the invention pertains to a methionine-producing and/or methionine derivatives-producing recombinant yeast, in the genome of which:

(A) at least one nucleic acid encoding an aspartate semi-aldehyde dehydrogenase HOM2 and/or at least one nucleic acid encoding an aspartate semi-aldehyde dehydrogenase HOM2 that can use as coenzyme both NAD and NADP is overexpressed and/or is under the control of an inducible or repressible promoter;

(B) at least one nucleic acid encoding an aspartokinase HOM3 is under the control of an inducible or repressible promoter; and (C) (i) a) at least one nucleic acid encoding an homoserine-O-acetyltransferase MET2 has been overexpressed and/or is under the control of an inducible or repressible promoter and/or at least one nucleic acid encoding an homoserine-O-acetyltransferase METX is overexpressed and/or is under the control of an inducible or repressible promoter, and b) at least one nucleic acid encoding an O-acetyl homoserine-O-acetyl serine sulfhydrylase MET17 is overexpressed and/or is under the control of an inducible or repressible promoter;

and/or (ii) a) at least one nucleic acid encoding an homoserine kinase THR1 is overexpressed and/or is under the control of an inducible or repressible promoter, and b) at least one nucleic acid encoding a cystathionine gamma-synthase 1 CGS1 that has an improved O-phospho-L-homoserine (OHPS) dependent methionine synthase activity is overexpressed and/or is under the control of an inducible or repressible promoter.

Specific Embodiments of a Methionine-Producing and/or Methionine Derivatives-Producing Recombinant Yeast Aspartate Transaminase Over Expression and/or Controlled Expression In preferred embodiments of a recombinant yeast according to the invention, at least one nucleic acid encoding an aspartate transaminase (AAT2) is overexpressed and/or is under the control of an inducible or repressible promoter.

The aspartate transaminase enzyme (also known as aspartate aminotransferase) is a protein which is described in the art for catalyzing the reaction of L-aspartate and 2-oxoglutarate for producing oxaloacetate and L-glutamate. The aspartate transaminase enzyme encoded by the genome Saccharomyces cerevisiae may be termed AAT2.

According to these embodiments, overexpression of an aspartate transaminase-encoding gene is obtained by inserting, at selected location(s) of the yeast genome, one or more copies of an expression cassette comprising an aspartate transaminase coding sequence. Aspartate transaminase and aspartate-transaminase-encoding gene that are encompassed by the invention are detailed elsewhere in the present specification.

In some of these embodiments, the said one or more copies of an expression cassette comprising an aspartate transaminase coding sequence comprise regulatory sequences allowing a strong expression of the aspartate transaminase, such as a strong promoter that is functional in yeast cells.

In addition to or as an alternative to these embodiments of a recombinant yeast according to the invention, at least one aspartate transaminase-encoding gene can be under the control of an inducible or repressible promoter that is functional in yeast cells.

Without wishing to be bound by any particular theory, the inventors believe that an over expression of an aspartate transaminase (AAT2) may induce a high level of conversion of oxaloacetate into aspartate. The same applies when at least one aspartate transaminase coding sequence is under the control of an inducible or repressible promoter.

A method implemented to measure the activity level of an aspartate transaminase belongs to the general knowledge of the one skilled in the art.

In this regard, the one skilled in the art may advantageously refer to the method described in Yagi et al. (1982, Biochem, VOl. 92: 35-43).

In some embodiments, the said aspartate transaminase-encoding gene is the gene from Saccharomyces cerevisiae, as shown in the examples herein.

In preferred embodiments, the aspartate transaminase is encoded by the A. Thaliana AAT2-gene.

In preferred embodiments, the said aspartate transaminase-encoding gene is placed under the control of the inducible or repressible promoter pSAM4 or of the inducible or repressible promoter pACU1 or of the strong promoter pADH1 or of the strong promoter pPGK1 or of the strong promoter pTEF3.

Illustratively, the aspartate transaminase gene may be inserted within the TRP1 gene and/or within the PYK1 gene and/or within the GNP1 gene and/or within the MUP3 gene, as it is shown in the examples herein.

Preferred aspartate transaminase in the present specification is known by the EC number 2.6.1.1.

The nucleic acid(s) encoding an aspartate transaminase may be nucleic acid(s) originating from organisms preferably selected in a group comprising prokaryotic organisms and eukaryotic organisms. In some embodiments, the nucleic acid(s) encoding an aspartate transaminase may be nucleic acid(s) originating from archaebacteria. In some preferred embodiments, the nucleic acid(s) encoding an aspartate transaminase may be nucleic acid(s) originate(s) from a yeast organism, and most preferably Saccharomyces cerevisiae.

According to a yet preferred embodiment, the nucleic acid(s) encoding an aspartate transaminase or AAT2 may be nucleic acid(s) selected from the group consisting of sequences having at least 39%, advantageously at least 65%, and preferably at least 80%, nucleic acid identity with the nucleic acid sequences of SEQ ID NO: 14, and also a biological activity of the same nature.

A biological activity of the same nature regarding this sequence is the capacity to code for an enzyme that catalyzes the reaction of L-aspartate and 2-oxoglutarate for producing oxaloacetate and L-glutamate.

As described herein, a nucleic acid sequence having at least 39% nucleotide identity with a reference nucleic acid sequence encompasses nucleic acid sequences having at least 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 14, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 14, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 14, and also a biological activity of the same nature.

For the amino acid sequence of the aspartate transaminase AAT2 from Saccharomyces cerevisiae, the one skilled in the art may refer to the accession number NP013127 in the UniProt database, or to SEQ ID NO. 15 described herein. Illustratively, the aspartate transaminase originating from E. coli has 39% amino acid identity with the aspartate transaminase AAT2 of SEQ ID NO. 15.

According to another particular embodiment, the nucleic acid(s) encoding an aspartate transaminase may be nucleic acid(s) encoding an amino acid sequence selected from the group consisting of sequences having at least 39%, advantageously at least 65%, preferably at least 80%, identity with the amino acid sequence of SEQ ID NO: 15, and also a biological activity of the same nature.

A biological activity of the same nature regarding this sequence is as described previously, i.e. the capacity to catalyze the reaction of L-aspartate and 2-oxoglutarate for producing oxaloacetate and L-glutamate.

As described herein, an amino acid sequence having at least 39% amino acid identity with a reference nucleic acid sequence encompasses amino acid sequences having at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 15, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 15, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 15, and also a biological activity of the same nature.

As above-mentioned, the expression level of the aspartate transaminase in the present invention is regulated by at least one promoter and at least one terminator, such as herein after defined more in details, which are present in 5' and 3' position respectively of the nucleic acid sequence encoding the aspartate transaminase.

In an embodiment of the invention, the genome of a recombinant yeast of the invention is such that at least one nucleic acid encoding an aspartate transaminase is overexpressed and/or is under the control of an inducible or repressible promoter.

In some embodiments, overexpression of aspartate transaminase may result from the control of the corresponding gene by a strong promoter within the said recombinant yeast.

In some other embodiments, overexpression of aspartate transaminase may result from the presence of a plurality of copies of an aspartate transaminase-encoding sequence within the genome the said recombinant yeast.

In still further embodiments, overexpression of aspartate transaminase may result from both (i) the control of the corresponding gene by a strong promoter within the said recombinant yeast and (ii) the presence of a plurality of copies of an aspartate transaminase-encoding sequence within the genome the said recombinant yeast.

Glutamate Dehydrogenase Over Expression and/or Controlled Expression

In preferred embodiments of a recombinant yeast according to the invention, at least one nucleic acid encoding a glutamate dehydrogenase-encoding gene (or NAD-specific glutamate dehydrogenase) is overexpressed and/or under the control of an inducible or repressible promoter.

In a particular embodiment, the genome of a recombinant yeast according to the invention is such that at least one nucleic acid encoding a glutamate dehydrogenase that converts oxo-glutarate to glutamate is overexpressed and/or is under the control of an inducible or repressible promoter.

The glutamate dehydrogenase enzyme (also known as NAD-specific glutamate dehydrogenase) is a protein which is described in the art for catalyzing the transformation of 2-oxoglutarate for producing L-glutamate. Thus, glutamate dehydrogenase is an enzyme specifically involved in the chemical reaction involving the conversion of 2-oxoglutarate to L-glutamate, in the presence of NADH.

According to these embodiments, over expression of a glutamate dehydrogenase enzyme-encoding gene is obtained by inserting, at selected location(s) of the yeast genome, one or more copies of an expression cassette comprising a glutamate dehydrogenase coding sequence. Glutamate dehydrogenase and a glutamate dehydrogenase-encoding gene that are encompassed by the invention are detailed elsewhere in the present specification.

In some of these embodiments, the said one or more copies of an expression cassette comprising a glutamate dehydrogenase coding sequence comprise regulatory sequences allowing a strong expression of the glutamate dehydrogenase, such as a strong promoter that is functional in yeast cells.

In addition to or as an alternative to these embodiments of a recombinant yeast according to the invention, at least one glutamate dehydrogenase-encoding gene can be under the control of an inducible or repressible promoter that is functional in yeast cells.

Without wishing to be bound by any particular theory the inventors believe that the over expression of the glutamate dehydrogenase, by converting oxoglutarate into glutamate, simultaneously generates NAD. The same applies when at least one glutamate dehydrogenase coding sequence is under the control of an inducible or repressible promoter.

A method implemented to measure the activity level of glutamate dehydrogenase belongs to the general knowledge of the one skilled in the art.

In this regard, the one skilled in the art may advantageously refer to the method described in Noor and Punekar (2005, Microbiology, Vol. 151: 1409-1419).

In preferred embodiments, the said glutamate dehydrogenase-encoding gene encodes for a glutamate dehydrogenase which uses NADH instead of NADPH, and is more particularly the GDH gene from *Entodinium caudatum* (GDH.eCa), as shown in the examples herein.

Preferred glutamate dehydrogenase in the present specification can in particular be the enzyme having the EC number no. EC 1.4.1.2.

In preferred embodiments, the said glutamate dehydrogenase-encoding gene is placed under the control of the strong promoter pTDH3.

Illustratively, the GDH gene may be inserted within the TRP1 gene, as it is shown in the examples herein, and/or within the HIS3 gene and/or within the SAM3 gene.

According to a preferred embodiment, the nucleic acid(s) encoding a glutamate dehydrogenase may be nucleic acid(s) originating from organisms preferably selected in a group comprising prokaryotic organisms and eukaryotic organisms. In some embodiments, the nucleic acid(s) encoding a glutamate dehydrogenase may be nucleic acid(s) originating from archaebacteria. In some embodiments, the nucleic acid(s) encoding a glutamate dehydrogenase may be nucleic acid(s) originating from organisms preferably selected from *Entodinium caudatum, Bacillus subtilis, Clostridium symbiosium.*

According to a yet preferred embodiment, the nucleic acid(s) encoding a glutamate dehydrogenase may be nucleic acid(s) selected from the group consisting of sequences having at least 49%, advantageously at least 65%, preferably at least 80%, nucleic acid identity with the nucleic acid sequences of SEQ ID NO: 16, and also a biological activity of the same nature. The nucleic acid of SEQ ID NO. 16 encodes a glutamate dehydrogenase originating from *Entodinium caudatum*, the said nucleic acid sequence being codon-optimized for its expression in yeast, and especially in *Saccharomyces cerevisiae*.

A biological activity of the same nature regarding this sequence is the capacity to code for an enzyme that catalyzes the transformation of 2-oxoglutarate for producing L-glutamate.

As described herein, a nucleic acid sequence having at least 49% nucleotide identity with a reference nucleic acid sequence encompasses nucleic acid sequences having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 16, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 16, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 16, and also a biological activity of the same nature.

For the amino acid sequence of the glutamate dehydrogenase from *Entodinium caudatum*, the one skilled in the art may refer to the accession number AAF15393 in the UniProt database, or to SEQ ID NO. 17 described herein. Illustratively, the glutamate dehydrogenase originating from *Giardia intestinalis* has 49% amino acid identity with the glutamate dehydrogenase of SEQ ID NO: 17.

According to another particular embodiment, the nucleic acid(s) encoding a glutamate dehydrogenase may be nucleic acid(s) encoding an amino acid sequence selected from the group consisting of sequences having at least 49%, advantageously at least 65%, preferably at least 80%, amino acid identity with the amino acid sequence of SEQ ID NO: 17, and also a biological activity of the same nature.

A biological activity of the same nature regarding this sequence is as described previously, i.e. the capacity to catalyze the transformation of 2-oxoglutarate for producing L-glutamate.

As described herein, an amino acid sequence having at least 49% amino acid identity with a reference nucleic acid sequence encompasses amino acid sequences having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 17, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 17, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 17, and also a biological activity of the same nature.

As above-mentioned, the expression level of the glutamate dehydrogenase in the present invention is regulated by at least one promoter and at least one terminator, such as herein after defined more in details, which are present in 5' and 3' position respectively of the nucleic acid sequence encoding the said glutamate dehydrogenase.

As it is specified elsewhere in the present description, the glutamate dehydrogenase is overexpressed in a recombinant yeast according to the invention.

In some embodiments, overexpression of the glutamate dehydrogenase may result from the control of the corresponding gene by a strong promoter within the said recombinant yeast.

In some other embodiments, overexpression of the glutamate dehydrogenase may result from the presence of a plurality of copies of a glutamate dehydrogenase-encoding sequence within the genome the said recombinant yeast.

In still further embodiments, overexpression of the glutamate dehydrogenase may result from both (i) the control of the corresponding gene by a strong promoter within the said recombinant yeast and (ii) the presence of a plurality of copies of a glutamate dehydrogenase-encoding sequence within the genome the said recombinant yeast.

Over Expression of a Homoserine Dehydrogenase

In some embodiments of a methionine-producing and/or methionine derivatives-producing recombinant yeast according to the invention, the said yeast is further defined as having a genome in which at least one nucleic acid encoding a homoserine dehydrogenase is overexpressed.

In preferred embodiments of a recombinant yeast according to the invention, over expression of a homoserine dehydrogenase-encoding gene is obtained by inserting, at selected location(s) of the yeast genome, one or more copies of an expression cassette comprising a homoserine dehydrogenase coding sequence. A homoserine dehydrogenase and a homoserine dehydrogenase-encoding gene that are encompassed by the invention are detailed elsewhere in the present specification.

In some of these embodiments, the said one or more copies of an expression cassette comprising a homoserine dehydrogenase coding sequence comprise regulatory sequences allowing a strong expression of the homoserine dehydrogenase, such as a strong promoter that is functional in yeast cells.

In other embodiments, the said one or more copies of an expression cassette comprising a homoserine dehydrogenase coding sequence comprise regulatory sequences allowing a strong expression of the homoserine dehydrogenase, such as a strong promoter that is functional in yeast cells.

Without wishing to be bound by any particular theory, the inventors believe that an over expression of a homoserine dehydrogenase increases the conversion of the intermediate metabolite aspartyl-semialdehyde into homoserine.

In some embodiments, it is made use of the homoserine dehydrogenase originating from a yeast, such as the HOM6- encoding gene from *Saccharomyces cerevisiae*. In some embodiments, it is introduced a plurality of copies of the HOM6-encoding gene in the yeast genome. In some embodiments, and especially in embodiments wherein sole one copy of the HOM6-encoding gene is present, the said HOM6-encoding gene is placed under the control of a strong promoter.

In preferred embodiments, the said homoserine dehydrogenase-encoding gene is the HOM6 gene from *Saccharomyces cerevisiae*, as shown in the examples herein.

In preferred embodiments, the said homoserine dehydrogenase-encoding gene is placed under the control of the strong promoter pRPLA1 or the strong promoter pADH1.

Illustratively, the homoserine dehydrogenase gene may be inserted within the HOM3 gene and/or within the MUP3 gene, as it is shown in the examples herein.

According to a preferred embodiment, the nucleic acid(s) encoding a homoserine dehydrogenase may be nucleic acid(s) originating from organisms preferably selected in a group comprising prokaryotic organisms and eukaryotic organisms. In some preferred embodiments, the nucleic acid(s) encoding a homoserine dehydrogenase may be nucleic acid(s) originating from a yeast, and especially from *Saccharomyces cerevisiae*.

According to a yet preferred embodiment, the nucleic acid(s) encoding a homoserine dehydrogenase may be nucleic acid(s) selected from the group consisting of sequences having at least 31%, advantageously at least 65%, preferably at least 80%, nucleic acid identity with a nucleic acid of SEQ ID NO: 18, and also a biological activity of the same nature. The nucleic acid of SEQ ID NO: 18 encodes a homoserine dehydrogenase originating from *Saccharomyces*, that may also be termed HOM6.

A biological activity of the same nature regarding this sequence is the capacity to code for an enzyme that catalyzes the conversion of the intermediate metabolite aspartyl-semialdehyde into homoserine.

As described herein, a nucleic acid sequence having at least 31% nucleotide identity with a reference nucleic acid sequence encompasses nucleic acid sequences having at least 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the with the nucleic acid sequence of SEQ ID NO: 18, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 18, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid sequence of SEQ ID NO: 18, and also a biological activity of the same nature.

For the amino acid sequence of the homoserine dehydrogenase from *Saccharomyces cerevisiae*, the one skilled in the art may refer to the accession number AJR75529 or NP012673 in the UniProt database, or to SEQ ID NO. 19 described herein.

According to another particular embodiment, the nucleic acid(s) encoding homoserine dehydrogenase may be nucleic acid(s) encoding an amino acid sequence selected from the group consisting of sequences having at least 31%, advantageously at least 65%, preferably at least 80%, amino acid identity with the amino acid sequence of SEQ ID NO: 19, and also a biological activity of the same nature. Illustratively, the homoserine dehydrogenase originating from *Stenotrophomonas maltophilia* has 31% amino acid identity with the homoserine dehydrogenase of SEQ ID NO. 19.

A biological activity of the same nature regarding this sequence is as described previously, i.e. the capacity to catalyze the conversion of the intermediate metabolite aspartyl-semialdehyde into homoserine.

As described herein, an amino acid sequence having at least 31% amino acid identity with a reference nucleic acid sequence encompasses amino acid sequences having at least 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 19, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 19, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 19, and also a biological activity of the same nature.

As above-mentioned, the expression level of the homoserine dehydrogenase in the present invention is regulated by at least one promoter and at least one terminator, such as herein after defined more in details, which are present in 5' and 3' position respectively of the nucleic acid sequence encoding the said homoserine dehydrogenase.

In a particular embodiment, the genome of a recombinant yeast of the invention is such that at least one nucleic acid encoding a homoserine dehydrogenase is overexpressed.

In some embodiments, overexpression of the homoserine dehydrogenase may result from the control of the corresponding gene by a strong promoter within the said recombinant yeast.

In some other embodiments, overexpression of the homoserine dehydrogenase may result from the presence of a plurality of copies of a homoserine dehydrogenase-encoding sequence within the genome the said recombinant yeast.

In still further embodiments, overexpression of the homoserine dehydrogenase may result from both (i) the control of the corresponding gene by a strong promoter within the said recombinant yeast and (ii) the presence of a plurality of copies of a homoserine dehydrogenase-encoding sequence within the genome the said recombinant yeast.

Under Expression of S-Adenosylmethionine Synthase 1 and 2 Genes

In some embodiments of a recombinant yeast according to the invention, the said recombinant yeast is further defined as having an under expression of (i) the gene encoding S-adenosylmethionine synthase 1 (also termed SAM1 herein), (ii) of the gene encoding S-adenosylmethionine synthase 2 (also termed SAM2 herein) or (iii) both the gene encoding S-adenosylmethionine synthase 1 and the gene encoding S-adenosylmethionine synthase 2.

Accordingly, in a particular embodiment, the genome of a yeast according to the invention is additionally such that, independently:

(i) at least one, preferably all, endogenous nucleic acid encoding a S-adenosyl methionine synthase SAM1 and/or SAM2 has been deleted, or (ii) at least one, preferably all, nucleic acid encoding a S-adenosyl methionine synthase SAM1 and/or SAM2 is under the control of an inducible or repressible promoter and/or is in a destabilized form.

SAM1 is the S-adenosylmethionine synthase 1 from *Saccharomyces cerevisiae*. For the amino acid sequence of SAM1, it may be referred to the access number NP_010790 in the UniProt database. For the nucleic acid sequence, it may be referred to the access number NM_001180810 in the NCBI database.

SAM2 is the S-adenosylmethionine synthase 2 from *Saccharomyces cerevisiae*. For the amino acid sequence of SAM2, it may be referred to the access number NP_013281 in the UniProt database. For the nucleic acid sequence, it may be referred to the access number NM_00118082067 in the NCBI database.

Without wishing to be bound by any particular theory, the inventors believe that an under expression of any of SAM1 gene, SAM2 gene, or both, shall increase methionine production by the recombinant yeast by reducing the consumption of the produced methionine by its conversion into S-adenosyl-methionine.

As regards, SAM1 and SAM2, under expression of these genes encompass a complete repression of their expression, e.g. by interruption or deletion of SAM1, SAM2 or both SAM1 and SAM2.

In some embodiments, under expression of SAM1, of SAM2, or of both SAM1 and SAM2 may be rendered conditional, for example by placing the expression of this (these) gene(s) under the control of repressible regulatory sequences, such as inducible or repressible promoters.

Methods for repressing gene expression, for interrupting target genes or for deleting target genes, are well known from the one skilled in the art.

As regards SAM1 and SAM2, under expression also encompasses the insertion of a nucleic acid encoding a destabilized SAM1 or the insertion of a nucleic acid encoding a destabilized SAM2, or both.

A destabilized SAM1 or SAM2 is a variant of SAM1 or SAM2, respectively, that is more rapidly degraded within the yeast cell than the parent SAM1 or SAM2.

In preferred embodiments, a destabilized SAM1 consists of a degron-tagged SAM1 protein.

In preferred embodiments, a destabilized SAM2 consists of a degron-tagged SAM2 protein.

As illustrated in the examples, the SAM1 gene can be interrupted by loxP, or for example by URA3.K1-loxP, and is thus deleted (which can also be termed inactivated).

Under Expression of Cystathionine Gamma-Lyase Gene

In some embodiments of a recombinant yeast according to the invention, the said recombinant yeast is further defined as having an under expression of the gene encoding the cystathionine gamma-lyase, that may be also termed CYS3 herein.

Accordingly, in a particular embodiment, a genome of a recombinant yeast according to the invention is such that at least one nucleic acid encoding a cystathionine gamma-lyase CYS3 is, independently, under the control of a weak promoter or of an inducible or repressible promoter and/or is in a destabilized form.

CYS3 is the cystathionine gamma-lyase from *Saccharomyces cerevisiae*. For the amino acid sequence of CYS3, it may be referred to the access number NP_009390 in the UniProt database. For the nucleic acid sequence, it may be referred to the access number NM_001178157 in the NCBI database.

Without wishing to be bound by any particular theory, the inventors believe that an under expression of any of CYS3 gene shall reduce the consumption of the produced methionine towards the synthesis of cysteine.

As regards, CYS3, under expression of this genes encompasses a complete repression of its expression, e.g. by interruption or deletion of CYS3.

In some embodiments, under expression of CYS3 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

As regards CYS3, under expression also encompasses the insertion of a nucleic acid encoding a destabilized CYS3 or the insertion of a nucleic acid encoding a destabilized CYS3, or both.

A destabilized CYS3 is a variant of CYS3 that is more rapidly degraded within the yeast cell than the parent CYS3.

In preferred embodiments, a destabilized CYS3 consists of a degron-tagged CYS3 protein.

Under Expression of Cystathionine Beta-Synthase Gene

In some embodiments of a recombinant yeast according to the invention, the said recombinant yeast is further defined as having an under expression of the gene encoding the cystathionine beta-synthase, that may be also termed CYS4 herein.

Accordingly, in a particular embodiment, a genome of a recombinant yeast according to the invention is such that at least one nucleic acid encoding a cystathionine beta-synthase CYS4 is, independently, under the control of a weak promoter or of an inducible or repressible promoter and/or is in a destabilized form.

CYS4 is the cystathionine beta-synthase from *Saccharomyces cerevisiae*. For the amino acid sequence of CYS4, it may be referred to the access number NP_011671 in the UniProt database. For the nucleic acid sequence, it may be referred to the access number NM_001181284 in the NCBI database.

Without wishing to be bound by any particular theory, the inventors believe that an under expression of any of cystathionine beta-synthase gene shall reduce the consumption of the produced methionine towards the synthesis of cysteine.

As regards, cystathionine beta-synthase, under expression of this genes encompasses a complete repression of its expression, e.g. by interruption or deletion of cystathionine beta-synthase.

In some embodiments, under expression of cystathionine beta-synthase may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

As regards cystathionine beta-synthase, under expression also encompasses the insertion of a nucleic acid encoding a destabilized cystathionine beta-synthase or the insertion of a nucleic acid encoding a destabilized cystathionine beta-synthase, or both.

A destabilized cystathionine beta-synthase is a variant of cystathionine beta-synthase that is more rapidly degraded within the yeast cell than the parent cystathionine beta-synthase.

In preferred embodiments, a destabilized cystathionine beta-synthase consists of a degron-tagged cystathionine beta-synthase protein.

Modification of the Expression of the Aromatic Aminotransferase I Gene (Aro8) and of the Cytosolic Branched-Chain Amino Acid (BCAA) Amino Transferase Gene (BAT2)

a. Production of Methionine

In embodiments where the production of methionine is sought, a recombinant yeast according to the invention is advantageously defined as having an under expression of (i) the gene encoding aromatic aminotransferase I gene (also named ARO8 herein), (ii) of the gene encoding cytosolic branched-chain amino acid (BCAA) amino transferase gene (also named BAT2 herein) or (iii) both the gene encoding aromatic aminotransferase I gene (Aro8) and the gene encoding cytosolic branched-chain amino acid (BCAA) amino transferase gene (BAT2).

In a particular embodiment, the genome of a recombinant yeast of the invention is such that, independently:

(i) at least one, preferably all, endogenous nucleic acid encoding an Aromatic aminotransferase I ARO8 and/or a Cytosolic branched-chain amino acid (BCAA) aminotransferase gene BAT2 has been deleted, or (ii) at least one, preferably all, nucleic acid encoding an Aromatic aminotransferase I ARO8 and/or a Cytosolic branched-chain amino acid (BCAA) aminotransferase gene BAT2 is under the control of an inducible or repressible promoter and/or is in a destabilized form.

ARO8 is the aromatic aminotransferase I from *Saccharomyces cerevisiae*. For the nucleic acid sequence, it may be referred to the access number NM_001181067.1 in the NCBI database.

According to a yet preferred embodiment, the nucleic acid(s) encoding an aromatic aminotransferase I may be nucleic acid(s) selected from the group consisting of sequences having at least 25%, advantageously at least 65%, preferably at least 80%, nucleic acid identity with a nucleic acid of SEQ ID NO: 20, and also a biological activity of the same nature.

A biological activity of the same nature regarding this sequence is the capacity to code for an enzyme that catalyzes the conversion of methionine into 2-keto-4-methylthiobutyric acid (KMB) and methionol.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid of SEQ ID NO: 20, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid of SEQ ID NO: 20, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid of SEQ ID NO: 20, and also a biological activity of the same nature.

For the amino acid sequence of ARO8, it may be referred to the access number NP_011313.1 in the UniProt database or to SEQ ID NO. 21 described herein.

According to another particular embodiment, the nucleic acid(s) encoding an aromatic aminotransferase I may be nucleic acid(s) encoding an amino acid sequence selected from the group consisting of sequences having at least 25%, advantageously at least 65%, preferably at least 80%, amino acid identity with the amino acid sequence of SEQ ID NO: 21, and also a biological activity of the same nature.

A biological activity of the same nature regarding this sequence is as described previously, i.e. the capacity to catalyze the conversion of methionine into 2-keto-4-methylthiobutyric acid (KMB) and methionol.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 21, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 21, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 21, and also a biological activity of the same nature.

BAT2 is the cytosolic branched-chain amino acid (BCAA) amino transferase from *Saccharomyces cerevisiae*.

For the nucleic acid sequence, it may be referred to the access number NM_001181806.1 in the NCBI database.

According to a yet preferred embodiment, the nucleic acid(s) encoding a cytosolic branched-chain amino acid (BCAA) amino transferase may be nucleic acid(s) selected from the group consisting of sequences having at least 25%, advantageously at least 65%, preferably at least 80%, nucleic acid identity with a nucleic acid of SEQ ID NO: 22, and also a biological activity of the same nature.

A biological activity of the same nature regarding this sequence is the capacity to code for an enzyme that catalyzes the conversion of methionine into 2-keto-4-methylthiobutyric acid (KMB) and methionol.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid of SEQ ID NO: 22, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid of SEQ ID NO: 22, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid of SEQ ID NO: 22, and also a biological activity of the same nature.

For the amino acid sequence of BAT2, it may be referred to the access number NP_012682.1 in the UniProt database or to the amino acid sequence of SEQ ID NO: 23.

According to another particular embodiment, the nucleic acid(s) encoding a cytosolic branched-chain amino acid (BCAA) amino transferase may be nucleic acid(s) encoding an amino acid sequence selected from the group consisting of sequences having at least 25%, advantageously at least 65%, preferably at least 80%, amino acid identity with the amino acid sequence of SEQ ID NO: 23, and also a biological activity of the same nature.

A biological activity of the same nature regarding this sequence is as described previously, i.e. the capacity to catalyze the conversion of methionine into 2-keto-4-methylthiobutyric acid (KMB) and methionol.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 23, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 23, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 23, and also a biological activity of the same nature.

Without wishing to be bound by any particular theory, the inventors believe that an under expression of any of ARO8 gene, BAT2 gene, or both, shall reduce the conversion of methionine into 2-keto-4-methylthiobutyric acid (KMB) and methionol.

As regards, ARO8 and BAT2, under expression of these genes encompass a complete repression of their expression, e.g. by interruption or deletion of ARO8, BAT2 or both ARO8 and BAT2.

In some embodiments, under expression of ARO8, of BAT2, or of both ARO8 and BAT2 may be rendered conditional, for example by placing the expression of this (these) gene(s) under the control of repressible regulatory sequences, such as inducible or repressible promoters.

Methods for repressing gene expression, for interrupting target genes or for deleting target genes, are well known from the one skilled in the art.

As regards ARO8 and BAT2, under expression also encompasses the insertion of a nucleic acid encoding a destabilized ARO8 or the insertion of a nucleic acid encoding a destabilized BAT2, or both.

A destabilized ARO8 or BAT2 is a variant of ARO8 or BAT2, respectively, that is more rapidly degraded within the yeast cell than the parent ARO8 or BAT2.

b. Production of Methionine Derivatives

On the contrary, in embodiments where the production of methionine derivatives is sought, a recombinant yeast according to the invention is advantageously defined as having an over expression and/or a controlled expression of (i) the gene encoding aromatic aminotransferase I gene (also named Aro8 herein), (ii) of the gene encoding cytosolic branched-chain amino acid (BCAA) amino transferase gene (also named BAT2 herein) or (iii) both the gene encoding aromatic aminotransferase I gene (ARO8) and the gene encoding cytosolic branched-chain amino acid (BCAA) amino transferase gene (BAT2).

Accordingly, in a particular embodiment, the genome of a recombinant yeast of the invention is such that, independently:

(i) at least one, preferably all, nucleic acid encoding an Aromatic aminotransferase I ARO8, and/or (ii) at least one, preferably all, nucleic acid encoding a Cytosolic branched-chain amino acid (BCAA) aminotransferase gene BAT2, is overexpressed and/or is under the control of an inducible or repressible promoter.

According to these embodiments, over expression of an aromatic aminotransferase I gene or of a cytosolic branched-chain amino acid (BCAA) amino transferase gene is obtained by inserting, at selected location(s) of the yeast genome, one or more copies of an expression cassette comprising, respectively, an aromatic aminotransferase I coding sequence or a cytosolic branched-chain amino acid (BCAA) amino transferase coding sequence.

In some of these embodiments, the said one or more copies of an expression cassette comprising an aromatic aminotransferase I coding sequence or a cytosolic branched-chain amino acid (BCAA) amino transferase coding sequence comprise regulatory sequences allowing a strong expression of the aromatic aminotransferase I or cytosolic branched-chain amino acid (BCAA) amino transferase, such as a strong promoter that is functional in yeast cells.

In addition to or as an alternative to these embodiments of a recombinant yeast according to the invention, at least one aromatic aminotransferase I encoding gene and/or at least one cytosolic branched-chain amino acid (BCAA) amino transferase encoding gene can be under the control of an inducible or repressible promoter that is functional in yeast cells.

Without wishing to be bound by any particular theory, the inventors believe that an over expression of any of ARO8 gene, BAT2 gene, or both, shall increase the conversion of methionine into 2-keto-4-methylthiobutyric acid (KMB).

A method implemented to measure the activity level of an aromatic aminotransferase I or of a cytosolic branched-chain amino acid (BCAA) amino transferase belongs to the general knowledge of the one skilled in the art.

In a further embodiment, the methionine derivative of interest is 2-keto-4-methylthiobutyric acid (KMB) and a recombinant yeast according to the invention having an over expression and/or a controlled expression of the gene encoding ARO8, of the gene encoding BAT2 or of both the gene encoding ARO8 and the gene encoding BAT2 is also defined as having an under expression of the phenylpyruvate decarboxylase gene (ARO10) and a non-expression of the 2-hydroxyacide dehydrogenase gene (KDH).

KDH is the 2-hydroxyacide dehydrogenase from *Lactococcus lactis*. For the nucleic acid sequence, it may be referred to the Enzyme Commission number E.C. 1.1.1.145.

According to a yet preferred embodiment, the nucleic acid(s) encoding a 2-hydroxyacide dehydrogenase may be nucleic acid(s) selected from the group consisting of sequences having at least 25%, advantageously at least 65%, preferably at least 80%, nucleic acid identity with a nucleic acid of SEQ ID NO: 24 and/or with a nucleic acid of SEQ ID NO: 25, and also a biological activity of the same nature.

A biological activity of the same nature regarding this sequence is the capacity to code for an enzyme that catalyzes the conversion of 2-keto-4-methylthiobutyric acid into 2-hydroxy-4-(methylthio) butanoic acid.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid of SEQ ID NO: 24 or of SEQ ID NO: 25, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid of SEQ ID NO: 24 or of SEQ ID NO: 25, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid of SEQ ID NO: 24 or of SEQ ID NO: 25, and also a biological activity of the same nature.

For the amino acid sequence of KDH, it may be referred to the access number WP_011835036.1. in the UniProt database and/or to the access number WP_010905887.1 in the UniProt database.

According to another particular embodiment, the nucleic acid(s) encoding 2-hydroxyacide dehydrogenase may be nucleic acid(s) encoding an amino acid sequence selected from the group consisting of sequences having at least 25%, advantageously at least 65%, preferably at least 80%, amino acid identity with the amino acid sequence of SEQ ID NO: 26 or with the amino acid sequence of SEQ ID NO: 27, and also a biological activity of the same nature.

A biological activity of the same nature regarding this sequence is as described previously, i.e. the capacity to catalyze the conversion of 2-keto-4-methylthiobutyric acid into 2-hydroxy-4-(methylthio) butanoic acid.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 26 or with the amino acid sequence of SEQ ID NO: 27, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 26 or with the amino acid sequence of SEQ ID NO: 27, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 26 or with the amino acid sequence of SEQ ID NO: 27, and also a biological activity of the same nature.

Optionally, the amino acid sequence can comprise an additional Serine inserted in position 2 of the protein, and accordingly, the corresponding nucleic acid sequence can comprise inserted nucleotides TCA or AGT in positions 4 to 6 of the nucleic acid sequence. A KDH having such sequence can be termed in the present text KDH1-0 and is present in some of the examples.

ARO10 is the phenylpyruvate decarboxylase from *Saccharomyces cerevisiae*. For the nucleic acid sequence, it may be referred to the access number NM_001180688.3 in the NCBI database.

According to a yet preferred embodiment, the nucleic acid(s) encoding a phenylpyruvate decarboxylase may be nucleic acid(s) selected from the group consisting of sequences having at least 25%, advantageously at least 65%, preferably at least 80%, nucleic acid identity with a nucleic acid of SEQ ID NO: 28, and also a biological activity of the same nature.

A biological activity of the same nature regarding this sequence is the capacity to code for an enzyme that catalyzes the decarboxylation of 2-keto-4-methylthiobutyric acid.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid of SEQ ID NO: 28, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid of SEQ ID NO: 28, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the nucleic acid of SEQ ID NO: 28, and also a biological activity of the same nature.

For the amino acid sequence of ARO10, it may be referred to the access number NP_010668.3 in the UniProt database or to the amino acid sequence of SEQ ID NO: 29.

According to another particular embodiment, the nucleic acid(s) encoding a phenylpyruvate decarboxylase may be nucleic acid(s) encoding an amino acid sequence selected from the group consisting of sequences having at least 25%, advantageously at least 65%, preferably at least 80%, amino acid identity with the amino acid sequence of SEQ ID NO: 29, and also a biological activity of the same nature.

A biological activity of the same nature regarding this sequence is as described previously, i.e. the capacity to catalyze the decarboxylation of 2-keto-4-methylthiobutyric acid.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 29, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 29, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the amino acid sequence of SEQ ID NO: 29, and also a biological activity of the same nature.

Optionally, the amino acid sequence can comprise an additional Serine inserted in position 2 of the protein, and accordingly, the corresponding nucleic acid sequence can comprise inserted nucleotides TCA or AGT in positions 4 to 6 of the nucleic acid sequence. A ARO10 having such sequence can be termed in the present text KDH1-0 and is present in some of the examples.

Without wishing to be bound by any particular theory, the inventors believe that an under expression of ARO10 gene shall reduce the conversion 2-keto-4-methylthiobutyric acid (KMB) and thus increase its availability. In particular, the inventors believe that an under expression of ARO10 reduces its conversion in methional.

As regards ARO10, under expression of this gene encompasses a complete repression of its expression, e.g. by interruption or deletion of ARO10.

In some embodiments, under expression of ARO10 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

As regards ARO10, under expression also encompasses the insertion of a nucleic acid encoding a destabilized ARO10.

A destabilized ARO10 is a variant of ARO10 that is more rapidly degraded within the yeast cell than the parent ARO10.

According to this embodiment where the methionine derivative of interest is 2-keto-4-methylthiobutyric acid (KMB), the recombinant yeast according to the invention defined here-above can also optionally be defined as having an over expression and/or a controlled expression of the gene encoding a water forming NADH oxidase (NOXE).

Preferred water forming NADH oxidase in the present invention are known by the EC number 1.6.3.1 and 1.6.99.3 (also known as NAD(P)H oxidase (H(2)O(2)-forming), dual oxidase, NAD(P)H oxidase, ThOX, THOX2, Thyroid NADPH oxidase, Thyroid oxidase Thyroid oxidase 2 for EC 1.6.3.1 and NADH dehydrogenase, Beta-NADH dehydrogenase dinucleotide, Cytochrome c reductase, Diaphorase, Dihydrocodehydrogenase I dehydrogenase, Dihydronicotinamide adenine dinucleotide dehydrogenase, Diphosphopyrinase, DPNH diaphorase, NADH diaphorase, NADH hydrogenase, NADH oxidoreductase, NADH-menadione oxidoreductase, NADH: cytochrome c oxidoreductase, Reduced diphosphopyridine nucleotide diaphorase, Type 1 dehydrogenase, Type I dehydrogenase for EC 1.6.99.3).

A water forming NADH oxidase which may be considered in the present invention is notably described in WO 2006/134277.

A method implemented to measure the activity level of a NADH oxidase according to the invention belongs to the general knowledge of the man of the art.

In this regard, the one skilled in the art may advantageously refer to the method described in Lopez DE FELIPE et al. (International Daily Journal, 2001, vol. 11: 37-44 (ISSN 0958-6946)).

According to a preferred embodiment, the nucleic acid(s) encoding a NADH oxidase or NOXE may be nucleic acid(s) selected from the group comprising *Streptococcus pneumoniae*, *Lactococcus lactis*, *Enterococcus faecalis*, *Lactobacillus brevis* and a mixture thereof, and preferably *Streptococcus pneumoniae*.

NOXE can in particular be the water forming NADH oxidase from *Lactococcus lactis*, having in particular the amino acid sequence having the NCBI reference number WP_012897225.1. For the nucleic acid sequence, it may be referred to the NCBI reference number YP003352913.1.

According to another preferred embodiment, the nucleic acid(s) encoding a NADH oxidase may be nucleic acid(s) selected from the group consisting of sequences having at least 78%, preferably at least 80%, nucleic acid identity with the nucleic acid sequences SEQ ID NO: 30, 31, 32 and 33, and also a biological activity of the same nature.

A biological activity of the same nature regarding this sequence is the capacity to code for a water forming NADH oxidase.

As described herein, a nucleic acid sequence having at least 78% nucleotide identity with a reference nucleic acid sequence encompasses nucleic acid sequences having at least 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

According to another particular embodiment, the nucleic acid(s) encoding a NADH oxidase may be nucleic acid(s) encoding an amino acid sequence selected from the group consisting of sequences having at least 78%, preferably at least 80%, identity with sequences SEQ ID NO: 34, 35, 36 and 37, and also a biological activity of the same nature.

A biological activity of the same nature regarding this sequence is as described previously, i.e. a water forming NADH oxidase.

As described herein, an amino acid sequence having at least 78% amino acid identity with a reference amino acid sequence encompasses amino acid sequences having at least 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

According to this embodiment of a recombinant yeast according to the invention, over expression of a NADH oxidase gene is obtained by inserting, at selected location(s) of the yeast genome, one or more copies of an expression cassette comprising a NADH oxidase coding sequence.

In some of these embodiments, the said one or more copies of an expression cassette comprising a NADH oxidase coding sequence comprise regulatory sequences allowing a strong expression of the NADH oxidase, such as a strong promoter that is functional in yeast cells.

In other preferred embodiments, the methionine derivative of interest is 2-hydroxy-4-(methylthio) butanoic acid (HMB), a recombinant yeast according to the invention having an over expression and/or a controlled expression of the gene encoding Aro8, of the gene encoding BAT2 or of both the gene encoding ARO8 and the gene encoding BAT2 is also defined as having an over expression and/or a controlled expression of the 2-hydroxyacide dehydrogenase gene (KDH) and preferably an under expression of ARO10.

Accordingly, in a particular embodiment, the genome of a recombinant yeast of the invention is such that at least one nucleic acid encoding 2-hydroxyacide dehydrogenase (KDH) is overexpressed and/or under the control of an inducible or repressible promoter.

HMB is not naturally produced by the yeasts according to the invention.

According to these embodiments of a recombinant yeast according to the invention, over expression of a 2-hydroxyacide dehydrogenase gene is obtained by inserting, at selected location(s) of the yeast genome, one or more copies of an expression cassette comprising a 2-hydroxyacide dehydrogenase coding sequence.

In some of these embodiments, the said one or more copies of an expression cassette comprising a 2-hydroxyacide dehydrogenase coding sequence comprise regulatory sequences allowing a strong expression of the 2-hydroxyacide dehydrogenase, such as a strong promoter that is functional in yeast cells.

In other embodiments, the said one or more copies of an expression cassette comprising a 2-hydroxyacide dehydrogenase coding sequence comprise regulatory sequences allowing a strong expression of the 2-hydroxyacide dehydrogenase, such as a strong promoter that is functional in yeast cells.

Export of the Compounds of Interest

In further embodiments of a recombinant yeast according to the invention, the export of the produced methionine and/or methionine derivatives outside of the yeast cell may be enhanced by (i) under expression of genes encoding yeast permeases, by (ii) over expression of genes encoding amino acid exporter proteins, or by (iii) both under expression of genes encoding yeast permeases and over expression of genes encoding amino acid exporter proteins.

Under Expression of Permease-Encoding Gene(s)

As it is described below, permease-encoding genes that may be under expressed in a recombinant yeast according to the invention encompass AGP1, AGP3, BAP3, BAP2, GAP1, GNP1, MUP3 and MUP1.

Accordingly, in a particular embodiment, a genome of a recombinant yeast according to the invention is such that at least one of the following modifications has been performed:
(A) at least one, preferably all, endogenous nucleic acid encoding a general amino acid permease AGP3 have been deleted from the genome of the yeast, and optionally:
    (i) at least one nucleic acid encoding a general amino acid permease AGP3 has been inserted and is under the control of an inducible or repressible promoter, and/or
    (ii) at least one nucleic acid encoding a destabilized general amino acid permease AGP3 has been inserted;

(B) at least one, preferably all, endogenous nucleic acid encoding a branched-chain amino-acid permease 3 BAP3 has been deleted from the genome of the yeast, and, optionally:
  (i) at least one nucleic acid encoding a branched-chain amino-acid permease 3 BAP3 has been inserted and is under the control of an inducible or repressible promoter, and/or
  (ii) at least one nucleic acid encoding a destabilized branched-chain amino-acid permease 3 BAP3 has been inserted;
(C) at least one, preferably all, endogenous nucleic acid encoding a branched-chain amino-acid permease 2 BAP2 has been deleted from the genome of the yeast, and, optionally:
  (i) at least one nucleic acid encoding a branched-chain amino-acid permease 2 BAP2 has been inserted and is under the control of an inducible or repressible promoter, and/or
  (ii) at least one nucleic acid encoding a destabilized branched-chain amino-acid permease 2 BAP2 has been inserted;
(D) at least one, preferably all, endogenous nucleic acid encoding a general amino acid permease GAP1 has been deleted from the genome of the yeast, and, optionally:
  (i) at least one nucleic acid encoding a general amino acid permease GAP1 has been inserted and is under the control of an inducible or repressible promoter, and/or
  (ii) at least one nucleic acid encoding a destabilized general amino acid permease GAP1 has been inserted;
(E) at least one, preferably all, endogenous nucleic acid encoding a high-affinity glutamine permease GNP1 has been deleted from the genome of the yeast, and, optionally:
  (i) at least one nucleic acid encoding a high-affinity glutamine permease GNP1 has been inserted and is under the control of an inducible or repressible promoter, and/or
  (ii) at least one nucleic acid encoding a destabilized high-affinity glutamine permease GNP1 has been inserted;
(F) at least one, preferably all, endogenous nucleic acid encoding a general amino acid permease AGP1 has been deleted from the genome of the yeast, and, optionally:
  (i) at least one nucleic acid encoding a general amino acid permease AGP1 has been inserted and is under the control of an inducible or repressible promoter, and/or
  (ii) at least one nucleic acid encoding a destabilized general amino acid permease AGP1 has been inserted;
(G) at least one, preferably all, endogenous nucleic acid encoding a low-affinity methionine permease MUP3 has been deleted from the genome of the yeast, and, optionally:
  (i) at least one nucleic acid encoding a low-affinity methionine permease MUP3 has been inserted and is under the control of an inducible or repressible promoter, and/or
  (ii) at least one nucleic acid encoding a destabilized low-affinity methionine permease MUP3 has been inserted;
(H) at least one, preferably all, endogenous nucleic acid encoding a high-affinity methionine permease MUP1 has been deleted from the genome of the yeast, and, optionally:
  (i) at least one nucleic acid encoding a high-affinity methionine permease MUP1 has been inserted and is under the control of an inducible or repressible promoter, and/or
  (ii) at least one nucleic acid encoding a destabilized high-affinity methionine permease MUP1 has been inserted;
(I) at least one nucleic acid encoding a probable transporter AQR1 is overexpressed; and/or
(J) at least one nucleic acid encoding a polyamine transporter 1 TPO1 is overexpressed.

In a particular embodiment, at least two, in particular at least three of these modifications have been performed in the genome of a yeast according to the invention.

AGP1 is the general amino acid permease 1 from *Saccharomyces cerevisiae*. For the amino acid sequence of AGP1 it may be referred to the access number NP_009905 in the UniProt database. For the nucleic acid sequence, it may be referred to the access number NM_001178671 in the NCBI database.

AGP3 is the general amino acid permease 3 from *Saccharomyces cerevisiae. For the amino acid sequence of AGP3 it may be referred to the access number NP_116600* in the UniProt database. For the nucleic acid sequence, it may be referred to the access number NM_001179912 in the NCBI database.

BAP3 is the valine amino acid permease from *Saccharomyces cerevisiae*. For the amino acid sequence of BAP3 it may be referred to the access number NP_010331 in the UniProt database. For the nucleic acid sequence, it may be referred to the access number NM_001180354 in the NCBI database.

BAP2 is the Leu/Val/Ile amino acid permease from *Saccharomyces cerevisiae*. For the amino acid sequence of BAP2 it may be referred to the access number NP_009624 in the UniProt database. For the nucleic acid sequence, it may be referred to the access number NM_001178416 in the NCBI database.

GAP1 is the general amino-acid permease from *Saccharomyces cerevisiae*. For the amino acid sequence of GAP1 it may be referred to the access number NP_012965.3 in the UniProt database. For the nucleic acid sequence, it may be referred to the access number NM_001179829 in the NCBI database.

GNP1 is the high-affinity glutamine permease from *Saccharomyces cerevisiae*. For the amino acid sequence of GNP1 it may be referred to the access number NP_010796 in the UniProt database. For the nucleic acid sequence, it may be referred to the access number NM_001180816 in the NCBI database.

MUP3 is the low-affinity methionine permease from *Saccharomyces cerevisiae*. For the amino acid sequence of MUP3 it may be referred to the access number NP_011827 in the UniProt database. For the nucleic acid sequence, it may be referred to the access number NM_001179116 in the NCBI database.

MUP1 is the low-affinity methionine permease from *Saccharomyces cerevisiae*. For the amino acid sequence of MUP it may be referred to the access number NP_011569 in the UniProt database. For the nucleic acid sequence, it may be referred to the access number NM_001181184 in the NCBI database.

In some embodiments of a recombinant yeast according to the invention, the said recombinant yeast is further defined as having an under expression one or more genes encoding a permease, that encompasses AGP1, AGP3, BAP3, BAP2, GAP1, GNP1, MUP3 and MUP1 permeases.

In a particular embodiment, the inserted at least one nucleic acid encoding a S-adenosyl methionine SAM1 and/or SAM2, a cystathionine gamma-lyase CYS3, a cystathionine beta-synthase CYS4, a homoserine kinase THR1, a general amino acid permease AGP3, a branched-chain amino-acid permease 3 BAP3, a branched-chain amino-acid permease 2 BAP2, a general amino acid permease GAP1, a high-affinity glutamine permease GNP1, a general amino acid permease AGP1, a low-affinity methionine permease MUP3 and a high-affinity methionine permease MUP1 are, independently, nucleic acid from a yeast, preferably from Saccharomyces cerevisiae.

Without wishing to be bound by any particular theory, the inventors believe that an under expression of any of the permease genes shall increase the excretion of the produced methionine and/or methionine derivatives outside the yeast cell, e.g. in the culture medium.

As regards permeases under expression of one or more of these genes encompasses a complete repression of their expression, e.g. by interruption or deletion of the said one or more permease genes.

In some embodiments, under expression of a permease-encoding gene may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

As regards a permease gene, under expression also encompasses the insertion of a nucleic acid encoding a destabilized permease protein or the insertion of a nucleic acid encoding a destabilized permease protein, or both.

A destabilized permease is a variant of a permease that is more rapidly degraded within the yeast cell than the parent permease.

In preferred embodiments, a destabilized permease consists of a degron-tagged permease protein.

As illustrated in the examples, the AGP3 gene, the BAP3 gene, the GAP1 gene, the GNP1 gene and the MUP3 gene can be interrupted by loxP and are thus deleted.

Over Expression of Amino Acid Exporter Protein-Encoding Gene(s)

As it is described below, exporter protein-encoding genes that may be over expressed in a recombinant yeast according to the invention encompass AQR1 and TPO1.

AQR1 is a transporter from Saccharomyces cerevisiae. For the amino acid sequence of AQR1 it may be referred to the access number NP_014334 in the UniProt database. For the nucleic acid sequence, it may be referred to the access number NM_001182903 in the NCBI database.

TPO1 is a polyamine transporter from Saccharomyces cerevisiae. For the amino acid sequence of TPO1 it may be referred to the access number NP_013072 in the UniProt database. For the nucleic acid sequence, it may be referred to the access number NM_001181848 in the NCBI database.

In preferred embodiments of a recombinant yeast according to the invention, over expression of a transporter-encoding gene is obtained by inserting, at selected location(s) of the yeast genome, one or more additional copies of an expression cassette comprising the said transporter coding sequence.

Without wishing to be bound by any particular theory, the inventors believe that an over expression of a transporter-encoding gene shall increase the excretion of the produced methionine and/or methionine derivatives outside the yeast cell, e.g. in the culture medium.

In some embodiments, over expression of a transporter-encoding gene is obtained by inserting, at selected location(s) of the yeast genome, one or more additional copies of an expression cassette comprising a transporter gene coding sequence. In some of these embodiments, the said one or more copies of an expression cassette comprising a transporter coding sequence comprise regulatory sequences allowing a strong expression of the said transporter, such as a strong promoter that is functional in yeast cells.

In some other embodiments, one copy of a transporter-encoding gene is inserted at a selected location of the yeast genome. In these other embodiments, the said one or more copies of an expression cassette comprising a transporter coding sequence comprise regulatory sequences allowing a strong expression of the said transporter, such as a strong promoter that is functional in yeast cells.

In preferred embodiments, the said amino acid exporter protein-encoding gene AQR1 is placed under the control of the strong promoter pTEF3.

Illustratively, the AQR1 gene may be inserted within the hom3 gene, as it is shown in the examples herein.

In preferred embodiments, the said amino acid exporter protein-encoding gene_TPO1 is placed under the control of the strong inducible or repressible promoter pSAM4 or the strong constitutive promoter pTEF1.

TPO1-1 can be used instead of TPO1. TPO1-1 is an artificial allele in which the lysines 10, 49, 86, 143, 144 and 145 are replaced by arginines.

It is believed by the inventors that these modifications protect TPO1 from degradation through the ubiquitin-proteasome pathway, thus stabilizing it.

Illustratively, the TPO1 gene may be inserted within the mae1 gene, as it is shown in the examples herein, and/or within the trp1 gene.

In view of further increasing methionine and/or methionine derivatives production, a recombinant yeast according to the invention may comprise additional genetic changes, such that they produce large quantities of the intermediate product oxaloacetate. These optional genetic changes are described here below.

Further Embodiments of a Methionine-Producing and/or Methionine Derivatives-Producing Recombinant Yeast According to some embodiments of a recombinant yeast according to the invention, production of methionine and/or methionine derivatives may be further increased by placing the said recombinant yeast in conditions leading to an increase production of the intermediate metabolite oxaloacetate.

Placing the said recombinant yeast in conditions leading to an increased production of oxaloacetate may be performed by introducing further genetic modifications in the yeast genome.

The present inventors have found that an optimally increased methionine and/or methionine derivatives production may be reached by introducing further genetic changes to the methionine-producing and/or methionine derivatives-producing recombinant yeast, that are described below.

First Further Embodiments of a Methionine-Producing and/or Methionine Derivatives-Producing Recombinant Yeast According to these first further embodiments of a methionine-producing and/or methionine derivatives-producing recombinant yeast according to the invention, further genetic engineering of the recombinant yeast is performed with the aim of increasing the production of the intermediate product phosphoenol-pyruvate (PEP).

Without wishing to be bound by any particular theory, the inventors believe that the further genetic changes introduced in the methionine-producing and/or methionine derivatives-producing recombinant yeast (i) cause an over-production of NADPH, (ii) cause a controlled and balanced conversion of phosphoenol pyruvate into oxaloacetate and pyruvate, respectively, and (iii) cause a reduced conversion of pyruvate into ethanol and a redirection towards conversion of phosphoenolpyruvate into oxaloacetate.

These further genetic changes introduced by genetic engineering in a methionine-producing and/or methionine derivatives-producing recombinant yeast according to the invention are specified in more detail below.

According to these embodiments, genetic changes are introduced so as to over-express a glucose-6-phosphate-1-dehydrogenase (also termed MET19 or ZWF1) and a 6-phosphogluconate dehydrogenase, decarboxylating 1 (also termed GND1). Without wishing to be bound by any particular theory, the inventors believe that an over expression of MET19 and GND1 causes an increase in NADPH production.

According to these embodiments, genetic changes are introduced so as to over-express a phosphoenolpyruvate carboxylase (also termed PEPC ou PPC) and/or a phosphoenolpyruvate carboxykinase [ATP] (also termed PCK1 or PEPCK).

According to these embodiments, genetic changes are introduced so as to under-express a pyruvate kinase 1 (also termed PYK1 or CDC19) and a pyruvate kinase 2 (also termed (PYK2). In some of these embodiments, PYK2 gene may be deleted rather than being under-expressed. In some embodiments, PYK1 gene may be deleted rather than being under-expressed. In particular embodiments, PYK1 gene and PYK2 gene may be deleted rather than being under-expressed.

In some of these embodiments, one or more of the genes encoding a pyruvate decarboxylase is (are) inactivated, preferably by deletion. Pyruvate decarboxylase-encoding genes encompass those termed PDC1, PDC5 and PDC6, respectively. According to some of these embodiments, PDC1 and/or PDC6 genes are inactivated, preferably by interruption or deletion, whereas the other pyruvate decarboxylase-encoding gene PDC5 is left unaltered; Or its expression is reduced by controlling it with a weak promoter.

In some of these embodiments, alcohol dehydrogenase activity of the recombinant yeast is reduced by altering the expression of one or more of the alcohol dehydrogenase-encoding genes. In some of these embodiments, the expression of ADH1 is reduced by placing the gene under the control of a weak promoter or by producing a destabilized ADH1 enzyme. In some of these embodiments, one or more of ADH3, ADH4 and ADH5 may be inactivated, preferably by interruption or deletion.

In some of these embodiments, an exogenous acetyl dehydrogenase-encoding gene (also termed MHPF) may be introduced in the yeast genome and over-expressed.

In some of these embodiments, an exogenous acetate kinase-encoding gene (also termed ACKA) may be introduced in the yeast genome and over-expressed.

In some of these embodiments, an exogenous phosphate acetyl transferase-encoding gene (also termed PTA) may be introduced in the yeast genome and over-expressed.

Glucose-6-Phosphate-1-Dehydrogenase

The glucose-6-phosphate-1-dehydrogenase enzyme is a protein which is described in the art for catalyzing D-glucose 6-phosphate to 6-phospho-D-glucono-1,5-lactone, with concomitant reduction of NADP to NADPH.

A method implemented to measure the activity level of glucose-6-phosphate-1-dehydrogenase belongs to the general knowledge of the one skilled in the art.

In this regard, the one skilled in the art may advantageously refer to the method described by Kuby, S. et al. (1966) Dehydrogenases and Oxidases Methods in Enzymology 9, 116-117.

Preferred glucose-6-phosphate-1-dehydrogenase in the present specification is an enzyme having an EC number of no. 1.1.1.49.

For the amino acid sequence of glucose-6-phosphate-1-dehydrogenase (also termed MET19), it may be referred to the access number NP_014158.1 in the UniProt database. For the nucleic acid sequence, it may be referred to the access number NM_001183079.1 in the UniProt database.

6-Phosphogluconate Dehydrogenase, Decarboxylating 1

The 6-phosphogluconate dehydrogenase, decarboxylating 1 enzyme is a protein which is described in the art for catalyzing the oxidative decarboxylation of 6-phosphogluconate to ribulose 5-phosphate and $CO_2$, with concomitant reduction of NADP to NADPH.

A method implemented to measure the activity level of 6-phosphogluconate dehydrogenase, decarboxylating 1 belongs to the general knowledge of the one skilled in the art.

In this regard, the one skilled in the art may advantageously refer to the method described by He W. et al. (2007) BMC Structural Biology, 7:38.

Preferred 6-phosphogluconate dehydrogenase, decarboxylating 1 in the present specification is an enzyme having an EC number of no. 1.1.1.44.

For the amino acid sequence of 6-phosphogluconate dehydrogenase, decarboxylating 1 (also termed GND1), it may be referred to the access number NP_012053 in the UniProt database. For the nucleic acid sequence, it may be referred to the access number NM_001179314 in the NCBI database.

Pyruvate Kinase 1

The pyruvate kinase 1 enzyme is a protein which is described in the art for catalyzing the conversion of pyruvate into phosphoenolpyruvate, in the presence of ATP.

A method implemented to measure the activity level of pyruvate kinase 1 belongs to the general knowledge of the one skilled in the art.

In this regard, the one skilled in the art may advantageously refer to the method described by Susan-resiga and Nowak (biochemistry, 2004, 43, 15230-15245).

Preferred pyruvate kinase 1 in the present specification is an enzyme having an EC number of no. 2.7.1.40.

For the amino acid sequence of pyruvate kinase 1 (also termed PYK1) it may be referred to the access number NP_009362 in the UniProt database. For the nucleic acid sequence, it may be referred to the access number NM_001178183 in the NCBI database.

Pyruvate Kinase 2

The pyruvate kinase 2 enzyme is a protein which is described in the art for catalyzing the conversion of pyruvate into phosphoenolpyruvate, in the presence of ATP. Pyruvate kinase 2 may be used by the yeast cell under conditions in which the level of glycolytic flux is very low.

A method implemented to measure the activity level of pyruvate kinase 2 belongs to the general knowledge of the one skilled in the art.

In this regard, the one skilled in the art may advantageously refer to the method described by Susan-resiga and Nowak (biochemistry, 2004, 43, 15230-15245).

Preferred pyruvate kinase 2 in the present specification is an enzyme having an EC number of no. 2.7.1.40.

For the amino acid sequence of pyruvate kinase 2 (also termed PYK2) it may be referred to the access number NP_014992 in the UniProt database. For the nucleic acid sequence, it may be referred to the access number NM_001183767 in the NCBI database.

Pyruvate Decarboxylase Isozyme 1

The pyruvate decarboxylase isozyme 1 is a protein which is described in the art for being involved in the non-oxidative conversion of pyruvate to acetaldehyde and carbon dioxide during alcoholic fermentation.

A method implemented to measure the activity level of the pyruvate decarboxylase isozyme 1 belongs to the general knowledge of the one skilled in the art.

In this regard, the one skilled in the art may advantageously refer to the method described by Wang et al. (Biochemistry, 2001, 40:1755-1763).

Preferred pyruvate decarboxylase isozyme 1 in the present specification is an enzyme having an EC number of no. 4.1.1.1.

For the amino acid sequence of pyruvate decarboxylase isozyme 1 (also termed PDC1) it may be referred to the access number NP_013145 in the UniProt database. For the nucleic acid sequence, it may be referred to the access number NM_001181931 in the NCBI database.

Pyruvate Decarboxylase Isozyme 2

The pyruvate decarboxylase isozyme 2 is a protein which is described in the art for being involved in the nonoxidative conversion of pyruvate to acetaldehyde and carbon dioxide during alcoholic fermentation.

A method implemented to measure the activity level of pyruvate decarboxylase isozyme 2 belongs to the general knowledge of the one skilled in the art.

In this regard, the one skilled in the art may advantageously refer to the method described by Wang et al. (Biochemistry, 2001, 40: 1755-1763).

Preferred pyruvate decarboxylase isozyme 2 in the present specification is an enzyme having an EC number of no. 4.1.1.1.

For the amino acid sequence of the pyruvate decarboxylase isozyme 2 from *Saccharomyces cerevisiae*, the one skilled in the art may refer to the accession number NP013235.1 in the UniProt database. For the nucleic acid sequence, it may be referred to the access number NM_001182021 in the NCBI database.

Pyruvate Decarboxylase Isozyme 3

The pyruvate decarboxylase isozyme 3 is a protein which is described in the art for being involved in the nonoxidative conversion of pyruvate to acetaldehyde and carbon dioxide during alcoholic fermentation.

A method implemented to measure the activity level of pyruvate decarboxylase isozyme 3 belongs to the general knowledge of the one skilled in the art.

In this regard, the one skilled in the art may advantageously refer to the method described by Wang et al. (Biochemistry, 2001, 40:1755-1763).

Preferred pyruvate decarboxylase isozyme 3 in the present specification is an enzyme having an EC number of no. 4.1.1.1.

For the amino acid sequence of pyruvate decarboxylase isozyme 3 (also termed PDC6) it may be referred to the access number NP011601.3 in the UniProt database. For the nucleic acid sequence, it may be referred to the access number NM_001181216.3 in the NCBI database.

Acetaldehyde Dehydrogenase

The acetaldehyde dehydrogenase is a protein which is described in the art for catalyzing the conversion of acetaldehyde to acetyl-CoA, using NAD and coenzyme A.

A method implemented to measure the activity level of acetaldehyde dehydrogenase belongs to the general knowledge of the one skilled in the art.

In this regard, the one skilled in the art may advantageously refer to the method described by Fisher et al. (2013) Chemi. Biol. Interact. 202 70-77.

Preferred acetaldehyde dehydrogenase in the present specification is an enzyme having an EC number of no. 1.1.1.10.

For the amino acid sequence of acetaldehyde dehydrogenase (also termed MHPF) it may be referred to the access number NP_414885 in the UniProt database. For the nucleic acid sequence, it may be referred to the one disclosed in the access number NC_000913.3 in the NCBI database.

Acetate Kinase

The acetate kinase is a protein which is described in the art for the formation of acetyl phosphate from acetate and ATP.

A method implemented to measure the activity level of acetate kinase belongs to the general knowledge of the one skilled in the art.

In this regard, the one skilled in the art may advantageously refer to the method described by Sagers et al. J. Bacteriology (1961) 82 233-238.

For the amino acid sequence of acetate kinase (also termed ACKA) it may be referred to the access number NP_416799 in the UniProt database. For the nucleic acid sequence, it may be referred to the one disclosed in the access number NC_000913.3 in the NCBI database.

Phosphate Acetyltransferase

The phosphate acetyltransferase is a protein which is described in the art for catalyzing the reversible interconversion of acetyl-CoA and acetyl phosphate.

A method implemented to measure the activity level of the phosphate acetyltransferase belongs to the general knowledge of the one skilled in the art.

In this regard, the one skilled in the art may advantageously refer to the method described by Castano-Cerezo and Canovas, Microbial Cell Factories 2009, 8:54.

Preferred phosphate acetyltransferase in the present specification is an enzyme having an EC number of no. 2.3.1.8.

For the amino acid sequence of phosphate acetyltransferase (also termed PTA) it may be referred to the access number NP_416800 in the UniProt database. For the nucleic acid sequence, it may be referred to the one disclosed in the access number NC_000913 in the NCBI database.

Alcohol Dehydrogenase 1

The alcohol dehydrogenase 1 is a protein which is described in the art for catalyzing the conversion of primary unbranched alcohols to their corresponding aldehydes.

A method implemented to measure the activity level of the alcohol dehydrogenase 1 belongs to the general knowledge of the one skilled in the art.

In this regard, the one skilled in the art may advantageously refer to the method described by Ganzhorn et al. (1987) The Journal of Biological Chemistry, 262, 3754-61

Preferred alcohol dehydrogenase 1 in the present specification is an enzyme having an EC number of no. 1.1.1.1.

For the amino acid sequence of alcohol dehydrogenase 1 (also termed ADH1) it may be referred to the access number NP_014555 in the UniProt database. For the nucleic acid sequence, it may be referred to the access number NM_001183340 in the NCBI database.

Alcohol Dehydrogenase 3

The alcohol dehydrogenase 3 is a protein which is described in the art for catalyzing the conversion of primary unbranched alcohols to their corresponding aldehydes.

A method implemented to measure the activity level of the alcohol dehydrogenase 3 belongs to the general knowledge of the one skilled in the art.

In this regard, the one skilled in the art may advantageously refer to the method described by Ganzhorn et al. (1987) The Journal of Biological Chemistry, 262, 3754-61.

Preferred alcohol dehydrogenase 3 in the present specification is an enzyme having an EC number of no. 1.1.1.1.

For the amino acid sequence of alcohol dehydrogenase 3 (also termed ADH3) it may be referred to the access number NP_013800 in the UniProt database. For the nucleic acid sequence, it may be referred to the access number NM_001182582 in the NCBI database.

Alcohol Dehydrogenase 4

The alcohol dehydrogenase 4 is a protein which is described in the art for catalyzing the conversion of primary unbranched alcohols to their corresponding aldehydes.

A method implemented to measure the activity level of the alcohol dehydrogenase 4 belongs to the general knowledge of the one skilled in the art.

In this regard, the one skilled in the art may advantageously refer to the method described by Ganzhorn et al. (1987) The Journal of Biological Chemistry, 262, 3754-61.

Preferred alcohol dehydrogenase 4 in the present specification is an enzyme having an EC number of no. 1.1.1.1.

For the amino acid sequence of alcohol dehydrogenase 4 (also termed ADH4) it may be referred to the access number NP_011258 in the UniProt database. For the nucleic acid sequence, it may be referred to the access number NM_001181122 in the NCBI database.

Alcohol Dehydrogenase 5

The alcohol dehydrogenase 5 is a protein which is described in the art for catalyzing the conversion of primary unbranched alcohols to their corresponding aldehydes.

A method implemented to measure the activity level of the alcohol dehydrogenase 5 belongs to the general knowledge of the one skilled in the art.

In this regard, the one skilled in the art may advantageously refer to the method described by Ganzhorn et al. (1987) The Journal of Biological Chemistry, 262, 3754-61.

Preferred alcohol dehydrogenase 5 in the present specification is an enzyme having an EC number of no. 1.1.1.1.

For the amino acid sequence of alcohol dehydrogenase 5 (also termed ADH5) it may be referred to the access number NP_009703 in the UniProt database. For the nucleic acid sequence, it may be referred to the access number NM_001178493 in the NCBI database.

Second Further Embodiments of a Methionine-Producing and/or Methionine Derivatives-Producing Recombinant Yeast According to these further embodiments of a methionine-producing and/or methionine derivatives-producing recombinant yeast according to the invention, further genetic engineering of the recombinant yeast is performed with the aim of increasing the production of the intermediate product phosphoenol-pyruvate (PEP).

Without wishing to be bound by any particular theory, the inventors believe that the further genetic changes introduced in the methionine-producing and/or methionine derivatives-producing recombinant yeast (i) cause an over-production of NADPH, (ii) cause a controlled and balanced conversion of phosphoenol pyruvate into oxaloacetate and pyruvate, respectively, and (iii) cause a reduced conversion of pyruvate into ethanol and a redirection towards conversion of phosphoenolpyruvate into oxaloacetate.

For this purpose, the inventors have conceived a completely novel metabolic pathway, starting from phosphenolpyruvate and ending with the production of oxaloacetate.

These further genetic changes introduced by genetic engineering in a methionine-producing and/or methionine derivatives-producing recombinant yeast according to the invention are specified in more detail below.

According to these embodiments, genetic changes are introduced so as to under express the pyruvate kinase 1 (also termed PYK1), and optionally also pyruvate kinase 2 (also termed PYK2). In some of these embodiments, PYK1 may be under-expressed by placing the gene under the control of a weak promoter or of an inducible or repressible promoter. In some of these embodiments, PYK2 may be inactivated, e.g. by interruption or deletion. In some embodiments, PYK1 gene may be deleted rather than being under-expressed. In particular embodiments, PYK1 gene and PYK2 gene may be deleted rather than being under-expressed.

According to these embodiments, genetic changes are introduced so as to over-express a phosphoenolpyruvate carboxykinase [ATP] (also termed PCK or PCKA or PEPCK), either (i) by constitutive over-expression or (ii) by inducible over-expression.

According to these embodiments, genetic changes are introduced so as over-express in the cytoplasm a malate dehydrogenase, such as a peroxisomal malate dehydrogenase (also termed MDH3), either (i) by constitutive over-expression or (ii) by inducible over-expression.

According to these embodiments, genetic changes are introduced so as over-express a NADP-dependent malic enzyme 3 (also termed ME3 or NADP-ME3), either (i) by constitutive over-expression or (ii) by inducible over-expression.

According to these embodiments, genetic changes are introduced so as to reduce expression of one or more alcohol dehydrogenase(s), preferably one or more alcohol dehydrogenase(s) selected in a group comprising alcohol dehydrogenase 1 (also termed ADH1), alcohol dehydrogenase 3 (also termed ADH3), alcohol dehydrogenase 4 (also termed ADH4) and alcohol dehydrogenase 5 (also termed ADH5), e.g. (i) by placing the corresponding coding sequence under the control of a weak promoter or of an inducible or repressible promoter, or (ii) by production of a destabilized form of the said alcohol dehydrogenase(s).

Still according to these embodiments, genetic changes are introduced so as to over-express an exogenous acetaldehyde dehydrogenase (also termed MHPF), either (i) by constitutive over-expression or (ii) by inducible over-expression.

Pyruvate kinase 1 and pyruvate kinase 2 are as defined previously.

Phosphoenolpyruvate Carboxykinase (PPCK)

The phosphoenol carboxykinase [ATP] enzyme is a protein which is described in the art for catalyzing the conversion of oxaloacetate to phosphoenolpyruvate through direct phosphoryl transfer between the nucleoside triphosphate and oxaloacetate.

A method implemented to measure the activity level of phosphoenol carboxykinase [ATP] belongs to the general knowledge of the one skilled in the art.

In this regard, the one skilled in the art may advantageously refer to the method described by Bazaes S. et al. (2007) The Protein Journal, 26, 265-269 and Mariët J. Van der Werf et al. (1997) Arch Microbiol 167: 332-342.

Preferred phosphoenol carboxykinase [ATP] in the present specification is an enzyme having an EC number of no. 4.1.1.49.

For the amino acid sequence of phosphoenol carboxykinase [ATP] (also termed PCKA) it may be referred to the access number NP_417862 in the UniProt database. For the nucleic acid sequence, it may be referred to the one disclosed in the access number NC_000913 in the NCBI database.

Preferred phosphoenol carboxykinase according to the invention can be selected from phosphoenolpyruvate carboxykinase PPCK such as PEPCK having an EC number of no. 4.1.1.32.

Malate Dehydrogenase

The malate dehydrogenase enzyme is a protein which is described in the art for catalyzing the conversion of malate to oaxaloacetate, in the presence of NADH.

A method implemented to measure the activity level of malate dehydrogenase belongs to the general knowledge of the one skilled in the art. Mention can for example be made of the commercial kit sold by Sigma entitled "Malate dehydrogenase assay kit" under the reference MAK196-1KT.

For the amino acid sequence of malate dehydrogenase (also termed MDH3) it may be referred to the access number NP_010205 in the UniProt database. For the nucleic acid sequence, it may be referred to the access number NM_00118037 in the NCBI database.

NADP-Dependent Malic Enzyme 3

The NADP-dependent malic enzyme 3 enzyme is a protein which is described in the art for catalyzing the conversion of malate to pyruvate, in the presence of NADP.

A method implemented to measure the activity level of NADP-dependent malic enzyme 3 belongs to the general knowledge of the one skilled in the art.

In this regard, the one skilled in the art may advantageously refer to the method described by Gerrard-Wheeler et al. FEBS Journal 276 (2009) 5665-5677.

Preferred NADP-dependent malic enzyme 3 in the present specification is an enzyme having an EC number of no. 1.1.1.40.

For the amino acid sequence of NADP-dependent malic enzyme 3 (also termed NADP-ME3 or ME3) it may be referred to the access number NP_197960 in the UniProt database. For the nucleic acid sequence, it may be referred to the access number NM_122489 in the NCBI database.

The alcohol dehydrogenase 1, alcohol dehydrogenase 3, alcohol dehydrogenase 4, acetaldehyde dehydrogenase and alcohol dehydrogenase 5 are as defined previously.

Promoters

As it is disclosed herein, the expression of the genes of interest that have been genetically engineered for obtaining a recombinant yeast according to the invention comprise appropriate regulatory sequences that are functional in yeast cells, including in *Saccharomyces cerevisiae*.

As disclosed in the present specification, various promoters may be used for the desired expression of the coding sequences of interest, which include (i) constitutive strong promoters (also called strong promoters in the present text), (ii) constitutive weak promoters (also called weak promoters in the present text) and (iii) inducible or repressible promoters. A list of yeast promoter with their relative activities in different media can be found in Keren et al. (2013) Molecular Systems Biology 9:701.

Promoters allowing the constitutive over-expression of a given gene, may be found in literature (Velculescu et al. (1997) Cell 88, 243-251).

Strong promoters more particularly interesting in the present invention may be selected from the group comprising:
pTDH3 (SEQ ID No. 38),
pENO2 (SEQ ID No. 39),
pTEF KI (SEQ ID No. 40),
pTEF3 (SEQ ID No. 41),
pTEF1 (SEQ ID No. 42),
pADH1 (SEQ ID No. 43),
pGMP1 (SEQ ID No. 44),
pFBA1 (SEQ ID No. 45),
pPDC1 (SEQ ID No. 46),
pCCW12 (SEQ ID No. 47), and
pGK1 (SEQ ID No. 48).

In a particular embodiment, the strong promoter according to the invention is, independently, selected from the group consisting of pTDH3, pENO2, pTEF-KI, pTEF3, pTEF1, pADH1, pGMP1, pFBA1, pPDC1, pCCW12 and pGK1.

Weak promoters more particularly interesting in the present invention may be selected from the group comprising:
pURA3 (SEQ ID No. 50),
pRPLA1 (SEQ ID No. 51)
pNUP57 (SEQ ID No. 130), and
pGAP1 (SEQ ID No. 131).

In a particular embodiment, the weak promoter according to the invention is, independently, selected from the group consisting of pURA3, pRPLA1, pNUP57 and pGAP1.

As previously mentioned, inducible or repressible promoters are promoters whose activity is controlled by the presence or absence of biotic or abiotic factors and also by the quantity of said factor. Accordingly, for some promoters, their activity will in particular be induced and thus increased when the quantity of a given factor increases or is increased, and, accordingly, the activity of these same promoters can be repressed and thus reduced when the quantity of said factor diminishes or is reduced. The quantity of said factor(s) in the culture medium of a recombinant yeast of the invention comprising inducible or repressible promoters can be decided and thus controlled by the man skilled in the art.

For example, increasing the quantity of methionine in a culture medium of a recombinant yeast according to the invention comprising a pSAM4 promoter will induce and thus increase transcription of the gene under the control of this promoter. On the contrary, reducing the quantity of methionine in said culture medium will lead to a repression, and thus a reduced, transcription of the gene under the control of this promoter.

In another example, increasing the quantity of copper in a culture medium of a recombinant yeast according to the invention comprising a pCTR1 promoter will repress and thus decrease transcription of the gene under the control of this promoter. On the contrary, reducing the quantity of copper in said culture medium will lead to an induced, and thus an increased, transcription of the gene under the control of this promoter.

For this reason, the following promoters are referred to in the present text as being "inducible or repressible promoters".

According to a first embodiment, inducible or repressible promoters according to the invention may be selected from the group comprising promoters inducible or repressible with copper, promoters inducible or repressible with methionine and promoters inducible or repressible with threonine, and are in particular selected from the group consisting of:
- pSAM4—methionine inducible or repressible (SEQ ID No. 52),
- pCUP1-1—copper inducible or repressible (SEQ ID No. 53),
- pCUP1.cgla—copper inducible or repressible (SEQ ID No. 54),
- pCUP1.sba—copper inducible or repressible (SEQ ID No. 55),
- pACU1—copper inducible or repressible (SEQ ID No. 56),
- pACU2—copper inducible or repressible (SEQ ID No. 57),
- pACU3p—copper inducible or repressible (SEQ ID No. 58),
- pACU4p—copper inducible or repressible (SEQ ID No. 59),
- pACU5—copper inducible or repressible (SEQ ID No. 60),
- pACU6—copper inducible or repressible (SEQ ID No. 61),
- pACU7—copper inducible or repressible (SEQ ID No. 62),
- pACU8—copper inducible or repressible (SEQ ID No. 63),
- pACU9—copper inducible or repressible (SEQ ID No. 64),
- pACU10p—copper inducible or repressible (SEQ ID No. 65),
- pACU11—copper inducible or repressible (SEQ ID No. 66),
- pACU12—copper inducible or repressible (SEQ ID No. 67),
- pACU13—copper inducible or repressible (SEQ ID No. 68),
- pACU14—copper inducible or repressible (SEQ ID No. 69),
- pACU15—copper inducible or repressible (SEQ ID No. 70),
- pGAL/CUP1p—copper inducible or repressible (SEQ ID No. 71),
- pCRS5—copper inducible or repressible (SEQ ID No. 72), and
- pCHA1—threonine inducible or repressible (SEQ ID No. 73).

According to this embodiment, the inducible or repressible promoter according of the invention can in particular, independently, be selected from the group consisting of pSAM4, pCUP1-1, pCUP1.Cgla, pCUP1.Sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, and pCHA1.

The activity of these promoters is thus induced by the increasing presence of methionine, copper or threonine as indicated above, and their activity diminishes, i.e. is repressed, when the quantity of methionine, copper or threonine is reduced.

According to a second embodiment, inducible or repressible promoters according to the invention may be selected from the group comprising promoters inducible or repressible with copper, promoters inducible or repressible with lysine and promoters inducible or repressible with methionine, and in particular selected from the group consisting of:
- pCTR1—copper inducible or repressible (SEQ ID No. 74),
- pCTR3—copper inducible or repressible (SEQ ID No. 75),
- pCUR1—copper inducible or repressible (SEQ ID No. 76),
- pCUR2—copper inducible or repressible (SEQ ID No. 77),
- pCUR3—copper inducible or repressible (SEQ ID No. 78),
- pCUR4—copper inducible or repressible (SEQ ID No. 79),
- pCUR5p—copper inducible or repressible (SEQ ID No. 80),
- pCUR6—copper inducible or repressible (SEQ ID No. 81),
- pCUR7—copper inducible or repressible (SEQ ID No. 82),
- pCUR8—copper inducible or repressible (SEQ ID No. 83),
- pCUR9—copper inducible or repressible (SEQ ID No. 84),
- pCUR10—copper inducible or repressible (SEQ ID No. 85),
- pCUR11—copper inducible or repressible (SEQ ID No. 86),
- pCUR12—copper inducible or repressible (SEQ ID No. 87),
- pCUR13—copper inducible or repressible (SEQ ID No. 88),
- pCUR14—copper inducible or repressible (SEQ ID No. 89),
- pCUR15—copper inducible or repressible (SEQ ID No. 90),
- pCUR16—copper inducible or repressible (SEQ ID No. 91),
- pCUR17—copper inducible or repressible (SEQ ID No. 92),
- pLYS1—lysine inducible or repressible (SEQ ID No. 93),
- pLYS4—lysine inducible or repressible (SEQ ID No. 94),
- pLYS9—lysine inducible or repressible (SEQ ID No. 95),
- pLYR1p—lysine inducible or repressible (SEQ ID No. 96),
- pLYR2p—lysine inducible or repressible (SEQ ID No. 97),
- pLYR3p—lysine inducible or repressible (SEQ ID No. 98),
- pLYR4p—lysine inducible or repressible (SEQ ID No. 99),
- pLYR5p—lysine inducible or repressible (SEQ ID No. 100), pLYR6p—lysine inducible or repressible (SEQ ID No. 101),
pLYR7p—lysine inducible or repressible (SEQ ID No. 102),
pLYR8—lysine inducible or repressible (SEQ ID No. 103),
pLYR9—lysine inducible or repressible (SEQ ID No. 104),
pLYR10—lysine inducible or repressible (SEQ ID No. 105),
pLYR11—lysine inducible or repressible (SEQ ID No. 106),
pMET17—methionine inducible or repressible (SEQ ID No. 107),
pMET6—methionine inducible or repressible (SEQ ID No. 108),
pMET14—methionine inducible or repressible (SEQ ID No. 109),
pMET3—methionine inducible or repressible (SEQ ID No. 110),
pSAM1—methionine inducible or repressible (SEQ ID No. 111), and
pSAM2—methionine inducible or repressible (SEQ ID No. 112),
pMDH2—glucose inducible or repressible (SEQ ID No. 49),
pJEN1—glucose inducible or repressible (SEQ ID No. 132),
pICL1—glucose inducible or repressible (SEQ ID No. 133),
pADH2—glucose inducible or repressible (SEQ ID No. 134), and
pMLS1—glucose inducible or repressible (SEQ ID No. 135).

According to this embodiment, the inducible or repressible promoter according to the invention can, independently, be selected from the group consisting of pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2 and pMLS1.

In a particular embodiment, inducible or repressible promoters according to the invention may be selected from the group comprising promoters inducible or repressible with copper, promoters inducible or repressible with glucose, promoters inducible or repressible with lysine, promoters inducible or repressible with methionine and promoters inducible or repressible with threonine.

The activity of these promoters is thus repressed by the increasing presence of methionine, copper, lysine or glucose as indicated above, and their activity increases, i.e. is induced, when the quantity of methionine, copper, lysine or glucose is reduced.

In a more particular embodiment, the inducible or repressible promoter according to the invention can, independently, be selected from the group consisting of pSAM4, pCUP1-1, pCUP1.Cgla, pCUP1.Sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, pCHA1, pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2 and pMLS1.

More particularly, said promoters, identical or different, may be preferably characterized by a sequence of nucleic acid selected from the group consisting of sequences having at least 80% identity with sequences SEQ ID NO: 38 to 112 and 130 to 135.

Synthetic promoters as described in Blazeck & Alper (2013) Biotechnol. J. 8 46-58 can also be used.

The strong, weak and inducible or repressible promoters of the invention can originate from any organism from the Saccharomycetes class and can in particular originate, independently, from an organism selected from the group consisting of *Saccharomyces cerevisiae, Saccharomyces boulardii, Saccharomyces castelii, Saccharomyces bayanus, Saccharomyces arboricola, Saccharomyces kudriavzevii, Ashbya gossypii, Kluveromyces lactis, Pichia pastoris, Candida glabrata, Candida tropicalis, Debaryomyces castelii, Yarrowia lipolitica* and *Cyberlindnera jadinii*.

The strong, weak and inducible or repressible promoters of the invention can preferably originate from an organism selected from the group consisting of *Saccharomyces cerevisiae, Saccharomyces castelii, Saccharomyces bayanus, Saccharomyces arboricola, Saccharomyces kudriavzevii* and *Kluveromyces lactis*.

Terminators

As it is disclosed herein, the expression of the genes of interest that have been genetically engineered for obtaining a recombinant yeast according to the invention comprise appropriate transcription terminator sequences that are functional in yeast cells, including in *Saccharomyces cerevisiae*.

Said transcription terminators, identical or different, may be found in literature Yamanishi et al., (2013) ACS synthetic biology 2, 337-347.

Terminators more particularly interesting in the present invention may be selected from the group comprising:
tTDH2 from the gene coding for Glyceraldehyde-3-phosphate dehydrogenase, isozyme 2 (TDH2 gene=Sequence SEQ ID No. 113),
tCYC1 (=Sequence SEQ ID No. 114),
tTDH3 (=Sequence SEQ ID No. 115), and
tADH1 from gene coding for the alcohol dehydrogenase (ADH1 gene=Sequence SEQ ID No. 116),
tADH2 from gene coding for the alcohol dehydrogenase (ADH2 gene=Sequence SEQ ID No. 117),
tTPI1 from the gene encoding for the Triose Phosphate Isomerase (TPI1 gene=Sequence SEQ ID No. 118),
tMET17 from the gene encoding for the O-acetyl homoserine-O-acetyl serine sulfhydrylase (Met17 gene=Sequence SEQ ID No. 119),
tENO2 from the gene coding for Enolase II (ENO2 gene=Sequence SEQ ID No. 120),
tMET3 (=Sequence SEQ ID No. 121), and
tPGK1 from the gene encoding for the 3-phosphoglycerate kinase (PGK1 gene=Sequence SEQ ID No. 122),
tDIT1 (=Sequence SEQ ID No. 123)
tRPL3 (=Sequence SEQ ID No. 124)
tRPL41B (=Sequence SEQ ID No. 125)
tRPL15A (=Sequence SEQ ID No. 126)
tIDP1 (=Sequence SEQ ID No. 127)

More particularly, said terminator, identical or different, may be preferably characterized by a sequence of nucleic acid selected from the group consisting of sequences having at least 80% identity with sequences SEQ ID NO: 113 to 127.

Recombinant Yeast

Generally, yeast can grow rapidly and can be cultivated at higher density as compared with bacteria, and does not require an aseptic environment in the industrial setting. Furthermore, yeast cells can be more easily separated from the culture medium compared to bacterial cells, greatly simplifying the process for product extraction and purification.

Preferentially, the yeast of the invention may be selected among the genus *Saccharomyces, CandidaAshbya, Dekkera, Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus* or *Malassezia.*

More preferentially, the yeast may be Crabtree positive yeast of genus of *Saccharomyces, Dekkera, Schizosaccharomyces, Kluyveromyces, Torulaspora Zigosaccharomyces,* or. *Brettanomycces*

More preferentially, the yeast may be from the species *Saccharomyces cerevisiae, Saccharomyces boulardii, Saccharomyces douglasii, Saccharomyces bayanus* or. or *Zigosaccharomyces bailii, Schizosaccharomyces pombe, Dekkera brucelensis, Dekkera intermedia, Brettanomycces custersii, Brettanomycces intermedius, Kluyveromyces themotolerens, Torulaspora globosa, Torulaspora glabrata*

More preferentially, the recombinant yeast may belong to the *Saccharomyces* genus, and preferably to the *Saccharomyces cerevisiae* species.

As above-mentioned, a recombinant yeast according to the invention has a pyruvate decarboxylase activity which is reduced by insertion of at least one DNA construct(s) selected from those disclosed in the present specification.

Methods implemented to insert a specific DNA construct within a gene belong to the general knowledge of a man skilled in the art. A related method is described in more details in the herein after examples.

Culture Conditions

The present invention also relates to the use of a recombinant yeast such as above-defined, for the production of methionine and/or of derivatives thereof.

The present invention further relates to a method of production of methionine and/or methionine derivatives comprising the following steps:
providing a recombinant microorganism as previously described, cultivating the recombinant microorganism in a culture medium containing a source of carbon, and recovering the methionine and/or methionine derivatives.

Typically, microorganisms of the invention are grown at a temperature in the range of about 20° C. to about 37° C., preferably at a temperature ranging from 27 to 34° C., in an appropriate culture medium.

When the recombinant yeast according to the invention belongs to the *S. cerevisiae* species, the temperature may advantageously range from 27 to 34° C., in an appropriate culture medium.

Suitable growth media for yeast are common commercially prepared media such as broth that includes yeast nitrogen base, ammonium sulfate, and dextrose as the carbon/energy source) or YPD Medium, a blend of peptone, yeast extract, and dextrose in optimal proportions for growing most. Other defined or synthetic growth media may also be used and the appropriate medium for growth of the particular microorganism will be known by one skilled in the art of microbiology or fermentation science.

The term "appropriate culture medium" is above-defined.

Examples of known culture media for a recombinant yeast according to the present invention are known to the person skilled in the art, and are presented in the following publication D. Burke et al., Methods in yeast Genetics—A cold spring harbor laboratory course Manual (2000).

Suitable pH ranges for the fermentation may be between pH 3.0 to pH 7.5, where pH 4.5 to pH 6.5 is preferred as the initial condition.

Fermentations may be performed under aerobic conditions or micro-aerobic conditions.

The amount of product in the fermentation medium can be determined using a number of methods known in the art, for example, high performance liquid chromatography (HPLC) or gas chromatography (GC).

The present process may employ a batch method of fermentation. A classical batch fermentation is a closed system where the composition of the medium is set at the beginning of the fermentation and not subject to artificial alterations during the fermentation. Thus, at the beginning of the fermentation, the medium is inoculated with the desired organism or organisms, and fermentation is permitted to occur without adding anything to the system. Typically, however, a "batch" fermentation is batch with respect to the addition of carbon source and attempts are often made at controlling factors such as temperature, pH and oxygen concentration. In batch systems, the metabolite and biomass compositions of the system change constantly up to the time when the fermentation is stopped. Within batch cultures cells progress through a static lag phase to a high growth log phase and finally to a stationary phase where growth rate is diminished or halted. If untreated, cells in the stationary phase will eventually die. Cells in log phase generally are responsible for the bulk of production of end product or intermediate.

A Fed-Batch system may also be used in the present invention. A Fed-Batch system is similar to a typical batch system with the exception that the carbon source substrate is added in increments as the fermentation progresses. Fed-Batch systems are useful when catabolite repression (e.g. glucose repression) is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$.

Fermentations are common and well known in the art and examples may be found in Sunderland et al., (1992), herein incorporated by reference. Although the present invention is performed in batch mode it is contemplated that the method would be adaptable to continuous fermentation.

Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to vary. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for production.

In order to still improve the methionine and/or methionine derivatives production, a particular embodiment may consist of culturing the recombinant yeast cells in an appropriate culture medium, such as above-mentioned, wherein the said culture medium comprises an optimal amount of carbon source, especially glucose.

Preferably, the cells are cultured in such an optimal culture medium during only a part of the whole culture duration. In some embodiments, the yeast cells are incubated in the said optimal culture medium 10 hours or more after initiation of the culture, which encompasses 11, 12, 13, 14, 15 or 16 hours or more after initiation of the culture.

Preferably, the cells are cultured in such an optimal culture medium during a time period ranging from 5 hours to 15 hours, which includes from 6 hours to 10 hours, e.g. 8 hours after initiation of the culture.

In preferred embodiments, the carbon source comprised in said optimal culture medium consists of glucose. In preferred embodiments, the said optimal culture medium comprises 12% w/w or more glucose, including 15% w/w or more glucose. In preferred embodiments, the said optimal culture medium comprises at most 40% w/w glucose, which includes at most 35% w/w glucose.

Thus, in the preferred embodiments described above, a method for producing methionine and/or methionine derivatives according to the invention may further comprise, between steps (a) and (c), an intermediate step (b) consisting of cultivating the yeast cells in the said optimal culture medium.

Purification of Methionine and/or of Methionine Derivatives

According to a specific aspect of the invention, the fermentative production of methionine and/or of methionine derivatives comprises a step of isolation of the methionine and/or of the methionine derivatives from the culture medium. Recovering the methionine and/or methionine derivatives from the culture medium is a routine task for a man skilled in the art. It may be achieved by a number of techniques well known in the art including but not limiting to distillation, gas-stripping, pervaporation, selective precipitation or liquid extraction. The expert in the field knows how to adapt parameters of each technique dependant on the characteristics of the material to be separated. The yeast as model of microorganism in the present invention has been retained in that the synthesized methionine and/or methionine derivatives is/are entirely exported outside the cells, thus simplifying the purification process.

The synthesized methionine and/or methionine derivatives may be collected by distillation. Distillation may involve an optional component different from the culture medium in order to facilitate the isolation of methionine and/or methionine derivatives by forming azeotrope and notably with water. This optional component is an organic solvent such as cyclohexane, pentane, butanol, benzene, toluene, trichloroethylene, octane, diethylether or a mixture thereof.

Gas stripping is achieved with a stripping gas chosen among helium, argon, carbon dioxide, hydrogen, nitrogen or mixture thereof.

Liquid extraction is achieved with organic solvent as the hydrophobic phase such as pentane, hexane, heptane or dodecane.

Methionine Derivatives

Methionine derivatives according to the invention are compounds that can be obtained from methionine after modification by at least one enzyme naturally and/or artificially present in the microorganism producing the methionine according to the invention, in particular in the yeast producing the methionine according to the invention.

Examples of such derivatives of methionine can for example be the 2-hydroxy-4-(methylthio) butanoic acid (HMB) or the 2-keto-4-methylthiobutyric acid (KMB).

Preferably, said methionine derivatives are selected from the 2-hydroxy-4-(methylthio) butanoic acid (HMB) and the 2-keto-4-methylthiobutyric acid (KMB), and preferably HMB.

These compounds can for example be obtained as represented in the FIGURE.

Throughout the description, including the claims, the expression "comprising a" should be understood as being synonymous with "comprising at least one", unless otherwise specified.

The terms "between . . . and . . . " and "ranging from . . . to . . . " should be understood as being inclusive of the limits, unless otherwise specified.

The examples and figures which follow are presented by way of illustration and without implied limitation of the invention.

EXAMPLES

Example 1: Protocol for Making a Recombinant *Saccharomyces cerevisiae* Strain According to the Invention All the hereinafter implemented recombinant *Saccharomyces cerevisiae* strains were constructed from standard strains using standard yeast molecular genetics procedure (Methods in yeast Genetics—A cold spring harbor laboratory course Manual (2000) by D. Burke, D. Dawson, T. Stearns CSHL Press).

Cluster of the following-mentioned genes were integrated in recombinant yeast at once using the ability of yeast to efficiently recombine free DNA ends which have sequence homology.

In addition, for a better comprehension of following genotypes:
  ade2, his3, leu2, trp1 and ura3 are auxotrophy marker genes.
  Lowercase letters mean that the considered gene is inactive, uppercase letters reflect an active gene.
  "::": following a gene name means that the gene is interrupted by what follows (if more than one gene are inserted, they are noted in brackets [ ]). The interruption of the gene is concomitant with an entire deletion of the coding sequence but preserves the promoter. In consequence the gene followed by "::" is inactive and is noted in lowercase. If not specified the transcription of the gene inserted is controlled by the promoter of the disrupted gene.
  "gene.Kl" means that the gene originates from *Kluyveromyces lactis*.

More particularly, the coding sequences to be cloned were artificially synthetized. For heterologous sequences (non-yeast), the nucleic sequences were modified in order to obtain a synonymous coding sequence using the yeast codon usage. Using restriction enzyme and classical cloning technology, each synthetic sequence was cloned in between a transcription promoter and a transcription terminator. Each promoter sequence is preceded by a 50 to 200 nucleotide sequence homologous to the sequence of the terminator of the upstream gene. Similarly, the terminator of each gene (a gene comprising the promoter-coding sequence-terminator) is followed by sequences homologous to the gene immediately following. So that each of the unit to be integrated have a 50-200 nucleotide overlap with both the unit upstream and the unit downstream. For the first unit, the promoter is preceded by 50-200 nucleotides homologous to the yeast chromosome nucleotide for the locus in which it will be integrated. Similarly, for the last unit, the terminator is followed by 50-200 nucleotides homologous to the yeast chromosome nucleotide for the locus in which it will be integrated.

Each unit are then PCR amplified from the plasmids constructs, yielding X unit of linear DNA having overlapping sequences. At least one of this gene is an auxotrophic marker, in order to select for recombination event. All the linear fragments are transformed in the yeast at once, and recombinant yeast are selected for the auxotrophy related to the marker used. The integrity of the sequence is then verified by PCR and sequencing.

Example 2: Comparative Examples for the Production of Methionine

A. Firstly, two recombinant strains are obtained: YA2326-14 and YA2408-27. These two strains have been recombined in order to only comprise a part of the modifications according to the invention.

Accordingly, these two strains are as follows:
Strain YA2326-14: Matα, ade2, agp3::loxP, bap3::loxP, can1-100, gap1::loxP, gnp1::loxP, his3::[pTDH3-MHPF.Ec-HIS3]×6, hom3::[pCUP1-1-HOM3-pADH1-HOM2-pADH1-MET2-pRPLA1-HOM6-pENO2-MET17-pTEF3-AQR1], leu2, mae1::[ADE2.K1-pENO2-PYC2-pTEF3-MET17-pTEF1-TPO1-1-pTDH3-METX.Cg], met19::[pENO2-MET19-pTEF3-GND1], mup3::loxP, pdc1::loxP, pdc6::loxP, sam1::loxP, trp1::[pTDH3-GDH-2.Eca-pCUP1-1-HOM3-TRP1]×5, ura3::[pTEF3-MET17-pTDH3-PPC-5.Ec-URA3]×7

Strain YA2408-27: Matα, ade2, agp3::loxP, bap3::loxP, gap1::loxP, gnp1::loxP, his3::[pTDH3-MHPF.Ec-HIS3]×6, hom3::[pCUP1-1-HOM3-pADH1-HOM2-pADH1-MET2-pRPLA1-HOM6-pENO2-MET17-pTEF3-AQR1], leu2, mae1::[ADE2.K1-pENO2-PYC2-pTEF3-MET17-pTEF1-TPO1-1-pTDH3-METX.Cg], met19::[pENO2-MET19-pTEF3-GND1], mup3::loxP, pdc1::loxP, pdc6::loxP, sam1::loxP, trp1::[pACU1-AAT2-pCUP1-1-HOM3-TRP1]×3, ura3::[pTEF3-MET17-pTDH3-PPC-5.Ec-URA3]×7

A third strain, DA705-1, is obtained comprising the combined modifications of the two strains YA2326-14 and YA2408-27. Accordingly, DA705-1 is a strain according to the invention.

DA705-1: (YA2408-27×YA2326-14): ade2/ade2, agp3::loxP/agp3::loxP, bap3::loxP/bap3::loxP, CAN1-100/can1-100, gap1::loxP/gap1::loxP, gnp1::loxP/gnp1::loxP, his3::[pTDH3-MHPF.Ec-HIS3]×6/his3::[pTDH3-MHPF.Ec-HIS3]×6, hom3::[pCUP1-1-HOM3-pADH1-HOM2-pADH1-MET2-pRPLA1-HOM6-pENO2-MET17-pTEF3-AQR1]/hom3::[pCUP1-1-HOM3-pADH1-HOM2-pADH1-MET2-pRPLA1-HOM6-pENO2-MET17-pTEF3-AQR1], leu2/leu2, mae1::[ADE2.K1-pENO2-PYC2-pTEF3-MET17-pTEF1-TPO1-1-pTDH3-METX.Cg]/mae1::[ADE2.K1-pENO2-PYC2-pTEF3-MET17-pTEF1-TPO1-1-pTDH3-METX.Cg], met19::[pENO2-MET19-pTEF3-GND1]/met19::[pENO2-MET19-pTEF3-GND1], mup3::loxP/mup3::loxP, pdc1::loxP/pdc1::loxP, pdc6::loxP/pdc6::loxP, sam1::loxP/sam1::loxP, trp1::[pACU1-AAT2-pCUP1-1-HOM3-TRP1]×3/trp1::[pTDH3-GDH-2.Eca-pCUP1-1-HOM3-TRP1]×5, ura3::[pTEF3-MET17-pTDH3-PPC-5.Ec-URA3]×7/ura3::[pTEF3-MET17-pTDH3-PPC-5.Ec-URA3]×7

PPC-5 is a more stable form of PPC wherein an alanine has been added in N+1.

All these strains were grown for 24 hours in YE (Yeast Extract) 2%, Glucose 8%, $(NH_4)_2SO_4$ 50 mM, and $CH_3SNa$ 1 g/L. 500 µM of $CuSO_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

The methionine amounts obtained with these different strains are respectively:
YA2326-14: 1.47 g/L$^{-1}$.
YA2408-27: 1.5 g/L$^{-1}$.
DA705-1: 1.9 g/L$^{-1}$.

It results from this comparative experiment that a recombinant strain comprising the modifications according to the invention produces a greater amount of methionine when cultured in the same conditions as other recombinant strains not comprising all the genetic modifications according to the invention.

B. Three other recombinant strains have also been obtained: YA1919-13, YA2058-33 and YA2058-27.

These three strains are as follows:
Strain YA1919-13: agp3::loxP, bap3::loxP, gap1::loxP, gnp1::loxP, mup3::loxP, pdc1::loxP, pdc6::loxP, sam1::loxP, hom3::[pCUP1-1-HOM3-pADH1-HOM2-pADH1-MET2-pRPLA1-HOM6-pENO2-MET17-pTEF3-AQR1], mae1::[ADE2.K1-pENO2-PYC2-pTEF3-MET17-pTEF1-TPO1-1-pTDH3-METX.Cg], met19::[pENO2-MET19-pTEF3-GND1], ura3::[pTEF3-MET17-pTDH3-PPC-5.Ec-URA3]×7, his3::[pTDH3-MHPF.Ec-HIS3]×6

YA2058-23: agp3::loxP, bap3::loxP, gap1::loxP, gnp1::loxP, mup3::loxP, pdc1::loxP, pdc6::loxP, sam1::loxP, hom3::[pCUP1-1-HOM3-pADH1-HOM2-pADH1-MET2-pRPLA1-HOM6-pENO2-MET17-pTEF3-AQR1], mae1::[ADE2.K1-pENO2-PYC2-pTEF3-MET17-pTEF1-TPO1-1-pTDH3-METX.Cg], met19::[pENO2-MET19-pTEF3-GND1], ura3::[pTEF3-MET17-pTDH3-PPC-5.Ec-URA3]×7, his3::[pTDH3-MHPF.Ec-HIS3]×6, trp1::[pCUP1-1-HOM3-TRP1]×2

YA2058-37: agp3::loxP, bap3::loxP, gap1::loxP, gnp1::loxP, mup3::loxP, pdc1::loxP, pdc6::loxP, sam1::loxP, hom3::[pCUP1-1-HOM3-pADH1-HOM2-pADH1-MET2-pRPLA1-HOM6-pENO2-MET17-pTEF3-AQR1], mae1::[ADE2.K1-pENO2-PYC2-pTEF3-MET17-pTEF1-TPO1-1-pTDH3-METX.Cg], met19::[pENO2-MET19-pTEF3-GND1], ura3::[pTEF3-MET17-pTDH3-PPC5.Ec-URA3]×7, his3::[pTDH3-MHPF.Ec-HIS3]×6, trp1::[pCUP1-1-HOM3-TRP1]×3

The three strains were grown for 48 hours in YE (Yeast Extract) 2%, Glucose 8%, $(NH_4)_2SO_4$ 50 mM, and MeSNa 1 g/L. 500 µM of $CuSO_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

The methionine amounts obtained with these three strains are respectively:

YA1919-13: 3.9 g/L$^{-1}$.
YA2058-23: 6.1 g/L$^{-1}$.
YA2058-37: 7.1 g/L$^{-1}$.

The controlled strong expression of HOM3 in the recombinant yeasts of the invention significantly improves their methionine production.

C. In addition to strain YA1919-13, two other recombinant strains have also been obtained: YA2160-40 and YA2230-9.

YA2160-40: agp3::loxP, bap3::loxP, gap1::loxP, gnp1::loxP, mup3::loxP, pdc1::loxP, pdc6::loxP, sam1::loxP, hom3::[pCUP1-1-HOM3-pADH1-HOM2-pADH1-MET2-pRPLA1-HOM6-pENO2-MET17-pTEF3-AQR1], mae1::[ADE2.K1-pENO2-PYC2-pTEF3-MET17-pTEF1-TPO1-1-pTDH3-METX.Cg], met19::[pENO2-MET19-pTEF3-GND1], ura3::[pTEF3-MET17-pTDH3-PPC-5.Ec-URA3]×7, his3::[pTDH3-MHPF.Ec-HIS3]×6, tip1::[pSAM4-TPO1-pCUP1-1-HOM3-TRP1]×5

YA2230-9: agp3::loxP, bap3::loxP, gap1::loxP, gnp1::loxP, mup3::loxP, pdc1::loxP, pdc6::loxP, sam1::loxP, hom3::[pCUP1-1-HOM3-pADH1-HOM2-pADH1-MET2-pRPLA1-HOM6-pENO2-MET17-pTEF3-AQR1], mae1::[ADE2.K1-pENO2-PYC2-pTEF3-MET17-pTEF1-TPO1-1-pTDH3-METX.Cg], met19::[pENO2-MET19-pTEF3-GND1], ura3::[pTEF3-MET17-pTDH3-PPC-5.Ec-URA3]×7, his3::[pTDH3-MHPF.Ec-HIS3]×6, trp1::[pTDH3-GDH.E.Ca-pCUP1-1-HOM3-TRP1]×5

The three strains were grown for 48 hours in YE (Yeast Extract) 2%, Glucose 8%, (NH$_4$)$_2$SO$_4$ 50 mM, and MeSNa 1 g/L. 500 µM of CuSO$_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

The methionine amounts obtained with these three strains are respectively:

YA1919-13: 3.9 g/L$^{-1}$.
YA2160-40: 7.4 g/L$^{-1}$.
YA2230-9: 9.6 g/L$^{-1}$.

The controlled strong expression of HOM3 in combination with the strong controlled expression of TPO1 in the recombinant yeasts of the invention significantly improves their methionine production.

Moreover, the strong controlled expression of HOM3 in combination with the constitutive strong over expression of GDH in the recombinant yeasts of the invention also significantly improves their methionine production.

D. In addition to strain YA1919-13, another recombinant strain has also been obtained: YA2231-8.

YA2231-8: agp3::loxP, bap3::loxP, gap1::loxP, gnp1::loxP, mup3::loxP, pdc1::loxP, pdc6::loxP, sam1::loxP, hom3::[pCUP1-1-HOM3-pADH1-HOM2-pADH1-MET2-pRPLA1-HOM6-pENO2-MET17-pTEF3-AQR1], mae1::[ADE2.K1-pENO2-PYC2-pTEF3-MET17-pTEF1-TPO1-1-pTDH3-METX.Cg], met19::[pENO2-MET19-pTEF3-GND1], ura3::[pTEF3-MET17-pTDH3-PPC-5.Ec-URA3]×7, his3::[pTDH3-MHPF.Ec-HIS3]×6, trp1::[pSAM4-AAT2-pCUP1-1-HOM3-TRP1]×4

The two strains were grown for 48 hours in YE (Yeast Extract) 2%, Glucose 8%, (NH$_4$)$_2$SO$_4$ 50 mM, and MeSNa 1 g/L. 500 µM of CuSO$_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

The methionine amounts obtained with these three strains are respectively:

YA1919-13: 3.9 g/L$^{-1}$.
YA2231-8: 7 g/L$^{-1}$.

The controlled strong expression of HOM3 in combination with the controlled strong expression of AAT2 in the recombinant yeasts of the invention significantly improves their methionine production.

E. Three additional recombinant strains according to the invention are obtained: YA2679-28, YA2687-142 and YA3083-58C.

Accordingly, these three strains are as follows:

YA2679-28: MAT-α, gnp1::[LEU2.K1, pENO2-ADH2-tIDP1, pADH1-AAT2-tRPL15A, pTEF3-MDH3-tRPL3, pPDC1-PEPCK.Ec-tMET17, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3, leu2, mup3::[LEU2.K1, pPGK1-AAT2-tTDH2, pENO2-TPO1-tMET17, pCCW12-MET17-tRPL41B, pTDH3-MET2-tRPL3, pCUP1-1-HOM3-tDIT1, pTDH3-MHPF.Ec-tTPI1, pCCW12-ME3.At-tRPL3, pTDH3-PEPCK.Ec-tIDP1, pTEF1-HOM2-tTDH3, pPDC1-MDH3-tRPL15A, pADH1-HOM6-tENO2], pyk1::[HIS5.Sp-pCUR3-PYK1-4], sam3::[pTDH3-GDH-2.Eca-tRPL3-pSAM4-HOM3-tTPI1]×9, trp1::[pTDH3-MHPF.Ec-tRPL3-pCUP1-1-HOM3-tIDP1-TRP1.Sc]×5, ura3::[pCCW12-ME3.At-tRPL3-pTEF3-MET17-tRPL15A-URA3. Sc]×11

YA2687-142: MAT-α, gnp1::[LEU2.K1, pENO2-ADH2-tIDP1, pADH1-AAT2-tRPL15A, pTEF3-MDH3-tRPL3, pPDC1-PEPCK.Ec-tMET17, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3, leu2, mup3::[LEU2.K1, pPGK1-AAT2-tTDH2, pENO2-TPO1-tMET17, pCCW12-MET17-tRPL41B, pTDH3-MET2-tRPL3, pCUP1-1-HOM3-tDIT1, pTDH3-MHPF.Ec-tTPI1, pCCW12-ME3.At-tRPL3, pTDH3-PEPCK.Ec-tIDP1, pTEF1-HOM2-tTDH3, pPDC1-MDH3-tRPL15A, pADH1-HOM6-tENO2], pyk1::[HIS5.Sp-pCUR3-PYK1-6], sam3::[pTDH3-GDH-2.Eca-tRPL3-pSAM4-HOM3-tTPI1].

PYK1-4 and PYK1-6 are destabilized forms of PYK1, destabilized according to the N-end rule, well known to the man skilled in the art (Gibbs et al. (2014) Trends in Cell Biology, 10, 603-610).

YA3083-58C: MAT-α, agp3::loxP, gap1::loxP, gnp1::loxP, his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET25-tPGK1, pTEF3-AQR1], leu2, lyp1::[pCUP1-1-MET17.Rp-tRPL15A-pACU6-METX-1.Cg-tTPI1]×7, mae1::[ADE2.K1-RS, pTEF3-MET17-tCYC1, pTEF1-TPO1-1-tADH1, pTDH3-METX.Cg-tADH2], met19::[pENO2-MET19-tCYC1, pTEF3-GND1], mup3::loxP, pdc1::loxP, pdc6::loxP, pyk2::[LEU2.K1-pCUP1-HOM2-1-tTDH3], sam1::loxP, trp1::[pTDH3-GDH.Eca-tRPL3-pCUP1-1-HOM3-tIDP1-TRP1]×5, ura3::[pTEF3-MET17-tRPL3-pTDH3-PPC-5.Ec-tDIT1-URA3]×7

The three strains were grown for 48 hours in YE (Yeast Extract) 2%, Glucose 8%, $(NH_4)_2SO_4$ 50 mM, and MeSNa 1 g/L. 500 µM of $CuSO_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

While the non-recombined corresponding yeasts do not produce a detectable quantity of methionine, the strain YA2679-28 produced 2 $g \cdot L^{-1}$ of methionine in 24 hours, the strain YA2687-142 produced in the same amount of time 2.2 $g \cdot L^{-1}$ of methionine and the strain YA3083-58C produced 2.2 $g \cdot L^{-1}$ of methionine in 24 hours.

F. Additional experiments have been performed in a fermenter with the two following recombinant strains obtained according to the invention:

DA964-31: MAT-a/MAT-α, ade2/ade2, agp3::loxP/agp3:: loxP, bap3::loxP/bap3::loxP, CAN1-100/can1-100, gap1:: loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET17-tPGK1, pTEF3-AQR1]/hom3::[pADH1-HOM2-tTPI1, pPDC1-MET2-tADH2, pRPLA1-HOM6-tTDH2, pENO2-MET17-tPGK1, pTEF3-AQR1], leu2/leu2, mae1::[ADE2.K1-RS, pTEF3-MET17-tCYC1, pTEF1-TPO1-1-tADH1, pTDH3-METX.Cg-tADH2]/mae1::[ADE2.K1-RS, pTEF3-MET17-tCYC1, pTEF1-TPO1-1-tADH1, pTDH3-METX.Cg-tADH2], met19::[pENO2-MET19-tCYC1, pTEF3-GND1]/met19::[pENO2-MET19-tCYC1, pTEF3-GND1], mup3::loxP/mup3::loxP, pdc1::loxP/pdc1::loxP, pdc6::loxP/pdc6::loxP, sam1::loxP/sam1::[LEU2.K1-pACU8-HOM2-1-tRPL15A, pACU5-TPO1-3-tTPI1], trp1::[pACU1-AAT2-tRPL3-pCUP1-1-HOM3-tIDP1]×3/trp 1::[pTDH3-GDH.Eca-tRPL3-pCUP1-1-HOM3-tIDP1-TRP1]×5, ura3::[pTEF3-MET17-tRPL3-pTDH3-PPC-5.Ec-tDIT1-URA3]×7/ura3::[pTEF3-MET17-tRPL3-pTDH3-PPC-5.Ec-tDIT1-URA3]×7

DA1047-1: MAT-a/MAT-α, ADE2/ADE2, agp3::loxP/agp3::loxP, BAP3/bap3::loxP, gap1::loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET17-tPGK1, pTEF3-AQR1]/hom3::[pADH1-HOM2-tTPI1, pPDC1-MET2-tADH2, pRPLA1-HOM6-tTDH2, pENO2-MET17-tPGK1, pTEF3-AQR1], leu2/leu2, LYP1/lyp1::[pCUP1-1-MET17.Rp-tRPL15A-pACU6-METX-1.Cg-tTPI1]×5, mae1::[ADE2.K1-RS, pTEF3-MET17-tCYC1, pTEF1-TPO1-1-tADH1, pTDH3-METX.Cg-tADH2]/mae1::[ADE2.K1-RS, pTEF3-MET17-tCYC1, pTEF1-TPO1-1-tADH1, pTDH3-METX.Cg-tADH2], met19::[pENO2-MET19-tCYC1, pTEF3-GND1]/met19::[pENO2-MET19-tCYC1, pTEF3-GND1], mup3::loxP/mup3::loxP, pdc1::loxP/pdc1::loxP, pdc6::loxP/pdc6::loxP, pyk2::[LEU2.K1-pCUP1-1-HOM2-1-tTDH3]/pyk2::[LEU2.K1-pCUP1-1-HOM2-1-tTDH3], sam1::loxP/sam1::loxP, trp1::[pACU1-AAT2-tRPL3-pCUP1-1-HOM3-tIDP1]×3/trp1::[pACU3p-HOM3-tRPL3-pACU3p-PPC-5.Ec-tIDP1]×8, ura3::[pTEF3-MET17-tRPL3-pTDH3-PPC-5.Ec-tDIT1-URA3]×7/ura3::[pTEF3-MET17-tRPL3-pTDH3-PPC-5.Ec-tDIT1-URA3]×7

These strains have been cultivated in a fermenter according to the "fed batch" technic such as described in Peng et al. (2017) biotechnology for buefuels 10-43 in YE (Yeast Extract) 2%, Glucose 8%, $(NH_4)_2SO_4$ 50 mM and 500 µM of $CuSO_4$.

Moreover, the culture medium contained either and 1 g/L of MeSH or and 1 g/L of MeSNA.

The production of methionine was then measured as previously described and the methionine amounts obtained with these two strains are respectively:

(i) in the presence of MeSH:
DA964-31: 32 $g/L^{-1}$ after 70 hours.
DA1047-1: 16 $g/L^{-1}$ after 50 hours.
(ii) in the presence of MeSNa:
DA964-31: 20 $g/L^{-1}$ after 63 hours.
DA1047-1: 11 $g/L^{-1}$ after 47 hours.

A higher quantity of methionine is obtained when the strains are cultivated in presence of MeSH instead of MeSNa. Here too, the corresponding non recombinant strains did not produced any measurable quantity of methionine.

G. Two further recombinant strains according to the invention, illustrated here-after, have also been assayed for methionine.

Strain YA3984-2: MAT-α, gap1::HIS5.Sp-loxP, gnp1::[RS-pENO2-ADH2-tIDP1, pADH1-AAT2-tRPL15A, pTEF3-MDH3-1-tRPL3, pPDC1-PEPCK-1.Ec-tMET17, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3, leu2, mup3::[pPGK1-AAT2-tTDH2, pENO2-TPO1-3-tMET17, pCCW12-MET17-tRPL41B, pTDH3-MET2-tRPL3, pCUP1-1-HOM3-tDIT1, pTDH3-MHPF.Ec-tTPI1, pCCW12-ME3.At-tRPL3, pTDH3-PEPCK-1.Ec-tIDP1, pTEF1-HOM2-tTDH3, pPDC1-MDH3-1-tRPL15A, pADH1-HOM6-tENO2], pyk1::[pCUR3-PYK1-7-tCYC1, HIS5.Sp-loxP], sam3::[pCUP1-1-MET17.Rp-tRPL15A-pACU6-METX.Cg-tTPI1]×4, trp1::[pTDH3-MHPF.Ec-tRPL3-pCUP1-1-HOM3-tIDP1-TRP1]×5, ura3::[pCCW12-ME3.At tRPL3-pTEF3-MET17-tRPL15A-URA3]×4

Strain YA4178: MAT-α, gap1::loxP, gnp1::[pENO2-ADH2-tIDP1, pADH1-AAT2-tRPL15A, pTEF3-MDH3-1-tRPL3, pPDC1-PEPCK-1.Ec-tMET17, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3, leu2, mup3::[pPGK1-AAT2-tTDH2, pENO2-TPO1-3-tMET17, pCCW12-MET17-tRPL41B, pTDH3-MET2-tRPL3, pCUP1-1-HOM3-tDIT1, pTDH3-MHPF.Ec-tTPI1, pCCW12-ME3.At-tRPL3, pTDH3-PEPCK-1.Ec-tIDP1, pTEF1-HOM2-tTDH3, pPDC1-MDH3-1-tRPL15A, pADH1-HOM6-tENO2], pyk1::[pCUR3-PYK1-7-tCYC1, HIS5.Sp-loxP], pyk1::[pCUR3-PYK1-7-tCYC1, HIS5.Sp-loxP], sam3:: [pCUP1-1-MET17.Rp-tRPL15A-pACU6-METX.Cg-tTPI1]×10, trp1::[pTDH3-MHPF.Ec-tRPL3-pCUP1-1-HOM3-tIDP1-TRP1]×5, ura3::[pCCW12-ME3.At tRPL3-pTEF3-MET17-tRPL15A-URA3]×4

PYK1-7 is an artificial allele of PYK1 that is tagged with a degron.

PEPCK-1 is a form of PEPCK stabilized by modification of the Arginine amino acid in position 2 by a Glycine.

These two strains were grown in 25 ml of Yeast extract 2%, Glucose 10%, Urea 50 mM, and $Cu(SO_4)$ 500 µM for seven hours, then a final concentration of 500 µM $Cu(SO_4)_2$ was added and 4 ml of $CH_3SNa$ (23 g/l) were slowly added (0.25 ml/h). The content of methionine in the medium was assayed after 25 h30 hours using the AccQ-Tag precolumn derivatization method for amino acid determination using an AccQ-Tag Ultra Derivatization Kit from Waters as advised by the manufacturer.

While the non-recombined corresponding yeasts do not produce a detectable quantity of methionine, the strain YA3984-2 produced 1.32 g·L$^{-1}$ of methionine in 25 h30, the strain YA4178 produced in the same amount of time 1.26 g·L$^{-1}$ of methionine.

Example 3: Strains Producing Methionine According to the Invention

Two recombinant strains according to the invention, illustrated here-after, have also been assayed for methionine.

Strain YA2573-36B: Mat a, agp3::loxP, gap1::loxP, gnp1::loxP, his3::[pTDH3-GDH-2.Eca-pPDC1-MHPF.Ec-HIS3]×5, hom3::[pCUP1-1-HOM3-pADH1-HOM2-pADH1-MET2-pRPLA1-HOM6-pENO2-MET17-pTEF3-AQR1], leu2, mae1::[ADE2.K1-pENO2-PYC2-pTEF3-MET17-pTEF1-TPO1-1-pTDH3-METX.Cg], met19::[pENO2-MET19-pTEF3-GND1], mup3::loxP, pdc1::loxP, pdc6::loxP, pyk1::[TRP1.K1-RS-pTEF3-AAT2-pCUP1-1-MET19-pACU1-PEPCK-1.Ec-pMET17-PYK1], pyk2::[LEU2.K1-RS-pADH1-HOM2-1], sam1::loxP, trp1::[pACU3p-HOM3-pACU3p-PPC-5.Ec-TRP1]×8, ura3::[pTEF3-MET17-pTDH3-PPC-5.Ec-URA3]×7

Strain YA2691-2: Mat a, agp3::loxP, gap1::loxP, gnp1::loxP, his3::[pTDH3-GDH-2.Eca-pPDC1-MHPF.Ec-HIS3]×5, hom3::[pCUP1-1-HOM3-pADH1-HOM2-pADH1-MET2-pRPLA1-HOM6-pENO2-MET17-pTEF3-AQR1], leu2, mae1::[ADE2.K1-pENO2-PYC2-pTEF3-MET17-pTEF1-TPO1-1-pTDH3-METX.Cg], met19::[pENO2-MET19-pTEF3-GND1], mup3::loxP, pdc1::loxP, pdc6::loxP, pyk1::[TRP1.K1-RS-pTEF3-AAT2-pCUP1-1-MET19-pACU1-PEPCK-1.Ec-pMET17-PYK1], pyk2::[LEU2.K1-RS-pADH1-HOM2-1], sam1::loxP, sam3::[pCUP1-1-CGS1-mut-pACU6-THR1-SAM3]×4, trp1::[pACU3p-HOM3-pACU3p-PPC-5.Ec-TRP1]×8, ura3::[pTEF3-MET17-pTDH3-PPC-5.Ec-URA3]×7

The two strains were grown for 24 hours in YE (Yeast Extract) 2%, Glucose 8%, (NH$_4$)$_2$SO$_4$ 50 mM, and CH$_3$SNa 1 g/L. 500 µM of CuSO$_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

The methionine amounts obtained with these two strains are respectively:
YA2573-36B: 1.8 g/L$^{-1}$.
YA2691-2: 2.1 g/L$^{-1}$.

Example 4: Strains Producing Methionine and Methionine Derivatives According to the Invention A. Two recombinant strains according to the invention, illustrated here-after, have also been assayed for methionine and KMB production.

These two strains are:

YA3344-12: MAT-α, ADE2, agp3::loxP, aro10::[pENO2-SAM2-pENO2-ARO8-tTDH3]×6, bap3::loxP, CAN1-100, gap1::loxP, gnp1::loxP, his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET17-tPGK1, pTEF3-AQR1], leu2, lyp1::[pCUP1-MET17.Rp-1-tRPL15A-pACU6-METX-1.Cg-tTPI1]×5, mae1::[ADE2.K1-RS, pTEF3-MET17-tCYC1, pTEF1-TPO1-1-tADH1, pTDH3-METX.Cg-tADH2], met19::[pENO2-MET19-tCYC1, pTEF3-GND1], mup3::loxP, pdc1::loxP, pdc6::loxP, sam1::loxP, sam2::[LEU2.K1-pACU8-HOM2-1-tRPL15A, pACU5-TPO1-3-tTPI1], trp1::[pTDH3-GDH.Eca-tRPL3-pCUP1-1-HOM3-tIDP1-TRP1]×5, ura3::[pTEF3-MET17-tRPL3-pTDH3-PPC-5.Ec-tDIT1-URA3]×7

DA1025-9: MAT-a/MAT-α, ade2/ade2, agp3::loxP/agp3::loxP, ARO10/aro10::[pENO2-SAM2-pENO2-ARO8-tTDH3]×11, bap3::loxP/bap3::loxP, CAN1-100/can1-100, gap1::loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET17-tPGK1, pTEF3-AQR1]/hom3::[pADH1-HOM2-tTPI1, pPDC1-MET2-tADH2, pRPLA1-HOM6-tTDH2, pENO2-MET17-tPGK1, pTEF3-AQR1], leu2/leu2, mae1::[ADE2.K1-RS, pTEF3-MET17-tCYC1, pTEF1-TPO1-1-tADH1, pTDH3-METX.Cg-tADH2]/mae1::[ADE2.K1-RS, pTEF3-MET17-tCYC1, pTEF1-TPO1-1-tADH1, pTDH3-METX.Cg-tADH2], met19::[pENO2-MET19-tCYC1, pTEF3-GND1]/met19::[pENO2-MET19-tCYC1, pTEF3-GND1], mup3::loxP/mup3::loxP, pdc1::loxP/pdc1::loxP, pdc6::loxP/pdc6::loxP, sam1::loxP/sam1::loxP, sam2::[LEU2.K1-pACU8-HOM2-1-tRPL15A]/sam2::[LEU2.K1-pACU8-HOM2-1-tRPL15A], trp1::[pACU1-AAT2-tRPL3-pCUP1-1-HOM3-tIDP1]×3/trp1::[pTDH3-GDH.Eca-tRPL3-pCUP1-1-HOM3-tIDP1-TRP1]×5, ura3::[pTEF3-MET17-tRPL3-pTDH3-PPC-5.Ec-tDIT1-URA3]×7/ura3::[pTEF3-MET17-tRPL3-pTDH3-PPC-5.Ec-tDIT1-URA3]×7

These strains have been cultivated in a fermenter according to the "fed batch" technic such as described in Peng et al. (2017) biotechnology for buefuels 10-43. doi: 10.1186/s13068-017-0728-x in YE (Yeast Extract) 2%, Glucose 8%, (NH$_4$)$_2$SO$_4$ 50 mM, 1 g/L of MeSNa and 500 µM of CuSO$_4$.

The production of methionine and of KMB was then measured as described previously and the methionine and KMB amounts obtained with these two strains are respectively:

(i) YA3344-12: 0.5 g/L$^{-1}$ of methionine and 1.2 g/L$^{-1}$ of KMB after 39 hours.

(ii) DA1025-9: 7.5 g/L$^{-1}$ of methionine and 8 g/L$^{-1}$ of KMB after 39 hours.

In these conditions of culture, the corresponding non-recombinant strains do not produce a detectable quantity of KMB.

B. Three recombinant strains according to the invention, illustrated here-after, have also been assayed for methionine and HMB production.

These three strains are:

DA1047-1: MAT-a/MAT-α, ADE2/ADE2, agp3::loxP/agp3::loxP, BAP3/bap3::loxP, gap1::loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET17-tPGK1, pTEF3-AQR1]/hom3::[pADH1-HOM2-tTPI1, pPDC1-MET2-tADH2, pRPLA1-HOM6-tTDH2, pENO2-MET17-tPGK1, pTEF3-AQR1], leu2/leu2, LYP1/lyp1::[pCUP1-1-MET17.Rp-tRPL15A-pACU6-METX-1.Cg-tTPI1]×5, mae1::[ADE2.K1-RS, pTEF3-MET17-tCYC1, pTEF1-TPO1-1-tADH1, pTDH3-METX.Cg-tADH2]/mae1::[ADE2.K1-RS, pTEF3-MET17-tCYC1, pTEF1-TPO1-1-tADH1, pTDH3-METX.Cg-tADH2], met19::[pENO2-MET19-tCYC1, pTEF3-GND1]/met19::[pENO2-MET19-tCYC1, pTEF3-GND1], mup3::loxP/mup3::loxP, pdc1::loxP/pdc1::loxP, pdc6::loxP/pdc6::loxP, pyk2::[LEU2.K1-pCUP1-1-HOM2-1-tTDH3]/pyk2::[LEU2.K1-pCUP1-1-HOM2-1-tTDH3], sam1::loxP/sam1::loxP, trp1::[pACU1-AAT2-tRPL3-pCUP1-1-HOM3- tIDP1]×3/trp1::[pACU3p-HOM3-tRPL3-pACU3p-PPC-5.Ec-tIDP1]×8, ura3::[pTEF3-MET17-tRPL3-pTDH3-PPC-5.Ec-tDIT1-URA3]×7/ura3::[pTEF3-MET17-tRPL3-pTDH3-PPC-5.Ec-tDIT1-URA3]×7

DA1555-2: MAT-a/MAT-α, ADE2/ADE2, agp3::loxP/agp3::loxP, BAP3/bap3::loxP, gap1::loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET17-tPGK1, pTEF3-AQR1]/hom3::[pADH1-HOM2-tTPI1, pPDC1-MET2-tADH2, pRPLA1-HOM6-tTDH2, pENO2-MET17-tPGK1, pTEF3-AQR1], leu2/leu2, LYP1/lyp1::[pCUP1-1-MET17.Rp-tRPL15A-pACU6-METX-1.Cg-tTPI1]×5, mae1::[ADE2.K1-RS, pTEF3-MET17-tCYC1, pTEF1-TPO1-1-tADH1, pTDH3-METX.Cg-tADH2]/mae1::[ADE2.K1-RS, pTEF3-MET17-tCYC1, pTEF1-TPO1-1-tADH1, pTDH3-METX.Cg-tADH2], met19::[pENO2-MET19-tCYC1, pTEF3-GND1]/met19::[pENO2-MET19-tCYC1, pTEF3-GND1], mup3::loxP/mup3::loxP, pdc1::loxP/pdc1::loxP, pdc6::loxP/pdc6::loxP, pyk2::[LEU2.K1-pCUP1-1-HOM2-1-tTDH3]/pyk2::[LEU2.K1-pCUP1-1-HOM2-1-tTDH3], sam1::loxP/sam1::loxP, sam3::[pCCW12-ARO8-tRPL15A-pTDH3-KDH1-0.L1-tTPI1]×1/sam3::[pCCW12-ARO8-tRPL15A-pTDH3-KDH1-0.L1-tTPI1]×2, trp1::[pACU1-AAT2-tRPL3-pCUP1-1-HOM3-tIDP1]×3/trp1::[pACU3p-HOM3-tRPL3-pACU3p-PPC-5.Ec-tIDP1]×8, ura3::[pTEF3-MET17-tRPL3-pTDH3-PPC-5.Ec-tDIT1-URA3]×7/ura3::[pTEF3-MET17-tRPL3-pTDH3-PPC-5.Ec-tDIT1-URA3]×7

DA1156-11: DA1555-2: MAT-a/MAT-α, ADE2/ADE2, agp3::loxP/agp3::loxP, BAP3/bap3::loxP, gap1::loxP/gap1::loxP, gnp1::loxP/gnp1::loxP, his3::[pTDH3-MHPF.Ec-tIDP1-HIS3]×6/his3::[pTDH3-MHPF.Ec-tIDP1-HIS3]×6, hom3::[pADH1-HOM2-tTPI1, pPDC1-MET2-tADH2, pRPLA1-HOM6-tTDH2, pENO2-MET17-tPGK1, pTEF3-AQR1]/hom3::[pADH1-HOM2-tTPI1,pPDC1-MET2-tADH2, pRPLA1-HOM6-tTDH2, pENO2-MET17-tPGK1, pTEF3-AQR1], leu2/leu2, LYP1/lyp1::[pCUP1-1-MET17.Rp-tRPL15A-pACU6-METX-1.Cg-tTPI1]×5, mae1::[ADE2.K1-RS, pTEF3-MET17-tCYC1, pTEF1-TPO1-1-tADH1, pTDH3-METX.Cg-tADH2]/mae1::[ADE2.K1-RS, pTEF3-MET17-tCYC1, pTEF1-TPO1-1-tADH1, pTDH3-METX.Cg-tADH2], met19::[pENO2-MET19-tCYC1, pTEF3-GND1]/met19::[pENO2-MET19-tCYC1, pTEF3-GND1], mup3::loxP/mup3::loxP, pdc1::loxP/pdc1::loxP, pdc6::loxP/pdc6::loxP, pyk2::[LEU2.K1-pCUP1-1-HOM2-1-tTDH3]/pyk2::[LEU2.K1-pCUP1-1-HOM2-1-tTDH3], sam1::loxP/sam1::loxP, sam3::[pCCW12-ARO8-tRPL15A-pTDH3-KDH2-0.L1-tTPI1]×1/sam3::[pCCW12-ARO8-tRPL15A-pTDH3-KDH2-0.L1-tTPI1]×2, trp1::[pACU1-AAT2-tRPL3-pCUP1-1-HOM3-tIDP1]×3/trp1::[pACU3p-HOM3-tRPL3-pACU3p-PPC-1.Ec-tIDP1]×8, ura3::[pTEF3-MET17-tRPL3-pTDH3-PPC-5.Ec-tDIT1-URA3]×7/ura3::[pTEF3-MET17-tRPL3-pTDH3-PPC-5.Ec-tDIT1-URA3]×7

The strains have been cultivated in erlenmeyer: Yeast extract 2%, Glucose 8%, CuSO$^4$ 500 µM, CH$_3$SNa 10 g/l for 24 h. Methionine, KMB and HMB are dosed in the culture supernatent by LC-MS (LC: Column: Hi-Plex H 300*7.7 mm Ref PL1170-6830 Agilent, eluant 85% Acide formique 0.5%, 15% Acetonitrile, ionisation ESI-, mass spectrometer Quattro Micro API Waters).

In these conditions of culture, the corresponding non-recombinant strains do not produce a detectable quantity of KMB and are not able to produce HMB.

The amounts of methionine, of KMB and of HMB obtained with these three strains are respectively:

(i) DA1047-1: 2.3 g/L$^{-1}$ of methionine, 0.3 g/L$^{-1}$ of KMB and 0.1 g/L$^{-1}$ of HMB (after 48 hours).

(ii) DA1555-2: 0.3 g/L$^{-1}$ of methionine, 0.15 g/L$^{-1}$ of KMB and 2.8 g/L$^{-1}$ of HMB after 36 hours.

(iii) DA1156-11: 0.4 g/L$^{-1}$ of methionine, 0.15 g/L$^{-1}$ of KMB and 2.4 g/L$^{-1}$ of HMB after 44 hours.

In can be seen that the over expression of ARO8 together with the over expression of different forms of KDH in recombinant strains according to the invention leads to the production of HMB. It can moreover be seen that the quantity of KMB not converted in HMB is very low in the present examples.

The invention claimed is:

1. A methionine-producing and/or methionine derivatives-producing recombinant yeast, in the genome of which:
   (A) at least one nucleic acid encoding an aspartate semi-aldehyde dehydrogenase and/or at least one nucleic acid encoding an aspartate semi-aldehyde dehydrogenase that can use as coenzyme both NAD and NADP is overexpressed or is under the control of an inducible or repressible promoter;
   (B) at least one nucleic acid encoding an aspartokinase is under the control of an inducible or repressible promoter; and
   (C) (i) a) at least one nucleic acid encoding an homoserine-O-acetyltransferase MET2 is overexpressed or is under the control of an inducible or repressible promoter;
      and/or at least one nucleic acid encoding an homoserine-O-acetyltransferase METX is overexpressed or is under the control of an inducible or repressible promoter, and
      b) at least one nucleic acid encoding a methionine synthase is overexpressed or is under the control of an inducible or repressible promoter; and/or
   ii) a) at least one nucleic acid encoding an homoserine kinase is overexpressed or is under the control of an inducible or repressible promoter, and
      b) at least one nucleic acid encoding a cystathionine gamma-synthase 1 that has an improved O-phospho-L-homoserine (OHPS) dependent methionine synthase activity is overexpressed or is under the control of an inducible or repressible promoter,
   wherein the yeast is selected from the species Saccharomyces cerevisiae, Saccharomyces boulardii, Saccharomyces douglasii, Saccharomyces bayanus, Zigosaccharomyces bailii, Dekkera brucelensis, Dekkera intermedia, Kluyveromyces themotolerens, Torulaspora globose and Torulaspora glabrata.

2. The recombinant yeast according to claim 1, in the genome of which at least one nucleic acid encoding an aspartate transaminase is overexpressed or is under the control of an inducible or repressible promoter.

3. The recombinant yeast according to claim 1, in the genome of which at least one nucleic acid encoding a glutamate dehydrogenase that converts oxo-glutarate to glutamate is overexpressed or is under the control of an inducible or repressible promoter.

4. The recombinant yeast according to claim 1, in the genome of which at least one nucleic acid encoding a homoserine dehydrogenase is overexpressed.

5. The recombinant yeast according to claim 1, in the genome of which, independently:
   (i) at least one endogenous nucleic acid encoding a S-adenosyl methionine synthase SAM1 and/or SAM2 has been deleted, or
   (ii) at least one nucleic acid encoding a S-adenosyl methionine synthase SAM1 and/or SAM2 is under the control of an inducible or repressible promoter or is in a destabilized form.

6. The recombinant yeast according to claim 1, in the genome of which, independently:
   (i) at least one endogenous nucleic acid encoding an Aromatic aminotransferase I ARO8 and/or a Cytosolic branched-chain amino acid (BCAA) aminotransferase gene BAT2 has been deleted, or
   (ii) at least one nucleic acid encoding an Aromatic aminotransferase I ARO8 and/or a Cytosolic branched-chain amino acid (BCAA) aminotransferase gene BAT2 is under the control of an inducible or repressible promoter or is in a destabilized form.

7. The recombinant yeast according to claim 1, in the genome of which, independently:
   (i) at least one nucleic acid encoding an Aromatic aminotransferase I ARO8, and/or
   (ii) at least one nucleic acid encoding a Cytosolic branched-chain amino acid (BCAA) aminotransferase gene BAT2, is overexpressed or is under the control of an inducible or repressible promoter.

8. The recombinant yeast according to claim 7, in the genome of which at least one nucleic acid encoding 2-hydroxyacid dehydrogenase (KDH) is overexpressed or under the control of an inducible or repressible promoter.

9. The recombinant yeast according to claim 1, in the genome of which at least one nucleic acid encoding a cystathionine gamma-lyase CYS3 is, independently, under the control of a weak promoter or of an inducible or repressible promoter or is in a destabilized form.

10. The recombinant yeast according to claim 1, in the genome of which at least one nucleic acid encoding a cystathionine beta-synthase CYS4 is, independently, under the control of a weak promoter or of an inducible or repressible promoter or is in a destabilized form.

11. The recombinant yeast according to claim 1, in the genome of which:
    a) at least one nucleic acid encoding an homoserine-O-acetyltransferase MET2 is overexpressed or under the control of an inducible or repressible promoter, and/or
    at least one nucleic acid encoding an homoserine-O-acetyltransferase METX is overexpressed or under the control of an inducible or repressible promoter, and
    b) at least one nucleic acid encoding an O-acetyl homoserine-O-acetyl serine sulfhydrylase MET17 is overexpressed or under the control of an inducible or repressible promoter.

12. The recombinant yeast according to claim 1, in the genome of which at least one nucleic acid encoding a homoserine kinase THR1 is, independently, under the control of an inducible or repressible promoter or is in a destabilized form.

13. The recombinant yeast according to claim 1, in the genome of which at least one of the following modifications has been performed:

(A) at least one endogenous nucleic acid encoding a general amino acid permease AGP3 have been deleted from the genome of the yeast, and optionally:
   (i) at least one nucleic acid encoding a general amino acid permease AGP3 has been inserted and is under the control of an inducible or repressible promoter, and/or
   (ii) at least one nucleic acid encoding a destabilized general amino acid permease AGP3 has been inserted;

(B) at least one endogenous nucleic acid encoding a branched-chain amino-acid permease 3 BAP3 has been deleted from the genome of the yeast, and, optionally:
   (i) at least one nucleic acid encoding a branched-chain amino-acid permease 3 BAP3 has been inserted and is under the control of an inducible or repressible promoter, and/or
   (ii) at least one nucleic acid encoding a destabilized branched-chain amino-acid permease 3 BAP3 has been inserted;

(C) at least one endogenous nucleic acid encoding a branched-chain amino-acid permease 2 BAP2 has been deleted from the genome of the yeast, and, optionally:
   (i) at least one nucleic acid encoding a branched-chain amino-acid permease 2 BAP2 has been inserted and is under the control of an inducible or repressible promoter, and/or
   (ii) at least one nucleic acid encoding a destabilized branched-chain amino-acid permease 2 BAP2 has been inserted;

(D) at least one endogenous nucleic acid encoding a general amino acid permease GAP1 has been deleted from the genome of the yeast, and, optionally:
   (i) at least one nucleic acid encoding a general amino acid permease GAP1 has been inserted and is under the control of an inducible or repressible promoter, and/or
   (ii) at least one nucleic acid encoding a destabilized general amino acid permease GAP1 has been inserted;

(E) at least one endogenous nucleic acid encoding a high-affinity glutamine permease GNP1 has been deleted from the genome of the yeast, and, optionally:
   (i) at least one nucleic acid encoding a high-affinity glutamine permease GNP1 has been inserted and is under the control of an inducible or repressible promoter, and/or
   (ii) at least one nucleic acid encoding a destabilized high-affinity glutamine permease GNP1 has been inserted;

(F) at least one endogenous nucleic acid encoding a general amino acid permease AGP1 has been deleted from the genome of the yeast, and, optionally:
   (i) at least one nucleic acid encoding a general amino acid permease AGP1 has been inserted and is under the control of an inducible or repressible promoter, and/or
   (ii) at least one nucleic acid encoding a destabilized general amino acid permease AGP1 has been inserted;

(G) at least one endogenous nucleic acid encoding a low-affinity methionine permease MUP3 has been deleted from the genome of the yeast, and, optionally:
   (i) at least one nucleic acid encoding a low-affinity methionine permease MUP3 has been inserted and is under the control of an inducible or repressible promoter, and/or (ii) at least one nucleic acid encoding a destabilized low-affinity methionine permease MUP3 has been inserted;

(H) at least one endogenous nucleic acid encoding a high-affinity methionine permease MUP1 has been deleted from the genome of the yeast, and, optionally:

(i) at least one nucleic acid encoding a high-affinity methionine permease MUP1 has been inserted and is under the control of an inducible or repressible promoter, and/or (ii) at least one nucleic acid encoding a destabilized high-affinity methionine permease MUP1 has been inserted;

(I) at least one nucleic acid encoding a probable transporter AQR1 is overexpressed; and/or (J) at least one nucleic acid encoding a polyamine transporter 1 TPO1 is overexpressed.

14. The recombinant yeast according to claim 13, in the genome of which at least two nucleic acid encoding 2-hydroxyacid dehydrogenase (KDH) is overexpressed and/or under the control of an inducible or repressible promoter have been performed.

15. The recombinant yeast according to claim 1, wherein the nucleic acid encoding an aspartokinase HOM3 are nucleic acid from a yeast.

16. The recombinant yeast according to claim 1, wherein the nucleic acid encoding an homoserine-O-acetyltransferase METX are nucleic acid from a bacterium.

17. The recombinant yeast according to claim 1, wherein the nucleic acid encoding a cystathionine gamma-synthase 1 CGS1 mutated are nucleic acid originating from a plant.

18. The recombinant yeast according to claim 1, wherein the inserted at least one nucleic acid encoding a S-adenosyl methionine SAM1 and/or SAM2, a cystathionine gamma-lyase CYS3, a cystathionine beta-synthase CYS4, a homoserine kinase THR1, a general amino acid permease AGP3, a branched-chain amino-acid permease 3 BAPS, a branched-chain amino-acid permease 2 BAP2, a general amino acid permease GAP1, a high-affinity glutamine permease GNP1, a general amino acid permease AGP1, a low-affinity methionine permease MUP3 and a high-affinity methionine permease MUP1 are, independently, nucleic acid from a yeast.

19. The recombinant yeast according to claim 1, wherein the strong promoter is, independently, selected from the group consisting of pTDH3 (SEQ ID No. 38), pENO2 (SEQ ID No. 39), pTEF-KI (SEQ ID No. 40), pTEF3 (SEQ ID No. 41), pTEF1 (SEQ ID No. 42), pADH1 (SEQ ID No. 43), pGMP1 (SEQ ID No. 44), pFBA1 (SEQ ID No. 45), pPDC1 (SEQ ID No. 46), pCCW12 (SEQ ID No. 47) and pGK1 (SEQ ID No. 48).

20. The recombinant yeast according to claim 1, wherein the inducible or repressible promoter is, independently, selected from the group consisting of promoters inducible or repressible with copper, promoters inducible or repressible with methionine and promoters inducible or repressible with threonine, selected from the group consisting of pSAM4 (SEQ ID No. 52), pCUP1-1 (SEQ ID No. 53), pCUP1.Cgla (SEQ ID No. 54), pCUP1.Sba (SEQ ID No. 55), pACU1 (SEQ ID No. 56), pACU2 (SEQ ID No. 57), pACU3p (SEQ ID No. 58), pACU4p (SEQ ID No. 59), pACU5 (SEQ ID No. 60), pACU6 (SEQ ID No. 61), pACU7 (SEQ ID No. 62), pACU8 (SEQ ID No. 63), pACU9 (SEQ ID No. 64), pACU10p (SEQ ID No. 65), pACU11 (SEQ ID No. 66), pACU12 (SEQ ID No. 67), pACU13 (SEQ ID No. 68), pACU14 (SEQ ID No. 69), pACU15 (SEQ ID No. 70), pGAL/CUP1p (SEQ ID No. 71), pCRS5 (SEQ ID No. 72), and pCHA1 (SEQ ID No. 73).

21. The recombinant yeast according to claim 1, wherein the weak promoter is, independently, selected from the group consisting of pURA3 (SEQ ID No. 50), pRPLA1 (SEQ ID No. 51), pNUP57 (SEQ ID No. 130) and pGAP1 (SEQ ID No. 131).

22. The recombinant yeast according to claim 1, wherein the inducible or repressible promoter is, independently, selected from the group consisting of promoters inducible or repressible with copper, promoters inducible or repressible with lysine and promoters inducible or repressible with methionine, selected from the group consisting of pCTR1 (SEQ ID No. 74), pCTR3 (SEQ ID No. 75), pCUR1 (SEQ ID No. 76), pCUR2 (SEQ ID No. 77), pCUR3 (SEQ ID No. 78), pCUR4 (SEQ ID No. 79), pCUR5p (SEQ ID No. 80), pCUR6 (SEQ ID No. 81), pCUR7 (SEQ ID No. 82), pCUR8 (SEQ ID No. 83), pCUR9 (SEQ ID No. 84), pCUR10 (SEQ ID No. 85), pCUR11 (SEQ ID No. 86), pCUR12 (SEQ ID No. 87), pCUR13 (SEQ ID No. 88), pCUR14 (SEQ ID No. 89), pCUR15 (SEQ ID No. 90), pCUR16 (SEQ ID No. 91), pCUR17 (SEQ ID No. 92), pLYS1 (SEQ ID No. 93), pLYS4 (SEQ ID No. 94), pLYS9 (SEQ ID No. 95), pLYR1p (SEQ ID No. 96), pLYR2p (SEQ ID No. 97), pLYR3p (SEQ ID No. 98), pLYR4p (SEQ ID No. 99), pLYR5p (SEQ ID No. 100), pLYR6p (SEQ ID No. 101), pLYR7p (SEQ ID No. 102), pLYR8 (SEQ ID No. 103), pLYR9 (SEQ ID No. 104), pLYR10 (SEQ ID No. 105), pLYR11 (SEQ ID No. 106), pMET17 (SEQ ID No. 107), pMET6 (SEQ ID No. 108), pMET14 (SEQ ID No. 109), pMET3 (SEQ ID No. 110), pSAM1 (SEQ ID No. 111), pSAM2 (SEQ ID No. 112), pMDH2 (SEQ ID No. 49), pJEN1 (SEQ ID No. 132), pICL1 (SEQ ID No. 133), pADH2 (SEQ ID No. 134) and pMLS1 (SEQ ID No. 135).

23. A method for producing methionine and/or at least one of its derivatives, said method comprising the steps of:

(a) culturing a recombinant yeast as defined in claim 1 in a culture medium, comprising methanethiol (MeSH), sodium methanethiolate (MeSNa) and/or dimethylthioether (MeSMe); and (b) recovering the methionine and/or at least one of its derivatives from said culture medium.

24. The method according to claim 23, wherein the culture medium comprises at least a carbon source.

* * * * *

SEQUENCE LISTING

```
<160> NUMBER OF SEQ ID NOS: 135

<210> SEQ ID NO 1
<211> LENGTH: 1098
<212> TYPE: DNA
<213> ORGANISM: Saccharomyces cerevisiae
<220> FEATURE:
<223> OTHER INFORMATION: ASPARTATE-SEMIALDEHYDE DEHYDROGENASE (HOM2)
<220> FEATURE:
<223> OTHER INFORMATION: ASPARTATE-SEMIALDEHYDE DEHYDROGENASE (HOM2)

<400> SEQUENCE: 1
atggctggaa agaaaattgc tggtgttttg ggtgctactg gttccgttgg tcaacgtttc      60
attctgttgt tggcaaatca ccctcatttc gaactgaaag ttcttggtgc ctcttctaga     120
tcagctggca agaaatacgt tgacgctgtg aactggaagc aaaccgattt gctaccggaa     180
tctgctaccg atattattgt ttccgaatgt aaatctgaat tctttaaaga gtgtgacatc     240
gtcttttccg gattggatgc tgactatgct ggcgctatcg aaaaggaatt catggaagct     300
ggtatcgcca ttgtttccaa tgccaagaat tatagaagag aacaagatgt gccattgatt     360
gttcctgttg tcaatcctga gcatttggat attgtagctc aaaagcttga caccgccaag     420
gctcaaggta agccaagacc agggttcatt atctgtattt ccaattgttc cactgcaggt     480
```

-continued

```
ttggttgcac cattgaagcc tttgattgaa aaattcggtc ctattgatgc tttgaccact     540
actactttgc aagcaatctc aggtgctggt ttctccccag gtgtaccagg tattgatatt     600
ctagacaata ttattccata cattggtggt gaagaagaca agatggaatg ggagaccaag     660
aaaatcttgg ctccattagc agaagacaag acacacgtca aactattgac tccagaagaa     720
atcaaagtct ctgctcaatg taacagagtc gctgtttccg atgggcacac cgaatgtatc     780
tctttgaggt tcaagaacag acctgctcca tccgtcgagc aagtcaagac atgcctaaaa     840
gaatacgtct gcgatgccta caaattaggc tgtcattctg ctccaaagca aactattcat     900
gttttggaac aaccagacag acctcaacca aggttggaca ggaacagaga cagcggttac     960
ggtgtttccg ttggtagaat cagagaagac ccattgttag atttcaaaat ggttgtcctt    1020
tcccacaaca ccattattgg tgccgctggt tctggtgtct tgattgccga aatcttacta    1080
gcaagaaact tgatttaa                                                  1098
```

<210> SEQ ID NO 2
<211> LENGTH: 1098
<212> TYPE: DNA
<213> ORGANISM: Saccharomyces cerevisiae
<220> FEATURE:
<223> OTHER INFORMATION: ASPARTATE-SEMIALDEHYDE DEHYDROGENASE (HOM2)
<220> FEATURE:
<223> OTHER INFORMATION: ASPARTATE-SEMIALDEHYDE DEHYDROGENASE (HOM2)

<400> SEQUENCE: 2

```
atggctggaa agaaaattgc tggtgttttg ggtgctactg gttccgttgg tcaacgtttc      60
attctgttgt tggcaaatca ccctcatttc gaactgaaag ttcttggtgc ctctgagaga     120
tcagctggca agaaatacgt tgacgctgtg aactggaagc aaaccgattt gctaccggaa     180
tctgctaccg atattattgt ttccgaatgt aaatctgaat tctttaaaga gtgtgacatc     240 gtctttttccg gattggatgc tgactatgct ggcgctatcg aaaaggaatt catggaagct     300
ggtatcgcca ttgtttccaa tgccaagaat tatagaagag aacaagatgt gccattgatt     360
gttcctgttg tcaatcctga gcatttggat attgtagctc aaaagcttga caccgccaag     420
gctcaaggta agccaagacc agggttcatt atctgtattt ccaattgttc cactgcaggt     480
ttggttgcac cattgaagcc tttgattgaa aaattcggtc ctattgatgc tttgaccact     540
actactttgc aagcaatctc aggtgctggt ttctccccag gtgtaccagg tattgatatt     600
ctagacaata ttattccata cattggtggt gaagaagaca agatggaatg ggagaccaag     660
aaaatcttgg ctccattagc agaagacaag acacacgtca aactattgac tccagaagaa     720
atcaaagtct ctgctcaatg taacagagtc gctgtttccg atgggcacac cgaatgtatc     780
tctttgaggt tcaagaacag acctgctcca tccgtcgagc aagtcaagac atgcctaaaa     840
gaatacgtct gcgatgccta caaattaggc tgtcattctg ctccaaagca aactattcat     900
gttttggaac aaccagacag acctcaacca aggttggaca ggaacagaga cagcggttac     960
ggtgtttccg ttggtagaat cagagaagac ccattgttag atttcaaaat ggttgtcctt    1020
tcccacaaca ccattattgg tgccgctggt tctggtgtct tgattgccga aatcttacta    1080
gcaagaaact tgatttaa                                                  1098
```

<210> SEQ ID NO 3
<211> LENGTH: 365
<212> TYPE: PRT
<213> ORGANISM: Saccharomyces cerevisiae
<220> FEATURE:

<223> OTHER INFORMATION: ASPARTATE-SEMIALDEHYDE DEHYDROGENASE (HOM2)
<220> FEATURE:
<223> OTHER INFORMATION: ASPARTATE-SEMIALDEHYDE DEHYDROGENASE (HOM2)

<400> SEQUENCE: 3

```
Met Ala Gly Lys Lys Ile Ala Gly Val Leu Gly Ala Thr Gly Ser Val
1               5                   10                  15

Gly Gln Arg Phe Ile Leu Leu Ala Asn His Pro His Phe Glu Leu
            20                  25                  30

Lys Val Leu Gly Ala Ser Ser Arg Ser Ala Gly Lys Lys Tyr Val Asp
        35                  40                  45

Ala Val Asn Trp Lys Gln Thr Asp Leu Leu Pro Glu Ser Ala Thr Asp
    50                  55                  60

Ile Ile Val Ser Glu Cys Lys Ser Glu Phe Phe Lys Glu Cys Asp Ile
65                  70                  75                  80

Val Phe Ser Gly Leu Asp Ala Asp Tyr Ala Gly Ala Ile Glu Lys Glu
                85                  90                  95

Phe Met Glu Ala Gly Ile Ala Ile Val Ser Asn Ala Lys Asn Tyr Arg
            100                 105                 110

Arg Glu Gln Asp Val Pro Leu Ile Val Pro Val Val Asn Pro Glu His
        115                 120                 125

Leu Asp Ile Val Ala Gln Lys Leu Asp Thr Ala Lys Ala Gln Gly Lys
130                 135                 140

Pro Arg Pro Gly Phe Ile Ile Cys Ile Ser Asn Cys Ser Thr Ala Gly
145                 150                 155                 160

Leu Val Ala Pro Leu Lys Pro Leu Ile Glu Lys Phe Gly Pro Ile Asp
                165                 170                 175

Ala Leu Thr Thr Thr Thr Leu Gln Ala Ile Ser Gly Ala Gly Phe Ser
            180                 185                 190

Pro Gly Val Pro Gly Ile Asp Ile Leu Asp Asn Ile Ile Pro Tyr Ile
        195                 200                 205

Gly Gly Glu Glu Asp Lys Met Glu Trp Glu Thr Lys Lys Ile Leu Ala
210                 215                 220

Pro Leu Ala Glu Asp Lys Thr His Val Lys Leu Leu Thr Pro Glu Glu
225                 230                 235                 240

Ile Lys Val Ser Ala Gln Cys Asn Arg Val Ala Val Ser Asp Gly His
                245                 250                 255

Thr Glu Cys Ile Ser Leu Arg Phe Lys Asn Arg Pro Ala Pro Ser Val
            260                 265                 270

Glu Gln Val Lys Thr Cys Leu Lys Glu Tyr Val Cys Asp Ala Tyr Lys
        275                 280                 285

Leu Gly Cys His Ser Ala Pro Lys Gln Thr Ile His Val Leu Glu Gln
    290                 295                 300

Pro Asp Arg Pro Gln Pro Arg Leu Asp Arg Asn Arg Asp Ser Gly Tyr
305                 310                 315                 320

Gly Val Ser Val Gly Arg Ile Arg Glu Asp Pro Leu Leu Asp Phe Lys
                325                 330                 335

Met Val Val Leu Ser His Asn Thr Ile Ile Gly Ala Ala Gly Ser Gly
            340                 345                 350

Val Leu Ile Ala Glu Ile Leu Leu Ala Arg Asn Leu Ile
        355                 360                 365
```

<210> SEQ ID NO 4
<211> LENGTH: 1583
<212> TYPE: DNA

<213> ORGANISM: Saccharomyces cerevisiae
<220> FEATURE:
<223> OTHER INFORMATION: ASPARTOKINASE (HOM3)
<220> FEATURE:
<223> OTHER INFORMATION: ASPARTOKINASE (HOM3)

<400> SEQUENCE: 4

```
atgccaatgg atttccaacc tacatcaagt cattcgaact gggtcgtgca aaagttcggt      60
ggtacatctg tcggtaaatt tcccgtccaa atagtggatg acattgtgaa gcactattct     120
aaacctgacg gcccaaacaa taatgtcgct gtcgtttgtt ccgcccgttc ttcatacacc     180
aaggctgaag gtaccacttc tcgtcttttg aaatgttgtg atttggcttc gcaagaatct     240
gaatttcaag acattatcga agttatcaga caagaccata tcgataatgc cgaccgcttc     300
attctcaatc ctgccttgca agccaagtta gtggatgata ccaataaaga acttgaactg     360
gtcaagaaat atttaaatgc ttcaaaagtt ttgggtgaag tgagttcacg tacagtagat     420
ctggtgatgt catgtggtga aagttgagt tgtttgttca tgactgcttt atgtaatgac      480
cgtggctgta aggccaaata tgtggatttg agccacattg ttccctctga tttcagtgcc     540
agcgctttgg ataacagttt ctacactttc ctggttcaag cattgaaaga aaaattggcc     600
cccttgtaa gtgctaaaga gcgtatcgtt ccagtcttta cagggttttt tggtttagtt      660
ccaactggtc ttctgaatgg tgttggtcgt ggctataccg atttatgtgc cgctttgata     720
gcagttgctg taaatgctga tgaactacaa gtttggaagg aagttgatgg tatatttact     780
gctgatcctc gtaaggttcc tgaagcacgt tgctagaca gtgttactcc agaagaagct     840
tctgaattaa catattatgg ttccgaagtt atacatcctt ttacgatgga acaagttatt     900
agggctaaga ttcctattag aatcaagaat gttcaaaatc cattaggtaa cggtaccatt     960
atctacccag ataatgtagc aaagaagggt gaatctactc caccacatcc tcctgagaac    1020
ttatcctcat ctttctatga aaagagaaag agaggtgcca ctgctatcac caccaaaaat    1080
gacattttcg tcatcaacat tcattccaat aagaaaaccc tatcccatgg tttcctagct    1140
caaatattta ccatcctgga taagtacaag ttagtcgtag atttaatatc tacttctgaa    1200
gttcatgttt cgatggcttt gcccattcca gatgcagact cattaaaatc tctgagacaa    1260
gctgaggaaa aattgagaat tttaggttct gttgatatca caaagaagtt gtctattgtt    1320
tcattagttg gtaaacatat gaaacaatac atcggcattg ctggtaccat gtttactact    1380
cttgctgaag aaggcatcaa cattgaaatg atttctcaag gggcaaatga aataaacata    1440
tcctgcgtta tcaatgaatc tgactccata aaagcgctac aatgtattca tgccaagtta    1500
ctaagtgagc ggacaaatac ttcaaaccaa tttgaacatg ccattgatga acgtttagaa    1560
caattgaaaa gacttggaat taa                                            1583
```

<210> SEQ ID NO 5
<211> LENGTH: 526
<212> TYPE: PRT
<213> ORGANISM: Saccharomyces cerevisiae
<220> FEATURE:
<223> OTHER INFORMATION: ASPARTOKINASE (HOM3)
<220> FEATURE:
<223> OTHER INFORMATION: ASPARTOKINASE (HOM3)

<400> SEQUENCE: 5

```
Pro Met Asp Phe Gln Pro Thr Ser Ser His Ser Asn Trp Val Val Gln
1               5                   10                  15

Lys Phe Gly Gly Thr Ser Val Gly Lys Phe Pro Val Gln Ile Val Asp
            20                  25                  30
```

```
Asp Ile Val Lys His Tyr Ser Lys Pro Asp Gly Pro Asn Asn Asn Val
             35                  40                  45

Ala Val Val Cys Ser Ala Arg Ser Ser Tyr Thr Lys Ala Glu Gly Thr
         50                  55                  60

Thr Ser Arg Leu Leu Lys Cys Cys Asp Leu Ala Ser Gln Glu Ser Glu
 65                  70                  75                  80

Phe Gln Asp Ile Ile Glu Val Ile Arg Gln Asp His Ile Asp Asn Ala
                     85                  90                  95

Asp Arg Phe Ile Leu Asn Pro Ala Leu Gln Ala Lys Leu Val Asp Asp
                100                 105                 110

Thr Asn Lys Glu Leu Glu Leu Val Lys Lys Tyr Leu Asn Ala Ser Lys
            115                 120                 125

Val Leu Gly Glu Val Ser Ser Arg Thr Val Asp Leu Val Met Ser Cys
        130                 135                 140

Gly Glu Lys Leu Ser Cys Leu Phe Met Thr Ala Leu Cys Asn Asp Arg
145                 150                 155                 160

Gly Cys Lys Ala Lys Tyr Val Asp Leu Ser His Ile Val Pro Ser Asp
                165                 170                 175

Phe Ser Ala Ser Ala Leu Asp Asn Ser Phe Tyr Thr Phe Leu Val Gln
                180                 185                 190

Ala Leu Lys Glu Lys Leu Ala Pro Phe Val Ser Ala Lys Glu Arg Ile
            195                 200                 205

Val Pro Val Phe Thr Gly Phe Phe Gly Leu Val Pro Thr Gly Leu Leu
        210                 215                 220

Asn Gly Val Gly Arg Gly Tyr Thr Asp Leu Cys Ala Ala Leu Ile Ala
225                 230                 235                 240

Val Ala Val Asn Ala Asp Glu Leu Gln Val Trp Lys Glu Val Asp Gly
                245                 250                 255

Ile Phe Thr Ala Asp Pro Arg Lys Val Pro Glu Ala Arg Leu Leu Asp
                260                 265                 270

Ser Val Thr Pro Glu Glu Ala Ser Glu Leu Thr Tyr Tyr Gly Ser Glu
            275                 280                 285

Val Ile His Pro Phe Thr Met Glu Gln Val Ile Arg Ala Lys Ile Pro
        290                 295                 300

Ile Arg Ile Lys Asn Val Gln Asn Pro Leu Gly Asn Gly Thr Ile Ile
305                 310                 315                 320

Tyr Pro Asp Asn Val Ala Lys Lys Gly Glu Ser Thr Pro His Pro
                325                 330                 335

Pro Glu Asn Leu Ser Ser Ser Phe Tyr Glu Lys Arg Lys Arg Gly Ala
            340                 345                 350

Thr Ala Ile Thr Thr Lys Asn Asp Ile Phe Val Ile Asn Ile His Ser
        355                 360                 365

Asn Lys Lys Thr Leu Ser His Gly Phe Leu Ala Gln Ile Phe Thr Ile
370                 375                 380

Leu Asp Lys Tyr Lys Leu Val Val Asp Leu Ile Ser Thr Ser Glu Val
385                 390                 395                 400

His Val Ser Met Ala Leu Pro Ile Pro Asp Ala Asp Ser Leu Lys Ser
                405                 410                 415

Leu Arg Gln Ala Glu Glu Lys Leu Arg Ile Leu Gly Ser Val Asp Ile
            420                 425                 430

Thr Lys Lys Leu Ser Ile Val Ser Leu Val Gly Lys His Met Lys Gln
        435                 440                 445
```

Tyr Ile Gly Ile Ala Gly Thr Met Phe Thr Thr Leu Ala Glu Glu Gly
            450                 455                 460

Ile Asn Ile Glu Met Ile Ser Gln Gly Ala Asn Glu Ile Asn Ile Ser
465                 470                 475                 480

Cys Val Ile Asn Glu Ser Asp Ser Ile Lys Ala Leu Gln Cys Ile His
                485                 490                 495

Ala Lys Leu Leu Ser Glu Arg Thr Asn Thr Ser Asn Gln Phe Glu His
            500                 505                 510

Ala Ile Asp Glu Arg Leu Glu Gln Leu Lys Arg Leu Gly Ile
            515                 520                 525

<210> SEQ ID NO 6
<211> LENGTH: 1461
<212> TYPE: DNA
<213> ORGANISM: Saccharomyces cerevisiae
<220> FEATURE:
<223> OTHER INFORMATION: HOMOSERINE O-ACETYLTRANSFERASE (MET2; METX)
<220> FEATURE:
<223> OTHER INFORMATION: HOMOSERINE O-ACETYLTRANSFERASE (MET2; METX)

<400> SEQUENCE: 6
atgtcgcata ctttaaaatc gaaaacgctc caagagctgg acattgagga gattaaggaa    60
actaacccat tgctcaaact agttcaaggg cagaggattg ttcaagttcc ggaactagtg   120
cttgagtctg gcgtggtcat aaataatttc cctattgctt ataagacgtg gggtacactg   180
aatgaagctg gtgataatgt tctggtaatt tgtcatgcct tgactgggtc cgcagatgtt   240
gctgactggt ggggccctct tctgggtaac gacttagcat tcgacccatc aaggtttttt   300
atcatatgtt taaactctat gggctctcca tatgggtctt tttcgccatt aacgataaat   360
gaggagacgg gcgttagata tggacccgaa ttcccattat gtactgtgcg cgatgacgtt   420
agagctcaca gaattgttct ggattctctg ggagtaaagt caatagcctg tgttattggt   480
ggctctatgg gggggatgct gagtttggaa tgggctgcca tgtatggtaa ggaatatgtg   540
aagaatatgg ttgctctggc gacatcagca agacattctg cctggtgcat atcgtggtct   600
gaggctcaaa gacaatcgat ttactcagat cccaactact tggacgggta ctatccggta   660
gaggagcaac ctgtggccgg actatcggct gcacgtatgt ctgcattgtt gacgtacagg   720
acaagaaaca gtttcgagaa caaattctcc agaagatctc cttcaatagc acaacaacaa   780
aaagctcaaa gggaggagac acgcaaacca tctactgtca gcgaacactc cctacaaatc   840
cacaatgatg ggtataaaac aaaagccagc actgccatcg ctggcatttc tgggcaaaaa   900
ggtcaaagcg tggtgtccac cgcatcttct tcggattcat tgaattcttc aacatcgatg   960
acttcggtaa gttctgtaac gggtgaagtg aaggacataa agcctgcgca gacgtatttt  1020
tctgcacaaa gttacttgag gtaccagggc acaaagttca tcaataggtt cgacgccaat  1080
tgttacattg ccatcacacg taaactggat acgcacgatt tggcaagaga cagagtagat  1140
gacatcactg aggtcctttc taccatccaa caaccatccc tgatcatcgg tatccaatct  1200
gatggactgt tcacatattc agaacaagaa ttttggctg agcacatacc gaagtcgcaa  1260
ttagaaaaaa ttgaatctcc cgaaggccac gatgccttcc tattggagtt taagctgata  1320
aacaaactga tagtacaatt tttaaaaacc aactgcaagg ccattaccga tgccgctcca  1380
agagcttggg gaggtgacgt tggtaacgat gaaacgaaga cgtctgtctt tggtgaggcc  1440
gaagaagtta ccaactggta g                                            1461

<210> SEQ ID NO 7

<211> LENGTH: 486
<212> TYPE: PRT
<213> ORGANISM: Saccharomyces cerevisiae
<220> FEATURE:
<223> OTHER INFORMATION: HOMOSERINE O-ACETYLTRANSFERASE (MET2; METX)
<220> FEATURE:
<223> OTHER INFORMATION: HOMOSERINE O-ACETYLTRANSFERASE (MET2; METX)

<400> SEQUENCE: 7

```
Met Ser His Thr Leu Lys Ser Lys Thr Leu Gln Glu Leu Asp Ile Glu
1               5                   10                  15

Glu Ile Lys Glu Thr Asn Pro Leu Leu Lys Leu Val Gln Gly Gln Arg
                20                  25                  30

Ile Val Gln Val Pro Glu Leu Val Leu Glu Ser Gly Val Val Ile Asn
            35                  40                  45

Asn Phe Pro Ile Ala Tyr Lys Thr Trp Gly Thr Leu Asn Glu Ala Gly
        50                  55                  60

Asp Asn Val Leu Val Ile Cys His Ala Leu Thr Gly Ser Ala Asp Val
65                  70                  75                  80

Ala Asp Trp Trp Gly Pro Leu Leu Gly Asn Asp Leu Ala Phe Asp Pro
                85                  90                  95

Ser Arg Phe Phe Ile Ile Cys Leu Asn Ser Met Gly Ser Pro Tyr Gly
                100                 105                 110

Ser Phe Ser Pro Leu Thr Ile Asn Glu Glu Thr Gly Val Arg Tyr Gly
            115                 120                 125

Pro Glu Phe Pro Leu Cys Thr Val Arg Asp Asp Val Arg Ala His Arg
130                 135                 140

Ile Val Leu Asp Ser Leu Gly Val Lys Ser Ile Ala Cys Val Ile Gly
145                 150                 155                 160

Gly Ser Met Gly Gly Met Leu Ser Leu Glu Trp Ala Ala Met Tyr Gly
                165                 170                 175

Lys Glu Tyr Val Lys Asn Met Val Ala Leu Ala Thr Ser Ala Arg His
                180                 185                 190

Ser Ala Trp Cys Ile Ser Trp Ser Glu Ala Gln Arg Gln Ser Ile Tyr
            195                 200                 205

Ser Asp Pro Asn Tyr Leu Asp Gly Tyr Tyr Pro Val Glu Glu Gln Pro
        210                 215                 220

Val Ala Gly Leu Ser Ala Ala Arg Met Ser Ala Leu Leu Thr Tyr Arg
225                 230                 235                 240

Thr Arg Asn Ser Phe Glu Asn Lys Phe Ser Arg Arg Ser Pro Ser Ile
                245                 250                 255

Ala Gln Gln Gln Lys Ala Gln Arg Glu Thr Arg Lys Pro Ser Thr
                260                 265                 270

Val Ser Glu His Ser Leu Gln Ile His Asn Asp Gly Tyr Lys Thr Lys
            275                 280                 285

Ala Ser Thr Ala Ile Ala Gly Ile Ser Gly Gln Lys Gly Gln Ser Val
        290                 295                 300

Val Ser Thr Ala Ser Ser Ser Asp Ser Leu Asn Ser Ser Thr Ser Met
305                 310                 315                 320

Thr Ser Val Ser Ser Val Thr Gly Glu Val Lys Asp Ile Lys Pro Ala
                325                 330                 335

Gln Thr Tyr Phe Ser Ala Gln Ser Tyr Leu Arg Tyr Gln Gly Thr Lys
                340                 345                 350

Phe Ile Asn Arg Phe Asp Ala Asn Cys Tyr Ile Ala Ile Thr Arg Lys
            355                 360                 365
```

Leu Asp Thr His Asp Leu Ala Arg Asp Arg Val Asp Asp Ile Thr Glu
370                 375                 380

Val Leu Ser Thr Ile Gln Gln Pro Ser Leu Ile Ile Gly Ile Gln Ser
385                 390                 395                 400

Asp Gly Leu Phe Thr Tyr Ser Glu Gln Glu Phe Leu Ala Glu His Ile
                405                 410                 415

Pro Lys Ser Gln Leu Glu Lys Ile Glu Ser Pro Glu Gly His Asp Ala
            420                 425                 430

Phe Leu Leu Glu Phe Lys Leu Ile Asn Lys Leu Ile Val Gln Phe Leu
                435                 440                 445

Lys Thr Asn Cys Lys Ala Ile Thr Asp Ala Ala Pro Arg Ala Trp Gly
450                 455                 460

Gly Asp Val Gly Asn Asp Glu Thr Lys Thr Ser Val Phe Gly Glu Ala
465                 470                 475                 480

Glu Glu Val Thr Asn Trp
                485

<210> SEQ ID NO 8
<211> LENGTH: 1335
<212> TYPE: DNA
<213> ORGANISM: Saccharomyces cerevisiae
<220> FEATURE:
<223> OTHER INFORMATION: HOMOCYSTEINE/CYSTEINE SYNTHASE (MET17)
<220> FEATURE:
<223> OTHER INFORMATION: HOMOCYSTEINE/CYSTEINE SYNTHASE (MET17)

<400> SEQUENCE: 8
atgccatctc atttcgatac tgttcaacta cacgccggcc aagagaaccc tggtgacaat    60
gctcacagat ccagagctgt accaatttac gccaccactt cttatgtttt cgaaaactct   120
aagcatggtt cgcaattgtt tggtctagaa gttccaggtc acgtctattc ccgtttccaa   180
aacccaacca gtaatgtttt ggaagaaaga attgctgctt tagaaggtgg tgctgctgct   240
ttggctgttt cctccggtca agccgctcaa acccttgcca tccaaggttt ggcacacact   300
ggtgacaaca tcgtttccac ttcttactta tacggtggta cttataacca gttcaaaatc   360
tcgttcaaaa gatttggtat cgaggctaga tttgttgaag gtgacaatcc agaagaattc   420
gaaaaggtct tgatgaaag accaaggct gtttatttgg aaaccattgg taatccaaag   480
tacaatgttc cggattttga aaaaattgtt gcaattgctc acaaacacgg tattccagtt   540
gtcgttgaca cacatttggg tgccggtggt tacttctgtc agccaattaa atacggtgct   600
gatattgtaa cacattctgc taccaaatgg attggtggtc atggtactac tatcggtggt   660
attattgttg actctggtaa gttcccatgg aaggactacc agaaaagtt ccctcaattc   720 tctcaacctg ccgaaggata tcacggtact atctacaatg aagcctacgg taacttggca   780
tacatcgttc atgttagaac tgaactatta agagatttgg gtccattgat gaacccattt   840
gcctctttct tgctactaca aggtgttgaa acattatctt tgagagctga agacacggt    900 gaaaatgcat tgaagttagc caaatggtta gaacaatccc catacgtatc ttgggtttca   960
tacactggtt tagcatctca ttctcatcat gaaaatgcta agaagtatct atctaacggt  1020
ttcggtggtg tcttatcttt cggtgtaaaa gacttaccaa atgccgacaa ggaaactgac  1080
ccattcaaac tttctggtgc tcaagttgtt gacaattaa agcttgcctc taacttggcc  1140
aatgttggtg atgccaagac cttagtcatt gctccatact tcactaccca caaacaatta  1200
aatgacaaag aaaagttggc atctggtgtt accaaggact taattcgtgt ctctgttggt  1260
atcgaattta ttgatgacat tattgcagac ttccagcaat cttttgaaac tgttttcgct  1320
ggccaaaaac catga 1335

<210> SEQ ID NO 9
<211> LENGTH: 444
<212> TYPE: PRT
<213> ORGANISM: Saccharomyces cerevisiae
<220> FEATURE:
<223> OTHER INFORMATION: HOMOCYSTEINE/CYSTEINE SYNTHASE (MET17)
<220> FEATURE:
<223> OTHER INFORMATION: HOMOCYSTEINE/CYSTEINE SYNTHASE (MET17)

<400> SEQUENCE: 9

Met Pro Ser His Phe Asp Thr Val Gln Leu His Ala Gly Gln Glu Asn
1               5                   10                  15

Pro Gly Asp Asn Ala His Arg Ser Arg Ala Val Pro Ile Tyr Ala Thr
            20                  25                  30

Thr Ser Tyr Val Phe Glu Asn Ser Lys His Gly Ser Gln Leu Phe Gly
        35                  40                  45

Leu Glu Val Pro Gly Tyr Val Tyr Ser Arg Phe Gln Asn Pro Thr Ser
    50                  55                  60

Asn Val Leu Glu Glu Arg Ile Ala Ala Leu Glu Gly Gly Ala Ala Ala
65                  70                  75                  80

Leu Ala Val Ser Ser Gly Gln Ala Ala Gln Thr Leu Ala Ile Gln Gly
                85                  90                  95

Leu Ala His Thr Gly Asp Asn Ile Val Ser Thr Ser Tyr Leu Tyr Gly
            100                 105                 110

Gly Thr Tyr Asn Gln Phe Lys Ile Ser Phe Lys Arg Phe Gly Ile Glu
        115                 120                 125

Ala Arg Phe Val Glu Gly Asp Asn Pro Glu Glu Phe Glu Lys Val Phe
    130                 135                 140

Asp Glu Arg Thr Lys Ala Val Tyr Leu Glu Thr Ile Gly Asn Pro Lys
145                 150                 155                 160

Tyr Asn Val Pro Asp Phe Glu Lys Ile Val Ala Ile Ala His Lys His
                165                 170                 175

Gly Ile Pro Val Val Asp Asn Thr Phe Gly Ala Gly Gly Tyr Phe
            180                 185                 190

Cys Gln Pro Ile Lys Tyr Gly Ala Asp Ile Val Thr His Ser Ala Thr
        195                 200                 205

Lys Trp Ile Gly Gly His Gly Thr Thr Ile Gly Gly Ile Ile Val Asp
    210                 215                 220

Ser Gly Lys Phe Pro Trp Lys Asp Tyr Pro Glu Lys Phe Pro Gln Phe
225                 230                 235                 240

Ser Gln Pro Ala Glu Gly Tyr His Gly Thr Ile Tyr Asn Glu Ala Tyr
                245                 250                 255

Gly Asn Leu Ala Tyr Ile Val His Val Arg Thr Glu Leu Leu Arg Asp
            260                 265                 270

Leu Gly Pro Leu Met Asn Pro Phe Ala Ser Phe Leu Leu Gln Gly
        275                 280                 285

Val Glu Thr Leu Ser Leu Arg Ala Glu Arg His Gly Glu Asn Ala Leu
    290                 295                 300

Lys Leu Ala Lys Trp Leu Glu Gln Ser Pro Tyr Val Ser Trp Val Ser
305                 310                 315                 320

Tyr Pro Gly Leu Ala Ser His Ser His His Glu Asn Ala Lys Lys Tyr
                325                 330                 335

Leu Ser Asn Gly Phe Gly Gly Val Leu Ser Phe Gly Val Lys Asp Leu

```
                340             345             350
Pro Asn Ala Asp Lys Glu Thr Asp Pro Phe Lys Leu Ser Gly Ala Gln
            355                 360                 365

Val Val Asp Asn Leu Lys Leu Ala Ser Asn Leu Ala Asn Val Gly Asp
        370                 375                 380

Ala Lys Thr Leu Val Ile Ala Pro Tyr Phe Thr His Lys Gln Leu
385                 390                 395                 400

Asn Asp Lys Glu Lys Leu Ala Ser Gly Val Thr Lys Asp Leu Ile Arg
                405                 410                 415

Val Ser Val Gly Ile Glu Phe Ile Asp Asp Ile Ile Ala Asp Phe Gln
            420                 425                 430

Gln Ser Phe Glu Thr Val Phe Ala Gly Gln Lys Pro
            435                 440

<210> SEQ ID NO 10
<211> LENGTH: 1074
<212> TYPE: DNA
<213> ORGANISM: Saccharomyces cerevisiae
<220> FEATURE:
<223> OTHER INFORMATION: HOMOSERINE KINASE (THR1)
<220> FEATURE:
<223> OTHER INFORMATION: HOMOSERINE KINASE (THR1)

<400> SEQUENCE: 10
atggttcgtg ccttcaaaat taaagttcca gcttcttccg ccaatatcgg ccctggttat      60
gatgttcttg gtgtcggtct ttctctattc ttggagttag atgtcaccat cgactccagc    120
caagctcagg aaacaaacga cgatcccaac aactgcaagc tgtcttacac taaagaaagt    180
gaaggctatt ctacggtccc attgcgttct gatgctaacc tgattaccag gactgcgtta    240
tatgtgttgc gttgcaacaa tattagaaac ttcccctccg gaaccaaagt tcacgtctcc    300
aacccaatcc cacttggccg tggattgggt tcctctggtg cagcagttgt ggcaggtgtt    360
attttaggta acgaagtggc ccaattgggt ttctctaagc aacgtatgtt ggactactgt    420
ttgatgattg aacgtcatcc agacaacata accgctgcta tgatgggagg cttttgcggt    480
tcattcctaa gggacttgac cccacaagag gtggaaagac gtgagattcc attggctgag    540
gtgcttccag aaccttctgg tggtgaagat accggtctgg ttccccatt acctcccacc     600 gatatcggta gacatgtcaa ataccaatgg aaccccgcca ttaaatgtat tgcgatcatc    660
ccacagttcg agttgtccac cgccgactcc agaggcgttc ttccaaaagc ctacccaacc    720
caggacttgg ttttcaatct acaaagattg gccgtcttga ccacagcttt gaccatggac    780
ccacctaatg ccgacttaat ctaccctgct atgcaagatc gtgtccacca accttataga    840
aagacattga tcccaggtct cacggaaatc ttatcatgtg tcaccccatc cacatacccct   900 ggcctattgg gtatctgctt gtcaggtgca ggcccaacta tcttggcttt ggccactgag    960
aatttcgaag aaatctctca gaaaattatc aacaggttcg ccaaaaacgg catcaagtgc   1020
tcctggaaac tactggagcc tgcctacgat ggtgctagcg tcgaacagca atga         1074

<210> SEQ ID NO 11
<211> LENGTH: 357
<212> TYPE: PRT
<213> ORGANISM: Saccharomyces cerevisiae
<220> FEATURE:
<223> OTHER INFORMATION: HOMOSERINE KINASE (THR1)
<220> FEATURE:
<223> OTHER INFORMATION: HOMOSERINE KINASE (THR1)

<400> SEQUENCE: 11
```

```
Met Val Arg Ala Phe Lys Ile Lys Val Pro Ala Ser Ala Asn Ile
1               5                   10                  15

Gly Pro Gly Tyr Asp Val Leu Gly Val Gly Leu Ser Leu Phe Leu Glu
            20                  25                  30

Leu Asp Val Thr Ile Asp Ser Ser Gln Ala Gln Glu Thr Asn Asp Asp
                35                  40                  45

Pro Asn Asn Cys Lys Leu Ser Tyr Thr Lys Glu Ser Glu Gly Tyr Ser
    50                  55                  60

Thr Val Pro Leu Arg Ser Asp Ala Asn Leu Ile Thr Arg Thr Ala Leu
65                  70                  75                  80

Tyr Val Leu Arg Cys Asn Asn Ile Arg Asn Phe Pro Ser Gly Thr Lys
                85                  90                  95

Val His Val Ser Asn Pro Ile Pro Leu Gly Arg Gly Leu Gly Ser Ser
                100                 105                 110

Gly Ala Ala Val Val Ala Gly Val Ile Leu Gly Asn Glu Val Ala Gln
            115                 120                 125

Leu Gly Phe Ser Lys Gln Arg Met Leu Asp Tyr Cys Leu Met Ile Glu
130                 135                 140

Arg His Pro Asp Asn Ile Thr Ala Ala Met Met Gly Gly Phe Cys Gly
145                 150                 155                 160

Ser Phe Leu Arg Asp Leu Thr Pro Gln Glu Val Glu Arg Arg Glu Ile
                165                 170                 175

Pro Leu Ala Glu Val Leu Pro Glu Pro Ser Gly Gly Glu Asp Thr Gly
            180                 185                 190

Leu Val Pro Pro Leu Pro Pro Thr Asp Ile Gly Arg His Val Lys Tyr
                195                 200                 205

Gln Trp Asn Pro Ala Ile Lys Cys Ile Ala Ile Ile Pro Gln Phe Glu
210                 215                 220

Leu Ser Thr Ala Asp Ser Arg Gly Val Leu Pro Lys Ala Tyr Pro Thr
225                 230                 235                 240

Gln Asp Leu Val Phe Asn Leu Gln Arg Leu Ala Val Leu Thr Thr Ala
                245                 250                 255

Leu Thr Met Asp Pro Pro Asn Ala Asp Leu Ile Tyr Pro Ala Met Gln
            260                 265                 270

Asp Arg Val His Gln Pro Tyr Arg Lys Thr Leu Ile Pro Gly Leu Thr
                275                 280                 285

Glu Ile Leu Ser Cys Val Thr Pro Ser Thr Tyr Pro Gly Leu Leu Gly
290                 295                 300

Ile Cys Leu Ser Gly Ala Gly Pro Thr Ile Leu Ala Leu Ala Thr Glu
305                 310                 315                 320

Asn Phe Glu Glu Ile Ser Gln Glu Ile Ile Asn Arg Phe Ala Lys Asn
                325                 330                 335

Gly Ile Lys Cys Ser Trp Lys Leu Leu Glu Pro Ala Tyr Asp Gly Ala
            340                 345                 350

Ser Val Glu Gln Gln
        355

<210> SEQ ID NO 12
<211> LENGTH: 2461
<212> TYPE: DNA
<213> ORGANISM: Arabidopsis thaliana
<220> FEATURE:
<223> OTHER INFORMATION: CYSTATHIONINE GAMMA SYNTHASE 1 (CGS1)
<220> FEATURE:
<223> OTHER INFORMATION: CYSTATHIONINE GAMMA SYNTHASE 1 (CGS1)
```

<400> SEQUENCE: 12

```
gttggaactt ggattgaaaa ctcaacaaca actcattgtt tggataagta agtagaaatc    60
tggcaataaa cgtattctat ttttgtaacg tagaaaatta gaaaataat agtaagagga    120
aaaggcatgg tttagtctgg tcaagttaat gtaaaccaga gtggttaaaa acaaaacgac    180
aaagcaattt ggcttcttaa aaacccgccc atggagaaag ccctcacgca cctctaaacc    240
acaaacaaaa agagagagaa gagaacgaga gaatcattga gaaacgaaac aacaatggcc    300
gtctcatcat tccagtgccc taccatcttc tcctcctcct caatctccgg ctttcaatgc    360
cgttctgatc cagatctcgt cggttctccc gtcggtggat catctcgccg tcgtgtccat    420
gcctccgccg ggatttcttc ctcattcacc ggggacgctg gattatcctc caggatctta    480
agatttcctc ctaatttcgt ccgtcagctg agcattaaag cccgtagaaa ctgtagcaac    540
atcggtgttg cacagatcgt ggcggctaag tggtccaaca acccatcctc cgcgttacct    600
tcggcggcgg cggctgctgc tacctcgtct gcatctgcgg tttcttccgc cgcatctgca    660
gccgcagcct cgtccgccgc cgccgcccct gtggctgccg cgcctcccgt cgtgctgaaa    720
agcgtcgatg aggaggttgt ggtggccgag gaggggatca gggagaagat aggtagtgta    780
cagctgacgg attccaaaca ttctttcttg agctccgatg ggagcctcac tgttcatgcc    840
ggtgaaagat taggccgtgg tatagtgacg gatgctatca ctactcctgt agtcaacaca    900
tctgcctact tcttcaagaa aactgctgag cttattgact tcaaggagaa aaggagtgtg    960
agtttcgagt atggtcgtta tggtaaccct acgactgtgg tacttgaaga taagataagt   1020
gcacttgaag gggctgaatc aactttggtt atggcatctg ggatgtgtgc aagcactgtt   1080
atgcttttgg cattggttcc tgctggtgga cacattgtca ctactactga ttgctacagg   1140
aagactagga tcttcatgga gaattttctt cccaagttgg ggatcactgt cactgtgatt   1200
gatcctgctg atatcgcagg gcttgaagct gcagtgaatg agttcaaggt atctctgttc   1260
ttcactgagt ccccgacaaa cccattcctt agatgtgtcg acattgagct agtttcaaaa   1320
atatgccaca agaggggaac tctggtttgc attgatggca cctttgcaac acctctgaat   1380
cagaaagccc ttgctcttgg tgctgatctt gtcgtgcact ctgctacaaa gtacattgga   1440
ggacacaatg atgttcttgc tggatgcatc tgtggttcac tgaagttggt ttcagaaatt   1500
cgcaatctgc atcatgtgtt gggaggaaca cttaacccaa acgctgcgta cctaatcatc   1560
cgaggcatga agacattgca tcttcgtgta cagcaacaga attcgaccgc ttttagaatg   1620
gccgaaattt tagaggcaca tcctaaggtg agtcatgtgt actatccagg ccttccaagt   1680
catcccgaac atgaactcgc caagcgacaa atgactggtt ttggaggtgt ggtcagtttc   1740
gagattgatg gagacattga aacgacaatc aagtttgtgg attctctaaa gattccttac   1800
attgcaccat ccttcggtgg ctgcgaaagc attgttgacc aacctgctat catgtcctac   1860
tgggatctgc cgcaagagga gagactaaag tatggaatca agataacttt ggttcgtttc   1920
agctttggag ttgaagactt tgaagatgtc aaagctgaca ttcttcaagc tctcgaagcc   1980
atctgaaaat gacacatcac acaaaaacgc tgtcgtttct tgtcccttta tttatctctc   2040
tttgctgttt tcagtcaccg taataatgat gtctttgaac tattgttccg cgacatttac   2100
gttccgaaat aatcgtgtac tattatgatg tttgttgtgc tatataataa attctgttta   2160
gttcgttttg cgtcttaaag aggttaaatt agataactgg tcccatgtga acgaccattg   2220
tggccattgc tttgtggtaa gaactccttg tgcttggaac ctcaaggtca cggcttcgaa   2280
```

```
caatggtcat gaccctctag cttctgcttc ttcttctctt tgtttcaaca acatataagg    2340
cattcataaa tgcctcgtct ttttttgttt tctttccttt caatacgtag ttcgatttcg    2400
atttcgattt gtagatctca gcaaaatcca tgtcttgaga gaatgattaa tgggcctttt    2460
t                                                                    2461
```

<210> SEQ ID NO 13
<211> LENGTH: 507
<212> TYPE: PRT
<213> ORGANISM: Arabidopsis thaliana
<220> FEATURE:
<223> OTHER INFORMATION: CYSTATHIONINE GAMMA SYNTHASE 1 (CGS1)
<220> FEATURE:
<223> OTHER INFORMATION: CYSTATHIONINE GAMMA SYNTHASE 1 (CGS1)

<400> SEQUENCE: 13

```
Met Ser Ser Arg Ile Leu Arg Phe Pro Pro Asn Phe Val Arg Gln Leu
1               5                   10                  15

Ser Ile Lys Ala Arg Arg Asn Cys Ser Asn Ile Ser Val Ala Gln Ile
            20                  25                  30

Val Ala Gly Lys Trp Ser Asn Asn Pro Ser Ser Ala Leu Pro Ser Ala
        35                  40                  45

Ala Ala Ala Ala Ala Thr Ser Ser Ala Ser Ala Val Ser Ser Ala Ala
    50                  55                  60

Ser Ala Ala Ala Ser Ser Ala Ala Ala Pro Val Ala Ala
65                  70                  75                  80

Pro Pro Val Val Leu Lys Ser Val Asp Glu Val Val Ala Glu
                85                  90                  95

Glu Gly Ile Arg Glu Lys Ile Gly Ser Val Gln Leu Thr Asp Ser Lys
                100                 105                 110

His Ser Phe Leu Ser Ser Asp Gly Ser Leu Thr Val His Ala Gly Glu
            115                 120                 125

Arg Leu Gly Arg Gly Ile Val Thr Asp Ala Ile Thr Thr Pro Val Val
    130                 135                 140

Asn Thr Ser Ala Tyr Phe Phe Lys Lys Thr Ala Glu Leu Ile Asp Phe
145                 150                 155                 160

Lys Glu Lys Arg Ser Val Ser Phe Glu Tyr Gly Arg Tyr Gly Asn Pro
                165                 170                 175

Thr Thr Val Val Leu Glu Asp Lys Ile Ser Ala Leu Glu Gly Ala Glu
            180                 185                 190

Ser Thr Leu Val Met Ala Ser Gly Met Cys Ala Ser Thr Val Met Leu
        195                 200                 205

Leu Ala Leu Val Pro Ala Gly Gly His Ile Val Thr Thr Asp Cys
    210                 215                 220

Tyr Arg Lys Thr Arg Ile Phe Met Glu Asn Phe Leu Pro Lys Leu Gly
225                 230                 235                 240

Ile Thr Val Thr Val Ile Asp Pro Ala Asp Ile Ala Gly Leu Glu Ala
                245                 250                 255

Ala Val Asn Glu Phe Lys Val Ser Leu Phe Phe Thr Glu Ser Pro Thr
            260                 265                 270

Asn Pro Phe Leu Arg Cys Val Asp Ile Glu Leu Val Ser Lys Ile Cys
        275                 280                 285

His Lys Arg Gly Thr Leu Val Cys Ile Asp Gly Thr Phe Ala Thr Pro
    290                 295                 300

Leu Asn Gln Lys Ala Leu Ala Leu Gly Ala Asp Leu Val Val His Ser
305                 310                 315                 320
```

```
Ala Thr Lys Tyr Ile Gly Gly His Asn Asp Val Leu Ala Cys Ile
                325                 330                 335

Cys Gly Ser Leu Lys Leu Val Ser Glu Ile Arg Asn Leu His Val
                340                 345                 350

Leu Gly Gly Pro Leu Asn Pro Asn Ala Ala Tyr Leu Ile Ile Arg Gly
                355                 360                 365

Met Lys Thr Leu His Leu Arg Val Gln Gln Asn Ser Thr Ala Phe
            370                 375                 380

Arg Met Ala Glu Ile Leu Glu Ala His Pro Lys Val Ser His Val Tyr
385                 390                 395                 400

Tyr Pro Gly Leu Pro Ser His Pro Glu His Glu Leu Ala Lys Arg Gln
                405                 410                 415

Met Thr Gly Phe Gly Gly Val Val Ser Phe Glu Ile Asp Gly Asp Ile
                420                 425                 430

Glu Thr Thr Ile Lys Phe Val Asp Ser Leu Lys Ile Pro Tyr Ile Ala
            435                 440                 445

Pro Ser Phe Gly Gly Cys Glu Ser Ile Val Asp Gln Pro Ala Ile Met
        450                 455                 460

Ser Tyr Trp Asp Leu Pro Gln Glu Glu Arg Leu Lys Tyr Gly Ile Lys
465                 470                 475                 480

Asp Asn Leu Val Arg Phe Ser Phe Gly Val Glu Asp Phe Glu Asp Val
                485                 490                 495

Lys Ala Asp Ile Leu Gln Ala Leu Glu Ala Ile
                500                 505
```

<210> SEQ ID NO 14
<211> LENGTH: 1257
<212> TYPE: DNA
<213> ORGANISM: Saccharomyces cerevisiae
<220> FEATURE:
<223> OTHER INFORMATION: ASPARTATE TRANSAMINASE (AAT2)
<220> FEATURE:
<223> OTHER INFORMATION: ASPARTATE TRANSAMINASE (AAT2)

<400> SEQUENCE: 14

```
atgtctgcca ctctgttcaa taacatcgaa ttgctgcccc ctgatgccct ttttggtatt      60
aagcaaaggt acgggcaaga tcaacgtgct accaaggtcg acttgggtat cggggcctac     120
agagacgaca acgtaaaacc atgggtcttg ccaagtgtta agccgccga aaagctaatt      180 cataacgaca gctcctacaa ccatgaatac ctcggtatta ccggtctgcc aagtttgaca     240
tctaacgccg ccaagatcat cttcggtacg caatccgatg cctttcagga agacagagta     300
atctcagtac aatcactgtc tggtacgggt gctcttcata tatctgcgaa gttttttca      360 aaattcttcc cagataaact ggtctatttg tctaagccta cttgggccaa ccacatggcc     420 attttttgaga atcaaggctt gaaaacggcg acttacccctt actgggccaa cgaaactaag    480
tctttggacc taaacggctt tctaaatgct attcaaaaag ctccagaggg ctccattttc     540
gttctgcact cttgcgccca taacccaact ggtctggacc tactagtga acaatgggtt      600 caaatcgttg atgctatcgc ctcaaagaac cacatcgcct tatttgacac cgcctaccaa     660
gggtttgcca ctggagattt ggacaaggat gcctatgctg tgcgtctagg tgtggagaag     720 cttctcaacgg tctctcccgt ctttgtctgt cagtcctttg ccaagaacgc cggtatgtac    780
ggtgagcgtg taggttgttt ccatctagca cttacaaaac aagctcaaaa caaaactata     840
aagcctgctg ttacatctca attggccaaa atcattcgta gtgaagtgtc caacccaccc     900
```

```
gcctacggcg ctaagattgt cgctaaactg ttggaaacgc cagaattaac ggaacagtgg    960
cacaaggata tggttaccat gtcctccaga attacgaaaa tgaggcacgc attaagagac   1020
catttagtca agttgggcac tcctggcaac tgggatcata tagtaaatca atgcgggatg   1080
ttctccttta cagggttgac tcctcaaatg gttaaacgac ttgaagaaac ccacgcagtt   1140
tacttggttg cctcaggtag agcttctatt gctggattga atcaaggaaa cgtggaatac   1200
gtggctaaag ccattgatga agtggtgcgc ttctatacta ttgaagctaa attgtaa     1257
```

<210> SEQ ID NO 15
<211> LENGTH: 418
<212> TYPE: PRT
<213> ORGANISM: Saccharomyces cerevisiae
<220> FEATURE:
<223> OTHER INFORMATION: ASPARTATE TRANSAMINASE (AAT2)
<220> FEATURE:
<223> OTHER INFORMATION: ASPARTATE TRANSAMINASE (AAT2)

<400> SEQUENCE: 15

```
Met Ser Ala Thr Leu Phe Asn Asn Ile Glu Leu Leu Pro Pro Asp Ala
1               5                   10                  15

Leu Phe Gly Ile Lys Gln Arg Tyr Gly Gln Asp Gln Arg Ala Thr Lys
            20                  25                  30

Val Asp Leu Gly Ile Gly Ala Tyr Arg Asp Asp Asn Gly Lys Pro Trp
        35                  40                  45

Val Leu Pro Ser Val Lys Ala Ala Glu Lys Leu Ile His Asn Asp Ser
    50                  55                  60

Ser Tyr Asn His Glu Tyr Leu Gly Ile Thr Gly Leu Pro Ser Leu Thr
65                  70                  75                  80

Ser Asn Ala Ala Lys Ile Ile Phe Gly Thr Gln Ser Asp Ala Phe Gln
                85                  90                  95

Glu Asp Arg Val Ile Ser Val Gln Ser Leu Ser Gly Thr Gly Ala Leu
            100                 105                 110

His Ile Ser Ala Lys Phe Phe Ser Lys Phe Phe Pro Asp Lys Leu Val
        115                 120                 125

Tyr Leu Ser Lys Pro Thr Trp Ala Asn His Met Ala Ile Phe Glu Asn
    130                 135                 140

Gln Gly Leu Lys Thr Ala Thr Tyr Pro Tyr Trp Ala Asn Glu Thr Lys
145                 150                 155                 160

Ser Leu Asp Leu Asn Gly Phe Leu Asn Ala Ile Gln Lys Ala Pro Glu
                165                 170                 175

Gly Ser Ile Phe Val Leu His Ser Cys Ala His Asn Pro Thr Gly Leu
            180                 185                 190

Asp Pro Thr Ser Glu Gln Trp Val Gln Ile Val Asp Ala Ile Ala Ser
        195                 200                 205

Lys Asn His Ile Ala Leu Phe Asp Thr Ala Tyr Gln Gly Phe Ala Thr
    210                 215                 220

Gly Asp Leu Asp Lys Asp Ala Tyr Ala Val Arg Leu Gly Val Glu Lys
225                 230                 235                 240

Leu Ser Thr Val Ser Pro Val Phe Val Cys Gln Ser Phe Ala Lys Asn
                245                 250                 255

Ala Gly Met Tyr Gly Glu Arg Val Gly Cys Phe His Leu Ala Leu Thr
            260                 265                 270

Lys Gln Ala Gln Asn Lys Thr Ile Lys Pro Ala Val Thr Ser Gln Leu
        275                 280                 285

Ala Lys Ile Ile Arg Ser Glu Val Ser Asn Pro Pro Ala Tyr Gly Ala
```

```
                290                 295                 300
Lys Ile Val Ala Lys Leu Leu Glu Thr Pro Glu Leu Thr Glu Gln Trp
305                 310                 315                 320

His Lys Asp Met Val Thr Met Ser Ser Arg Ile Thr Lys Met Arg His
                325                 330                 335

Ala Leu Arg Asp His Leu Val Lys Leu Gly Thr Pro Gly Asn Trp Asp
                340                 345                 350

His Ile Val Asn Gln Cys Gly Met Phe Ser Phe Thr Gly Leu Thr Pro
            355                 360                 365

Gln Met Val Lys Arg Leu Glu Glu Thr His Ala Val Tyr Leu Val Ala
            370                 375                 380

Ser Gly Arg Ala Ser Ile Ala Gly Leu Asn Gln Gly Asn Val Glu Tyr
385                 390                 395                 400

Val Ala Lys Ala Ile Asp Glu Val Val Arg Phe Tyr Thr Ile Glu Ala
                405                 410                 415

Lys Leu

<210> SEQ ID NO 16
<211> LENGTH: 1317
<212> TYPE: DNA
<213> ORGANISM: Entodinium caudatum
<220> FEATURE:
<223> OTHER INFORMATION: GLUTAMATE DESHYDROGENASE (GDH)
<220> FEATURE:
<223> OTHER INFORMATION: GLUTAMATE DESHYDROGENASE (GDH)

<400> SEQUENCE: 16
atgatagatt tagaagcgag aaaccctgct caacccgaat tcattcaagc cagtagagaa      60
gtaatcgaat cgatcattga tgttgttaat agcaatccga atacctggaa aacaaaatt     120 ttggagagaa ttacggaacc aaacctaatt cacgaattca agtcgaatg ggagaatgac     180 aagcacgaaa tcatggtgaa caaaggttat cgtattcagt tcaataatgc gataggtccc     240
tataagggag gcctaaggtt tcacagagca gtcactctag gtactctgaa attccttggt     300
tttgaacaga tatttaagaa ttccttgaca ggattaccta tgggaggtgg caaaggtggt     360
tcagattttg atcctagagg taaatcagat gccgagattt taagattctg taggtctttt     420
atgacttcgt tgttcaaata tattgggcca gagatagatg ttcctgctgg agatataggt     480
gtcggaggta gggaaattgg ttacttgttt ggccaataca aaagactgac caacaacat     540 gaaggagttc taactggtaa gggtcttaac tggggtggct ctcttgttag acctgaagcc     600
acaggttttg aacgatgta tttgctaac gaagtcttac atgcacatgg tgacgacatc     660
aaggggaaaa ccattgccat atccggattt ggtaatgttg cctttggtgc tgtcttaaaa     720
gcgaaacaat taggcgctaa ggtagtcact atatctggcc cagatggtta catttatgac     780
gagaatggga taaacaccga cgagaaaatc aactacatgt tggaattaag agcctcaaat     840
aatgatgtgg ttgcgccatt tgcagagaag tttggtgcaa aattcatacc agggaagaag     900
ccatgggaag ttccagtgga tatggctttt ccctgtgcca ttcagaacga attgaatgcc     960
gaagatgctg ccactttaca taagaatgga gtgaaatatg tgatcgagac atccaatatg    1020
ggctgtacag cagatgctgt gcaatacttc attaagaacc gtattgtttt cgctccgggt    1080
aaagcagcta atgctggtgg tgttgcagta tctgggttgg aaatgagcca aaactcaatg    1140
aagttgaact ggacagctga agaagttgac gctaaattga gaatatcat gaccaatatt    1200 catgcaagtt gcgtaaagga aggaaaagag agtgacgggt atatcaatta cgttaaaggc    1260
```
gcaaatatag caggcttcaa gaaagtagct gatgcaatgg tagatcttgg ctattaa        1317

<210> SEQ ID NO 17
<211> LENGTH: 438
<212> TYPE: PRT
<213> ORGANISM: Entodinium caudatum
<220> FEATURE:
<223> OTHER INFORMATION: GLUTAMATE DESHYDROGENASE (GDH)
<220> FEATURE:
<223> OTHER INFORMATION: GLUTAMATE DESHYDROGENASE (GDH)

<400> SEQUENCE: 17

```
Met Ile Asp Leu Glu Ala Arg Asn Pro Ala Gln Pro Glu Phe Ile Gln
1               5                   10                  15

Ala Ser Arg Glu Val Ile Glu Ser Ile Ile Asp Val Val Asn Ser Asn
            20                  25                  30

Pro Lys Tyr Leu Glu Asn Lys Ile Leu Glu Arg Ile Thr Glu Pro Asn
        35                  40                  45

Leu Ile His Glu Phe Lys Val Glu Trp Glu Asn Asp Lys His Glu Ile
    50                  55                  60

Met Val Asn Lys Gly Tyr Arg Ile Gln Phe Asn Asn Ala Ile Gly Pro
65                  70                  75                  80

Tyr Lys Gly Gly Leu Arg Phe His Arg Ala Val Thr Leu Gly Thr Leu
                85                  90                  95

Lys Phe Leu Gly Phe Glu Gln Ile Phe Lys Asn Ser Leu Thr Gly Leu
            100                 105                 110

Pro Met Gly Gly Gly Lys Gly Gly Ser Asp Phe Asp Pro Arg Gly Lys
        115                 120                 125

Ser Asp Ala Glu Ile Leu Arg Phe Cys Arg Ser Phe Met Thr Ser Leu
    130                 135                 140

Phe Lys Tyr Ile Gly Pro Glu Ile Asp Val Pro Ala Gly Asp Ile Gly
145                 150                 155                 160

Val Gly Gly Arg Glu Ile Gly Tyr Leu Phe Gly Gln Tyr Lys Arg Leu
                165                 170                 175

Thr Gln Gln His Glu Gly Val Leu Thr Gly Lys Gly Leu Asn Trp Gly
            180                 185                 190

Gly Ser Leu Val Arg Pro Glu Ala Thr Gly Phe Gly Thr Met Tyr Phe
        195                 200                 205

Ala Asn Glu Val Leu His Ala His Gly Asp Asp Ile Lys Gly Lys Thr
    210                 215                 220

Ile Ala Ile Ser Gly Phe Gly Asn Val Ala Phe Gly Ala Val Leu Lys
225                 230                 235                 240

Ala Lys Gln Leu Gly Ala Lys Val Val Thr Ile Ser Gly Pro Asp Gly
                245                 250                 255

Tyr Ile Tyr Asp Glu Asn Gly Ile Asn Thr Asp Glu Lys Ile Asn Tyr
            260                 265                 270

Met Leu Glu Leu Arg Ala Ser Asn Asn Asp Val Val Ala Pro Phe Ala
        275                 280                 285

Glu Lys Phe Gly Ala Lys Phe Ile Pro Gly Lys Lys Pro Trp Glu Val
    290                 295                 300

Pro Val Asp Met Ala Phe Pro Cys Ala Ile Gln Asn Glu Leu Asn Ala
305                 310                 315                 320

Glu Asp Ala Ala Thr Leu His Lys Asn Gly Val Lys Tyr Val Ile Glu
                325                 330                 335

Thr Ser Asn Met Gly Cys Thr Ala Asp Ala Val Gln Tyr Phe Ile Lys
            340                 345                 350
```

Asn Arg Ile Val Phe Ala Pro Gly Lys Ala Ala Asn Ala Gly Gly Val
          355                 360                 365

Ala Val Ser Gly Leu Glu Met Ser Gln Asn Ser Met Lys Leu Asn Trp
    370                 375                 380

Thr Ala Glu Glu Val Asp Ala Lys Leu Lys Asn Ile Met Thr Asn Ile
385                 390                 395                 400

His Ala Ser Cys Val Lys Glu Gly Lys Glu Ser Asp Gly Tyr Ile Asn
                405                 410                 415

Tyr Val Lys Gly Ala Asn Ile Ala Gly Phe Lys Lys Val Ala Asp Ala
            420                 425                 430

Met Val Asp Leu Gly Tyr
            435

<210> SEQ ID NO 18
<211> LENGTH: 1080
<212> TYPE: DNA
<213> ORGANISM: Saccharomyces cerevisiae
<220> FEATURE:
<223> OTHER INFORMATION: HOMOSERINE DESHYDROGENASE (HOM6)
<220> FEATURE:
<223> OTHER INFORMATION: HOMOSERINE DESHYDROGENASE (HOM6)

<400> SEQUENCE: 18

```
atgagcacta aagttgttaa tgttgccgtt atcggtgccg gtgttgttgg ttcagctttc      60
ttggatcaat tgttagccat gaagtctacc attacttaca atctagttct tttggctgaa     120
gctgagcgtt ctttaatctc caaggacttt tctccattaa atgttggttc tgattggaag     180
gctgctttag cagcctccac tactaaaacg ttgcctttgg atgatttaat tgctcatttg     240
aagacttcac ctaagccagt catttttggtt gataacactt ccagcgctta cattgctggt     300
ttttacacta gtttgtcga aatggtatt tccattgcta ctccaaacaa gaaggccttt       360
tcctctgatt tggctacctg gaaggctctt ttctcaaata agccaactaa cggttttgtc     420
tatcatgaag ctaccgtcgg tgctggtttg cctatcatca gtttcttaag agaaattatt     480
caaaccggtg acgaagttga aaaaattgaa ggtatcttct ctggtactct atcttatatt     540
ttcaacgagt tctccactag tcaagctaac gacgtcaaat tctctgatgt tgtcaaagtt     600
gctaaaaaat tgggttatac tgaaccagat ccaagagatg atttgaatgg ttggatgtt      660 gctagaaagg ttaccattgt tggtaggata tctggtgtgg aagttgaatc tccaacttcc     720
ttccctgtcc agtctttgat tccaaaacca ttggaatctg tcaagtctgc tgatgaattc     780
ttggaaaaat tatctgatta cgataaagat ttgactcaat tgaagaagga agctgccact     840
gaaaataagg tattgagatt cattggtaaa gtcgatgttg ccaccaaatc tgtgtctgta     900
ggaattgaaa agtacgatta ctcacaccca ttcgcatcat tgaagggatc agataacgtt     960
atttccatca agactaagcg ttacaccaat cctgttgtca ttcaaggtgc cggtgccggt    1020
gctgccgtta ctgccgctgg tgttttgggt gatgttatca agattgctca aagactttaa   1080
```

<210> SEQ ID NO 19
<211> LENGTH: 308
<212> TYPE: PRT
<213> ORGANISM: Saccharomyces cerevisiae
<220> FEATURE:
<223> OTHER INFORMATION: HOMOSERINE DESHYDROGENASE (HOM6)
<220> FEATURE:
<223> OTHER INFORMATION: HOMOSERINE DESHYDROGENASE (HOM6)

<400> SEQUENCE: 19

Met Ser Thr Lys Val Asn Val Ala Val Ile Gly Ala Gly Val Val
1               5                   10                  15

Gly Ser Ala Phe Leu Asp Gln Leu Leu Ala Met Lys Ser Thr Ile Thr
            20                  25                  30

Tyr Asn Leu Val Leu Leu Ala Glu Ala Glu Arg Ser Leu Ile Ser Lys
                35                  40                  45

Asp Phe Ser Pro Leu Asn Val Gly Ser Asp Trp Lys Ala Ala Leu Ala
    50                  55                  60

Ala Ser Thr Thr Lys Thr Leu Pro Leu Asp Leu Ile Ala His Leu
65                  70                  75                  80

Lys Thr Ser Pro Lys Pro Val Ile Leu Val Asp Asn Thr Ser Ser Ala
                85                  90                  95

Tyr Ile Ala Gly Phe Tyr Thr Lys Phe Val Glu Asn Gly Ile Ser Ile
                100                 105                 110

Ala Thr Pro Asn Lys Lys Ala Phe Ser Ser Asp Leu Ala Thr Trp Lys
            115                 120                 125

Ala Leu Phe Ser Asn Lys Pro Thr Asn Gly Phe Val Tyr His Glu Ala
    130                 135                 140

Thr Val Gly Ala Gly Leu Pro Ile Ile Ser Phe Leu Arg Glu Ile Ile
145                 150                 155                 160

Gln Thr Gly Asp Glu Val Glu Lys Ile Glu Gly Ile Phe Ser Gly Thr
                165                 170                 175

Leu Ser Tyr Ile Phe Asn Glu Phe Ser Thr Ser Gln Ala Asn Asp Val
            180                 185                 190

Lys Phe Ser Asp Val Val Lys Val Ala Lys Lys Leu Gly Tyr Thr Glu
    195                 200                 205

Pro Asp Pro Arg Asp Asp Leu Asn Gly Leu Asp Val Ala Arg Lys Val
210                 215                 220

Thr Ile Val Gly Arg Ile Ser Gly Val Glu Val Glu Ser Pro Thr Ser
225                 230                 235                 240

Phe Pro Val Gln Ser Leu Ile Pro Lys Pro Leu Glu Ser Val Lys Ser
                245                 250                 255

Ala Asp Glu Phe Leu Glu Lys Leu Ser Asp Tyr Asp Lys Asp Leu Thr
            260                 265                 270

Gln Leu Lys Lys Glu Ala Ala Thr Glu Asn Lys Val Leu Arg Phe Ile
    275                 280                 285

Gly Lys Val Asp Val Ala Thr Lys Ser Val Ser Val Gly Ile Glu Lys
290                 295                 300

Tyr Asp Tyr Ser
305

<210> SEQ ID NO 20
<211> LENGTH: 1503
<212> TYPE: DNA
<213> ORGANISM: Saccharomyces cerevisiae
<220> FEATURE:
<223> OTHER INFORMATION: Aromatic aminotransferase I (ARO8)
<220> FEATURE:
<223> OTHER INFORMATION: Aromatic aminotransferase I (ARO8)

<400> SEQUENCE: 20
atgactttac ctgaatcaaa agactttttct tacttgtttt cggatgaaac caatgctcgt      60
aaaccatccc cattgaaaac ctgcatccat cttttccaag atcctaacat tatcttttg      120 ggtggtggcc tgccattaaa agattattc ccatgggata atctatctgt agattcaccc      180
aagcctcctt ttccccaggg tattggagct ccaattgacg agcagaattg cataaaatac      240

```
accgtcaaca aagattacgc tgataaaagt gccaatcctt ccaacgatat tcctttgtca    300
agagctttgc aatacgggtt cagtgctggt caacctgaac tattaaactt cattagagat    360
cataccaaga ttatccacga tttgaagtat aaggactggg acgttttagc cactgcaggt    420
aacacaaatg cctgggaatc tactttaaga gtcttttgta accgaggtga tgtcatctta    480
gttgaggcac attcttttc ctcttcattg gcttctgcag aggctcaagg tgtcattacc    540
ttccccgtgc caattgacgc tgatggtatc attcctgaaa aattagctaa agtcatggaa    600
aactggacac ctggtgctcc taaaccaaag ttgttataca ctattccaac gggccaaaat    660
ccaactggta cttccattgc agaccataga aggaggcaa tttacaagat cgctcaaaag    720
tacgacttcc taattgtgga agatgaacct tattatttct tacaaatgaa tccctacatc    780
aaagacttga aggaaagaga gaaggcacaa agttctccaa agcaggacca tgacgaattt    840
ttgaagtcct tggcaaacac ctttccttcc ttggatacag aaggccgtgt tattagaatg    900
gattccttt caaagttttt ggccccaggg acaagattgg ttggattac tggttcatcc    960
aaaatcttga agccttactt gagtttgcat gaaatgacga ttcaagcccc agcaggtttt   1020
acacaagttt tggtcaacgc tacgctatcc aggtggggtc aaaagggtta cttggactgg   1080
ttgcttggcc tgcgtcatga atacactttg aaacgtgact gtgccatcga tgcctttac    1140
aagtatctac acaatctga tgctttcgtg atcaatcctc caattgcagg tatgtttttc   1200
accgtgaaca ttgacgcatc tgtccaccct gagtttaaaa caaaatacaa ctcagaccct   1260
taccagctag aacagagtct ttaccacaaa gtggttgaac gtggtgtttt agtggttccc   1320
ggttcttggt tcaagagtga gggtgagacg gaacctcctc aacccgctga atctaaagaa   1380
gtcagtaatc caaacataat tttcttcaga ggtacctatg cagctgtctc tcctgagaaa   1440
ctgactgaag gtctgaagag attaggtgat actttatacg aagaatttgg tatttccaaa   1500
tag                                                                 1503
```

<210> SEQ ID NO 21
<211> LENGTH: 500
<212> TYPE: PRT
<213> ORGANISM: Saccharomyces cerevisiae
<220> FEATURE:
<223> OTHER INFORMATION: Aromatic aminotransferase I (ARO8)
<220> FEATURE:
<223> OTHER INFORMATION: Aromatic aminotransferase I (ARO8)

<400> SEQUENCE: 21

```
Met Thr Leu Pro Glu Ser Lys Asp Phe Ser Tyr Leu Phe Ser Asp Glu
1               5                   10                  15

Thr Asn Ala Arg Lys Pro Ser Pro Leu Lys Thr Cys Ile His Leu Phe
            20                  25                  30

Gln Asp Pro Asn Ile Ile Phe Leu Gly Gly Leu Pro Leu Lys Asp
        35                  40                  45

Tyr Phe Pro Trp Asp Asn Leu Ser Val Asp Ser Pro Lys Pro Phe
    50                  55                  60

Pro Gln Gly Ile Gly Ala Pro Ile Asp Glu Gln Asn Cys Ile Lys Tyr
65                  70                  75                  80

Thr Val Asn Lys Asp Tyr Ala Asp Lys Ser Ala Asn Pro Ser Asn Asp
                85                  90                  95

Ile Pro Leu Ser Arg Ala Leu Gln Tyr Gly Phe Ser Ala Gly Gln Pro
            100                 105                 110

Glu Leu Leu Asn Phe Ile Arg Asp His Thr Lys Ile Ile His Asp Leu
```

```
            115                 120                 125
Lys Tyr Lys Asp Trp Asp Val Leu Ala Thr Ala Gly Asn Thr Asn Ala
    130                 135                 140

Trp Glu Ser Thr Leu Arg Val Phe Cys Asn Arg Gly Asp Val Ile Leu
145                 150                 155                 160

Val Glu Ala His Ser Phe Ser Ser Leu Ala Ser Ala Glu Ala Gln
                165                 170                 175

Gly Val Ile Thr Phe Pro Val Pro Ile Asp Ala Asp Gly Ile Ile Pro
            180                 185                 190

Glu Lys Leu Ala Lys Val Met Glu Asn Trp Thr Pro Gly Ala Pro Lys
    195                 200                 205

Pro Lys Leu Leu Tyr Thr Ile Pro Thr Gly Gln Asn Pro Thr Gly Thr
210                 215                 220

Ser Ile Ala Asp His Arg Lys Glu Ala Ile Tyr Lys Ile Ala Gln Lys
225                 230                 235                 240

Tyr Asp Phe Leu Ile Val Glu Asp Glu Pro Tyr Tyr Phe Leu Gln Met
                245                 250                 255

Asn Pro Tyr Ile Lys Asp Leu Lys Glu Arg Glu Lys Ala Gln Ser Ser
            260                 265                 270

Pro Lys Gln Asp His Asp Glu Phe Leu Lys Ser Leu Ala Asn Thr Phe
    275                 280                 285

Leu Ser Leu Asp Thr Glu Gly Arg Val Ile Arg Met Asp Ser Phe Ser
290                 295                 300

Lys Val Leu Ala Pro Gly Thr Arg Leu Gly Trp Ile Thr Gly Ser Ser
305                 310                 315                 320

Lys Ile Leu Lys Pro Tyr Leu Ser Leu His Glu Met Thr Ile Gln Ala
                325                 330                 335

Pro Ala Gly Phe Thr Gln Val Leu Val Asn Ala Thr Leu Ser Arg Trp
            340                 345                 350

Gly Gln Lys Gly Tyr Leu Asp Trp Leu Leu Gly Leu Arg His Glu Tyr
    355                 360                 365

Thr Leu Lys Arg Asp Cys Ala Ile Asp Ala Leu Tyr Lys Tyr Leu Pro
370                 375                 380

Gln Ser Asp Ala Phe Val Ile Asn Pro Pro Ile Ala Gly Met Phe Phe
385                 390                 395                 400

Thr Val Asn Ile Asp Ala Ser Val His Pro Glu Phe Lys Thr Lys Tyr
                405                 410                 415

Asn Ser Asp Pro Tyr Gln Leu Glu Gln Ser Leu Tyr His Lys Val Val
            420                 425                 430

Glu Arg Gly Val Leu Val Val Pro Gly Ser Trp Phe Lys Ser Glu Gly
    435                 440                 445

Glu Thr Glu Pro Pro Gln Pro Ala Glu Ser Lys Val Ser Asn Pro
450                 455                 460

Asn Ile Ile Phe Phe Arg Gly Thr Tyr Ala Ala Val Ser Pro Glu Lys
465                 470                 475                 480

Leu Thr Glu Gly Leu Lys Arg Leu Gly Asp Thr Leu Tyr Glu Glu Phe
                485                 490                 495

Gly Ile Ser Lys
            500

<210> SEQ ID NO 22
<211> LENGTH: 1134
<212> TYPE: DNA
<213> ORGANISM: Saccharomyces cerevisiae
```

<220> FEATURE:
<223> OTHER INFORMATION: Cytosolic branched-chain amino acid (BCAA) aminotransferase (BAT2)
<220> FEATURE:
<223> OTHER INFORMATION: Cytosolic branched-chain amino acid (BCAA) aminotransferase (BAT2)

<400> SEQUENCE: 22

```
atgatgacct tggcacccct agacgcctcc aaagttaaga taactaccac acaacatgca    60
tctaagccaa aaccgaacag tgagttagtg tttggcaaga gcttcacgga ccacatgtta   120
actgcggaat ggacagctga aaaagggtgg ggtaccccag agattaaacc ttatcaaaat   180
ctgtctttag acccttccgc ggtggttttc cattatgctt ttgagctatt cgaagggatg   240
aaggcttaca gaacggtgga caacaaaatt acaatgtttc gtccagatat gaatatgaag   300
cgcatgaata gtctgctca gagaatctgt ttgccaacgt tcgacccaga gagttgatt    360
accctaattg ggaaactgat ccagcaagat aagtgcttag ttcctgaagg aaaaggttac   420
tctttatata tcaggcctac attaatcggc actacggccg gtttaggggt tccacgcct    480
gatagagcct tgctatatgt catttgctgc cctgtgggtc cttattacaa actggatt    540
aaggcggtca gactggaagc cactgattat gccacaagag cttggccagg aggctgtggt   600
gacaagaaac taggtgcaaa ctacgccccc tgcgtcctgc acaattgca agctgcttca   660
aggggttacc aacaaaattt atggctattt ggtccaaata caacattac tgaagtcggc   720
accatgaatg ctttttttcgt gtttaaagat agtaaaacgg gcaagaagga actagttact   780
gctccactag acggtaccat tttggaaggt gttactaggg attccatttt aaatcttgct   840
aaagaaagac tcgaaccaag tgaatggacc attagtgaac gctacttcac tataggcgaa   900
gttactgaga gatccaagaa cggtgaacta cttgaagcct ttggttctgg tactgctgcg   960
attgtttctc ccattaagga aatcggctgg aaaggcgaac aaattaatat tccgttgttg  1020
cccggcgaac aaaccggtcc attggccaaa gaagttgcac aatggattaa tggaatccaa  1080
tatgggcgaga ctgagcatgg caattggtca agggttgtta ctgatttgaa ctga        1134
```

<210> SEQ ID NO 23
<211> LENGTH: 377
<212> TYPE: PRT
<213> ORGANISM: Saccharomyces cerevisiae
<220> FEATURE:
<223> OTHER INFORMATION: Cytosolic branched-chain amino acid (BCAA) aminotransferase (BAT2)
<220> FEATURE:
<223> OTHER INFORMATION: Cytosolic branched-chain amino acid (BCAA) aminotransferase (BAT2)

<400> SEQUENCE: 23

```
Met Met Thr Leu Ala Pro Leu Asp Ala Ser Lys Val Lys Ile Thr Thr
  1               5                  10                  15

Thr Gln His Ala Ser Lys Pro Lys Pro Asn Ser Glu Leu Val Phe Gly
                 20                  25                  30

Lys Ser Phe Thr Asp His Met Leu Thr Ala Glu Trp Thr Ala Glu Lys
             35                  40                  45

Gly Trp Gly Thr Pro Glu Ile Lys Pro Tyr Gln Asn Leu Ser Leu Asp
         50                  55                  60

Pro Ser Ala Val Val Phe His Tyr Ala Phe Glu Leu Phe Glu Gly Met
 65                  70                  75                  80

Lys Ala Tyr Arg Thr Val Asp Asn Lys Ile Thr Met Phe Arg Pro Asp
                 85                  90                  95
```

```
Met Asn Met Lys Arg Met Asn Lys Ser Ala Gln Arg Ile Cys Leu Pro
            100                 105                 110

Thr Phe Asp Pro Glu Glu Leu Ile Thr Leu Ile Gly Lys Leu Ile Gln
        115                 120                 125

Gln Asp Lys Cys Leu Val Pro Glu Gly Lys Gly Tyr Ser Leu Tyr Ile
    130                 135                 140

Arg Pro Thr Leu Ile Gly Thr Thr Ala Gly Leu Gly Val Ser Thr Pro
145                 150                 155                 160

Asp Arg Ala Leu Leu Tyr Val Ile Cys Cys Pro Val Gly Pro Tyr Tyr
                165                 170                 175

Lys Thr Gly Phe Lys Ala Val Arg Leu Glu Ala Thr Asp Tyr Ala Thr
            180                 185                 190

Arg Ala Trp Pro Gly Gly Cys Gly Asp Lys Lys Leu Gly Ala Asn Tyr
        195                 200                 205

Ala Pro Cys Val Leu Pro Gln Leu Gln Ala Ala Ser Arg Gly Tyr Gln
    210                 215                 220

Gln Asn Leu Trp Leu Phe Gly Pro Asn Asn Ile Thr Glu Val Gly
225                 230                 235                 240

Thr Met Asn Ala Phe Phe Val Phe Lys Asp Ser Lys Thr Gly Lys Lys
                245                 250                 255

Glu Leu Val Thr Ala Pro Leu Asp Gly Thr Ile Leu Glu Gly Val Thr
            260                 265                 270

Arg Asp Ser Ile Leu Asn Leu Ala Lys Glu Arg Leu Glu Pro Ser Glu
        275                 280                 285

Trp Thr Ile Ser Glu Arg Tyr Phe Thr Ile Gly Glu Val Thr Glu Arg
    290                 295                 300

Ser Lys Asn Gly Glu Leu Leu Glu Ala Phe Gly Ser Gly Thr Ala Ala
305                 310                 315                 320

Ile Val Ser Pro Ile Lys Glu Ile Gly Trp Lys Gly Glu Gln Ile Asn
                325                 330                 335

Ile Pro Leu Leu Pro Gly Glu Gln Thr Gly Pro Leu Ala Lys Glu Val
            340                 345                 350

Ala Gln Trp Ile Asn Gly Ile Gln Tyr Gly Glu Thr Glu His Gly Asn
        355                 360                 365

Trp Ser Arg Val Val Thr Asp Leu Asn
    370                 375

<210> SEQ ID NO 24
<211> LENGTH: 939
<212> TYPE: DNA
<213> ORGANISM: Lactococcus lactis
<220> FEATURE:
<223> OTHER INFORMATION: 2-hydroxyacide dehydrogenase (KDH)
<220> FEATURE:
<223> OTHER INFORMATION: 2-hydroxyacide dehydrogenase (KDH)

<400> SEQUENCE: 24
atgcgaatta cgatagcggg tgctggtgct atgggctctc gcttcggatt aatgcttcac      60
cgcggtggca atgaagttac cctagtggat ggatggttgg aacatgttac agccatcaaa     120
gagcatggat acaggcgaa tttcaatggt gaagagataa cggctcacct ttctgtagaa      180
ctccaatcca atattagcag tgaggagaaa acagacctca ttatactctt caccaaggca     240
atgcagttgg ataaaatgct tcaagacatc aagcccttga tagccgaaca tacgaaggtg     300
ctgtgcctct taaatggcat aggccatgaa gacattattg aaaagtatgt gagtaagaac     360
aatattttca tcggtaatac tatgtggaca gccggacttg aaggaccggg aaaggccaaa     420
```

```
ttattcggca atgggagcgt agaactacaa aacttcattc ctggtgagga agagacggcc    480
aagaaactag ctgacatcct gagcgcctct gggttaaatg ccaattattc cgacaacatc    540
cattactcaa tttaccggaa agcatgcgtt aacggcacca tgaacggctt gtgcacaatc    600
ttggacacca acatggccgg tctgggtgcc acaaagccag cgcatgacat ggtggttaca    660
attgtaaagg agtttgccgc tgtggcaaaa cacgaggatg ttaatcttga catagacgaa    720
gtggttgaac atgtagaaac atgcttcgat cccgaaacta ttggcttgca ctacccatcg    780
atgtatcaag acctgattaa taacaatcgt tgactgaga tagactacat aaatggagct    840
gtttctagga agggcaagaa gtaccaaatc gccacccctt attgtgactt cttgactcaa    900
ttagttcata gtaaagagga gttgctcaaa gcaaaataa                          939

<210> SEQ ID NO 25
<211> LENGTH: 939
<212> TYPE: DNA
<213> ORGANISM: Lactococcus lactis
<220> FEATURE:
<223> OTHER INFORMATION: 2-hydroxyacide dehydrogenase (KDH)
<220> FEATURE:
<223> OTHER INFORMATION: 2-hydroxyacide dehydrogenase (KDH)

<400> SEQUENCE: 25
atgagaatca caatcgccgg agccggggct atgggatctc gctttggact tatgttacat     60
aagggtggaa atgaagtaac gttaatcgac ggttggccag agcatgtaaa agcaatcaaa    120
gaacatggct tgagagctaa ctataacggt gaagaattga cagctcactt gtctgtggag    180
cttcaaagcg aaatcagttc taagaaaag accgacctca tcatactgtt cacgaaagct    240
atgcagcttg ataagatgct ccaagatata aaacccctga tagatgagca cacgaaggtc    300
ctatgtcttt taaatggcat tggacacgag gacacgattg aaaagtatgt gtccaagaat    360
aacatttcca ttggaaacac aatgtggact gcggggttgg aaggccctgg taaagctaag    420
ttgttcggag atggttctgt ggaactacaa aaccttatta gcggggaaga agaaaccgca    480
aagaagctcg cagaaattct ttcggaatca ggtctaaatg caaatatttc caacaacatt    540
cattactcaa tctaccgtaa ggcgtgcgtt aatggaacca tgaatggttt gtgtacaatt    600
ttagacacga atatggccgg tttaggcgag acaaagcctg cgcatgatat ggtcgttacc    660
atcgtcaatg aatttgctgc cgtggctaag tttgagaatg ttaatctcga cattgctgaa    720
gtggtacagc atgttgaaac ttgcttcgat ccgtccacaa ttggcttaca ttacccatct    780
atgtatcagg acttaatcaa gaataatcgt cttacagaga ttgattatat aaatggcgcc    840
gtttcccgaa agggcaagaa gtacaacgtc gcaactccat attgtgactt cttgactcag    900
ttagtacata gtaaagagga actgctaaag gcaaagtaa                          939

<210> SEQ ID NO 26
<211> LENGTH: 312
<212> TYPE: PRT
<213> ORGANISM: Lactococcus lactis
<220> FEATURE:
<223> OTHER INFORMATION: 2-hydroxyacide dehydrogenase (KDH)
<220> FEATURE:
<223> OTHER INFORMATION: 2-hydroxyacide dehydrogenase (KDH)

<400> SEQUENCE: 26

Met Arg Ile Thr Ile Ala Gly Ala Gly Ala Met Gly Ser Arg Phe Gly
 1               5                  10                  15

Leu Met Leu His Arg Gly Gly Asn Glu Val Thr Leu Val Asp Gly Trp
```

```
            20                  25                  30
Leu Glu His Val Thr Ala Ile Lys Glu His Gly Leu Gln Ala Asn Phe
            35                  40                  45

Asn Gly Glu Glu Ile Thr Ala His Leu Ser Val Glu Leu Gln Ser Asn
        50                  55                  60

Ile Ser Ser Glu Glu Lys Thr Asp Leu Ile Ile Leu Phe Thr Lys Ala
65                  70                  75                  80

Met Gln Leu Asp Lys Met Leu Gln Asp Ile Lys Pro Leu Ile Ala Glu
                85                  90                  95

His Thr Lys Val Leu Cys Leu Leu Asn Gly Ile Gly His Glu Asp Ile
            100                 105                 110

Ile Glu Lys Tyr Val Ser Lys Asn Asn Ile Phe Ile Gly Asn Thr Met
            115                 120                 125

Trp Thr Ala Gly Leu Glu Gly Pro Gly Lys Ala Lys Leu Phe Gly Asn
        130                 135                 140

Gly Ser Val Glu Leu Gln Asn Phe Ile Pro Gly Glu Glu Thr Ala
145                 150                 155                 160

Lys Lys Leu Ala Asp Ile Leu Ser Ala Ser Gly Leu Asn Ala Asn Tyr
                165                 170                 175

Ser Asp Asn Ile His Tyr Ser Ile Tyr Arg Lys Ala Cys Val Asn Gly
            180                 185                 190

Thr Met Asn Gly Leu Cys Thr Ile Leu Asp Thr Asn Met Ala Gly Leu
        195                 200                 205

Gly Ala Thr Lys Pro Ala His Asp Met Val Val Thr Ile Val Lys Glu
    210                 215                 220

Phe Ala Ala Val Ala Lys His Glu Asp Val Asn Leu Asp Ile Asp Glu
225                 230                 235                 240

Val Val Glu His Val Glu Thr Cys Phe Asp Pro Glu Thr Ile Gly Leu
                245                 250                 255

His Tyr Pro Ser Met Tyr Gln Asp Leu Ile Asn Asn Asn Arg Leu Thr
            260                 265                 270

Glu Ile Asp Tyr Ile Asn Gly Ala Val Ser Arg Lys Gly Lys Lys Tyr
        275                 280                 285

Gln Ile Ala Thr Pro Tyr Cys Asp Phe Leu Thr Gln Leu Val His Ser
    290                 295                 300

Lys Glu Glu Leu Leu Lys Ala Lys
305                 310

<210> SEQ ID NO 27
<211> LENGTH: 312
<212> TYPE: PRT
<213> ORGANISM: Lactococcus lactis
<220> FEATURE:
<223> OTHER INFORMATION: 2-hydroxyacide dehydrogenase (KDH)
<220> FEATURE:
<223> OTHER INFORMATION: 2-hydroxyacide dehydrogenase (KDH)

<400> SEQUENCE: 27

Met Arg Ile Thr Ile Ala Gly Ala Gly Ala Met Gly Ser Arg Phe Gly
1               5                   10                  15

Leu Met Leu His Lys Gly Gly Asn Glu Val Thr Leu Ile Asp Gly Trp
            20                  25                  30

Pro Glu His Val Lys Ala Ile Lys Glu His Gly Leu Arg Ala Asn Tyr
            35                  40                  45

Asn Gly Glu Glu Leu Thr Ala His Leu Ser Val Glu Leu Gln Ser Glu
        50                  55                  60
```

```
Ile Ser Ser Lys Glu Lys Thr Asp Leu Ile Ile Leu Phe Thr Lys Ala
 65                 70                  75                  80

Met Gln Leu Asp Lys Met Leu Gln Asp Ile Lys Pro Leu Ile Asp Glu
                 85                  90                  95

His Thr Lys Val Leu Cys Leu Leu Asn Gly Ile Gly His Glu Asp Thr
            100                 105                 110

Ile Glu Lys Tyr Val Ser Lys Asn Asn Ile Phe Ile Gly Asn Thr Met
        115                 120                 125

Trp Thr Ala Gly Leu Glu Gly Pro Gly Lys Ala Lys Leu Phe Gly Asp
130                 135                 140

Gly Ser Val Glu Leu Gln Asn Leu Ile Ser Gly Glu Glu Thr Ala
145                 150                 155                 160

Lys Lys Leu Ala Glu Ile Leu Ser Glu Ser Gly Leu Asn Ala Lys Tyr
                165                 170                 175

Ser Asn Asn Ile His Tyr Ser Ile Tyr Arg Lys Ala Cys Val Asn Gly
            180                 185                 190

Thr Met Asn Gly Leu Cys Thr Ile Leu Asp Thr Asn Met Ala Gly Leu
        195                 200                 205

Gly Glu Thr Lys Pro Ala His Asp Met Val Thr Ile Val Asn Glu
210                 215                 220

Phe Ala Ala Val Ala Lys Phe Glu Asn Val Asn Leu Asp Ile Ala Glu
225                 230                 235                 240

Val Val Gln His Val Glu Thr Cys Phe Asp Pro Ser Thr Ile Gly Leu
                245                 250                 255

His Tyr Pro Ser Met Tyr Gln Asp Leu Ile Lys Asn Asn Arg Leu Thr
            260                 265                 270

Glu Ile Asp Tyr Ile Asn Gly Ala Val Ser Arg Lys Gly Lys Lys Tyr
        275                 280                 285

Asn Val Ala Thr Pro Tyr Cys Asp Phe Leu Thr Gln Leu Val His Ser
290                 295                 300

Lys Glu Glu Leu Leu Lys Ala Lys
305                 310
```

<210> SEQ ID NO 28
<211> LENGTH: 1908
<212> TYPE: DNA
<213> ORGANISM: Saccharomyces cerevisiae
<220> FEATURE:
<223> OTHER INFORMATION: Phenylpyruvate decarboxylase (ARO10)
<220> FEATURE:
<223> OTHER INFORMATION: Phenylpyruvate decarboxylase (ARO10)

<400> SEQUENCE: 28

```
atggcacctg ttacaattga aaagttcgta aatcaagaag aacgacacct tgtttccaac    60
cgatcagcaa caattccgtt tggtgaatac atatttaaaa gattgttgtc catcgatacg   120
aaatcagttt tcggtgttcc tggtgacttc aacttatctc tattagaata tctctattca   180
cctagtgttg aatcagctgg cctaagatgg gtcggcacgt gtaatgaact gaacgccgct   240
tatgcggccg acggatattc ccgttactct aataagattg ctgtttaat aaccacgtat   300
ggcgttggtg aattaagcgc cttgaacggt atagccggtt cgttcgctga aatgtcaaa   360
gttttgcaca ttgttggtgt ggccaagtcc atagattcgc gttcaagtaa ctttagtgat   420
cggaacctac atcatttggt cccacagcta catgattcaa attttaaagg gccaaatcat   480
aaagtatatc atgatatggt aaaagataga gtcgcttgct cggtagccta cttggaggat   540
```

```
attgaaactg catgtgacca agtcgataat gttatccgcg atatttacaa gtattctaaa    600
cctggttata tttttgttcc tgcagatttt gcggatatgt ctgttacatg tgataatttg    660
gttaatgttc cacgtatatc tcaacaagat tgtatagtat acccttctga aaaccaattg    720
tctgacataa tcaacaagat tactagttgg atatattcca gtaaaacacc tgcgatcctt    780
ggagacgtac tgactgatag gtatggtgtg agtaacttt tgaacaagct tatctgcaaa     840
actgggattt ggaattttc cactgttatg ggaaaatctg taattgatga gtcaaaccca     900
acttatatgg gtcaatataa tggtaaagaa ggttttaaaac aagtctatga acattttgaa   960
ctgtgcgact tggtcttgca tttttggagtc gacatcaatg aaattaataa tgggcattat  1020
acttttactt ataaaccaaa tgctaaaatc attcaattc atccgaatta tattcgcctt    1080
gtggacacta ggcagggcaa tgagcaaatg ttcaaaggaa tcaatttgc ccctatttta    1140 aaagaactat acaagcgcat tgacgtttct aaactttctt tgcaatatga ttcaaatgta   1200
actcaatata cgaacgaaac aatgcggtta gaagatccta ccaatggaca atcaagcatt   1260
attacacaag ttcacttaca aaagacgatg cctaaatttt tgaaccctgg tgatgttgtc   1320
gtttgtgaaa caggctcttt tcaattctct gttcgtgatt tcgcgtttcc ttcgcaatta   1380
aaatatatat cgcaaggatt tttcctttcc attggcatgg cccttcctgc cgccctaggt   1440
gttggaattg ccatgcaaga ccactcaaac gctcacatca atggtggcaa cgtaaaagag   1500
gactataagc aagattaat tttgtttgaa ggtgacggtg cagcacagat gacaatccaa   1560
gaactgagca ccattctgaa gtgcaatatt ccactagaag ttatcatttg gaacaataac   1620
ggctacacta ttgaaagagc catcatgggc cctaccaggt cgtataacga cgttatgtct   1680
tggaaatgga ccaaactatt tgaagcattc ggagacttcg acggaaagta tactaatagc   1740
actctcattc aatgtccctc taaattagca ctgaaattgg aggagcttaa gaattcaaac   1800
aaaagaagcg ggatagaact tttagaagtc aaattaggcg aattggattt ccccgaacag   1860
ctaaagtgca tggttgaagc agcggcactt aaaagaaata aaaaatag                 1908
```

<210> SEQ ID NO 29
<211> LENGTH: 635
<212> TYPE: PRT
<213> ORGANISM: Saccharomyces cerevisiae
<220> FEATURE:
<223> OTHER INFORMATION: Phenylpyruvate decarboxylase (ARO10)
<220> FEATURE:
<223> OTHER INFORMATION: Phenylpyruvate decarboxylase (ARO10)

<400> SEQUENCE: 29

```
Met Ala Pro Val Thr Ile Glu Lys Phe Val Asn Gln Glu Glu Arg His
1               5                   10                  15

Leu Val Ser Asn Arg Ser Ala Thr Ile Pro Phe Gly Glu Tyr Ile Phe
            20                  25                  30

Lys Arg Leu Leu Ser Ile Asp Thr Lys Ser Val Phe Gly Val Pro Gly
        35                  40                  45

Asp Phe Asn Leu Ser Leu Leu Glu Tyr Leu Tyr Ser Pro Ser Val Glu
    50                  55                  60

Ser Ala Gly Leu Arg Trp Val Gly Thr Cys Asn Glu Leu Asn Ala Ala
65                  70                  75                  80

Tyr Ala Ala Asp Gly Tyr Ser Arg Tyr Ser Asn Lys Ile Gly Cys Leu
                85                  90                  95

Ile Thr Thr Tyr Gly Val Gly Glu Leu Ser Ala Leu Asn Gly Ile Ala
            100                 105                 110
```

```
Gly Ser Phe Ala Glu Asn Val Lys Val Leu His Ile Gly Val Ala
        115                 120                 125
Lys Ser Ile Asp Ser Arg Ser Asn Phe Ser Asp Arg Asn Leu His
130                 135                 140
His Leu Val Pro Gln Leu His Asp Ser Asn Phe Lys Gly Pro Asn His
145                 150                 155                 160
Lys Val Tyr His Asp Met Val Lys Asp Arg Val Ala Cys Ser Val Ala
                165                 170                 175
Tyr Leu Glu Asp Ile Glu Thr Ala Cys Asp Gln Val Asp Asn Val Ile
                180                 185                 190
Arg Asp Ile Tyr Lys Tyr Ser Lys Pro Gly Tyr Ile Phe Val Pro Ala
195                 200                 205
Asp Phe Ala Asp Met Ser Val Thr Cys Asp Asn Leu Val Asn Val Pro
        210                 215                 220
Arg Ile Ser Gln Gln Asp Cys Ile Val Tyr Pro Ser Glu Asn Gln Leu
225                 230                 235                 240
Ser Asp Ile Ile Asn Lys Ile Thr Ser Trp Ile Tyr Ser Ser Lys Thr
                245                 250                 255
Pro Ala Ile Leu Gly Asp Val Leu Thr Asp Arg Tyr Gly Val Ser Asn
                260                 265                 270
Phe Leu Asn Lys Leu Ile Cys Lys Thr Gly Ile Trp Asn Phe Ser Thr
        275                 280                 285
Val Met Gly Lys Ser Val Ile Asp Glu Ser Asn Pro Thr Tyr Met Gly
        290                 295                 300
Gln Tyr Asn Gly Lys Glu Gly Leu Lys Gln Val Tyr Glu His Phe Glu
305                 310                 315                 320
Leu Cys Asp Leu Val Leu His Phe Gly Val Asp Ile Asn Glu Ile Asn
                325                 330                 335
Asn Gly His Tyr Thr Phe Thr Tyr Lys Pro Asn Ala Lys Ile Ile Gln
                340                 345                 350
Phe His Pro Asn Tyr Ile Arg Leu Val Asp Thr Arg Gln Gly Asn Glu
        355                 360                 365
Gln Met Phe Lys Gly Ile Asn Phe Ala Pro Ile Leu Lys Glu Leu Tyr
        370                 375                 380
Lys Arg Ile Asp Val Ser Lys Leu Ser Leu Gln Tyr Asp Ser Asn Val
385                 390                 395                 400
Thr Gln Tyr Thr Asn Glu Thr Met Arg Leu Glu Asp Pro Thr Asn Gly
                405                 410                 415
Gln Ser Ser Ile Ile Thr Gln Val His Leu Gln Lys Thr Met Pro Lys
                420                 425                 430
Phe Leu Asn Pro Gly Asp Val Val Cys Glu Thr Gly Ser Phe Gln
        435                 440                 445
Phe Ser Val Arg Asp Phe Ala Phe Pro Ser Gln Leu Lys Tyr Ile Ser
        450                 455                 460
Gln Gly Phe Phe Leu Ser Ile Gly Met Ala Leu Pro Ala Ala Leu Gly
465                 470                 475                 480
Val Gly Ile Ala Met Gln Asp His Ser Asn Ala His Ile Asn Gly Gly
                485                 490                 495
Asn Val Lys Glu Asp Tyr Lys Pro Arg Leu Ile Leu Phe Glu Gly Asp
                500                 505                 510
Gly Ala Ala Gln Met Thr Ile Gln Glu Leu Ser Thr Ile Leu Lys Cys
                515                 520                 525
Asn Ile Pro Leu Glu Val Ile Ile Trp Asn Asn Asn Gly Tyr Thr Ile
```

```
              530             535             540
Glu Arg Ala Ile Met Gly Pro Thr Arg Ser Tyr Asn Asp Val Met Ser
545             550             555             560

Trp Lys Trp Thr Lys Leu Phe Glu Ala Phe Gly Asp Phe Asp Gly Lys
            565             570             575

Tyr Thr Asn Ser Thr Leu Ile Gln Cys Pro Ser Lys Leu Ala Leu Lys
            580             585             590

Leu Glu Glu Leu Lys Asn Ser Asn Lys Arg Ser Gly Ile Glu Leu Leu
            595             600             605

Glu Val Lys Leu Gly Glu Leu Asp Phe Pro Glu Gln Leu Lys Cys Met
610             615             620

Val Glu Ala Ala Ala Leu Lys Arg Asn Lys Lys
625             630             635

<210> SEQ ID NO 30
<211> LENGTH: 1341
<212> TYPE: DNA
<213> ORGANISM: Lactococcus lactis
<220> FEATURE:
<223> OTHER INFORMATION: NADH oxidase (NOXE)
<220> FEATURE:
<223> OTHER INFORMATION: NADH oxidase (NOXE)

<400> SEQUENCE: 30
```

| | | | | | |
|---|---|---|---|---|---|
| atgggtattg | tcgtaatagg | tactaaccat | gccggaatag | ctacagcaaa | taccttaatc       60 |
| gaccaatatc | caggacatga | aattgttatg | attgacagaa | actcgaatat | gagttatctt      120 |
| ggctgtggta | cagcgatttg | ggttgggaga | caaatcgaga | aacctgatga | acttttctat      180 |
| gcaaaagcag | aagatttcga | aaagaagggt | gttaaaatcc | tgaccgagac | tgaagtgtca      240 |
| gaaatcgact | ttaccaacaa | aatgatatat | gccaaaagca | agactgggga | aaaatcacg       300 |
| gaatcttatg | ataagctagt | attggcaaca | ggaagcagac | caatcatacc | caatttgcct      360 |
| ggtaaagatc | ttaaaggaat | tcatttctta | aagttattcc | aggaaggtca | agccattgac      420 |
| gaagaattcg | caaagaatga | cgtgaaaaga | atcgcggtaa | ttggtgctgg | ttatattgga      480 |
| acagagatag | ctgaagcagc | taaacgtaga | gggaaagaag | tgttgttgtt | tgatgctgaa      540 |
| agtacctcat | tagcgtcata | ctacgacgaa | gaatttgcca | aaggcatgga | tgaaaatttg      600 |
| gcacaacacg | ggattgagtt | gcactttggt | gaacttgccc | aagagttcaa | ggcaaatgaa      660 |
| gaaggtcatg | tctcccagat | tgttacaaac | aaatccactt | atgatgtgga | tctggtcatc      720 |
| aattgcatag | atttactgc | caattcagcc | ttagctggtg | agcatctaga | aacgtttaag      780 |
| aacggtgcca | taaggttaa | taagcatcaa | caatctagtg | atccagacgt | gtatgcagtt      840 |
| ggtgatgttg | caactatcta | ctctaacgct | ttgcaagact | ttacttacat | cgctttagct      900 |
| agcaatgctg | ttagatcagg | cattgttgct | ggacacaata | ttggcggtaa | atccatagaa      960 |
| tctgtcggtg | ttcagggtag | taacggcatt | tctatattcg | gatacaatat | gacaagtact     1020 |
| ggtttatcag | taaaagctgc | taagaagatt | ggtctagaag | tctccttttc | tgattttgaa     1080 |
| gataagcaaa | aggcttggtt | tctgcatgag | aacaatgatt | cggtcaaaat | aaggatcgta     1140 |
| tacgaaacaa | aatccaggag | aataattggc | gcacaattgg | catcgaaatc | agagattata     1200 |
| gcgggcaaca | ttaacatgtt | ctctttagcc | attcaggaaa | agaaaacgat | tgatgagtta     1260 |
| gccctattgg | atttgttctt | tctgcctcac | tttaactctc | cgtacaatta | tatgaccgta     1320 |
| gctgcgttga | atgctaaata | a | | |     1341 |

<210> SEQ ID NO 31
<211> LENGTH: 1380
<212> TYPE: DNA
<213> ORGANISM: Streptococcus pneumoniae
<220> FEATURE:
<223> OTHER INFORMATION: NADH oxidase (NOXE)
<220> FEATURE:
<223> OTHER INFORMATION: NADH oxidase (NOXE)

<400> SEQUENCE: 31

| | | | | | |
|---|---|---|---|---|---|
| atgtctaaga | tagtggtagt | tggtgctaac | catgcaggaa | ctgcttgcat | caatacgatg | 60 |
| ttggataatt | tcggcaatga | aaatgagata | gtggtgtttg | atcagaattc | caacatcagc | 120 |
| tttctaggtt | gtggtatggc | gttatggatt | ggggagcaaa | tagatggtgc | tgaagggttg | 180 |
| ttttactcag | acaaagagaa | attggaagcc | aaaggtgcca | agtctacat | gaattcgcca | 240 |
| gtcctgagta | tagactatga | caacaaagtg | gtaactgcag | aagtagaagg | caaagagcac | 300 |
| aaagaatcct | atgagaaact | gatctttgct | actggttcaa | caccgatttt | accacctatt | 360 |
| gaaggagtcg | agatcgttaa | aggtaataga | gaatttaagg | ccacacttga | aaacgtacaa | 420 |
| tttgttaagt | tgtatcagaa | tgctgaagaa | gtcatcaaca | agctttcaga | taaaagccag | 480 |
| catttagata | ggattgctgt | tgttggaggt | ggatacattg | tgttgaatt | ggctgaagcc | 540 |
| tttgaaagac | taggaaaaga | agttgtgtta | gttgacattg | tggacactgt | cttaaacggg | 600 |
| tattatgaca | agatttcac | ccaaatgatg | gccaagaatc | ttgaggatca | aacattaga | 660 |
| cttgctttag | gccaaacagt | gaaggctatt | gaaggcgatg | gtaaggtaga | aaggttgatt | 720 |
| acagacaagg | agtctttcga | tgttgacatg | gtcattttag | cagtaggatt | tagaccaaac | 780 |
| actgctttgg | cagatgggaa | aattgaattg | tttagaaatg | gtgcttttct | ggtggataag | 840 |
| aaacaagaaa | cttcaatacc | cgatgtttat | gcagttggtg | attgtgcaac | agtctatgat | 900 |
| aatgccagaa | aggatacttc | ctacatagca | ttggcatcta | atgcagttag | aacgggcatt | 960 |
| gttggtgctt | ataatgcctg | tggtcatgaa | ttggagggca | ttggtgtcca | aggttctaat | 1020 |
| ggtatatcga | tttatggcct | tcatatggtt | agtaccggat | tgactctgga | aaggccaaa | 1080 |
| gctgctggat | acaatgcgac | agaaacaggt | ttcaacgatt | tacagaagcc | agagtttatg | 1140 |
| aaacacgaca | accatgaagt | agcgatcaaa | atcgtatttg | acaaggattc | tcgtgaaatt | 1200 |
| ctagggggcac | aaatggtttc | acacgatata | gcgataagta | tgggcatcca | tatgttctct | 1260 |
| ctagcgattc | aagaacatgt | taccatagat | aaattagcat | taaccgatct | attcttcttg | 1320 |
| cctcatttca | caaaccttta | caattacatc | acgatggcag | ctttgaccgc | cgaaaagtaa | 1380 |

<210> SEQ ID NO 32
<211> LENGTH: 1341
<212> TYPE: DNA
<213> ORGANISM: Enterococcus faecalis
<220> FEATURE:
<223> OTHER INFORMATION: NADH oxidase (NOXE)
<220> FEATURE:
<223> OTHER INFORMATION: NADH oxidase (NOXE)

<400> SEQUENCE: 32

| | | | | | |
|---|---|---|---|---|---|
| atgtctgtgg | ttgtcgtagg | ctgtacacat | gctggtacta | gtgcagtgaa | atctatccta | 60 |
| gctaatcatc | ccgaagctga | agtcactgtt | tatgaacgta | atgacaacat | atccttcttg | 120 |
| tcttgtggaa | ttgcacttta | tgttggaggt | gtagttaaga | atgctgccga | cttattttac | 180 |
| agcaatcctg | aggaattagc | cagtttagga | gccactgtga | aaatggaaca | caacgtagaa | 240 |
| gagatcaatg | tcgatgataa | gacagttacg | gcaaagaatc | tacaaacagg | tgcaacagaa | 300 |

```
accgtatcct acgataagtt ggtcatgact actggaagtt ggcctataat tccaccaata       360
cccggaattg atgctgagaa cattctactt tgcaagaatt attctcaagc gaatgtcatt       420
atcgaaaagg ccaaagatgc gaaaagagtc gttgtcgttg gtggtggcta tattggtata       480
gagttagttg aagcttttgt tgaaagcggt aaacaggtga ccctagttga tggtctagac       540
aggattttga acaagtattt ggacaaaccg tttactgatg ttttagaaaa ggagttagtt       600
gatagaggtg tgaacttagc cttaggtgaa aatgtccaac agtttgtagc tgatgaacag       660
ggaaaagttg caaaagttat cactccatct caagaattcg aagcagacat ggtcataatg       720
tgtgttggct ttagaccaaa taccgaactt ttgaaagaca agttgatat gttgcctaac        780
ggtgcaattg aggttaacga gtatatgcaa acgtccaatc cagatatctt tgctgctggt       840
gattcagccg tagtgcatta caccccatcg caaacgaaga attatattcc cttagcgact       900
aatgcagtaa gacagggtat gttggtgggg agaaacttga cagaacagaa acttgcctat       960
agaggcaccc aaggtacgtc tggcttgtac ttgttcggtt ggaaaattgg ctcaacagga      1020
gtaaccaaag aatcggcaaa attgaatggg ttagatgttg aagctacagt ctttgaggat      1080
aactatagac ctgaattcat gccaacaacc gaaaaggtgc tgatggagct ggtgtacgaa      1140
aaggggactc aaaggatagt aggtgggcaa ttgatgtcca aatacgatat cactcaatca      1200
gcgaatacac tttcattggc tgtacagaac aaaatgaccg ttgaagatct ggctatttca      1260
gacttcttct ttcaaccgca ctttgaccgt ccttggaatt acttaaattt gctagcccaa      1320
gcagctctgg agaacatgta a                                                1341

<210> SEQ ID NO 33
<211> LENGTH: 1356
<212> TYPE: DNA
<213> ORGANISM: Lactobacillus brevis
<220> FEATURE:
<223> OTHER INFORMATION: NADH oxidase (NOXE)
<220> FEATURE:
<223> OTHER INFORMATION: NADH oxidase (NOXE)

<400> SEQUENCE: 33
atgtctaagg ttaccgtggt aggttgtaca catgccggta cttttgcaat caaacagatt        60
ttggcagaac atcctgatgc agaagtaaca gtctatgaga gaaatgacgt gattagcttc       120
ttgtcgtgtg gcatagcgtt gtacttgggt gggaaagttg ctgaccctca agggcttttc       180
tactcatcac cagaagagtt acaaaagctt ggggcgaatg tccaaatgaa ccacaacgtt       240
ttagcgatag atccagatca aaagactgtt actgttgaag atctaacgag tcatgctcag       300
acaacagaat cctatgacaa gttagtcatg acttcaggtt cttggccgat agttcccaaa       360
ataccaggta ttgactccga tagagtcaag ctgtgcaaga attgggctca tgcacaagct       420
ttgattgaag atgctaaaga agcgaaaaga attactgtca ttggcgctgg ttatatcggt       480
gccgaattgg ccgaagcgta ttctactaca ggtcacgacg taacgttgat agacgcaatg       540
gatagagtaa tgcccaaata ctttgatgca gattttaccg atgtcattga gcaagattat       600
cgtgatcatg gagtgcaatt agccttgagt gaaactgttg aatcgtttac agacagtgct       660
acaggattga ccataaagac tgacaagaat agttacgaaa cagatcttgc catcttatgc       720
attggcttta gaccaaatac ggatctgctg aaaggaaaag ttgatatggc accaaatggt       780
gctattatta ccgatgacta tatgcgttcc tctaatccgg acatatttgc tgcaggagac       840
tctgctgcag ttcactataa ccctacacac cagaatgcat atatcccact agccacaaat       900
gctgtgagac aaggtatatt agtaggcaag aatttggtca aaccgaccgt taaatacatg       960
```

```
ggtacgcaaa gctcttcagg tcttgccctg tacgatagga ctattgtttc gaccggctta   1020
acgctagcag cagctaaaca acagggtgtt aatgctgaac aggtgatcgt tgaggacaat   1080
tatagacctg agtttatgcc ttcaactgaa cccgtgctaa tgagcttagt ctttgatcca   1140
gatactcata ggatcttagg aggagctttg atgtccaaat acgatgtatc ccagtctgca   1200
aacaccttgt ctgtgtgtat ccaaaacgag aatactattg atgacttagc catggttgat   1260
atgcttttcc aacctaactt cgatagacca ttcaactatc taaacatttt ggctcaagct   1320
gctcaagcca aagtagctca atcagtaaac gcctag                             1356
```

<210> SEQ ID NO 34
<211> LENGTH: 446
<212> TYPE: PRT
<213> ORGANISM: Lactobacillus lactis
<220> FEATURE:
<223> OTHER INFORMATION: NADH oxidase (NOXE)
<220> FEATURE:
<223> OTHER INFORMATION: NADH oxidase (NOXE)

<400> SEQUENCE: 34

```
Met Gly Ile Val Val Ile Gly Thr Asn His Ala Gly Ile Ala Thr Ala
1               5                   10                  15

Asn Thr Leu Ile Asp Gln Tyr Pro Gly His Glu Ile Val Met Ile Asp
                20                  25                  30

Arg Asn Ser Asn Met Ser Tyr Leu Gly Cys Gly Thr Ala Ile Trp Val
            35                  40                  45

Gly Arg Gln Ile Glu Lys Pro Asp Glu Leu Phe Tyr Ala Lys Ala Glu
        50                  55                  60

Asp Phe Glu Lys Lys Gly Val Lys Ile Leu Thr Glu Thr Glu Val Ser
65                  70                  75                  80

Glu Ile Asp Phe Thr Asn Lys Met Ile Tyr Ala Lys Ser Lys Thr Gly
                85                  90                  95

Glu Lys Ile Thr Glu Ser Tyr Asp Lys Leu Val Leu Ala Thr Gly Ser
            100                 105                 110

Arg Pro Ile Ile Pro Asn Leu Pro Gly Lys Asp Leu Lys Gly Ile His
        115                 120                 125

Phe Leu Lys Leu Phe Gln Glu Gly Gln Ala Ile Asp Glu Glu Phe Ala
    130                 135                 140

Lys Asn Asp Val Lys Arg Ile Ala Val Ile Gly Ala Gly Tyr Ile Gly
145                 150                 155                 160

Thr Glu Ile Ala Glu Ala Ala Lys Arg Arg Gly Lys Glu Val Leu Leu
                165                 170                 175

Phe Asp Ala Glu Ser Thr Ser Leu Ala Ser Tyr Tyr Asp Glu Glu Phe
            180                 185                 190

Ala Lys Gly Met Asp Glu Asn Leu Ala Gln His Gly Ile Glu Leu His
        195                 200                 205

Phe Gly Glu Leu Ala Gln Glu Phe Lys Ala Asn Glu Glu Gly His Val
    210                 215                 220

Ser Gln Ile Val Thr Asn Lys Ser Thr Tyr Asp Val Asp Leu Val Ile
225                 230                 235                 240

Asn Cys Ile Gly Phe Thr Ala Asn Ser Ala Leu Ala Gly Glu His Leu
                245                 250                 255

Glu Thr Phe Lys Asn Gly Ala Ile Lys Val Asn Lys His Gln Gln Ser
            260                 265                 270

Ser Asp Pro Asp Val Tyr Ala Val Gly Asp Val Ala Thr Ile Tyr Ser
```

```
                    275                 280                 285
Asn Ala Leu Gln Asp Phe Thr Tyr Ile Ala Leu Ala Ser Asn Ala Val
    290                 295                 300
Arg Ser Gly Ile Val Ala Gly His Asn Ile Gly Gly Lys Ser Ile Glu
305                 310                 315                 320
Ser Val Gly Val Gln Gly Ser Asn Gly Ile Ser Ile Phe Gly Tyr Asn
                325                 330                 335
Met Thr Ser Thr Gly Leu Ser Val Lys Ala Ala Lys Ile Gly Leu
            340                 345                 350
Glu Val Ser Phe Ser Asp Phe Glu Asp Lys Gln Lys Ala Trp Phe Leu
            355                 360                 365
His Glu Asn Asn Asp Ser Val Lys Ile Arg Ile Val Tyr Glu Thr Lys
            370                 375                 380
Ser Arg Arg Ile Ile Gly Ala Gln Leu Ala Ser Lys Ser Glu Ile Ile
385                 390                 395                 400
Ala Gly Asn Ile Asn Met Phe Ser Leu Ala Ile Gln Glu Lys Lys Thr
                405                 410                 415
Ile Asp Glu Leu Ala Leu Leu Asp Leu Phe Phe Leu Pro His Phe Asn
            420                 425                 430
Ser Pro Tyr Asn Tyr Met Thr Val Ala Ala Leu Asn Ala Lys
            435                 440                 445

<210> SEQ ID NO 35
<211> LENGTH: 459
<212> TYPE: PRT
<213> ORGANISM: Streptococcus pneumoniae
<220> FEATURE:
<223> OTHER INFORMATION: NADH oxidase (NOXE)
<220> FEATURE:
<223> OTHER INFORMATION: NADH oxidase (NOXE)

<400> SEQUENCE: 35

Met Ser Lys Ile Val Val Gly Ala Asn His Ala Gly Thr Ala Cys
1               5                   10                  15

Ile Asn Thr Met Leu Asp Asn Phe Gly Asn Glu Asn Glu Ile Val Val
                20                  25                  30

Phe Asp Gln Asn Ser Asn Ile Ser Phe Leu Gly Cys Gly Met Ala Leu
            35                  40                  45

Trp Ile Gly Glu Gln Ile Asp Gly Ala Glu Gly Leu Phe Tyr Ser Asp
    50                  55                  60

Lys Glu Lys Leu Glu Ala Lys Gly Ala Lys Val Tyr Met Asn Ser Pro
65                  70                  75                  80

Val Leu Ser Ile Asp Tyr Asp Asn Lys Val Val Thr Ala Glu Val Glu
                85                  90                  95

Gly Lys Glu His Lys Glu Ser Tyr Glu Lys Leu Ile Phe Ala Thr Gly
            100                 105                 110

Ser Thr Pro Ile Leu Pro Pro Ile Glu Gly Val Glu Ile Val Lys Gly
            115                 120                 125

Asn Arg Glu Phe Lys Ala Thr Leu Glu Asn Val Gln Phe Val Lys Leu
    130                 135                 140

Tyr Gln Asn Ala Glu Glu Val Ile Asn Lys Leu Ser Asp Lys Ser Gln
145                 150                 155                 160

His Leu Asp Arg Ile Ala Val Val Gly Gly Gly Tyr Ile Gly Val Glu
                165                 170                 175

Leu Ala Glu Ala Phe Glu Arg Leu Gly Lys Glu Val Val Leu Val Asp
            180                 185                 190
```

```
Ile Val Asp Thr Val Leu Asn Gly Tyr Tyr Asp Lys Asp Phe Thr Gln
        195                 200                 205

Met Met Ala Lys Asn Leu Glu Asp His Asn Ile Arg Leu Ala Leu Gly
    210                 215                 220

Gln Thr Val Lys Ala Ile Glu Gly Asp Gly Lys Val Glu Arg Leu Ile
225                 230                 235                 240

Thr Asp Lys Glu Ser Phe Asp Val Asp Met Val Ile Leu Ala Val Gly
                245                 250                 255

Phe Arg Pro Asn Thr Ala Leu Ala Asp Gly Lys Ile Glu Leu Phe Arg
            260                 265                 270

Asn Gly Ala Phe Leu Val Asp Lys Lys Gln Glu Thr Ser Ile Pro Asp
        275                 280                 285

Val Tyr Ala Val Gly Asp Cys Ala Thr Val Tyr Asp Asn Ala Arg Lys
    290                 295                 300

Asp Thr Ser Tyr Ile Ala Leu Ala Ser Asn Ala Val Arg Thr Gly Ile
305                 310                 315                 320

Val Gly Ala Tyr Asn Ala Cys Gly His Glu Leu Glu Gly Ile Gly Val
                325                 330                 335

Gln Gly Ser Asn Gly Ile Ser Ile Tyr Gly Leu His Met Val Ser Thr
            340                 345                 350

Gly Leu Thr Leu Glu Lys Ala Lys Ala Ala Gly Tyr Asn Ala Thr Glu
        355                 360                 365

Thr Gly Phe Asn Asp Leu Gln Lys Pro Glu Phe Met Lys His Asp Asn
    370                 375                 380

His Glu Val Ala Ile Lys Ile Val Phe Asp Lys Asp Ser Arg Glu Ile
385                 390                 395                 400

Leu Gly Ala Gln Met Val Ser His Asp Ile Ala Ile Ser Met Gly Ile
                405                 410                 415

His Met Phe Ser Leu Ala Ile Gln Glu His Val Thr Ile Asp Lys Leu
            420                 425                 430

Ala Leu Thr Asp Leu Phe Phe Leu Pro His Phe Asn Lys Pro Tyr Asn
        435                 440                 445

Tyr Ile Thr Met Ala Ala Leu Thr Ala Glu Lys
    450                 455

<210> SEQ ID NO 36
<211> LENGTH: 446
<212> TYPE: PRT
<213> ORGANISM: Enterococcus faecalis
<220> FEATURE:
<223> OTHER INFORMATION: NADH oxidase (NOXE)
<220> FEATURE:
<223> OTHER INFORMATION: NADH oxidase (NOXE)

<400> SEQUENCE: 36

Met Ser Val Val Val Gly Cys Thr His Ala Gly Thr Ser Ala Val
1               5                   10                  15

Lys Ser Ile Leu Ala Asn His Pro Glu Ala Glu Val Thr Val Tyr Glu
            20                  25                  30

Arg Asn Asp Asn Ile Ser Phe Leu Ser Cys Gly Ile Ala Leu Tyr Val
                35                  40                  45

Gly Gly Val Val Lys Asn Ala Ala Asp Leu Phe Tyr Ser Asn Pro Glu
        50                  55                  60

Glu Leu Ala Ser Leu Gly Ala Thr Val Lys Met Glu His Asn Val Glu
65                  70                  75                  80
```

Glu Ile Asn Val Asp Lys Thr Val Thr Ala Lys Asn Leu Gln Thr
                85                  90                  95

Gly Ala Thr Glu Thr Val Ser Tyr Asp Lys Leu Val Met Thr Thr Gly
            100                 105                 110

Ser Trp Pro Ile Ile Pro Pro Ile Gly Ile Asp Ala Glu Asn Ile
            115                 120                 125

Leu Leu Cys Lys Asn Tyr Ser Gln Ala Asn Val Ile Ile Glu Lys Ala
            130                 135                 140

Lys Asp Ala Lys Arg Val Val Val Gly Gly Tyr Ile Gly Ile
145                 150                 155                 160

Glu Leu Val Glu Ala Phe Val Glu Ser Gly Lys Gln Val Thr Leu Val
                165                 170                 175

Asp Gly Leu Asp Arg Ile Leu Asn Lys Tyr Leu Asp Lys Pro Phe Thr
            180                 185                 190

Asp Val Leu Glu Lys Glu Leu Val Asp Arg Gly Val Asn Leu Ala Leu
            195                 200                 205

Gly Glu Asn Val Gln Gln Phe Val Ala Asp Glu Gln Gly Lys Val Ala
            210                 215                 220

Lys Val Ile Thr Pro Ser Gln Glu Phe Glu Ala Asp Met Val Ile Met
225                 230                 235                 240

Cys Val Gly Phe Arg Pro Asn Thr Glu Leu Leu Lys Asp Lys Val Asp
                245                 250                 255

Met Leu Pro Asn Gly Ala Ile Glu Val Asn Glu Tyr Met Gln Thr Ser
            260                 265                 270

Asn Pro Asp Ile Phe Ala Ala Gly Asp Ser Ala Val Val His Tyr Asn
            275                 280                 285

Pro Ser Gln Thr Lys Asn Tyr Ile Pro Leu Ala Thr Asn Ala Val Arg
290                 295                 300

Gln Gly Met Leu Val Gly Arg Asn Leu Thr Glu Gln Lys Leu Ala Tyr
305                 310                 315                 320

Arg Gly Thr Gln Gly Thr Ser Gly Leu Tyr Leu Phe Gly Trp Lys Ile
                325                 330                 335

Gly Ser Thr Gly Val Thr Lys Glu Ser Ala Lys Leu Asn Gly Leu Asp
            340                 345                 350

Val Glu Ala Thr Val Phe Glu Asp Asn Tyr Arg Pro Glu Phe Met Pro
            355                 360                 365

Thr Thr Glu Lys Val Leu Met Glu Leu Val Tyr Glu Lys Gly Thr Gln
370                 375                 380

Arg Ile Val Gly Gly Gln Leu Met Ser Lys Tyr Asp Ile Thr Gln Ser
385                 390                 395                 400

Ala Asn Thr Leu Ser Leu Ala Val Gln Asn Lys Met Thr Val Glu Asp
                405                 410                 415

Leu Ala Ile Ser Asp Phe Phe Phe Gln Pro His Phe Asp Arg Pro Trp
            420                 425                 430

Asn Tyr Leu Asn Leu Leu Ala Gln Ala Leu Glu Asn Met
            435                 440                 445

<210> SEQ ID NO 37
<211> LENGTH: 451
<212> TYPE: PRT
<213> ORGANISM: Lactobacillus brevis
<220> FEATURE:
<223> OTHER INFORMATION: NADH oxidase (NOXE)
<220> FEATURE:
<223> OTHER INFORMATION: NADH oxidase (NOXE)

```
<400> SEQUENCE: 37

Met Ser Lys Val Thr Val Gly Cys Thr His Ala Gly Thr Phe Ala
1               5                   10                  15

Ile Lys Gln Ile Leu Ala Glu His Pro Asp Ala Glu Val Thr Val Tyr
                20                  25                  30

Glu Arg Asn Asp Val Ile Ser Phe Leu Ser Cys Gly Ile Ala Leu Tyr
            35                  40                  45

Leu Gly Gly Lys Val Ala Asp Pro Gln Gly Leu Phe Tyr Ser Ser Pro
    50                  55                  60

Glu Glu Leu Gln Lys Leu Gly Ala Asn Val Gln Met Asn His Asn Val
65                  70                  75                  80

Leu Ala Ile Asp Pro Asp Gln Lys Thr Val Thr Val Glu Asp Leu Thr
                85                  90                  95

Ser His Ala Gln Thr Thr Glu Ser Tyr Asp Lys Leu Val Met Thr Ser
            100                 105                 110

Gly Ser Trp Pro Ile Val Pro Lys Ile Pro Gly Ile Asp Ser Asp Arg
    115                 120                 125

Val Lys Leu Cys Lys Asn Trp Ala His Ala Gln Ala Leu Ile Glu Asp
130                 135                 140

Ala Lys Glu Ala Lys Arg Ile Thr Val Ile Gly Ala Gly Tyr Ile Gly
145                 150                 155                 160

Ala Glu Leu Ala Glu Ala Tyr Ser Thr Thr Gly His Asp Val Thr Leu
                165                 170                 175

Ile Asp Ala Met Asp Arg Val Met Pro Lys Tyr Phe Asp Ala Asp Phe
            180                 185                 190

Thr Asp Val Ile Glu Gln Asp Tyr Arg Asp His Gly Val Gln Leu Ala
    195                 200                 205

Leu Ser Glu Thr Val Glu Ser Phe Thr Asp Ser Ala Thr Gly Leu Thr
210                 215                 220

Ile Lys Thr Asp Lys Asn Ser Tyr Glu Thr Asp Leu Ala Ile Leu Cys
225                 230                 235                 240

Ile Gly Phe Arg Pro Asn Thr Asp Leu Leu Lys Gly Lys Val Asp Met
                245                 250                 255

Ala Pro Asn Gly Ala Ile Ile Thr Asp Asp Tyr Met Arg Ser Ser Asn
            260                 265                 270

Pro Asp Ile Phe Ala Ala Gly Asp Ser Ala Ala Val His Tyr Asn Pro
    275                 280                 285

Thr His Gln Asn Ala Tyr Ile Pro Leu Ala Thr Asn Ala Val Arg Gln
290                 295                 300

Gly Ile Leu Val Gly Lys Asn Leu Val Lys Pro Thr Val Lys Tyr Met
305                 310                 315                 320

Gly Thr Gln Ser Ser Ser Gly Leu Ala Leu Tyr Asp Arg Thr Ile Val
                325                 330                 335

Ser Thr Gly Leu Thr Leu Ala Ala Ala Lys Gln Gln Gly Val Asn Ala
            340                 345                 350

Glu Gln Val Ile Val Glu Asp Asn Tyr Arg Pro Glu Phe Met Pro Ser
    355                 360                 365

Thr Glu Pro Val Leu Met Ser Leu Val Phe Asp Pro Asp Thr His Arg
370                 375                 380

Ile Leu Gly Gly Ala Leu Met Ser Lys Tyr Asp Val Ser Gln Ser Ala
385                 390                 395                 400

Asn Thr Leu Ser Val Cys Ile Gln Asn Glu Asn Thr Ile Asp Asp Leu
                405                 410                 415
```

```
Ala Met Val Asp Met Leu Phe Gln Pro Asn Phe Asp Arg Pro Phe Asn
            420                 425                 430

Tyr Leu Asn Ile Leu Ala Gln Ala Ala Gln Ala Lys Val Ala Gln Ser
        435                 440                 445

Val Asn Ala
    450

<210> SEQ ID NO 38
<211> LENGTH: 554
<212> TYPE: DNA
<213> ORGANISM: Saccharomyces cerevisiae
<220> FEATURE:
<223> OTHER INFORMATION: pTDH3" <223> "pTDH3
<220> FEATURE:
<223> OTHER INFORMATION: pTDH3
<220> FEATURE:
<223> OTHER INFORMATION: pTDH3

<400> SEQUENCE: 38
ccaaaatagg gggcgggtta cacagaatat ataacatcgt aggtgtctgg gtgaacagtt    60
tattcctggc atccactaaa tataatggag cccgcttttt aagctggcat ccagaaaaaa   120
aaagaatccc agcaccaaaa tattgttttc ttcaccaacc atcagttcat aggtccattc   180
tcttagcgca actacagaga acaggggcac aaacaggcaa aaacgggca caacctcaat   240 ggagtgatgc aacctgcctg gagtaaatga tgacacaagg caattgaccc acgcatgtat   300
ctatctcatt ttcttacacc ttctattacc ttctgctctc tctgatttgg aaaaagctga   360
aaaaaaaggt tgaaaccagt tccctgaaat tattccccta cttgactaat aagtatataa   420
agacggtagg tattgattgt aattctgtaa atctatttct taaacttctt aaattctact   480
tttatagtta gtctttttt tagttttaaa acaccaagaa cttagtttcg aataaacaca   540
cataaacaaa caaa                                                    554

<210> SEQ ID NO 39
<211> LENGTH: 550
<212> TYPE: DNA
<213> ORGANISM: Saccharomyces cerevisiae
<220> FEATURE:
<223> OTHER INFORMATION: pENO2" <223> "pENO2
<220> FEATURE:
<223> OTHER INFORMATION: pENO2
<220> FEATURE:
<223> OTHER INFORMATION: pENO2

<400> SEQUENCE: 39
cgctcagcat ctgcttcttc ccaaagatga acgcggcgtt atgtcactaa cgacgtgcac    60
caacttgcgg aaagtggaat cccgttccaa aactggcatc cactaattga tacatctaca   120
caccgcacgc cttttttctg aagcccactt tcgtggactt tgccatatgc aaaattcatg   180
aagtgtgata ccaagtcagc atacacctca ctagggtagt ttctttggtt gtattgatca   240
tttggttcat cgtggttcat taattttttt tctccattgc tttctggctt tgatcttact   300
atcatttgga tttttgtcga aggttgtaga attgtatgtg acaagtggca ccaagcatat   360
ataaaaaaaa aaagcattat cttcctacca gagttgattg ttaaaaacgt atttatagca   420
aacgcaattg taattaattc ttattttgta tcttttcttc ccttgtctca atcttttatt   480
tttattttat ttttctttc ttagtttctt tcataacacc aagcaactaa tactataaca   540
tacaataata                                                         550
```

<210> SEQ ID NO 40
<211> LENGTH: 419
<212> TYPE: DNA
<213> ORGANISM: Saccharomyces cerevisiae
<220> FEATURE:
<223> OTHER INFORMATION: pTEF Kl" <223> "pTEF Kl
<220> FEATURE:
<223> OTHER INFORMATION: pTEF Kl
<220> FEATURE:
<223> OTHER INFORMATION: pTEF Kl

<400> SEQUENCE: 40

```
ctctctcgca ataacaatga acactgggtc aatcatagcc tacacaggtg aacagagtag      60 cgttatataca gggtttatac ggtgattcct acggcaaaaa ttttcattt ctaaaaaaaa     120 aaagaaaaat ttttctttcc aacgctagaa ggaaagaaaa aatctaatta aattgatttg     180
gtgattttct gagagttccc tttttcatat atcgaatttt gaatataaaa ggagatcgaa     240
aaaatttttc tattcaatct gttttctggt tttatttgat agttttttttg tgtattatta    300 ttatggatta gtactggttt atatgggttt ttctgtataa cttcttttta ttttagtttg     360
tttaatctta ttttgagtta cattatagtt ccctaactgc aagagaagta acattaaaa      419
```

<210> SEQ ID NO 41
<211> LENGTH: 598
<212> TYPE: DNA
<213> ORGANISM: Saccharomyces cerevisiae
<220> FEATURE:
<223> OTHER INFORMATION: pTEF3" <223> "pTEF3
<220> FEATURE:
<223> OTHER INFORMATION: pTEF3
<220> FEATURE:
<223> OTHER INFORMATION: pTEF3

<400> SEQUENCE: 41

```
ggctgataat agcgtataaa caatgcatac tttgtacgtt caaaatacaa tgcagtagat      60
atatttatgc atattacata taatacatat cacataggaa gcaacaggcg cgttggactt     120
ttaattttcg aggaccgcga atccttacat cacacccaat cccccacaag tgatccccca     180
cacaccatag cttcaaaatg tttctactcc ttttttactc ttccagattt tctcggactc     240
cgcgcatcgc cgtaccactt caaaacaccc aagcacagca tactaaattt ccctctcttc     300
ttcctctagg gtgtcgttaa ttacccgtac taaaggtttg gaaaagaaaa aagagaccgc     360
ctcgtttctt tttcttcgtc gaaaaaggca ataaaaattt ttatcacgtt tcttttttctt    420 gaaaattttt tttttttgatt ttttttctctt tcgatgacct cccattgata tttaagttaa   480
taaacggtct tcaatttctc aagtttcagt ttcatttttc ttgttctatt acaacttttt     540
ttacttcttg ctcattagaa agaaagcata gcaatctaat ctaagtttta attacaaa       598
```

<210> SEQ ID NO 42
<211> LENGTH: 383
<212> TYPE: DNA
<213> ORGANISM: Saccharomyces cerevisiae
<220> FEATURE:
<223> OTHER INFORMATION: pTEF1" <223> "pTEF1
<220> FEATURE:
<223> OTHER INFORMATION: pTEF1
<220> FEATURE:
<223> OTHER INFORMATION: pTEF1

<400> SEQUENCE: 42

```
gtttagcttg cctcgtcccc gccgggtcac ccggccagcg acatggaggc ccagaatacc      60
ctccttgaca gtcttgacgt gcgcagctca ggggcatgat gtgactgtcg cccgtacatt     120
```

```
tagcccatac atccccatgt ataatcattt gcatccatac attttgatgg ccgcacggcg    180
cgaagcaaaa attacggctc ctcgctgcag acctgcgagc agggaaacgc tccctcaca    240 gacgcgttga attgtcccca cgccgcgccc ctgtagagaa atataaaagg ttaggatttg    300
ccactgaggt tcttctttca tatacttcct tttaaaatct tgctacgata cagttctcac    360
atcacatccg aacataaaca acc                                           383

<210> SEQ ID NO 43
<211> LENGTH: 700
<212> TYPE: DNA
<213> ORGANISM: Saccharomyces cerevisiae
<220> FEATURE:
<223> OTHER INFORMATION: pADH1" <223> "pADH1
<220> FEATURE:
<223> OTHER INFORMATION: pADH1
<220> FEATURE:
<223> OTHER INFORMATION: pADH1

<400> SEQUENCE: 43
gggtgtacaa tatggacttc ctcttttctg gcaaccaaac ccatacatcg ggattcctat     60
aataccttcg ttggtctccc taacatgtag gtggcggagg ggagatatac aatagaacag    120
ataccagaca agacataatg ggctaaacaa gactacacca attacactgc ctcattgatg    180
gtggtacata acgaactaat actgtagccc tagacttgat agccatcatc atatcgaagt    240
ttcactaccc tttttccatt tgccatctat tgaagtaata ataggcgcat gcaacttctt    300 ttctttttt ttcttttctc tctccccgt tgttgtctca ccatatccgc aatgacaaaa    360
aaatgatgga agacactaaa ggaaaaaatt aacgacaaag acagcaccaa cagatgtcgt    420
tgttccagag ctgatgaggg gtatctcgaa gcacacgaaa cttttttcctt ccttcattca    480 cgcacactac tctctaatga gcaacggtat acggccttcc ttccagttac ttgaatttga    540
aataaaaaaa agtttgctgt cttgctatca agtataaata gacctgcaat tattaatctt    600
ttgtttcctc gtcattgttc tcgttcccct tcttccttgt ttcttttttct gcacaatatt    660 tcaagctata ccaagcatac aatcaactat ctcatataca                          700

<210> SEQ ID NO 44
<211> LENGTH: 549
<212> TYPE: DNA
<213> ORGANISM: Saccharomyces cerevisiae
<220> FEATURE:
<223> OTHER INFORMATION: pGPM 1" <223> "pGPM 1
<220> FEATURE:
<223> OTHER INFORMATION: pGPM 1
<220> FEATURE:
<223> OTHER INFORMATION: pGPM 1

<400> SEQUENCE: 44
gccaaacttt tcggttaaca catgcagtga tgcacgcgcg atggtgctaa gttacatata     60
tatatatata tatatatata tatatatata gccatagtga tgtctaagta acctttatgg    120
tatatttctt aatgtggaaa gatactagcg cgcgcaccca cacacaagct tcgtcttttc    180
ttgaagaaaa gaggaagctc gctaaatggg attccacttt ccgttccctg ccagctgatg    240 gaaaaggtt agtggaacga tgaagaataa aagagagat ccactgaggt gaaatttcag    300
ctgacagcga gtttcatgat cgtgatgaac aatggtaacg agttgtggct gttgccaggg    360
agggtggttc tcaactttta atgtatggcc aaatcgctac ttgggtttgt tatataacaa    420
agaagaaata atgaactgat tctcttcctc cttcttgtcc tttcttaatt ctgttgtaat    480
taccttcctt tgtaattttt tttgtaatta ttcttcttaa taatccaaac aaacacacat    540
```

<210> SEQ ID NO 45
<211> LENGTH: 650
<212> TYPE: DNA
<213> ORGANISM: Saccharomyces cerevisiae
<220> FEATURE:
<223> OTHER INFORMATION: pFBA1" <223> "pFBA1
<220> FEATURE:
<223> OTHER INFORMATION: pFBA1
<220> FEATURE:
<223> OTHER INFORMATION: pFBA1

<400> SEQUENCE: 45

```
acgcaagccc taagaaatga ataacaatac tgacagtact aaataattgc ctacttggct      60
tcacatacgt tgcatacgtc gatatagata ataatgataa tgacagcagg attatcgtaa     120
tacgtaatag ttgaaaatct caaaaatgtg tgggtcatta cgtaaataat gataggaatg     180
ggattcttct attttttcctt tttccattct agcagccgtc gggaaaacgt ggcatcctct     240
ctttcgggct caattggagt cacgctgccg tgagcatcct ctctttccat atctaacaac     300
tgagcacgta accaatggaa aagcatgagc ttagcgttgc tccaaaaaag tattggatgg     360
ttaataccat ttgtctgttc tcttctgact ttgactcctc aaaaaaaaaa aatctacaat     420
caacagatcg cttcaattac gccctcacaa aaactttttt ccttcttctt cgcccacgtt     480
aaattttatc cctcatgttg tctaacggat ttctgcactt gatttattat aaaaagacaa     540
agacataata cttctctatc aatttcagtt attgttcttc cttgcgttat tcttctgttc     600
ttcttttttct tttgtcatat ataaccataa ccaagtaata catattcaaa     650
```

<210> SEQ ID NO 46
<211> LENGTH: 700
<212> TYPE: DNA
<213> ORGANISM: Saccharomyces cerevisiae
<220> FEATURE:
<223> OTHER INFORMATION: pPDC1" <223> "pPDC1
<220> FEATURE:
<223> OTHER INFORMATION: pPDC1
<220> FEATURE:
<223> OTHER INFORMATION: pPDC1

<400> SEQUENCE: 46

```
ttatttacct atctctaaac ttcaacacct tatatcataa ctaatatttc ttgagataag      60
cacactgcac ccataccttc cttaaaaacg tagcttccag ttttttggtgg ttccggcttc    120
cttcccgatt ccgcccgcta aacgcatatt tttgttgcct ggtggcattt gcaaaatgca    180
taacctatgc atttaaaaga ttatgtatgc tcttctgact tttcgtgtga tgaggctcgt    240
ggaaaaaatg aataatttat gaatttgaga acaattttgt gttgttacgg tattttacta    300
tggaataatc aatcaattga ggattttatg caaatatcgt ttgaatattt ttccgaccct    360
ttgagtactt tcttcataa ttgcataata ttgtccgctg ccccttttc tgttagacgg    420
tgtcttgatc tacttgctat cgttcaacac caccttattt tctaactatt tttttttag    480
ctcatttgaa tcagcttatg gtgatggcac atttttgcat aaacctagct gtcctcgttg    540
aacataggaa aaaaaaatat ataaacaagg ctctttcact ctccttgcaa tcagatttgg    600
gtttgttccc tttatttca tatttcttgt catattcctt tctcaattat tattttctac    660
tcataacctc acgcaaaata acacagtcaa atcaatcaaa                          700
```

<210> SEQ ID NO 47

```
<211> LENGTH: 998
<212> TYPE: DNA
<213> ORGANISM: Saccharomyces cerevisiae
<220> FEATURE:
<223> OTHER INFORMATION: pCCW12" <223> "pCCW12
<220> FEATURE:
<223> OTHER INFORMATION: pCCW12
<220> FEATURE:
<223> OTHER INFORMATION: pCCW12

<400> SEQUENCE: 47
aaccagggca aagcaaaata aaagaaactt aatacgttat gccgtaatga agggctacca      60
aaaacgataa tctcaactgt aaacaggtac aatgcggacc cttttgccac aaaacataca    120
tcattcattg ccggaaaaag aaagaagtga agacagcagt gcagccagcc atgttgcgcc    180
aatctaatta tagatgctgg tgccctgagg atgtatctgg agccagccat ggcatcatgc    240
gctaccgccg gatgtaaaat ccgacacgca aaagaaaacc ttcgaggttg cgcacttcgc    300
ccacccatga accacacggt tagtccaaaa ggggcagttc agattccaga tgcgggaatt    360
agcttgctgc caccctcacc tcactaacgc tgcggtgtgc ggatacttca tgctattat    420 agacgcgcgt gtcggaatca gcacgcgcaa gaaccaaatg gaaaatcgg aatgggtcca    480 gaactgcttt gagtgctggc tattggcgtc tgatttccgt tttgggaatc ctttgccgcg    540
cgcccctctc aaaactccgc acaagtccca gaaagcggga agaaataaa acgccaccaa    600 aaaaaaaaat aaaagccaat cctcgaagcg tgggtggtag gccctggatt atcccgtaca    660
agtatttctc aggagtaaaa aaaccgtttg ttttggaatt ccccatttcg cggccaccta    720
cgccgctatc tttgcaacaa ctatctgcga taactcagca aattttgcat attcgtgttg    780
cagtattgcg ataatgggag tcttacttcc aacataacgg cagaaagaaa tgtgagaaaa    840
ttttgcatcc tttgcctccg ttcaagtata aaagtcggc atgcttgata atctttcttt    900
ccatcctaca ttgttctaat tattcttatt ctcctttatt ctttcctaac ataccaagaa    960
attaatcttc tgtcattcgc ttaaacacta tatcaata                            998

<210> SEQ ID NO 48
<211> LENGTH: 700
<212> TYPE: DNA
<213> ORGANISM: Saccharomyces cerevisiae
<220> FEATURE:
<223> OTHER INFORMATION: pGK1" <223> "pGK1
<220> FEATURE:
<223> OTHER INFORMATION: pGK1
<220> FEATURE:
<223> OTHER INFORMATION: pGK1

<400> SEQUENCE: 48
gtgagtaagg aaagagtgag gaactatcgc atacctgcat ttaaagatgc cgatttgggc     60
gcgaatcctt tattttggct tcaccctcat actattatca gggccagaaa aggaagtgt    120 ttccctcctt cttgaattga tgttaccctc ataaagcacg tggcctctta tcgagaaaga    180
aattaccgtc gctcgtgatt tgtttgcaaa aagaacaaaa ctgaaaaaac ccagacacgc    240
tcgacttcct gtcttcctat tgattgcagc ttccaatttc gtcacacaac aaggtcctag    300
cgacggctca caggttttgt aacaagcaat cgaaggttct ggaatggcgg gaaagggttt    360
agtaccacat gctatgatgc ccactgtgat ctccagagca agttcgttc gatcgtactg    420 ttactctctc tctttcaaac agaattgtcc gaatcgtgtg acaacaacag cctgttctca    480
cacactcttt tcttctaacc aagggggtgg tttagtttag tagaacctcg tgaaacttac    540
atttacatat atataaactt gcataaattg gtcaatgcaa gaaatacata tttggtcttt    600
```

```
tctaattcgt agtttttcaa gttcttagat gctttctttt tctcttttttt acagatcatc    660 aaggaagtaa ttatctactt tttacaacaa atataaaaca                          700

<210> SEQ ID NO 49
<211> LENGTH: 913
<212> TYPE: DNA
<213> ORGANISM: Saccharomyces cerevisiae
<220> FEATURE:
<223> OTHER INFORMATION: pMDH2" <223> "pMDH2
<220> FEATURE:
<223> OTHER INFORMATION: pMDH2
<220> FEATURE:
<223> OTHER INFORMATION: pMDH2

<400> SEQUENCE: 49
ccttcgctaa ataataaacc tgaactgtac ttagcgaagc cttcatagca cctacgtaca     60
cgtatatata gacattttac gtaatggaga aactgaggtt tttgttttca cttttttttct  120 ttcttttca ctattgctcg aaccgcctgc gatgagctaa gaaaaaaaag tgaaagaaat    180
catagaaagc aaaaatgaga ttatatagcc cagagccctc ttctggcgcc tgtcccaagg   240
cggaccaaca acaacacttg cccaaaccta agaaaatccc ctcatacttt tccgtttgta   300
tctcctactt tcttacttcc ttttttttctt ctttatttgc ttggtttacc attgaagtcc   360 attttttacta cagacaatag ctagtcattc gctatcttcc gtttgtcact tttttttcaaa  420 tttctcatct atatagcgaa gtacggaaaa gatgtcactt gccggcatct cggccttccc   480
cggccaaatg gactcatcat ctacgatacg gcccctttaa tccgcaatta ctttgcccat   540
tcggccgtag ccgttctaaa gccgccgtgc cttgccccca atactcccct aatgatccgg   600
gaagttccgg ttttttttcct tgtttagtg gcattttgtg ttgcccaagg ttgggaaggt    660
ccgatttgac tttaaggaac tacggaaggt atctaaggtt tctaaaaaca atatacacgc   720
gcgtgcgtag atatataaag ataaagattt atcgatatga gataaagatt gctgcatgat   780
tctccttctg attcttttttc cctgtatata ttttctcccc ttctgtataa atcgtacagt    840
cagaagtagt ccagaatata gtgctgcaga ctattacaaa agttcaatac aatatcataa    900
aagttatagt aac                                                     913

<210> SEQ ID NO 50
<211> LENGTH: 406
<212> TYPE: DNA
<213> ORGANISM: Saccharomyces cerevisiae
<220> FEATURE:
<223> OTHER INFORMATION: pURA3" <223> "pURA3
<220> FEATURE:
<223> OTHER INFORMATION: pURA3
<220> FEATURE:
<223> OTHER INFORMATION: pURA3

<400> SEQUENCE: 50
ggtacccaaa ccgaagttat ctgatgtaga aaaggattaa agatgctaag agatagtgat     60
gatatttcat aaataatgta attctatata tgttaattac cttttttgcg aggcatattt   120
atggtgaagg ataagttttg accatcaaag aaggttaatg tggctgtggt ttcagggtcc   180
ataaagcttt tcaattcatc ttttttttttt ttgttctttt ttttgattcc ggtttctttg    240
aaattttttt gattcggtaa tctccgagca gaaggaagaa cgaaggaagg agcacagact   300
tagattggta tatatacgca tatgtggtgt tgaagaaaca tgaaattgcc cagtattctt   360
aacccaactg cacagaacaa aaacctgcag gaaacgaaga taaatc                 406
```

<210> SEQ ID NO 51
<211> LENGTH: 535
<212> TYPE: DNA
<213> ORGANISM: Saccharomyces cerevisiae
<220> FEATURE:
<223> OTHER INFORMATION: pRPLA1" <223> "pRPLA1
<220> FEATURE:
<223> OTHER INFORMATION: pRPLA1
<220> FEATURE:
<223> OTHER INFORMATION: pRPLA1

<400> SEQUENCE: 51

```
tcaagttgga tactgatctg atctctccgc cctactacca gggaccctca tgattaccgc     60
tcgaatgcga cgtttcctgc ctcataaaac tggcttgaaa atatttattc gctgaacagt    120
agcctagctt ataaaaattt catttaatta atgtaatatg aaaactcaca tgccttctgt    180
ttctaaaatt gtcacagcaa gaaataacat taccatacgt gatcttatta aactctagta    240
tcttgtctaa tacttcattt aaagaagcc ttaaccctgt agcctcatct atgtctgcta     300
catatcgtga ggtacgaata tcgtaagatg ataccacgca actttgtaat gattttttt    360
ttttcatttt ttaaagaatg cctttacatg gtatttgaaa aaaatatctt tataaagttt    420
gcgatctctt ctgttctgaa taattttag taaaagaaat caaaagaata agaaatagt      480
ccgctttgtc caatacaaca gcttaaaccg attatctcta aaataacaag aagaa         535
```

<210> SEQ ID NO 52
<211> LENGTH: 400
<212> TYPE: DNA
<213> ORGANISM: Saccharomyces cerevisiae
<220> FEATURE:
<223> OTHER INFORMATION: pSAM4" <223> "pSAM4
<220> FEATURE:
<223> OTHER INFORMATION: pSAM4
<220> FEATURE:
<223> OTHER INFORMATION: pSAM4

<400> SEQUENCE: 52

```
agattttggt gttagatggt actcttgcat atgtaacctt taataaattt tgcaaatcga     60
attcctttgt aacgtgcaaa gcattttata gcctggcgct cgcattgtta agcaacaggc    120
ggtgcggcaa cgttgaaatg tttcacgcag ggttttttac gtactgcacg gcattctgga    180
gtgaaaaaaa atgaaaagta cagctcgaag ttttttgtcc atcggttgta ctttgcagag    240
tattagtcat ttttgatatc agagtactac tatcgaagca tttttacgct tgaataactt    300
gaatattatt gaaagcttag ttcaaccaag ctgaaaagaa ccattattca acataattgg    360
aaatcatttc gttactaaat cgtccgaaaa ttgcagaaaa                          400
```

<210> SEQ ID NO 53
<211> LENGTH: 505
<212> TYPE: DNA
<213> ORGANISM: Saccharomyces cerevisiae
<220> FEATURE:
<223> OTHER INFORMATION: pCUP1-1" <223> "pCUP1-1
<220> FEATURE:
<223> OTHER INFORMATION: pCUP1-1
<220> FEATURE:
<223> OTHER INFORMATION: pCUP1-1

<400> SEQUENCE: 53

```
cggcaaactt caacgatttc tatgatgcat tttataatta gtaagccgat cccattaccg     60
acatttgggc gctatacgtg catatgttca tgtatgtatc tgtatttaaa acacttttgt    120
attattttc ctcatatatg tgtataggtt tatacggatg atttaattat tacttcacca    180
```

-continued

```
cccctttattt caggctgata tcttagcctt gttactagtt agaaaaagac attttttgctg    240 tcagtcactg tcaagagatt cttttgctgg catttcttcc agaagcaaaa agagcgatgc    300
gtcttttccg ctgaaccgtt ccagcaaaaa agactaccaa cgcaatatgg attgtcagaa    360
tcatataaaa gagaagcaaa taactccttg tcttgtatca attgcattat aatatcttct    420
tgttagtgca atatcatata gaagtcatcg aaatagatat taagaaaaac aaactgtaca    480
atcaatcaat caatcatcac ataaa                                         505
```

<210> SEQ ID NO 54
<211> LENGTH: 500
<212> TYPE: DNA
<213> ORGANISM: Candida glabrata
<220> FEATURE:
<223> OTHER INFORMATION: pCUP1.Cgla" <223> "pCUP1.Cgla
<220> FEATURE:
<223> OTHER INFORMATION: pCUP1.Cgla
<220> FEATURE:
<223> OTHER INFORMATION: pCUP1.Cgla

<400> SEQUENCE: 54

```
cacaccacac aaccgtcagc accccggctg tacgtctgtg aaggctgcgg tatagacacg     60
gactgcgata cagaactcat gacttatatc tgtagactcc tctgcttcaa tgcgaactcc    120
aggatcaccg aatagcatgc gatgagctgt tgattcttat atataattat ctattgcatt    180
ttttttttaa tgctgcatgg gggggcctag taaatcaccc gtacaagtca cgcgtgagag    240
aaagagaagg gcccttttcgt cgtggaagcg tggatcgtga cgacctgtt tctaaatata    300 gcttttgggt aggatattat attaagtgaa attttattag agggtaaatg tatgtgaaag    360
ttatgtataa tatgttgcta aattagcgat cgtgaatgca tagaatctaa tcgttataga    420
aaaccgcaac ttgtgctgtt ttgttgtgtt ttcttgtcgt ttttttatat tatttatcta    480
gtattttgct ttagttgtta                                               500
```

<210> SEQ ID NO 55
<211> LENGTH: 425
<212> TYPE: DNA
<213> ORGANISM: Saccharomyces bayanus
<220> FEATURE:
<223> OTHER INFORMATION: pCUP1.Sba" <223> "pCUP1.Sba
<220> FEATURE:
<223> OTHER INFORMATION: pCUP1.Sba
<220> FEATURE:
<223> OTHER INFORMATION: pCUP1.Sba

<400> SEQUENCE: 55

```
agaaggaggg gtcctattac caatacttgg acgctatacg tgcatatgta catgtacgta     60
tctgtattta aacacttttg tattattttc tttatatatg tgtataggtt tacatggttg    120
acttttatca ttgtttgtgc acatttgcaa tggccatttt tttgtttttg agaaaggtat    180
tattgctgtc actattcgag atgcttttgc tgacattcct cctagaagcc aaaaggccga    240
tgcgtttttt ccgctgagag gataccagca aaaaaagcta ccagtacaag atgggacggc    300
aaaagcgtat aaaagaagaa gcaaaatgac cagatatgct ttcaatttca tcaatgtttc    360 tttctcctg ttatgatcca gaagaataat caaaagcaaa acatctattc aatcaatctc    420
ataaa                                                               425
```

<210> SEQ ID NO 56
<211> LENGTH: 741
<212> TYPE: DNA

<213> ORGANISM: Artificial Sequence
<220> FEATURE:
<223> OTHER INFORMATION: pACU1" <223> "pACU1
<220> FEATURE:
<223> OTHER INFORMATION: pACU1
<220> FEATURE:
<223> OTHER INFORMATION: pACU1

<400> SEQUENCE: 56

```
ttacattatc aatccttgcg tttcagcttc cactaattta gatgactatt tctcatcatt      60
tgcgtcatct tctaacaccg tatatgataa tatactagta acgtaaatac tagttagtag     120
atgatagttg attttattc caacactaag aaataattc gccatttctt gaatgtattt       180
aaagatattt aatgctataa tagacattta aatccaattc ttccaacata caatgggagt     240
ttggccgagt ggtttaaggc gtcagattta ggtggattta acctctaaaa tctctgatat     300
cttcggatgc aagggttcga atcccttagc tctcattatt ttttgctttt tctcttgaat     360
tcgaaaaaga cattttttgct gtcagtcact gtcaagagat tcttttgctg gcatttcttc   420
cagaagcaaa aagagcgatg cgtctttttcc gctgaaccgt tccagcaaaa aagactacca   480
acgaattcta attaagttag tcaaggcgcc atcctcatga aaactgtgta acataataac    540
cgaagtgtcg aaaggtggc accttgtcca attgaacacg ctcgatgaaa aaataagat      600
atatataagg ttaagtaaag cgtctgttag aaaggaagtt tttcctttttt cttgctctct  660
tgtcttttca tctactattt ccttcgtgta atacagggtc gtcagataca tagatacaat    720
tctattaccc ccatccatac a                                               741
```

<210> SEQ ID NO 57
<211> LENGTH: 757
<212> TYPE: DNA
<213> ORGANISM: Artificial Sequence
<220> FEATURE:
<223> OTHER INFORMATION: pACU2" <223> "pACU2
<220> FEATURE:
<223> OTHER INFORMATION: pACU2
<220> FEATURE:
<223> OTHER INFORMATION: pACU2

<400> SEQUENCE: 57

```
ttacattatc aatccttgcg tttcagcttc cactaattta gatgactatt tctcatcatt      60
tgcgtcatct tctaacaccg tatatgataa tatactagta acgtaaatac tagttagtag     120
atgatagttg attttattc caacactaag aaataattc gccatttctt gaatgtattt       180
aaagatattt aatgctataa tagacattta aatccaattc ttccaacata caatgggagt     240
ttggccgagt ggtttaaggc gtcagattta ggtggattta acctctaaaa tctctgatat     300
cttcggatgc aagggttcga atcccgaatt cgaaaaagac attttgctg tcagtcactg    360
tcaagagatt cttttgctgg catttcttcc agaagcaaaa agagcgatgc gtctttttccg  420
ctgaaccgtt ccagcaaaaa agactaccaa cgaattccac gtgaagctgt cgatattggg   480
gaactgtggt ggttggcaaa tgactaatta agttagtcaa ggcgccatcc tcatgaaaac   540
tgtgtaacat aataaccgaa gtgtcgaaaa ggtggcacct tgtccaattg aacacgctcg   600
atgaaaaaaa taagatatat ataaggttaa gtaaagcgtc tgttagaaag gaagtttttc   660
ctttttcttg ctctcttgtc ttttcatcta ctatttcctt cgtgtaatac agggtcgtca   720
gatacataga tacaattcta ttaccccat ccataca                              757
```

<210> SEQ ID NO 58
<211> LENGTH: 498

```
<212> TYPE: DNA
<213> ORGANISM: Artificial Sequence
<220> FEATURE:
<223> OTHER INFORMATION: pACU3p" <223> "pACU3p
<220> FEATURE:
<223> OTHER INFORMATION: pACU3p
<220> FEATURE:
<223> OTHER INFORMATION: pACU3p

<400> SEQUENCE: 58
ttatattgaa ttttcaaaaa ttcttacttt ttttttggat ggacgcaaag aagtttaata      60
atcatattac atggcattac caccatatac atatccatat ctaatcttac ttatatgttg     120
tggaaatgta aagagcccga attcgaaaaa gacattttg ctgtcagtca ctgtcaagag      180
attcttttgc tggcatttct tccagaagca aaaagagcga tgcgtctttt ccgctgaacc     240
gttccagcaa aaagactac caacgaattc ggatgataat gcgattagtt ttttagcctt     300
atttctgggg taattaatca gcgaagcgat gattttgat ctattaacag atatataaat     360
ggaaaagctg cataaccact ttaactaata cttt caacat tttcagtttg tattacttct     420
tattcaaatg tcataaaagt atcaacaaaa aattgttaat atacctctat actttaacgt     480
caaggagaaa aaactata                                                   498

<210> SEQ ID NO 59
<211> LENGTH: 498
<212> TYPE: DNA
<213> ORGANISM: Artificial Sequence
<220> FEATURE:
<223> OTHER INFORMATION: pACU4p" <223> "pACU4p
<220> FEATURE:
<223> OTHER INFORMATION: pACU4p
<220> FEATURE:
<223> OTHER INFORMATION: pACU4p

<400> SEQUENCE: 59
ttatattgaa ttttcaaaaa ttcttacttt ttttttggat ggacgcaaag aagtttaata      60
atcatattac atggcattac caccatatac atatccatat ctaatcttac ttatatgttg     120
tggaaatgta aagagcccga attcgttggt agtctttttt gctggaacgg ttcagcggaa     180
aagacgcatc gctcttttg cttctggaag aaatgccagc aaaagaatct cttgacagtg      240
actgacagca aaatgtctt tttcgaattc ggatgataat gcgattagtt ttttagcctt      300
atttctgggg taattaatca gcgaagcgat gattttgat ctattaacag atatataaat     360
ggaaaagctg cataaccact ttaactaata ctttcaacat tttcagtttg tattacttct     420
tattcaaatg tcataaaagt atcaacaaaa aattgttaat atacctctat actttaacgt     480
caaggagaaa aaactata                                                   498

<210> SEQ ID NO 60
<211> LENGTH: 530
<212> TYPE: DNA
<213> ORGANISM: Artificial Sequence
<220> FEATURE:
<223> OTHER INFORMATION: pACU5" <223> "pACU5
<220> FEATURE:
<223> OTHER INFORMATION: pACU5
<220> FEATURE:
<223> OTHER INFORMATION: pACU5

<400> SEQUENCE: 60
ggaggacgaa acaaaaaagt gaaaaaaaat gaaaattttt ttggaaaacc aagaaatgaa      60
ttatatttcc gtgtgagacg acatcgtcga atatgattca gggtaacagt attgatgtaa    120
```

| | |
|---|---|
| tcaatttcct acctgaatct aaaattcccg gaattcgaaa aagacattt tgctgtcagt | 180 |
| cactgtcaag agattctttt gctggcattt cttccagaag caaaagagc gatgcgtctt | 240 |
| ttccgctgaa ccgttccagc aaaaaagact accaacgaat tccgagcaga tccgccaggc | 300 |
| gtgtatatat agcgtggatg gccaggcaac tttagtgctg acacatacag gcatatatat | 360 |
| atgtgtgcga cgacacatga tcatatggca tgcatgtgct ctgtatgtat ataaaactct | 420 |
| tgttttcttc ttttctctaa atattctttc cttatacatt aggacctttg cagcataaat | 480 |
| tactatactt ctatagacac acaaacacaa atacacacac taaattaata | 530 |

<210> SEQ ID NO 61
<211> LENGTH: 867
<212> TYPE: DNA
<213> ORGANISM: Artificial Sequence
<220> FEATURE:
<223> OTHER INFORMATION: pACU6" <223> "pACU6
<220> FEATURE:
<223> OTHER INFORMATION: pACU6
<220> FEATURE:
<223> OTHER INFORMATION: pACU6

<400> SEQUENCE: 61

| | |
|---|---|
| ttacattatc aatccttgcg tttcagcttc cactaattta gatgactatt tctcatcatt | 60 |
| tgcgtcatct tctaacaccg tatatgataa tatactagta acgtaaatac tagttagtag | 120 |
| atgatagttg atttttattc caacactaag aaataaattc gccatttctt gaatgtattt | 180 |
| aaagatattt aatgctataa tagacattta aatccaattc ttccaacata caatgggagt | 240 |
| ttggccgagt ggtttaaggc gtcagattta ggtggattta acctctaaaa tctctgatat | 300 |
| cttcggatgc aagggttcga atcccttagc tctcattatt ttttgctttt tctcttgaat | 360 |
| tcgaaaaaga catttttgct gtcagtcact gtcaagagat tcttttgctg gcatttcttc | 420 |
| cagaagcaaa aagagcgatg cgtcttttcc gctgaaccgt tccagcaaaa aagactacca | 480 |
| acgaattcga aaaagacatt tttgctgtca gtcactgtca agagattctt ttgctggcat | 540 |
| ttcttccaga agcaaaaaga gcgatgcgtc ttttccgctg aaccgttcca gcaaaaaaga | 600 |
| ctaccaacga attctaatta agttagtcaa ggcgccatcc tcatgaaaac tgtgtaacat | 660 |
| aataaccgaa gtgtcgaaaa ggtggcacct tgtccaattg aacacgctcg atgaaaaaaa | 720 |
| taagatatat ataaggttaa gtaaagcgtc tgttagaaag gaagttttc ctttttcttg | 780 |
| ctctcttgtc ttttcatcta ctatttcctt cgtgtaatac agggtcgtca gatacataga | 840 |
| tacaattcta ttaccccat ccataca | 867 |

<210> SEQ ID NO 62
<211> LENGTH: 867
<212> TYPE: DNA
<213> ORGANISM: Artificial Sequence
<220> FEATURE:
<223> OTHER INFORMATION: pACU7" <223> "pACU7
<220> FEATURE:
<223> OTHER INFORMATION: pACU7
<220> FEATURE:
<223> OTHER INFORMATION: pACU7

<400> SEQUENCE: 62

| | |
|---|---|
| ttacattatc aatccttgcg tttcagcttc cactaattta gatgactatt tctcatcatt | 60 |
| tgcgtcatct tctaacaccg tatatgataa tatactagta acgtaaatac tagttagtag | 120 |
| atgatagttg atttttattc caacactaag aaataaattc gccatttctt gaatgtattt | 180 |
| aaagatattt aatgctataa tagacattta aatccaattc ttccaacata caatgggagt | 240 |

```
ttggccgagt ggtttaaggc gtcagattta ggtggattta acctctaaaa tctctgatat        300
cttcggatgc aagggttcga atcccttagc tctcattatt ttttgctttt tctcttgaat        360
tcgttggtag tctttttgc tggaacggtt cagcggaaaa gacgcatcgc tcttttttgct       420 tctggaagaa atgccagcaa aagaatctct tgacagtgac tgacagcaaa aatgtctttt        480
tcgaattcgt tggtagtctt ttttgctgga acggttcagc ggaaaagacg catcgctctt       540
tttgcttctg gaagaaatgc cagcaaaaga atctcttgac agtgactgac agcaaaaatg       600 tcttttttcga attctaatta agttagtcaa ggcgccatcc tcatgaaaac tgtgtaacat      660
aataaccgaa gtgtcgaaaa ggtggcacct tgtccaattg aacacgctcg atgaaaaaaa      720
taagatatat ataaggttaa gtaaagcgtc tgttagaaag gaagttttc cttttttcttg       780 ctctcttgtc ttttcatcta ctatttcctt cgtgtaatac agggtcgtca gatacataga      840
tacaattcta ttaccccccat ccataca                                           867

<210> SEQ ID NO 63
<211> LENGTH: 1119
<212> TYPE: DNA
<213> ORGANISM: Artificial Sequence
<220> FEATURE:
<223> OTHER INFORMATION: pACU8" <223> "pACU8
<220> FEATURE:
<223> OTHER INFORMATION: pACU8
<220> FEATURE:
<223> OTHER INFORMATION: pACU8

<400> SEQUENCE: 63
ttacattatc aatccttgcg tttcagcttc cactaattta gatgactatt tctcatcatt        60
tgcgtcatct tctaacaccg tatatgataa tatactagta acgtaaatac tagttagtag       120
atgatagttg attttttattc caacactaag aaataattc gccatttctt gaatgtattt       180
aaagatattt aatgctataa tagacattta aatccaattc ttccaacata caatgggagt       240
ttggccgagt ggtttaaggc gtcagattta ggtggattta acctctaaaa tctctgatat        300
cttcggatgc aagggttcga atcccttagc tctcattatt ttttgctttt tctcttgaat        360
tcgaaaaaga cattttttgct gtcagtcact gtcaagagat tcttttgctg gcatttcttc     420
cagaagcaaa aagagcgatg cgtctttttcc gctgaaccgt tccagcaaaa aagactacca     480
acgaattcga aaaagacatt ttttgctgtca gtcactgtca agagattctt ttgctggcat    540
ttcttccaga agcaaaaaga gcgatgcgtc ttttccgctg aaccgttcca gcaaaaaaga     600
ctaccaacga attcgaaaaa gacatttttg ctgtcagtca ctgtcaagag attcttttgc      660
tggcatttct tccagaagca aaaagagcga tgcgtctttt ccgctgaacc gttccagcaa      720 aaagactac caacgaattc gaaaagaca tttttgctgt cagtcactgt caagagattc       780
ttttgctggc atttcttcca gaagcaaaaa gagcgatgcg tcttttccgc tgaaccgttc      840
cagcaaaaaa gactaccaac gaattctaat taagttagtc aaggcgccat cctcatgaaa     900
actgtgtaac ataataaccg aagtgtcgaa aaggtggcac cttgtccaat tgaacacgct       960
cgatgaaaaa aataagatat ataaggtt aagtaaagcg tctgttagaa aggaagtttt       1020 tccttttct tgctctcttg tcttttcatc tactatttcc ttcgtgtaat acagggtcgt       1080
cagatacata gatacaattc tattaccccc atccataca                              1119

<210> SEQ ID NO 64
<211> LENGTH: 624
<212> TYPE: DNA
```

<213> ORGANISM: Artificial Sequence
<220> FEATURE:
<223> OTHER INFORMATION: pACU9" <223> "pACU9
<220> FEATURE:
<223> OTHER INFORMATION: pACU9
<220> FEATURE:
<223> OTHER INFORMATION: pACU9

<400> SEQUENCE: 64

```
tatagttttt tctccttgac gttaaagtat agaggtatat taacaatttt ttgttgatac    60
ttttatgaca tttgaataag aagtaataca aactgaaaat gttgaaagta ttagttaaag   120
tggttatgca gcttttccat ttatatatct gttaatagat caaaaatcat cgcttcgctg   180
attaattacc ccagaaataa ggctaaaaaa ctaatcgcat tatcatccga attcgaaaaa   240
gacattttg ctgtcagtca ctgtcaagag attcttttgc tggcatttct tccagaagca    300
aaaagagcga tgcgtctttt ccgctgaacc gttccagcaa aaaagactac caacgaattc   360
gaaaaagaca ttttgctgt cagtcactgt caagagattc ttttgctggc atttcttcca    420
gaagcaaaaa gagcgatgcg tcttttccgc tgaaccgttc cagcaaaaaa gactaccaac   480
gaattcgggc tctttacatt tccacaacat ataagtaaga ttagatatgg atatgtatat   540
ggtggtaatg ccatgtaata tgattattaa acttctttgc gtccatccaa aaaaaagta   600
agaattttg aaaattcaat ataa                                            624
```

<210> SEQ ID NO 65
<211> LENGTH: 876
<212> TYPE: DNA
<213> ORGANISM: Artificial Sequence
<220> FEATURE:
<223> OTHER INFORMATION: pACU10p" <223> "pACU10p
<220> FEATURE:
<223> OTHER INFORMATION: pACU10p
<220> FEATURE:
<223> OTHER INFORMATION: pACU10p

<400> SEQUENCE: 65

```
ttatattgaa ttttcaaaaa ttcttacttt ttttttggat ggacgcaaag aagtttaata    60
atcatattac atggcattac caccatatac atatccatat ctaatcttac ttatatgttg   120
tggaaatgta aagagcccga attggttggt agtctttttt gctggaacgg ttcagcggaa   180
aagacgcatc gctctttttg cttctggaag aaatgccagc aaaagaatct cttgacagtg   240
actgacagca aaaatgtctt tttcgaattc gttggtagtc ttttttgctg gaacggttca   300
gcggaaaaga cgcatcgctc ttttgcttc tggaagaaat gccagcaaaa gaatctcttg    360
acagtgactg acagcaaaaa tgtcttttc gaattcgttg gtagtctttt ttgctggaac   420
ggttcagcgg aaaagacgca tcgctctttt tgcttctgga agaaatgcca gcaaaagaat   480
ctcttgacag tgactgacag caaaaatgtc tttttcgaat tcgttggtag tctttttgc    540
tggaacggtt cagcggaaaa gacgcatcgc tctttttgct tctggaagaa atgccagcaa   600
aagaatctct tgacagtgac tgacagcaaa aatgtctttt tccaattcgg atgataatgc   660
gattagtttt ttagccttat ttctggggta attaatcagc gaagcgatga ttttgatct    720
attaacagat atataaatgg aaaagctgca taaccacttt aactaatact ttcaacattt   780
tcagtttgta ttacttctta ttcaaatgtc ataaagtat caacaaaaaa ttgttaatat    840
acctctatac tttaacgtca aggagaaaaa actata                             876
```

<210> SEQ ID NO 66
<211> LENGTH: 633

```
<212> TYPE: DNA
<213> ORGANISM: Artificial Sequence
<220> FEATURE:
<223> OTHER INFORMATION: pACU11" <223> "pACU11
<220> FEATURE:
<223> OTHER INFORMATION: pACU11
<220> FEATURE:
<223> OTHER INFORMATION: pACU11

<400> SEQUENCE: 66
gctcagcatc tgcttcttcc caaagatgaa cgcggcgtta tgtcactaac gacgtgcacc      60
aacttgcggg aattcgaaaa agacatttt gctgtcagtc actgtcaaga gattcttttg     120
ctggcatttc ttccagaagc aaaaagagcg atgcgtcttt ccgctgaac cgttccagca     180
aaaaagacta ccaacgaatt ccaccgcacg ccttttttct gaagcccact ttcgtggact     240
ttgccatata tgcaaaattc atgaagtgtg ataccaagtc agcatacacc tcactagggt     300
agtttctttg gttgtattga tcatttggtt catcgtggtt cattaattt ttttctccat      360
tgctttctgg ctttgatctt actatcattt ggattttgt cgaaggttgt agaattgtat      420
gtgacaagtg gcaccaagca tatataaaaa aaaaagcat tatcttccta ccagagttga     480
ttgttaaaaa cgtatttata gcaaacgcaa ttgtaattaa ttcttatttt gtatctttc      540
ttcccttgtc tcaatctttt atttttattt tatttttctt ttcttagttt ctttcataac     600
accaagcaac taatactata acatacaata ata                                 633

<210> SEQ ID NO 67
<211> LENGTH: 1119
<212> TYPE: DNA
<213> ORGANISM: Artificial Sequence
<220> FEATURE:
<223> OTHER INFORMATION: pACU12" <223> "pACU12
<220> FEATURE:
<223> OTHER INFORMATION: pACU12
<220> FEATURE:
<223> OTHER INFORMATION: pACU12

<400> SEQUENCE: 67
ttacattatc aatccttgcg tttcagcttc cactaattta gatgactatt tctcatcatt      60
tgcgtcatct tctaacaccg tatatgataa tatactagta acgtaaatac tagttagtag     120
atgatagttg attttattc caacactaag aaataatttc gccatttctt gaatgtattt      180
aaagatattt aatgctataa tagacatttta aatccaattc ttccaacata caatgggagt     240
ttggccgagt ggtttaaggc gtcagattta ggtggattta acctctaaaa tctctgatat     300
cttcggatgc aagggttcga atcccttagc tctcattatt ttttgctttt tctcttgaat     360
tggttggtag tctttttgc tggaacggtt cagcggaaaa gacgcatcgc tctttttgct      420
tctgaagaa atgccagcaa aagaatctct tgacagtgac tgacagcaaa atgtctttt      480
tcgaattcgt tggtagtctt ttttgctgga acggttcagc ggaaaagacg catcgctctt     540
tttgcttctg gaagaaatgc cagcaaaaga atctcttgac agtgactgac agcaaaatg     600
tcttttttcga attcgttggt agtcttttt gctggaacgg ttcagcggaa aagacgcatc     660
gctcttttg cttctggaag aaatgccagc aaaagaatct cttgacagtg actgacagca     720
aaaatgtctt tttcgaattc gttggtagtc ttttttgctg gaacggttca gcggaaaaga     780
cgcatcgctc ttttttgcttc tggaagaaat gccagcaaaa gaatctcttg acagtgactg     840
acagcaaaaa tgtcttttc caattctaat taagttagtc aaggcgccat cctcatgaaa     900
actgtgtaac ataataaccg aagtgtcgaa aaggtggcac cttgtccaat tgaacacgct     960
```

```
cgatgaaaaa aataagatat atataaggtt aagtaaagcg tctgttagaa aggaagtttt    1020 tccttttttct tgctctcttg tcttttcatc tactatttcc ttcgtgtaat acagggtcgt   1080
cagatacata gatacaattc tattaccccc atccataca                           1119
```

<210> SEQ ID NO 68
<211> LENGTH: 1497
<212> TYPE: DNA
<213> ORGANISM: Artificial Sequence
<220> FEATURE:
<223> OTHER INFORMATION: pACU13" <223> "pACU13
<220> FEATURE:
<223> OTHER INFORMATION: pACU13
<220> FEATURE:
<223> OTHER INFORMATION: pACU13

<400> SEQUENCE: 68

```
ttacattatc aatccttgcg tttcagcttc cactaattta gatgactatt tctcatcatt      60
tgcgtcatct tctaacaccg tatatgataa tatactagta acgtaaatac tagttagtag    120
atgatagttg atttttattc caacactaag aaataaattc gccatttctt gaatgtattt    180
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tggttggtag tcttttttgc tggaacggtt cagcggaaaa gacgcatcgc tcttttttgct   420 tctggaagaa atgccagcaa aagaatctct tgacagtgac tgacagcaaa aatgtctttt    480
tcgaattcgt tggtagtctt ttttgctgga acggttcagc ggaaaagacg catcgctctt    540
tttgcttctg gaagaaatgc cagcaaaaga atctcttgac agtgactgac agcaaaaatg    600 tcttttttcga attcgttggt agtctttttt gctggaacgg ttcagcggaa aagacgcatc    660 gctcttttttg cttctggaag aaatgccagc aaaagaatct cttgacagtg actgacagca    720
aaaatgtctt tttcgaattc gttggtagtc ttttttgctg gaacggttca gcggaaaaga    780
cgcatcgctc ttttttgcttc tggaagaaat gccagcaaaa gaatctcttg acagtgactg    840
acagcaaaaa tgtctttttc gaattcgttg gtagtctttt ttgctggaac ggttcagcgg    900
aaaagacgca tcgctcttttt tgcttctgga agaaatgcca gcaaaagaat ctcttgacag   960
tgactgacag caaaaatgtc ttttttcgaat tcgttggtag tctttttttgc tggaacggtt   1020 cagcggaaaa gacgcatcgc tcttttttgct tctggaagaa atgccagcaa aagaatctct    1080
tgacagtgac tgacagcaaa aatgtctttt tcgaattcgt tggtagtctt ttttgctgga    1140
acggttcagc ggaaaagacg catcgctctt tttgcttctg gaagaaatgc cagcaaaaga   1200
atctcttgac agtgactgac agcaaaaatg tcttttttcca attctaatta agttagtcaa    1260
ggcgccatcc tcatgaaaac tgtgtaacat aataaccgaa gtgtcgaaaa ggtggcacct    1320
tgtccaattg aacacgctcg atgaaaaaaa taagatatat ataaggttaa gtaaagcgtc    1380
tgttagaaag gaagttttttc cttttttcttg ctctcttgtc ttttcatcta ctatttcctt    1440
cgtgtaatac agggtcgtca gatacataga tacaattcta ttaccccat ccataca       1497
```

<210> SEQ ID NO 69
<211> LENGTH: 1011
<212> TYPE: DNA
<213> ORGANISM: Artificial Sequence
<220> FEATURE:
<223> OTHER INFORMATION: pACU14" <223> "pACU14
<220> FEATURE:
<223> OTHER INFORMATION: pACU14

<220> FEATURE:
<223> OTHER INFORMATION: pACU14

<400> SEQUENCE: 69

```
gctcagcatc tgcttcttcc caaagatgaa cgcggcgtta tgtcactaac gacgtgcacc      60
aacttgcggg aattggaaaa agacatttt gctgtcagtc actgtcaaga gattcttttg     120
ctggcatttc ttccagaagc aaaaagagcg atgcgtcttt tccgctgaac cgttccagca    180
aaaaagacta ccaacgaatt cgaaaaagac attttttgctg tcagtcactg tcaagagatt    240
cttttgctgg catttcttcc agaagcaaaa agagcgatgc gtcttttccg ctgaaccgtt     300
ccagcaaaaa agactaccaa cgaattcgaa aaagacattt tgctgtcag tcactgtcaa     360
gagattcttt tgctggcatt tcttccagaa gcaaaaagag cgatgcgtct tttccgctga     420
accgttccag caaaaaagac taccaacgaa ttcgaaaaag acattttttgc tgtcagtcac    480
tgtcaagaga ttcttttgct ggcatttctt ccagaagcaa aaagagcgat gcgtcttttc     540
cgctgaaccg ttcagcaaaa aagactacc aaccaattcc accgcacgcc ttttttctga     600
agcccactttt cgtggacttt gccatatatg caaaattcat gaagtgtgat accaagtcag     660
catacacctc actagggtag tttctttggt tgtattgatc atttggttca tcgtggttca     720
ttaatttttt ttctccattg ctttctggct ttgatcttac tatcatttgg attttttgtcg     780
aaggttgtag aattgtatgt gacaagtggc accaagcata tataaaaaaa aaaagcatta     840
tcttcctacc agagttgatt gttaaaaacg tatttatagc aaacgcaatt gtaattaatt     900
cttattttgt atcttttctt cccttgtctc aatcttttat tttttattta ttttttctttt    960
cttagtttct ttcataacac caagcaacta atactataac atacaataat a            1011
```

<210> SEQ ID NO 70
<211> LENGTH: 398
<212> TYPE: DNA
<213> ORGANISM: Artificial Sequence
<220> FEATURE:
<223> OTHER INFORMATION: pACU15" <223> "pACU15
<220> FEATURE:
<223> OTHER INFORMATION: pACU15
<220> FEATURE:
<223> OTHER INFORMATION: pACU15

<400> SEQUENCE: 70

```
tatagttttt tctccttgac gttaaagtat agaggtatat taacaatttt ttgttgatac      60
ttttatgaca tttgaataag aagtaataca aactgaaaat gttgaaagta ttagttaaag     120
tggttatgca gcttttccat ttatatatct gttaatagat caaaaatcat cgcttcgctg     180
attaattacc ccagaaataa ggctaaaaaa ctaatcgcat tatcatccga attcgttggt     240
agtcttttt gctggaacgg ttcagcgaa aagacgcatc gctctttttg cttctggaag      300
aaatgccagc aaaagaatct cttgacagtg actgacagca aaaatgtctt tttcgaattc     360
gggctcttta catttccaca acatataagt aagattag                            398
```

<210> SEQ ID NO 71
<211> LENGTH: 428
<212> TYPE: DNA
<213> ORGANISM: Artificial Sequence
<220> FEATURE:
<223> OTHER INFORMATION: pGAL/CUP1p" <223> "pGAL/CUP1p
<220> FEATURE:
<223> OTHER INFORMATION: pGAL/CUP1p
<220> FEATURE:
<223> OTHER INFORMATION: pGAL/CUP1p

<400> SEQUENCE: 71

| ttatattgaa | ttttcaaaaa | ttcttactttt | ttttttggat | ggacgcaaag | aagtttaata | 60 |
| atcatattac | atggcattac | caccatatac | atatccatat | ctaatcttac | ttatatgttg | 120 |
| tggaaatgta | aagagcccga | attcgaaaaa | gacattttg | ctgtcagtca | ctgtcaagag | 180 |
| attcttttgc | tggcatttct | tccagaagca | aaaagagcga | tgcgtctttt | ccgctgaacc | 240 |
| gttccagcaa | aaaagactac | caacgcaata | tggattgtca | gaatcatata | aaagagaagc | 300 |
| aaataactcc | ttgtcttgta | tcaattgcat | tataatatct | tcttgttagt | gcaatatcat | 360 |
| atagaagtca | tcgaaataga | tattaagaaa | acaaactgt | acaatcaatc | aatcaatcat | 420 |
| cacataaa | | | | | | 428 |

<210> SEQ ID NO 72
<211> LENGTH: 518
<212> TYPE: DNA
<213> ORGANISM: Saccharomyces cerevisiae
<220> FEATURE:
<223> OTHER INFORMATION: pCRS5" <223> "pCRS5
<220> FEATURE:
<223> OTHER INFORMATION: pCRS5
<220> FEATURE:
<223> OTHER INFORMATION: pCRS5

<400> SEQUENCE: 72

| gtggacgaaa | agacataact | gcagaagtac | agctgccttt | atttcttgtg | gtcatttatt | 60 |
| gcttttattt | tcaagtcaga | tatacaagaa | aatcaaatcc | catcgtcaac | gtcacgtata | 120 |
| aacgattaat | ttacagtaat | accatactct | accaacatta | ttttagtccg | acgttcagtc | 180 |
| ctgtaggtgt | tccaaatcct | tctggcattg | acttctgtgc | agaaacccttt | caaaatgagt | 240 |
| tccactttac | gtcagatcgc | ataacaaccg | gtcatatatt | ttttctttt | gctaaacccc | 300 |
| ctactgcaag | cacttttaag | aaaagaaca | ataaatgcgt | ctttattgct | gtgtggaagt | 360 |
| gattttgtc | tttcggacaa | aaaaaggata | gggatgcgag | agggctgtga | agtagtgatc | 420 |
| aagcgggggcc | tatataagaa | gggcgcacat | cgtcccccct | aagaatagcg | aagcgatatt | 480 |
| acactgaaca | ctacaatgtc | aaatagtact | caataaat | | | 518 |

<210> SEQ ID NO 73
<211> LENGTH: 510
<212> TYPE: DNA
<213> ORGANISM: Saccharomyces cerevisiae
<220> FEATURE:
<223> OTHER INFORMATION: pCHA1" <223> "pCHA1
<220> FEATURE:
<223> OTHER INFORMATION: pCHA1
<220> FEATURE:
<223> OTHER INFORMATION: pCHA1

<400> SEQUENCE: 73

| gatctctgct | gacgttgtat | ccacagatct | aattgcaaga | tagcctcttg | cgaccttatt | 60 |
| aaaagcctct | ccgtgatatc | ctctagggct | tgggttgcca | ttaatcgatg | tgtccttgtt | 120 |
| tccttatgcg | agctgtttct | tatctatctt | atggtcccat | tctttactgc | actgtttaca | 180 |
| ttttgatcaa | ttgcgaaatg | ttcctactat | ttttctttt | ctcttttcgc | gagtactaat | 240 |
| caccgcgaac | ggaaactaat | gagtcctctg | cgcggagaca | tgattccgca | tgggcggctc | 300 |
| ctgttaagcc | ccagcggaaa | tgtaattcca | ctgagtgtca | ttaaatagtg | ccaaagcttt | 360 |
| atcaaattgt | ttgcgatgag | ataagataaa | agggacaata | tgaggaggaa | cacaggtata | 420 |
| taaatatcgc | caaataaaag | gaaaatgttt | atacagtttt | ctcttttta | agtgctggat | 480 |

```
agacaagaga caggaaaatt aaccagcgag                                    510
```

```
<210> SEQ ID NO 74
<211> LENGTH: 601
<212> TYPE: DNA
<213> ORGANISM: Saccharomyces cerevisiae
<220> FEATURE:
<223> OTHER INFORMATION: pCTR1" <223> "pCTR1
<220> FEATURE:
<223> OTHER INFORMATION: pCTR1
<220> FEATURE:
<223> OTHER INFORMATION: pCTR1

<400> SEQUENCE: 74
caagtccgat tgttcctctt caggagcttc ctgaaccaaa cttttccgc aaggccgcat     60 tttgaaccgt attttgctcg ttccagcctt tccacgtttt tgttatctaa gcaacttggc    120
acatttccct actatactac aaaccgatac gtaaatactt ccctaaatag catatgaatt    180
attcagtaat ttttaaggat cgaaactgca cctcaactat tcgttactgt ggttatgttc    240
tcatgtattg atgcaaatca tgggatattt gctcaagacg acggtaaaat gagcaaaaat    300
ggcacgatcc tgaaaagagc acttttcaag attcgggcta caaatgcaa cataaaaaat     360 gttgtattgt catctcgaca gggtcttgta tgttttattc ctcttatgat tagttcacat    420
tagtaaaaca gatacgcagt gtgctcttaa taaacaacta ctccatagct ttatttgcat    480
aacaaaactt ttaagcacaa acttaaacag gtggagtaat agttcggcgg cgactcaaat    540
tacatttgtt ggaagaatcg aatagaaaat aaaaaaaagt gtattatatt tgacattcaa    600
a                                                                    601
```

```
<210> SEQ ID NO 75
<211> LENGTH: 522
<212> TYPE: DNA
<213> ORGANISM: Saccharomyces cerevisiae
<220> FEATURE:
<223> OTHER INFORMATION: pCTR3" <223> "pCTR3
<220> FEATURE:
<223> OTHER INFORMATION: pCTR3
<220> FEATURE:
<223> OTHER INFORMATION: pCTR3

<400> SEQUENCE: 75
gatgtgatga caaaacctct tccgataaaa acatttaaac tattaacaaa caaatggatt     60
cattagatct attacattat gggtggtatg ttggaataaa aatcaactat catctactaa    120
ctagtattta cgttactagt atattatcat atacggtgtt agaagatgac gcaaatgatg    180
agaaatagtc atctaaatta gtggaagctg aaacgcaagg attgataatg taataggatc    240
aatgaatatt aacatataaa acgatgataa taatatttat agaattgtgt agaattgcag    300 attcccttt atggattcct aaatcctcca ggagaacttc tagtatatct acatacctaa     360
tattattgcc ttattaaaaa tggaatccca acaattacat caaaatccac attctcttca    420
cttctccgat agacttgtaa tttatcttat ttcatttcct aacactttga tcgaagaaga    480
gggataacaa cagacgaaaa cacatttaag ggctatacaa ag                        522
```

```
<210> SEQ ID NO 76
<211> LENGTH: 675
<212> TYPE: DNA
<213> ORGANISM: Artificial Sequence
<220> FEATURE:
<223> OTHER INFORMATION: pCUR1" <223> "pCUR1
<220> FEATURE:
```

<223> OTHER INFORMATION: pCUR1
<220> FEATURE:
<223> OTHER INFORMATION: pCUR1

<400> SEQUENCE: 76

```
ttacattatc aatccttgcg tttcagcttc cactaattta gatgactatt tctcatcatt      60
tgcgtcatct tctaacaccg tatatgataa tatactagta acgtaaatac tagttagtag     120
atgatagttg attttattc caacactaag aaataaattc gccatttctt gaatgtattt      180
aaagatattt aatgctataa tagacattta aatccaattc ttccaacata caatgggagt     240
ttggccgagt ggtttaaggc gtcagattta ggtggattta acctctaaaa tctctgatat     300
cttcggatgc aagggttcga atcccttagc tctcattatt ttttgctttt tctcttgaat     360
tgtcatggga tatttgctca agacgacggt aaaatgagca aatatggcac gatcctcaat     420
tctaattaag ttagtcaagg cgccatcctc atgaaaactg tgtaacataa taaccgaagt     480
gtcgaaaagg tggcaccttg tccaattgaa cacgctcgat gaaaaaaata agatatatat     540
aaggttaagt aaagcgtctg ttagaaagga agttttccct ttttcttgct ctcttgtctt     600
ttcatctact atttccttcg tgtaatacag ggtcgtcaga tacatagata caattctatt     660
accccccatcc ataca                                                    675
```

<210> SEQ ID NO 77
<211> LENGTH: 674
<212> TYPE: DNA
<213> ORGANISM: Artificial Sequence
<220> FEATURE:
<223> OTHER INFORMATION: pCUR2" <223> "pCUR2
<220> FEATURE:
<223> OTHER INFORMATION: pCUR2
<220> FEATURE:
<223> OTHER INFORMATION: pCUR2

<400> SEQUENCE: 77

```
ttacattatc aatccttgcg tttcagcttc cactaattta gatgactatt tctcatcatt      60
tgcgtcatct tctaacaccg tatatgataa tatactagta acgtaaatac tagttagtag     120
atgatagttg attttattc caacactaag aaataaattc gccatttctt gaatgtattt      180
aaagatattt aatgctataa tagacattta aatccaattc ttccaacata caatgggagt     240
ttggccgagt ggtttaaggc gtcagattta ggtggattta acctctaaaa tctctgatat     300
cttcggatgc aagggttcga atcccttagc tctcattatt ttttgctttt tctcttgatt     360
gaggatcgtg ccatatttgc tcattttacc gtcgtcttga gcaaatatcc catgacaatt     420
ctaattaagt tagtcaaggc gccatcctca tgaaaactgt gtaacataat aaccgaagtg     480
tcgaaaaggt ggcaccttgt ccaattgaac acgctcgatg aaaaaaataa gatatatata     540
aggttaagta aagcgtctgt tagaaaggaa gttttccctt tttcttgctc tcttgtcttt     600
tcatctacta tttccttcgt gtaatacagg gtcgtcagat acatagatac aattctatta     660
ccccccatcca taca                                                     674
```

<210> SEQ ID NO 78
<211> LENGTH: 794
<212> TYPE: DNA
<213> ORGANISM: Artificial Sequence
<220> FEATURE:
<223> OTHER INFORMATION: pCUR3" <223> "pCUR3
<220> FEATURE:
<223> OTHER INFORMATION: pCUR3
<220> FEATURE:
<223> OTHER INFORMATION: pCUR3

<400> SEQUENCE: 78

```
ttacattatc aatccttgcg tttcagcttc cactaattta gatgactatt tctcatcatt        60
tgcgtcatct tctaacaccg tatatgataa tatactagta acgtaaatac tagttagtag       120
atgatagttg atttttattc caacactaag aaataaattc gccatttctt gaatgtattt       180
aaagatattt aatgctataa tagacattta aatccaattc ttccaacata caatgggagt       240
ttggccgagt ggtttaaggc gtcagattta ggtggattta acctctaaaa tctctgatat       300
cttcggatgc aagggttcga atcccttagc tctcattatt ttttgctttt tctcttgaat       360
taggatcgtg ccatatttgc tcattttacc gtcgtcttga gcaaatatcc catgacaatt       420
gaggatcgtg ccatatttgc tcattttacc gtcgtcttga gcaaatatcc catgacaatt       480
gaggatcgtg ccatatttgc tcattttacc gtcgtcttga gcaaatatcc catgacaatt       540
ctaattaagt tagtcaaggc gccatcctca tgaaaactgt gtaacataat aaccgaagtg       600
tcgaaaaggt ggaccttgt ccaattgaac acgctcgatg aaaaaaataa gatatatata        660
aggttaagta aagcgtctgt tagaaaggaa gttttccctt tttcttgctc tcttgtcttt       720
tcatctacta tttccttcgt gtaatacagg gtcgtcagat acatagatac aattctatta       780
cccccatcca taca                                                         794
```

<210> SEQ ID NO 79
<211> LENGTH: 850
<212> TYPE: DNA
<213> ORGANISM: Artificial Sequence
<220> FEATURE:
<223> OTHER INFORMATION: pCUR4" <223> "pCUR4
<220> FEATURE:
<223> OTHER INFORMATION: pCUR4
<220> FEATURE:
<223> OTHER INFORMATION: pCUR4

<400> SEQUENCE: 79

```
ttacattatc aatccttgcg tttcagcttc cactaattta gatgactatt tctcatcatt        60
tgcgtcatct tctaacaccg tatatgataa tatactagta acgtaaatac tagttagtag       120
atgatagttg atttttattc caacactaag aaataaattc gccatttctt gaatgtattt       180
aaagatattt aatgctataa tagacattta aatccaattc ttccaacata caatgggagt       240
ttggccgagt ggtttaaggc gtcagattta ggtggattta acctctaaaa tctctgatat       300
cttcggatgc aagggttcga atcccttagc tctcattatt ttttgctttt tctcttgaat       360
tgtcatggga tatttgctca agacgacggt aaaatgagca atatggcac gatcctcaat       420
tgtcatggga tatttgctca agacgacggt aaaatgagca atatggcac gatcctcaat       480
gtcatggat atttgctcaa gacgacggta aaatgagcaa atatggcacg atcctcaatt       540
gtcatggat atttgctcaa gacgacggta aaatgagcaa atatcccatg acaattctaa       600
ttaagttagt caaggcgcca tcctcatgaa aactgtgtaa cataataacc gaagtgtcga       660
aaaggtggca ccttgtccaa ttgaacacgc tcgatgaaaa aaataagata tatataaggt       720
taagtaaagc gtctgttaga aaggaagttt tcctttttc ttgctctctt gtcttttcat        780
ctactatttc cttcgtgtaa tacagggtcg tcagatacat agatacaatt ctattacccc       840
catccataca                                                              850
```

<210> SEQ ID NO 80
<211> LENGTH: 491
<212> TYPE: DNA

<213> ORGANISM: Artificial Sequence
<220> FEATURE:
<223> OTHER INFORMATION: pCUR5p" <223> "pCUR5p
<220> FEATURE:
<223> OTHER INFORMATION: pCUR5p
<220> FEATURE:
<223> OTHER INFORMATION: pCUR5p

<400> SEQUENCE: 80

```
ttatattgaa ttttcaaaaa ttcttacttt tttttttggat ggacgcaaag aagtttaata    60
atcatattac atggcattac caccatatac atatccatat ctaatcttac ttatatgttg   120
tggaaatgta aagagcccga attgtcatgg gatatttgct caagacgacg gtaaaatgag   180
caaatatggc acgatcctca attgtcatgg gatatttgct caagacgacg gtaaaatgag   240
caaatatggc acgatcccaa ttcggatgat aatgcgatta gttttttagc cttatttctg   300
gggtaattaa tcagcgaagc gatgattttt gatctattaa cagatatata aatggaaaag   360
ctgcataacc actttaacta atactttcaa cattttcagt ttgtattact tcttattcaa   420
atgtcataaa agtatcaaca aaaaattgtt aatatacctc tactttaa cgtcaaggag    480
aaaaaactat a                                                       491
```

<210> SEQ ID NO 81
<211> LENGTH: 833
<212> TYPE: DNA
<213> ORGANISM: Artificial Sequence
<220> FEATURE:
<223> OTHER INFORMATION: pCUR6" <223> "pCUR6
<220> FEATURE:
<223> OTHER INFORMATION: pCUR6
<220> FEATURE:
<223> OTHER INFORMATION: pCUR6

<400> SEQUENCE: 81

```
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttttattc caacactaag aaataaattc gccatttctt gaatgtattt   180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccgaatt gaggatcgtg ccatatttgc tcattttacc   360
gtcgtcttga gcaaatatcc catgacaatt gaggatcgtg ccatatttgc tcattttacc   420
gtcgtcttga gcaaatatcc catgacaatt gaggatcgtg ccatatttgc tcattttacc   480
gtcgtcttga gcaaatatcc catgacaatt catgatcgca aaatggcaaa tggcacgtga   540
agctgtcgat attggggaac tgtggtggtt ggcaaatgac taattaagtt agtcaaggcg   600
ccatcctcat gaaaactgtg taacataata accgaagtgt cgaaaaggtg gcaccttgtc   660
caattgaaca cgctcgatga aaaaaataag atatatataa ggttaagtaa agcgtctgtt   720
agaaaggaag tttttccttt ttcttgctct cttgtctttt catctactat ttccttcgtg   780
taatacaggg tcgtcagata catagataca attctattac ccccatccat aca           833
```

<210> SEQ ID NO 82
<211> LENGTH: 803
<212> TYPE: DNA
<213> ORGANISM: Artificial Sequence
<220> FEATURE:
<223> OTHER INFORMATION: pCUR7" <223> "pCUR7
<220> FEATURE:
<223> OTHER INFORMATION: pCUR7

<220> FEATURE:
<223> OTHER INFORMATION: pCUR7

<400> SEQUENCE: 82

| | | | | | |
|---|---|---|---|---|---|
| gtgagtaagg | aaagagtgag | gaactatcgc | atacctgcat | ttaaagatgc | cgatttgggc | 60 |
| gcgaatcctt | tattttggct | tcaccctcat | actattatca | gggccagaaa | aaggaagtgt | 120 |
| ttccctcctt | cttgaattga | tgttaccctc | ataaagcacg | tggcctctta | tcgagaaaga | 180 |
| aattaccgtc | gctcgtgatt | tgtttgcaaa | aagaacaaaa | ctgaattcag | gatcgtgcca | 240 |
| tatttgctca | ttttaccgtc | gtcttgagca | aatatcccat | gacaattgag | gatcgtgcca | 300 |
| tatttgctca | ttttaccgtc | gtcttgagca | aatatcccat | gagaattctt | cctgtcttcc | 360 |
| tattgattgc | agcttccaat | ttcgtcacac | aacaaggtcc | tagcgacggc | tcacaggttt | 420 |
| tgtaacaagc | aatcgaaggt | tctggaatgg | cgggaaaggg | tttagtacca | catgctatga | 480 |
| tgcccactgt | gatctccaga | gcaaagttcg | ttcgatcgta | ctgttactct | ctctctttca | 540 |
| aacagaattg | tccgaatcgt | gtgacaacaa | cagcctgttc | tcacacactc | ttttcttcta | 600 |
| accaagggg | tggtttagtt | tagtagaacc | tcgtgaaact | tacatttaca | tatatataaa | 660 |
| cttgcataaa | ttggtcaatg | caagaaatac | atatttggtc | ttttctaatt | cgtagttttt | 720 |
| caagttctta | gatgctttct | ttttctcttt | tttacagatc | atcaaggaag | taattatcta | 780 |
| cttttttacaa | caaatataaa | aca | | | | 803 |

<210> SEQ ID NO 83
<211> LENGTH: 863
<212> TYPE: DNA
<213> ORGANISM: Artificial Sequence
<220> FEATURE:
<223> OTHER INFORMATION: pCUR8" <223> "pCUR8
<220> FEATURE:
<223> OTHER INFORMATION: pCUR8
<220> FEATURE:
<223> OTHER INFORMATION: pCUR8

<400> SEQUENCE: 83

| | | | | | |
|---|---|---|---|---|---|
| gtgagtaagg | aaagagtgag | gaactatcgc | atacctgcat | ttaaagatgc | cgatttgggc | 60 |
| gcgaatcctt | tattttggct | tcaccctcat | actattatca | gggccagaaa | aaggaagtgt | 120 |
| ttccctcctt | cttgaattga | tgttaccctc | ataaagcacg | tggcctctta | tcgagaaaga | 180 |
| aattaccgtc | gctcgtgatt | tgtttgcaaa | aagaacaaaa | ctgaattcag | gatcgtgcca | 240 |
| tatttgctca | ttttaccgtc | gtcttgagca | aatatcccat | gacaattgag | gatcgtgcca | 300 |
| tatttgctca | ttttaccgtc | gtcttgagca | aatatcccat | gacaattgag | gatcgtgcca | 360 |
| tatttgctca | ttttaccgtc | gtcttgagca | aatatcccat | gagaattctt | cctgtcttcc | 420 |
| tattgattgc | agcttccaat | ttcgtcacac | aacaaggtcc | tagcgacggc | tcacaggttt | 480 |
| tgtaacaagc | aatcgaaggt | tctggaatgg | cgggaaaggg | tttagtacca | catgctatga | 540 |
| tgcccactgt | gatctccaga | gcaaagttcg | ttcgatcgta | ctgttactct | ctctctttca | 600 |
| aacagaattg | tccgaatcgt | gtgacaacaa | cagcctgttc | tcacacactc | ttttcttcta | 660 |
| accaagggg | tggtttagtt | tagtagaacc | tcgtgaaact | tacatttaca | tatatataaa | 720 |
| cttgcataaa | ttggtcaatg | caagaaatac | atatttggtc | ttttctaatt | cgtagttttt | 780 |
| caagttctta | gatgctttct | ttttctcttt | tttacagatc | atcaaggaag | taattatcta | 840 |
| cttttttacaa | caaatataaa | aca | | | | 863 |

<210> SEQ ID NO 84

-continued

```
<211> LENGTH: 863
<212> TYPE: DNA
<213> ORGANISM: Artificial Sequence
<220> FEATURE:
<223> OTHER INFORMATION: pCUR9" <223> "pCUR9
<220> FEATURE:
<223> OTHER INFORMATION: pCUR9
<220> FEATURE:
<223> OTHER INFORMATION: pCUR9

<400> SEQUENCE: 84
gtgagtaagg aaagagtgag gaactatcgc atacctgcat ttaaagatgc cgatttgggc      60
gcgaatcctt tattttggct tcaccctcat actattatca gggccagaaa aaggaagtgt     120
ttccctcctt cttgaattga tgttaccctc ataaagcacg tggcctctta tcgagaaaga    180
aattaccgtc gctcgtgatt tgtttgcaaa aagaacaaaa ctgaattctc atgggatatt    240
tgctcaagac gacggtaaaa tgagcaaata tggcacgatc tcaattgtc atgggatatt     300 tgctcaagac gacggtaaaa tgagcaaata tggcacgatc tcaattgtc atgggatatt     360 tgctcaagac gacggtaaaa tgagcaaata tggcacgatc ctgaattctt cctgtcttcc    420
tattgattgc agcttccaat ttcgtcacac aacaaggtcc tagcgacggc tcacaggttt    480
tgtaacaagc aatcgaaggt tctggaatgg cgggaaaggg tttagtacca catgctatga    540
tgcccactgt gatctccaga gcaaagttcg ttcgatcgta ctgttactct ctctctttca    600
aacagaattg tccgaatcgt gtgacaacaa cagcctgttc tcacacactc ttttcttcta    660
accaaggggg tggtttagtt tagtagaacc tcgtgaaact tacatttaca tatatataaa    720
cttgcataaa ttggtcaatg caagaaatac atatttggtc ttttctaatt cgtagttttt    780
caagttctta gatgctttct tttctctctt tttacagatc atcaaggaag taattatcta    840 cttttttacaa caaatataaa aca                                            863

<210> SEQ ID NO 85
<211> LENGTH: 923
<212> TYPE: DNA
<213> ORGANISM: Artificial Sequence
<220> FEATURE:
<223> OTHER INFORMATION: pCUR10" <223> "pCUR10
<220> FEATURE:
<223> OTHER INFORMATION: pCUR10
<220> FEATURE:
<223> OTHER INFORMATION: pCUR10

<400> SEQUENCE: 85
gtgagtaagg aaagagtgag gaactatcgc atacctgcat ttaaagatgc cgatttgggc      60
gcgaatcctt tattttggct tcaccctcat actattatca gggccagaaa aaggaagtgt     120
ttccctcctt cttgaattga tgttaccctc ataaagcacg tggcctctta tcgagaaaga    180
aattaccgtc gctcgtgatt tgtttgcaaa aagaacaaaa ctgaattctc atgggatatt    240
tgctcaagac gacggtaaaa tgagcaaata tggcacgatc tcaattgtc atgggatatt     300 tgctcaagac gacggtaaaa tgagcaaata tggcacgatc tcaattgtc atgggatatt     360 tgctcaagac gacggtaaaa tgagcaaata tggcacgatc tcaattgtc atgggatatt     420 tgctcaagac gacggtaaaa tgagcaaata tggcacgatc ctgaattctt cctgtcttcc    480
tattgattgc agcttccaat ttcgtcacac aacaaggtcc tagcgacggc tcacaggttt    540
tgtaacaagc aatcgaaggt tctggaatgg cgggaaaggg tttagtacca catgctatga    600
tgcccactgt gatctccaga gcaaagttcg ttcgatcgta ctgttactct ctctctttca    660
aacagaattg tccgaatcgt gtgacaacaa cagcctgttc tcacacactc ttttcttcta    720
```

```
accaaggggg tggtttagtt tagtagaacc tcgtgaaact tacatttaca tatatataaa    780
cttgcataaa ttggtcaatg caagaaatac atatttggtc ttttctaatt cgtagttttt    840
caagttctta gatgctttct ttttctcttt tttacagatc atcaaggaag taattatcta    900 cttttttacaa caaatataaa aca                                          923
```

<210> SEQ ID NO 86
<211> LENGTH: 983
<212> TYPE: DNA
<213> ORGANISM: Artificial Sequence
<220> FEATURE:
<223> OTHER INFORMATION: pCUR11" <223> "pCUR11
<220> FEATURE:
<223> OTHER INFORMATION: pCUR11
<220> FEATURE:
<223> OTHER INFORMATION: pCUR11

<400> SEQUENCE: 86

```
gtgagtaagg aaagagtgag gaactatcgc atacctgcat ttaaagatgc cgatttgggc     60
gcgaatcctt tattttggct tcaccctcat actattatca gggccagaaa aaggaagtgt    120
ttccctcctt cttgaattga tgttaccctc ataaagcacg tggcctctta tcgagaaaga    180
aattaccgtc gctcgtgatt tgtttgcaaa aagaacaaaa ctgaattctc atgggatatt    240
tgctcaagac gacggtaaaa tgagcaaata tggcacgatc ctcaattgtc atgggatatt    300
tgctcaagac gacggtaaaa tgagcaaata tggcacgatc ctcaattgtc atgggatatt    360
tgctcaagac gacggtaaaa tgagcaaata tggcacgatc ctcaattgtc atgggatatt    420
tgctcaagac gacggtaaaa tgagcaaata tggcacgatc ctcaattgtc atgggatatt    480
tgctcaagac gacggtaaaa tgagcaaata tggcacgatc ctgaattctt cctgtcttcc    540
tattgattgc agcttccaat ttcgtcacac aacaaggtcc tagcgacggc tcacaggttt    600
tgtaacaagc aatcgaaggt tctggaatgg cgggaaaggg tttagtacca catgctatga    660
tgcccactgt gatctccaga gcaaagttcg ttcgatcgta ctgttactct ctctctttca    720
aacagaattg tccgaatcgt gtgacaacaa cagcctgttc tcacacactc ttttcttcta    780
accaaggggg tggtttagtt tagtagaacc tcgtgaaact tacatttaca tatatataaa    840
cttgcataaa ttggtcaatg caagaaatac atatttggtc ttttctaatt cgtagttttt    900
caagttctta gatgctttct ttttctcttt tttacagatc atcaaggaag taattatcta    960 cttttttacaa caaatataaa aca                                          983
```

<210> SEQ ID NO 87
<211> LENGTH: 1043
<212> TYPE: DNA
<213> ORGANISM: Artificial Sequence
<220> FEATURE:
<223> OTHER INFORMATION: pCUR12" <223> "pCUR12
<220> FEATURE:
<223> OTHER INFORMATION: pCUR12
<220> FEATURE:
<223> OTHER INFORMATION: pCUR12

<400> SEQUENCE: 87

```
gtgagtaagg aaagagtgag gaactatcgc atacctgcat ttaaagatgc cgatttgggc     60
gcgaatcctt tattttggct tcaccctcat actattatca gggccagaaa aaggaagtgt    120
ttccctcctt cttgaattga tgttaccctc ataaagcacg tggcctctta tcgagaaaga    180
aattaccgtc gctcgtgatt tgtttgcaaa aagaacaaaa ctgaattcag gatcgtgcca    240
```

```
tatttgctca ttttaccgtc gtcttgagca aatatcccat gacaattgag gatcgtgcca      300
tatttgctca ttttaccgtc gtcttgagca aatatcccat gacaattgag gatcgtgcca      360
tatttgctca ttttaccgtc gtcttgagca aatatcccat gagaattcag gatcgtgcca      420
tatttgctca ttttaccgtc gtcttgagca aatatcccat gacaattgag gatcgtgcca      480
tatttgctca ttttaccgtc gtcttgagca aatatcccat gacaattgag gatcgtgcca      540
tatttgctca ttttaccgtc gtcttgagca aatatcccat gagaattctt cctgtcttcc      600
tattgattgc agcttccaat ttcgtcacac aacaaggtcc tagcgacggc tcacaggttt      660
tgtaacaagc aatcgaaggt tctggaatgg cgggaaaggg tttagtacca catgctatga      720
tgcccactgt gatctccaga gcaaagttcg ttcgatcgta ctgttactct ctctctttca      780
aacagaattg tccgaatcgt gtgacaacaa cagcctgttc tcacacactc ttttcttcta      840 accaagggg tggtttagtt tagtagaacc tcgtgaaact tacatttaca tatatataaa      900
cttgcataaa ttggtcaatg caagaaatac atatttggtc ttttctaatt cgtagttttt      960
caagttctta gatgctttct ttttctcttt tttacagatc atcaaggaag taattatcta     1020 cttttttacaa caaatataaa aca                                            1043

<210> SEQ ID NO 88
<211> LENGTH: 1043
<212> TYPE: DNA
<213> ORGANISM: Artificial Sequence
<220> FEATURE:
<223> OTHER INFORMATION: pCUR13" <223> "pCUR13
<220> FEATURE:
<223> OTHER INFORMATION: pCUR13
<220> FEATURE:
<223> OTHER INFORMATION: pCUR13

<400> SEQUENCE: 88
gtgagtaagg aaagagtgag gaactatcgc atacctgcat ttaaagatgc cgatttgggc       60
gcgaatcctt tattttggct tcaccctcat actattatca gggccagaaa aaggaagtgt      120
ttccctcctt cttgaattga tgttaccctc ataaagcacg tggcctctta tcgagaaaga      180
aattaccgtc gctcgtgatt tgtttgcaaa aagaacaaaa ctgaattctc atgggatatt      240
tgctcaagac gacggtaaaa tgagcaaata tggcacgatc ctcaattgtc atgggatatt      300
tgctcaagac gacggtaaaa tgagcaaata tggcacgatc ctcaattgtc atgggatatt      360
tgctcaagac gacggtaaaa tgagcaaata tggcacgatc ctgaattctc atgggatatt      420
tgctcaagac gacggtaaaa tgagcaaata tggcacgatc ctcaattgtc atgggatatt      480
tgctcaagac gacggtaaaa tgagcaaata tggcacgatc ctcaattgtc atgggatatt      540
tgctcaagac gacggtaaaa tgagcaaata tggcacgatc ctgaattctt cctgtcttcc      600
tattgattgc agcttccaat ttcgtcacac aacaaggtcc tagcgacggc tcacaggttt      660
tgtaacaagc aatcgaaggt tctggaatgg cgggaaaggg tttagtacca catgctatga      720
tgcccactgt gatctccaga gcaaagttcg ttcgatcgta ctgttactct ctctctttca      780
aacagaattg tccgaatcgt gtgacaacaa cagcctgttc tcacacactc ttttcttcta      840 accaagggg tggtttagtt tagtagaacc tcgtgaaact tacatttaca tatatataaa      900
cttgcataaa ttggtcaatg caagaaatac atatttggtc ttttctaatt cgtagttttt      960
caagttctta gatgctttct ttttctcttt tttacagatc atcaaggaag taattatcta     1020 cttttttacaa caaatataaa aca                                            1043
```

<210> SEQ ID NO 89
<211> LENGTH: 1223
<212> TYPE: DNA
<213> ORGANISM: Artificial Sequence
<220> FEATURE:
<223> OTHER INFORMATION: pCUR14" <223> "pCUR14
<220> FEATURE:
<223> OTHER INFORMATION: pCUR14
<220> FEATURE:
<223> OTHER INFORMATION: pCUR14

<400> SEQUENCE: 89

| | | | | | |
|---|---|---|---|---|---|
| gtgagtaagg | aaagagtgag | gaactatcgc | atacctgcat | ttaaagatgc | cgatttgggc | 60 |
| gcgaatcctt | tattttggct | tcaccctcat | actattatca | gggccagaaa | aaggaagtgt | 120 |
| ttccctcctt | cttgaattga | tgttaccctc | ataaagcacg | tggcctctta | tcgagaaaga | 180 |
| aattaccgtc | gctcgtgatt | tgtttgcaaa | aagaacaaaa | ctgaattctc | atgggatatt | 240 |
| tgctcaagac | gacggtaaaa | tgagcaaata | tggcacgatc | ctcaattgtc | atgggatatt | 300 |
| tgctcaagac | gacggtaaaa | tgagcaaata | tggcacgatc | ctcaattgtc | atgggatatt | 360 |
| tgctcaagac | gacggtaaaa | tgagcaaata | tggcacgatc | ctgaattctc | atgggatatt | 420 |
| tgctcaagac | gacggtaaaa | tgagcaaata | tggcacgatc | ctcaattgtc | atgggatatt | 480 |
| tgctcaagac | gacggtaaaa | tgagcaaata | tggcacgatc | ctcaattgtc | atgggatatt | 540 |
| tgctcaagac | gacggtaaaa | tgagcaaata | tggcacgatc | ctgaattctc | atgggatatt | 600 |
| tgctcaagac | gacggtaaaa | tgagcaaata | tggcacgatc | ctcaattgtc | atgggatatt | 660 |
| tgctcaagac | gacggtaaaa | tgagcaaata | tggcacgatc | ctcaattgtc | atgggatatt | 720 |
| tgctcaagac | gacggtaaaa | tgagcaaata | tggcacgatc | ctgaattctt | cctgtcttcc | 780 |
| tattgattgc | agcttccaat | ttcgtcacac | aacaaggtcc | tagcgacggc | tcacaggttt | 840 |
| tgtaacaagc | aatcgaaggt | tctggaatgg | cgggaaaggg | tttagtacca | catgctatga | 900 |
| tgcccactgt | gatctccaga | gcaaagttcg | ttcgatcgta | ctgttactct | ctctcttca | 960 |
| aacagaattg | tccgaatcgt | gtgacaacaa | cagcctgttc | tcacacactc | ttttcttcta | 1020 |
| accaagggg | tggtttagtt | tagtagaacc | tcgtgaaact | tacatttaca | tatatataaa | 1080 |
| cttgcataaa | ttggtcaatg | caagaaatac | atatttggtc | ttttctaatt | cgtagttttt | 1140 |
| caagttctta | gatgctttct | ttttctcttt | tttacagatc | atcaaggaag | taattatcta | 1200 |
| cttttttacaa | caaatataaa | aca | | | | 1223 |

<210> SEQ ID NO 90
<211> LENGTH: 1283
<212> TYPE: DNA
<213> ORGANISM: Artificial Sequence
<220> FEATURE:
<223> OTHER INFORMATION: pCUR15" <223> "pCUR15
<220> FEATURE:
<223> OTHER INFORMATION: pCUR15
<220> FEATURE:
<223> OTHER INFORMATION: pCUR15

<400> SEQUENCE: 90

| | | | | | |
|---|---|---|---|---|---|
| gtgagtaagg | aaagagtgag | gaactatcgc | atacctgcat | ttaaagatgc | cgatttgggc | 60 |
| gcgaatcctt | tattttggct | tcaccctcat | actattatca | gggccagaaa | aaggaagtgt | 120 |
| ttccctcctt | cttgaattga | tgttaccctc | ataaagcacg | tggcctctta | tcgagaaaga | 180 |
| aattaccgtc | gctcgtgatt | tgtttgcaaa | aagaacaaaa | ctgaattcag | gatcgtgcca | 240 |
| tatttgctca | ttttaccgtc | gtcttgagca | aatatcccat | gacaattgag | gatcgtgcca | 300 |

-continued

| | |
|---|---|
| tatttgctca ttttaccgtc gtcttgagca aatatcccat gacaattgag gatcgtgcca | 360 |
| tatttgctca ttttaccgtc gtcttgagca aatatcccat gacaattgag gatcgtgcca | 420 |
| tatttgctca ttttaccgtc gtcttgagca aatatcccat gagaattcag gatcgtgcca | 480 |
| tatttgctca ttttaccgtc gtcttgagca aatatcccat gacaattgag gatcgtgcca | 540 |
| tatttgctca ttttaccgtc gtcttgagca aatatcccat gacaattgag gatcgtgcca | 600 |
| tatttgctca ttttaccgtc gtcttgagca aatatcccat gagaattcag gatcgtgcca | 660 |
| tatttgctca ttttaccgtc gtcttgagca aatatcccat gacaattgag gatcgtgcca | 720 |
| tatttgctca ttttaccgtc gtcttgagca aatatcccat gacaattgag gatcgtgcca | 780 |
| tatttgctca ttttaccgtc gtcttgagca aatatcccat gagaattctt cctgtcttcc | 840 |
| tattgattgc agcttccaat ttcgtcacac aacaaggtcc tagcgacggc tcacaggttt | 900 |
| tgtaacaagc aatcgaaggt tctggaatgg cgggaaaggg tttagtacca catgctatga | 960 |
| tgcccactgt gatctccaga gcaaagttcg ttcgatcgta ctgttactct ctctctttca | 1020 |
| aacagaattg tccgaatcgt gtgacaacaa cagcctgttc tcacacactc tttcttcta | 1080 |
| accaagggg tggtttagtt tagtagaacc tcgtgaaact tacatttaca tatatataaa | 1140 |
| cttgcataaa ttggtcaatg caagaaatac atatttggtc ttttctaatt cgtagttttt | 1200 |
| caagttctta gatgctttct ttttctcttt tttacagatc atcaaggaag taattatcta | 1260 |
| cttttttacaa caaatataaa aca | 1283 |

<210> SEQ ID NO 91
<211> LENGTH: 686
<212> TYPE: DNA
<213> ORGANISM: Artificial Sequence
<220> FEATURE:
<223> OTHER INFORMATION: pCUR16" <223> "pCUR16
<220> FEATURE:
<223> OTHER INFORMATION: pCUR16
<220> FEATURE:
<223> OTHER INFORMATION: pCUR16

<400> SEQUENCE: 91

| | |
|---|---|
| gctcagcatc tgcttcttcc caaagatgaa cgcggcgtta tgtcactaac gacgtgcacc | 60 |
| aacttgcggg aattctcatg ggatatttgc tcaagacgac ggtaaaatga gcaaatatgg | 120 |
| cacgatcctc aattgtcatg ggatatttgc tcaagacgac ggtaaaatga gcaaatatgg | 180 |
| cacgatcctc aatgtcatgg gatatttgct caagacgacg gtaaaatgag caaatatggc | 240 |
| acgatcctga attccaccgc acgccttttt tctgaagccc actttcgtgg actttgccat | 300 |
| atatgcaaaa ttcatgaagt gtgataccaa gtcagcatac acctcactag ggtagtttct | 360 |
| ttggttgtat tgatcatttg gttcatcgtg gttcattaat ttttttttctc cattgctttc | 420 |
| tggctttgat cttactatca tttggatttt tgtcgaaggt tgtagaattg tatgtgacaa | 480 |
| gtggcaccaa gcatatataa aaaaaaaaag cattatcttc ctaccagagt tgattgttaa | 540 |
| aaacgtattt atagcaaacg caattgtaat taattccttat tttgtatctt tcttcccctt | 600 |
| gtctcaatct tttattttta ttttattttt cttttcttag tttctttcat aacaccaagc | 660 |
| aactaatact ataacataca ataata | 686 |

<210> SEQ ID NO 92
<211> LENGTH: 747
<212> TYPE: DNA
<213> ORGANISM: Artificial Sequence
<220> FEATURE:
<223> OTHER INFORMATION: pCUR17" <223> "pCUR17

<220> FEATURE:
<223> OTHER INFORMATION: pCUR17
<220> FEATURE:
<223> OTHER INFORMATION: pCUR17

<400> SEQUENCE: 92

```
gctcagcatc tgcttcttcc caaagatgaa cgcggcgtta tgtcactaac gacgtgcacc      60
aacttgcggg aattctcatg ggatatttgc tcaagacgac ggtaaaatga gcaaatatgg     120
cacgatcctc aattgtcatg ggatatttgc tcaagacgac ggtaaaatga gcaaatatgg     180
cacgatcctc aattctcatg ggatatttgc tcaagacgac ggtaaaatga gcaaatatgg     240
cacgatcctc aattctcatg ggatatttgc tcaagacgac ggtaaaatga gcaaatatgg     300
cacgatcctg aattccaccg cacgcctttt ttctgaagcc cactttcgtg gactttgcca     360
tatatgcaaa attcatgaag tgtgatacca agtcagcata cacctcacta gggtagtttc     420
tttggttgta ttgatcattt ggttcatcgt ggttcattaa ttttttttct ccattgcttt     480
ctggctttga tcttactatc atttggattt ttgtcgaagg ttgtagaatt gtatgtgaca     540
agtggcacca agcatatata aaaaaaaaaa gcattatctt cctaccagag ttgattgtta     600
aaaacgtatt tatagcaaac gcaattgtaa ttaattctta ttttgtatct tttcttccct     660
tgtctcaatc tttattttt attttatttt tcttttctta gtttctttca taacaccaag     720
caactaatac tataacatac aataata                                         747
```

<210> SEQ ID NO 93
<211> LENGTH: 500
<212> TYPE: DNA
<213> ORGANISM: Saccharomyces cerevisiae
<220> FEATURE:
<223> OTHER INFORMATION: pLYS1" <223> "pLYS1
<220> FEATURE:
<223> OTHER INFORMATION: pLYS1
<220> FEATURE:
<223> OTHER INFORMATION: pLYS1

<400> SEQUENCE: 93

```
gcaagttaac attagggaga acgtggggcc ttcctccatg agtgcagagc aattgaagat      60
gtttagaggt ttaaaggaga ataaccagtt gctggatagc tctgtgccag ctacagttta     120
tgccaaattg gcccttcatg gtattcctga cggtgttaat ggacagtact tgagctataa     180
tgaccctgcc ttggcggact ttatgccttg aggatagcag gtacatataa attgttacat     240
actaagtcga tgagtcaaaa aagactctta tacatttata cattttgcat tattattttt     300
tttttccagc ggaatttgga attccgctct caaccgccaa aattcccctg cgatttcagc     360
gacaaagagt cataaagtca tcctcgagaa accacgatga aatatataaa aagcccatct     420
tccctgacgg aaactggtat tttaggaggc ataccataag ataacaacga aaacgcttta     480
tttttcacac aaccgcaaaa                                                 500
```

<210> SEQ ID NO 94
<211> LENGTH: 650
<212> TYPE: DNA
<213> ORGANISM: Saccharomyces cerevisiae
<220> FEATURE:
<223> OTHER INFORMATION: pLYS4" <223> "pLYS4
<220> FEATURE:
<223> OTHER INFORMATION: pLYS4
<220> FEATURE:
<223> OTHER INFORMATION: pLYS4

<400> SEQUENCE: 94

```
ttgaaaaatg cgaagttgaa gtgccataga agagaaacag cccacacagg ggagaagccc    60
actggaaagg gggcactgac caactttaaa taggaaacag aagataccac aagccagcga   120
tacaacagca ccaaacaccg aaaagaatag ccaaagctgt cctctggtgt tggaaaaact   180
ggaaaaaacg caactgcgtt ggctgctacg gtgaaaaatt ttcctatgac ttttttcact   240
gcttgttcgt gcgaaattac cgcaaacccg gtaaaatgta cacgtatcaa gtgataaaca   300
atttcgtgtc aagtgagcag aatggagcga tttggaaaaa aaaattttt attgttttt    360 cccccgggat tttgctcgag atgactgaaa ttttgtaatc gatgagtcta taccagaggc   420
agcaaatatc accaacatac acaggtatac acaatctcat gtccacacac acgtacagac   480
acgcacatat atatatatat atatatatcc ccataggtat ttatatatac aaaagaatcc   540
tcgtgtgttt gtgtgtgcaa tagctagttt tgcgctgcct cttatagtag acaatatcac   600
tttttcaata aaatagaact tgcaaggaaa caaaattgta tcgcttcaag              650
```

<210> SEQ ID NO 95
<211> LENGTH: 500
<212> TYPE: DNA
<213> ORGANISM: Saccharomyces cerevisiae
<220> FEATURE:
<223> OTHER INFORMATION: pLYS9" <223> "pLYS9
<220> FEATURE:
<223> OTHER INFORMATION: pLYS9
<220> FEATURE:
<223> OTHER INFORMATION: pLYS9

<400> SEQUENCE: 95

```
acatatgcaa gagtcttatg tatcgtatct aagtgccacg taggggattc ccatcatttg    60
atgatttcca aatataatac ctgtagagag cggtggagca aaagtcaaat tttaatcgca   120
actgcagaca agtcaagctg aggaaattgt ggatgatctc ttgtttcttt tgatattcac   180
cacaacagaa gtgaagagtg tgattgcggt tactactgac cacgaagcaa tgcgtttagt   240
agtgaaaaga attactcata ctctggaatc gaaattccgt tggaaaaatt cgctttgtag   300
tgaaaaataa agatgtcaat aaagggtatt gagaatttcc aatggaatta tcagcaatag   360
atgatagaaa gtagcacaga atttggctta atggtatata aaccgtaggg tcctggtaaa   420
attacatggg aaggatcctt aggcagtagg gaaaacttat caggacaatt gagttatatt   480
aacgtattat atattttaat                                                 500
```

<210> SEQ ID NO 96
<211> LENGTH: 494
<212> TYPE: DNA
<213> ORGANISM: Artificial Sequence
<220> FEATURE:
<223> OTHER INFORMATION: pLYR1p" <223> "pLYR1p
<220> FEATURE:
<223> OTHER INFORMATION: pLYR1p
<220> FEATURE:
<223> OTHER INFORMATION: pLYR1p

<400> SEQUENCE: 96

```
ttatattgaa ttttcaaaaa ttcttacttt ttttttggat ggacgcaaag aagtttaata    60
atcatattac atggcattac caccatatac atatccatat ctaatcttac ttatatgttg   120
tggaaatgta aagagcccga attcctcata ctctggaatc gaaattccgt tggaaaaatt   180
cgctttgtag tgaaaaataa agatgtcaat aaagggtatt gagaatttcc aatggaatta   240
tcagcaatag atgatagaaa gaattcggat gataatgcga ttagtttttt agccttattt   300
ctggggtaat taatcagcga agcgatgatt tttgatctat taacagatat ataaatggaa   360
```

```
aagctgcata accactttaa ctaatacttt caacattttc agtttgtatt acttcttatt      420
caaatgtcat aaaagtatca acaaaaaatt gttaatatac ctctatactt taacgtcaag      480
gagaaaaaac tata                                                         494

<210> SEQ ID NO 97
<211> LENGTH: 494
<212> TYPE: DNA
<213> ORGANISM: Artificial Sequence
<220> FEATURE:
<223> OTHER INFORMATION: pLYR2p" <223> "pLYR2p
<220> FEATURE:
<223> OTHER INFORMATION: pLYR2p
<220> FEATURE:
<223> OTHER INFORMATION: pLYR2p

<400> SEQUENCE: 97
ttatattgaa ttttcaaaaa ttcttacttt tttttttggat ggacgcaaag aagtttaata      60
atcatattac atggcattac caccatatac atatccatat ctaatcttac ttatatgttg     120
tggaaatgta aagagcccga attctttcta tcatctattg ctgataattc cattggaaat     180
tctcaatacc ctttattgac atctttattt ttcactacaa agcgaatttt tccaacggaa     240
tttcgattcc agagtatgag gaattcggat gataatgcga ttagtttttt agccttattt     300
ctggggtaat taatcagcga agcgatgatt tttgatctat taacagatat ataaatggaa     360
aagctgcata accactttaa ctaatacttt caacattttc agtttgtatt acttcttatt     420
caaatgtcat aaaagtatca acaaaaaatt gttaatatac ctctatactt taacgtcaag     480
gagaaaaaac tata                                                        494

<210> SEQ ID NO 98
<211> LENGTH: 616
<212> TYPE: DNA
<213> ORGANISM: Artificial Sequence
<220> FEATURE:
<223> OTHER INFORMATION: pLYR3p" <223> "pLYR3p
<220> FEATURE:
<223> OTHER INFORMATION: pLYR3p
<220> FEATURE:
<223> OTHER INFORMATION: pLYR3p

<400> SEQUENCE: 98
ttatattgaa ttttcaaaaa ttcttacttt tttttttggat ggacgcaaag aagtttaata      60
atcatattac atggcattac caccatatac atatccatat ctaatcttac ttatatgttg     120
tggaaatgta aagagcccga attcctcata ctctggaatc gaaattccgt tggaaaaatt     180
cgctttgtag tgaaaaataa agatgtcaat aaagggtatt gagaatttcc aatggaatta     240
tcagcaatag atgatagaaa gaattcctca tactctggaa tcgaattcc gttggaaaaa      300 ttcgctttgt agtgaaaaat aaagatgtca ataaggggta ttgagaattt ccaatggaat     360
tatcagcaat agatgataga agaattcgg atgataatgc gattagtttt ttagccttat     420
ttctggggta attaatcagc gaagcgatga ttttgatct attaacagat atataaatgg     480
aaaagctgca taaccactttt aactaatact ttcaacattt tcagtttgta ttacttctta    540
ttcaaatgtc ataaaagtat caacaaaaaa ttgttaatat acctctatac tttaacgtca    600
aggagaaaaa actata                                                      616

<210> SEQ ID NO 99
<211> LENGTH: 616
<212> TYPE: DNA
```

<213> ORGANISM: Artificial Sequence
<220> FEATURE:
<223> OTHER INFORMATION: pLYR4p" <223> "pLYR4p
<220> FEATURE:
<223> OTHER INFORMATION: pLYR4p
<220> FEATURE:
<223> OTHER INFORMATION: pLYR4p

<400> SEQUENCE: 99

| | | | | | |
|---|---|---|---|---|---|
| ttatattgaa | ttttcaaaaa | ttcttacttt | tttttttggat | ggacgcaaag | aagtttaata | 60 |
| atcatattac | atggcattac | caccatatac | atatccatat | ctaatcttac | ttatatgttg | 120 |
| tggaaatgta | aagagcccga | attctttcta | tcatctattg | ctgataattc | cattggaaat | 180 |
| tctcaatacc | ctttattgac | atctttatttt | ttcactacaa | agcgaatttt | tccaacggaa | 240 |
| tttcgattcc | agagtatgag | gaattctttc | tatcatctat | tgctgataat | tccattggaa | 300 |
| attctcaata | ccctttattg | acatctttat | ttttcactac | aaagcgaatt | tttccaacgg | 360 |
| aatttcgatt | ccagagtatg | aggaattcgg | atgataatgc | gattagtttt | ttagccttat | 420 |
| ttctgggta | attaatcagc | gaagcgatga | ttttgatct | attaacagat | atataaatgg | 480 |
| aaaagctgca | taaccacttt | aactaatact | ttcaacattt | tcagtttgta | ttacttctta | 540 |
| ttcaaatgtc | ataaaagtat | caacaaaaaa | ttgttaatat | acctctatac | tttaacgtca | 600 |
| aggagaaaaa | actata | | | | | 616 |

<210> SEQ ID NO 100
<211> LENGTH: 738
<212> TYPE: DNA
<213> ORGANISM: Artificial Sequence
<220> FEATURE:
<223> OTHER INFORMATION: pLYR5p" <223> "pLYR5p
<220> FEATURE:
<223> OTHER INFORMATION: pLYR5p
<220> FEATURE:
<223> OTHER INFORMATION: pLYR5p

<400> SEQUENCE: 100

| | | | | | |
|---|---|---|---|---|---|
| ttatattgaa | ttttcaaaaa | ttcttacttt | tttttttggat | ggacgcaaag | aagtttaata | 60 |
| atcatattac | atggcattac | caccatatac | atatccatat | ctaatcttac | ttatatgttg | 120 |
| tggaaatgta | aagagcccga | attctttcta | tcatctattg | ctgataattc | cattggaaat | 180 |
| tctcaatacc | ctttattgac | atctttatttt | ttcactacaa | agcgaatttt | tccaacggaa | 240 |
| tttcgattcc | agagtatgag | gaattctttc | tatcatctat | tgctgataat | tccattggaa | 300 |
| attctcaata | ccctttattg | acatctttat | ttttcactac | aaagcgaatt | tttccaacgg | 360 |
| aatttcgatt | ccagagtatg | aggaattctt | tctatcatct | attgctgata | attccattgg | 420 |
| aaattctcaa | tacccttttat | tgacatcttt | attttttcact | acaaagcgaa | tttttccaac | 480 |
| ggaatttcga | ttccagagta | tgaggaattc | ggatgataat | gcgattagtt | ttttagcctt | 540 |
| atttctgggg | taattaatca | gcgaagcgat | gattttgat | ctattaacag | atatataaat | 600 |
| ggaaaagctg | cataaccact | ttaactaata | ctttcaacat | tttcagtttg | tattacttct | 660 |
| tattcaaatg | tcataaaagt | atcaacaaaa | aattgttaat | atacctctat | actttaacgt | 720 |
| caaggagaaa | aaactata | | | | | 738 |

<210> SEQ ID NO 101
<211> LENGTH: 1104
<212> TYPE: DNA
<213> ORGANISM: Artificial Sequence
<220> FEATURE:
<223> OTHER INFORMATION: pLYR6p" <223> "pLYR6p
<220> FEATURE:
<223> OTHER INFORMATION: pLYR6p
<220> FEATURE:
<223> OTHER INFORMATION: pLYR6p

<400> SEQUENCE: 101

```
ttatattgaa ttttcaaaaa ttcttacttt tttttggat ggacgcaaag aagtttaata      60
atcatattac atggcattac caccatatac atatccatat ctaatcttac ttatatgttg    120
tggaaatgta aagagcccga attgctcata ctctggaatc gaaattccgt tggaaaaatt    180
cgctttgtag tgaaaaataa agatgtcaat aaagggtatt gagaatttcc aatggaatta    240
tcagcaatag atgatagaaa gaattcctca tactctggaa tcgaaattcc gttggaaaaa    300
ttcgctttgt agtgaaaaat aaagatgtca ataagggta ttgagaattt ccaatggaat    360
tatcagcaat agatgataga agaattcct catactctgg aatcgaaatt ccgttggaaa    420
aattcgcttt gtagtgaaaa ataaagatgt caataaaggg tattgagaat tccaatgga    480
attatcagca atagatgata gaaacaattg ctcatactct ggaatcgaaa ttccgttgga    540
aaaattcgct ttgtagtgaa aataaagat gtcaataaag ggtattgaga atttccaatg    600
gaattatcag caatagatga tagaaagaat tcctcatact ctggaatcga aattccgttg    660
gaaaaattcg ctttgtagtg aaaataaag atgtcaataa agggtattga gaatttccaa    720
tggaattatc agcaatagat gatagaaaga attcctcata ctctggaatc gaaattccgt    780
tggaaaaatt cgctttgtag tgaaaaataa agatgtcaat aaagggtatt gagaatttcc    840
aatggaatta tcagcaatag atgatagaaa caattcggat gataatgcga ttagttttt    900
agccttattt ctggggtaat taatcagcga agcgatgatt tttgatctat aacagatat    960
ataaatggaa agctgcata accactttaa ctaatacttt caacattttc agtttgtatt   1020
acttcttatt caaatgtcat aaaagtatca acaaaaaatt gttaatatac ctctatactt   1080
taacgtcaag gagaaaaaac tata                                          1104
```

<210> SEQ ID NO 102
<211> LENGTH: 1836
<212> TYPE: DNA
<213> ORGANISM: Artificial Sequence
<220> FEATURE:
<223> OTHER INFORMATION: pLYR7p" <223> "pLYR7p
<220> FEATURE:
<223> OTHER INFORMATION: pLYR7p
<220> FEATURE:
<223> OTHER INFORMATION: pLYR7p

<400> SEQUENCE: 102

```
ttatattgaa ttttcaaaaa ttcttacttt tttttggat ggacgcaaag aagtttaata      60
atcatattac atggcattac caccatatac atatccatat ctaatcttac ttatatgttg    120
tggaaatgta aagagcccga attgtttcta tcatctattg ctgataattc cattggaaat    180
tctcaatacc cttattgac atctttattt ttcactacaa agcgaatttt tccaacggaa    240
tttcgattcc agagtatgag gaattctttc tatcatctat tgctgataat tccattggaa    300
attctcaata ccctttattg acatcttat ttttcactac aaagcgaatt tttccaacgg    360
aatttcgatt ccagagtatg aggaattctt tctatcatct attgctgata attccattgg    420
aaattctcaa tacccttat tgacatcttt atttttcact acaaagcgaa ttttttccaac    480
ggaatttcga ttccagagta tgagcaattg tttctatcat ctattgctga taattccatt    540
ggaaattctc aatacccttt attgacatct ttatttttca ctacaaagcg aattttttcca    600
```

```
acggaatttc gattccagag tatgaggaat tctttctatc atctattgct gataattcca      660
ttggaaattc tcaataccct ttattgacat ctttattttt cactacaaag cgaattttc       720 caacggaatt tcgattccag agtatgagga attcttccta tcatctattg ctgataattc      780
cattggaaat tctcaatacc ctttattgac atctttattt ttcactacaa agcgaatttt      840
tccaacggaa tttcgattcc agagtatgag caattgtttc tatcatctat tgctgataat      900
tccattggaa attctcaata ccctttattg acatctttat ttttcactac aaagcgaatt      960
tttccaacgg aatttcgatt ccagagtatg aggaattctt ctatcatct attgctgata      1020 attccattgg aaattctcaa tacccttttat tgacatcttt attttcact acaaagcgaa      1080 ttttccaac ggaatttcga ttccagagta tgaggaattc tttctatcat ctattgctga      1140
taattccatt ggaaattctc aatacccttt attgacatct ttattttca ctacaaagcg      1200 aattttccca acggaatttc gattccagag tatgagcaat gtttctatc atctattgct      1260 gataattcca ttggaaattc tcaataccct ttattgacat ctttattttt cactacaaag      1320 cgaattttc caacggaatt tcgattccag agtatgagga attcttccta tcatctattg      1380
ctgataattc cattggaaat tctcaataccc ctttattgac atctttattt tcactacaa      1440 agcgaatttt tccaacggaa tttcgattcc agagtatgag gaattcttc tatcatctat       1500 tgctgataat tccattggaa attctcaata ccctttattg acatctttat ttttcactac      1560
aaagcgaatt tttccaacgg aatttcgatt ccagagtatg agcaattcgg atgataatgc      1620 gattagttt ttagccttat ttctggggta attaatcagc gaagcgatga ttttgatct      1680 attaacagat atataaatgg aaaagctgca taaccacttt aactaatact ttcaacattt      1740
tcagtttgta ttacttctta ttcaaatgtc ataaagtat caacaaaaaa ttgttaatat      1800
acctctatac ttaacgtca aggagaaaaa actata                                1836
```

<210> SEQ ID NO 103
<211> LENGTH: 981
<212> TYPE: DNA
<213> ORGANISM: Artificial Sequence
<220> FEATURE:
<223> OTHER INFORMATION: pLYR8" <223> "pLYR8
<220> FEATURE:
<223> OTHER INFORMATION: pLYR8
<220> FEATURE:
<223> OTHER INFORMATION: pLYR8

<400> SEQUENCE: 103

```
ttacattatc aatccttgcg tttcagcttc cactaattta gatgactatt tctcatcatt       60
tgcgtcatct tctaacaccg tatatgataa tatactagta acgtaaatac tagttagtag      120
atgatagttg attttttattc caacactaag aaataaattc gccatttctt gaatgtatt      180 aaagatattt aatgctataa tagacattta atccaattc ttccaacata caatgggagt      240
ttggccgagt ggtttaaggc gtcagattta ggtggattta acctctaaaa tctctgatat      300
cttcggatgc aagggttcga atcccttagc tctcattatt ttttgctttt tctcttgaat      360
tgctcatact ctggaatcga aattccgttg gaaaaattcg ctttgtagtg aaaaataaag      420
atgtcaataa agggtattga gaatttccaa tggaattatc agcaatagat gatagaaaga      480
attcctcata ctctggaatc gaaattccgt tggaaaaatt cgctttgtag tgaaaaataa      540
agatgtcaat aaagggtatt gagaatttcc aatggaatta tcagcaatag atgatagaaa      600
gaattcctca tactctggaa tcgaaattcc gttggaaaaa ttcgctttgt agtgaaaaat      660
aaagatgtca taaagggta ttgagaatttt ccaatggaat tatcagcaat agatgataga      720
```

```
aacaattcta attaagttag tcaaggcgcc atcctcatga aaactgtgta acataataac    780
cgaagtgtcg aaaaggtggc accttgtcca attgaacacg ctcgatgaaa aaataagat    840 atatataagg ttaagtaaag cgtctgttag aaaggaagtt tttcctttt  cttgctctct    900 tgtcttttca tctactattt ccttcgtgta atacagggtc gtcagataca tagatacaat    960
tctattaccc ccatccatac a                                              981
```

<210> SEQ ID NO 104
<211> LENGTH: 981
<212> TYPE: DNA
<213> ORGANISM: Artificial Sequence
<220> FEATURE:
<223> OTHER INFORMATION: pLYR9" <223> "pLYR9
<220> FEATURE:
<223> OTHER INFORMATION: pLYR9
<220> FEATURE:
<223> OTHER INFORMATION: pLYR9

<400> SEQUENCE: 104

```
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg attttattc caacactaag aaataaattc gccatttctt gaatgtattt     180
aaagatattt aatgctataa tagacattta atccaattc ttccaacata caatgggagt     240
ttggccgagt ggtttaaggc gtcagattta ggtggattta acctctaaaa tctctgatat    300
cttcggatgc aagggttcga atcccttagc tctcattatt ttttgctttt tctcttgaat    360
tgtttctatc atctattgct gataattcca ttggaaattc tcaatacct ttattgacat     420 ctttattttt cactacaaag cgaattttc caacggaatt tcgattccag agtatgagga    480 attcttttcta tcatctattg ctgataattc cattggaaat tctcaatacc ctttattgac    540
atctttattt ttcactacaa agcgaatttt tccaacggaa tttcgattcc agagtatgag    600
gaattctttc tatcatctat tgctgataat tccattggaa attctcaata cccttttattg    660 acatctttat tttcactac aaagcgaatt tttccaacgg aatttcgatt ccagagtatg    720
agcaattcta attaagttag tcaaggcgcc atcctcatga aaactgtgta acataataac    780
cgaagtgtcg aaaaggtggc accttgtcca attgaacacg ctcgatgaaa aaataagat    840 atatataagg ttaagtaaag cgtctgttag aaaggaagtt tttccttttt cttgctctct    900
tgtcttttca tctactattt ccttcgtgta atacagggtc gtcagataca tagatacaat    960
tctattaccc ccatccatac a                                              981
```

<210> SEQ ID NO 105
<211> LENGTH: 1225
<212> TYPE: DNA
<213> ORGANISM: Artificial Sequence
<220> FEATURE:
<223> OTHER INFORMATION: pLYR10" <223> "pLYR10
<220> FEATURE:
<223> OTHER INFORMATION: pLYR10
<220> FEATURE:
<223> OTHER INFORMATION: pLYR10

<400> SEQUENCE: 105

```
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg attttattc caacactaag aaataaattc gccatttctt gaatgtattt     180
```

```
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tgtttctatc atctattgct gataattcca ttggaaattc tcaatacccct ttattgacat    420 ctttattttt cactacaaag cgaattttc caacggaatt tcgattccag agtatgagga    480
attctttcta tcatctattg ctgataattc cattggaaat tctcaatacc ctttattgac    540
atctttattt ttcactacaa agcgaatttt tccaacgaa tttcgattcc agagtatgag    600
gaattctttc tatcatctat tgctgataat tccattggaa attctcaata cccctttattg    660 acatctttat ttttcactac aaagcgaatt tttccaacgg aatttcgatt ccagagtatg    720
aggaattctt tctatcatct attgctgata attccattgg aaattctcaa taccctttat    780
tgacatcttt atttttcact acaaagcgaa tttttccaac ggaatttcga ttccagagta    840
tgaggaattc tttctatcat ctattgctga taattccatt ggaaattctc aatacccttt    900
attgacatct ttatttttca ctacaaagcg aattttttcca acggaatttc gattccagag    960
tatgagcaat tctaattaag ttagtcaagg cgccatcctc atgaaaactg tgtaacataa    1020
taaccgaagt gtcgaaaagg tggcaccttg tccaattgaa cacgctcgat gaaaaaaata    1080
agatatatat aaggttaagt aaagcgtctg ttagaaagga agttttttcct ttttcttgct    1140 ctcttgtctt ttcatctact atttccttcg tgtaatacag ggtcgtcaga tacatagata    1200
caattctatt accccccatcc ataca                                         1225
```

<210> SEQ ID NO 106
<211> LENGTH: 1347
<212> TYPE: DNA
<213> ORGANISM: Artificial Sequence
<220> FEATURE:
<223> OTHER INFORMATION: pLYR11" <223> "pLYR11
<220> FEATURE:
<223> OTHER INFORMATION: pLYR11
<220> FEATURE:
<223> OTHER INFORMATION: pLYR11

<400> SEQUENCE: 106

```
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg atttttattc caacactaag aaataaattc gccatttctt gaatgtatt    180 aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tgctcatact ctggaatcga aattccgttg gaaaaattcg ctttgtagtg aaaaataaag    420
atgtcaataa agggtattga gaatttccaa tggaattatc agcaatagat gatagaaaga    480
attcctcata ctctggaatc gaaattccgt tggaaaaatt cgctttgtag tgaaaaataa    540
agatgtcaat aaagggtatt gagaatttcc aatggaatta tcagcaatag atgatagaaa    600
gaattcctca tactctggaa tcgaaattcc gttggaaaaa ttcgctttgt agtgaaaaat    660
aaagatgtca ataaagggta ttgagaattt ccaatggaat tatcagcaat agatgataga    720
aagaattcct catactctgg aatcgaaatt ccgttggaaa aattcgcttt gtagtgaaaa    780
ataaagatgt caataaaggg tattgagaat ttccaatgga attatcagca atagatgata    840
gaaagaattc ctcatactct ggaatcgaaa ttccgttgga aaaattcgct ttgtagtgaa    900
```

```
aaataaagat gtcaataaag ggtattgaga atttccaatg gaattatcag caatagatga    960
tagaaagaat tcctcatact ctggaatcga attccgttg gaaaaattcg ctttgtagtg    1020
aaaaataaag atgtcaataa agggtattga gaatttccaa tggaattatc agcaatagat    1080
gatagaaaca attctaatta agttagtcaa ggcgccatcc tcatgaaaac tgtgtaacat    1140
aataaccgaa gtgtcgaaaa ggtggcacct tgtccaattg aacacgctcg atgaaaaaaa    1200
taagatatat ataaggttaa gtaaagcgtc tgttagaaag gaagttttc cttttcttg     1260 ctctcttgtc ttttcatcta ctatttcctt cgtgtaatac agggtcgtca gatacataga    1320
tacaattcta ttaccccat ccataca                                        1347
```

<210> SEQ ID NO 107
<211> LENGTH: 686
<212> TYPE: DNA
<213> ORGANISM: Saccharomyces cerevisiae
<220> FEATURE:
<223> OTHER INFORMATION: pMET17" <223> "pMET17
<220> FEATURE:
<223> OTHER INFORMATION: pMET17
<220> FEATURE:
<223> OTHER INFORMATION: pMET17

<400> SEQUENCE: 107

```
ttacattatc aatccttgcg tttcagcttc cactaattta gatgactatt tctcatcatt     60
tgcgtcatct tctaacaccg tatatgataa atactagta acgtaaatac tagttagtag    120
atgatagttg atttttattc caacactaag aaataaattc gccatttctt gaatgtattt    180
aaagatattt aatgctataa tagacattta atccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgagg    360
tcacatgatc gcaaaatggc aaatggcacg tgaagctgtc gatattgggg aactgtggtg    420
gttggcaaat gactaattaa gttagtcaag gcgccatcct catgaaaact gtgtaacata    480
ataaccgaag tgtcgaaaag gtggcaccct gtccaattga acacgctcga tgaaaaaaat    540
aagatatata taaggttaag taaagcgtct gttagaaagg aagtttcc ttttcttgc      600 tctcttgtct tttcatctac tatttccttc gtgtaataca gggtcgtcag atacatagat    660
acaattctat taccccatc cataca                                         686
```

<210> SEQ ID NO 108
<211> LENGTH: 510
<212> TYPE: DNA
<213> ORGANISM: Saccharomyces cerevisiae
<220> FEATURE:
<223> OTHER INFORMATION: pMET6" <223> "pMET6
<220> FEATURE:
<223> OTHER INFORMATION: pMET6
<220> FEATURE:
<223> OTHER INFORMATION: pMET6

<400> SEQUENCE: 108

```
ccacaggaaa tatttcacgt gacttacaaa cagagtcgta cgtcaggacc ggagtcaggt     60 gaaaaatgt gggccggtaa agggaaaaaa ccagaaacgg gactactatc gaactcgttt    120
agtcgcgaac gtgcaaaagg ccaatatttt tcgctagagt catcgcagtc atggcagctc    180
tttcgctcta tctcccggtc gcaaaactgt ggtagtcata gctcgttctg ctcaattgag    240
aactgtgaat gtgaatatgg aacaaatgcg atagatgcac taatttaagg gaagctagct    300
```

```
agttttccca actgcgaaag aaaaaaagga agaaaaaaa aattctatat aagtgataga    360
tatttccatc tttactagca ttagtttctc ttttacgtat tcaatatttt tgttaaactc   420
ttcctttatc ataaaaaagc aagcatctaa gagcattgac aacactctaa gaaacaaaat   480
accaatataa tttcaaagta catatcaaaa                                    510
```

<210> SEQ ID NO 109
<211> LENGTH: 508
<212> TYPE: DNA
<213> ORGANISM: Saccharomyces cerevisiae
<220> FEATURE:
<223> OTHER INFORMATION: pMET14" <223> "pMET14
<220> FEATURE:
<223> OTHER INFORMATION: pMET14
<220> FEATURE:
<223> OTHER INFORMATION: pMET14

<400> SEQUENCE: 109

```
cctatgcatg tttagagcaa gcgcctttgt gagccctccc ggttacgacg ccttggcaat     60
gtagcagata actctgcact tctagaatca ttccactacg acatttggct catcaccagc    120
tcgcgagaaa tgtaaataag ccaacaacca agaatgcgta acattaaaga atacagttgc    180
tttcatttcg gcgtgatggt acggcaccca cggttcctta cattattctc gaaaaatagc    240
tgcacgcttt tccaggaata aaagaccgtg ccactaattt cacgtgatca atatatttac    300
aagccacctc aaaaaatgtg gcaatggaga agaggatgaa cgactcaata tgacttcaac    360
ttcatgaatt tgtcaaaata tctatataag atgcaaaatt tctatacaac atcagttgcg    420
tatccgttaa tgtcgttcat tttctctctt tgttcgaact tgacatcaag aaaagttgga    480
attatttctc caagcacact gtacacca                                       508
```

<210> SEQ ID NO 110
<211> LENGTH: 552
<212> TYPE: DNA
<213> ORGANISM: Saccharomyces cerevisiae
<220> FEATURE:
<223> OTHER INFORMATION: pMET3" <223> "pMET3
<220> FEATURE:
<223> OTHER INFORMATION: pMET3
<220> FEATURE:
<223> OTHER INFORMATION: pMET3

<400> SEQUENCE: 110

```
aacgatatgt acgtagtggt ataaggtgag ggggtccaca gatataacat cgtttaattt     60
agtactaaca gagacttttg tcacaactac atataagtgt acaaatatag tacagatatg    120
acacacttgt agcgccaacg cgcatcctac ggattgctga cagaaaaaaa ggtcacgtga    180
ccagaaaagt cacgtgtaat tttgtaactc accgcattct agcggtccct gtcgtgcaca    240
ctgcactcaa caccataaac cttagcaacc tccaaaggaa atcaccgtat aacaaagcca    300
cagttttaca acttagtctc ttatgaagtt acttaccaat gagaaataga ggctctttct    360
cgacaaatat gaatatggat atatatatat atatatatat atatatatat atatatatgt    420
aaacttggtt ctttttttagc ttgtgatctc tagcttgggt ctctctctgt cgtaacagtt    480
gtgatatcgt ttcttaacaa ttgaaaagga actaagaaag tataataata acaagaataa    540
agtataatta ac                                                        552
```

<210> SEQ ID NO 111
<211> LENGTH: 363
<212> TYPE: DNA
<213> ORGANISM: Saccharomyces cerevisiae

```
<220> FEATURE:
<223> OTHER INFORMATION: pSAM1" <223> "pSAM1
<220> FEATURE:
<223> OTHER INFORMATION: pSAM1
<220> FEATURE:
<223> OTHER INFORMATION: pSAM1

<400> SEQUENCE: 111
gaaacggacg taagacggaa atagaatttg aagataaagt tatatatcac tacacacgaa     60
tactttcttt ttttttttc acaggaaaac tgtggtggcg cccttgccta ctagtgcatt    120
tcttttttcg ggttcttgtc tcgacgaaat tttagcctca tcgtagtttt tcactctggt    180
atcgatgaaa aagggaagag taaaaagttt tccgtttagt acttaatggg attggtttgg    240
gacgtatata tcgactggtg ttgtctgtta ttcatcgttg tttttcggtt agcttcgaaa    300
aaaaaataga gtaaaaacca ggaatttacc ctaaaaacaa gaaaaaataa gataaacgaa    360
aat                                                                  363

<210> SEQ ID NO 112
<211> LENGTH: 500
<212> TYPE: DNA
<213> ORGANISM: Saccharomyces cerevisiae
<220> FEATURE:
<223> OTHER INFORMATION: pSAM2" <223> "pSAM2
<220> FEATURE:
<223> OTHER INFORMATION: pSAM2
<220> FEATURE:
<223> OTHER INFORMATION: pSAM2

<400> SEQUENCE: 112
gagctttgct ctattatata agataaaata tgcactaaaa gtttgcattt ctttacataa     60
ctaaaactaa gacattatgc atagcttacc tgatcaaaaa gtatgtaaac ttgttaacat    120
cttcacatgt gattcatctg gtcgtacttt cttgcggtgc agtgtaatat ttctacccac    180
gtgactataa ttgagcttga aaactgtggc gttttccac cgatgggtcc acgccagata    240
ttaaccgaag ccaaaatacc gatgaaattt ctgagatagc tcttgtaaac gacgtcaaat    300
cttcatatgc aaggagatct tgatttcttt ttggtagtca tctgtcgtct tgaggcgtat    360
aagaaggagg ttatatctgt cctttctaca aagtattttc gagaatcttg cttctgcccc    420
tttttctttt ttttaaaagg tttaaaaaac ataactgtct tcaatatatc cagtatttac    480
gacaatatac aaacataatc                                                500

<210> SEQ ID NO 113
<211> LENGTH: 300
<212> TYPE: DNA
<213> ORGANISM: Saccharomyces cerevisiae
<220> FEATURE:
<223> OTHER INFORMATION: tTDH2" <223> "tTHD2
<220> FEATURE:
<223> OTHER INFORMATION: tTDH2
<220> FEATURE:
<223> OTHER INFORMATION: tTHD2

<400> SEQUENCE: 113
atttaactcc ttaagttact ttaatgattt agttttttatt attaataatt catgctcatg     60
acatctcata tacgcgttta taaaacttaa atagattgaa aatgtattaa agattcctca    120
gggattcgat tttttggaa gttttttgttt tttttttcctt gagatgctgt agtatttggg    180
aacaattata caatcgaaag atatatgctt acattcgacc gttttagccg tgatcattat    240
cctatagtaa cataacctga agcataactg acactactat catcaatact tgtcacatga    300
```

```
<210> SEQ ID NO 114
<211> LENGTH: 300
<212> TYPE: DNA
<213> ORGANISM: Saccharomyces cerevisiae
<220> FEATURE:
<223> OTHER INFORMATION: tCYC1" <223> "tCYC1
<220> FEATURE:
<223> OTHER INFORMATION: tCYC1
<220> FEATURE:
<223> OTHER INFORMATION: tCYC1

<400> SEQUENCE: 114
acaggcccct tttcctttgt cgatatcatg taattagtta tgtcacgctt acattcacgc    60
cctcctccca catccgctct aaccgaaaag gaaggagtta gacaacctga agtctaggtc   120
cctatttatt ttttttaata gttatgttag tattaagaac gttatttata tttcaaattt   180 ttctttttt tctgtacaaa cgcgtgtacg catgtaacat tatactgaaa accttgcttg   240
agaaggtttt gggacgctcg aaggctttaa tttgcaagct tcgcagttta cactctcatc   300

<210> SEQ ID NO 115
<211> LENGTH: 300
<212> TYPE: DNA
<213> ORGANISM: Saccharomyces cerevisiae
<220> FEATURE:
<223> OTHER INFORMATION: tTDH3" <223> "tTDH3
<220> FEATURE:
<223> OTHER INFORMATION: tTDH3
<220> FEATURE:
<223> OTHER INFORMATION: tTDH3

<400> SEQUENCE: 115
gtgaatttac tttaaatctt gcatttaaat aaattttctt tttatagctt tatgacttag    60
tttcaattta tatactattt taatgacatt ttcgattcat tgattgaaag ctttgtgttt   120
tttcttgatg cgctattgca ttgttcttgt cttttcgcc acatgtaata tctgtagtag   180
atacctgata cattgtggat gctgagtgaa atttagtta ataatggagg cgctcttaat   240
aattttgggg atattggctt ttttttttaa agtttacaaa tgaattttt ccgccaggat   300

<210> SEQ ID NO 116
<211> LENGTH: 354
<212> TYPE: DNA
<213> ORGANISM: Saccharomyces cerevisiae
<220> FEATURE:
<223> OTHER INFORMATION: tADH1" <223> "tADH1
<220> FEATURE:
<223> OTHER INFORMATION: tADH1
<220> FEATURE:
<223> OTHER INFORMATION: tADH1

<400> SEQUENCE: 116
actagttcta gagcggccgc caccgcggtg ggcgaatttc ttatgattta tgatttttat    60
tattaaataa gttataaaaa aaataagtgt atacaaattt taaagtgact cttaggtttt   120
aaaacgaaaa ttcttattct tgagtaactc tttcctgtag gtcaggttgc tttctcaggt   180
atagcatgag gtcgctctta ttgaccacac ctctaccggc atgccgagca aatgcctgca   240
aatcgctccc catttcaccc aattgtagat atgctaactc cagcaatgag ttgatgaatc   300
tcggtgtgta ttttatgtcc tcagaggaca acacctgttg taatcgttct tcca          354

<210> SEQ ID NO 117
<211> LENGTH: 301
<212> TYPE: DNA
<213> ORGANISM: Saccharomyces cerevisiae
```

```
<220> FEATURE:
<223> OTHER INFORMATION: tADH2" <223> "tADH2
<220> FEATURE:
<223> OTHER INFORMATION: tADH2
<220> FEATURE:
<223> OTHER INFORMATION: tADH2

<400> SEQUENCE: 117
gcggatctct tatgtcttta cgatttatag ttttcattat caagtatgcc tatattagta      60
tatagcatct ttagatgaca gtgttcgaag tttcacgaat aaaagataat attctacttt     120
ttgctcccac cgcgtttgct agcacgagtg aacaccatcc ctcgcctgtg agttgtaccc     180
attcctctaa actgtagaca tggtagcttc agcagtgttc gttatgtacg gcatcctcca     240
acaaacagtc ggttatagtt tgtcctgctc ctctgaatcg tctccctcga tatttctcat     300
t                                                                    301

<210> SEQ ID NO 118
<211> LENGTH: 299
<212> TYPE: DNA
<213> ORGANISM: Saccharomyces cerevisiae
<220> FEATURE:
<223> OTHER INFORMATION: tTPI1" <223> "tTPI1
<220> FEATURE:
<223> OTHER INFORMATION: tTPI1
<220> FEATURE:
<223> OTHER INFORMATION: tTPI1

<400> SEQUENCE: 118
gattaatata attatataaa aatattatct tcttttcttt atatctagtg ttatgtaaaa      60
taaattgatg actacggaaa gcttttttat attgtttctt tttcattctg agccacttaa     120
atttcgtgaa tgttcttgta agggacggta gatttacaag tgatacaaca aaaagcaagg     180 cgcttttttct aataaaaaga agaaaagcat ttaacaattg aacacctcta tatcaacgaa    240
gaatattact ttgtctctaa atccttgtaa aatgtgtacg atctctatat gggttactc     299

<210> SEQ ID NO 119
<211> LENGTH: 299
<212> TYPE: DNA
<213> ORGANISM: Saccharomyces cerevisiae
<220> FEATURE:
<223> OTHER INFORMATION: tMET17" <223> "tMET17
<220> FEATURE:
<223> OTHER INFORMATION: tMET17
<220> FEATURE:
<223> OTHER INFORMATION: tMET17

<400> SEQUENCE: 119
gtgtgcgtaa tgagttgtaa aattatgtat aaacctactt tctctcacaa gtactatact      60
tttataaaac gaactttatt gaatgaata tccttttttt cccttgttac atgtcgtgac      120
tcgtactttg aacctaaatt gttctaacat caaagaacag tgttaattcg cagtcgagaa     180
gaaaaatatg gtgaacaaga ctcatctact tcatgagact actttacgcc tcctataaag     240
ctgtcacact ggataaattt attgtaggac caagttacaa aagaggatga tggaggttt     299

<210> SEQ ID NO 120
<211> LENGTH: 305
<212> TYPE: DNA
<213> ORGANISM: Saccharomyces cerevisiae
<220> FEATURE:
<223> OTHER INFORMATION: tENO2" <223> "tENO2
<220> FEATURE:
<223> OTHER INFORMATION: tENO2
<220> FEATURE:
```

<223> OTHER INFORMATION: tENO2

<400> SEQUENCE: 120

| ggatcctaaa gtgcttttaa ctaagaatta ttagtctttt ctgcttattt tttcatcata | 60 |
| gtttagaaca ctttatatta acgaatagtt tatgaatcta tttaggttta aaaattgata | 120 |
| cagttttata agttactttt tcaaagactc gtgctgtcta ttgcataatg cactggaagg | 180 |
| ggaaaaaaaa ggtgcacacg cgtggctttt tcttgaattt gcagtttgaa aaataactac | 240 |
| atggatgata agaaaacatg gagtacagtc actttgagaa ccttcaatca gctggtaacg | 300 |
| tcttc | 305 |

<210> SEQ ID NO 121
<211> LENGTH: 300
<212> TYPE: DNA
<213> ORGANISM: Saccharomyces cerevisiae
<220> FEATURE:
<223> OTHER INFORMATION: tMET3" <223> "tMET3
<220> FEATURE:
<223> OTHER INFORMATION: tMET3
<220> FEATURE:
<223> OTHER INFORMATION: tMET3

<400> SEQUENCE: 121

| tcgtcataaa atgctcccat ctcaaaagta gggcaaaatt catgatcgac cgcgcaaaat | 60 |
| aaatagattt gcaaataagt tttgtatgta catttattaa tatatataat atatcaaaag | 120 |
| aaaaaaatca aaaaaaaaaa aaaaaaaaaa ttgcactctt attcagtcat caattacaaa | 180 |
| acctagagat agcgatggtg catattcaat aaaaaactcc ttatactgtc gagaaagctt | 240 |
| attattggta cttctcgaag atactaaaaa aggttaattt ttggagacgg aggcaatagc | 300 |

<210> SEQ ID NO 122
<211> LENGTH: 301
<212> TYPE: DNA
<213> ORGANISM: Saccharomyces cerevisiae
<220> FEATURE:
<223> OTHER INFORMATION: tPGK1" <223> "tPGK1
<220> FEATURE:
<223> OTHER INFORMATION: tPGK1
<220> FEATURE:
<223> OTHER INFORMATION: tPGK1

<400> SEQUENCE: 122

| attgaattga attgaaatcg atagatcaat ttttttcttt tctctttccc catcctttac | 60 |
| gctaaaataa tagtttattt tattttttga atatttttta tttatatacg tatatataga | 120 |
| ctattattta tcttttaatg attattaaga ttttttattaa aaaaaaattc gctcctcttt | 180 |
| taatgccttt atgcagtttt tttttcccat tcgatatttc tatgttcggg ttcagcgtat | 240 |
| tttaagttta ataactcgaa aattctgcgt tcgttaaagc tttcgagaag gatattattt | 300 |
| a | 301 |

<210> SEQ ID NO 123
<211> LENGTH: 300
<212> TYPE: DNA
<213> ORGANISM: Saccharomyces cerevisiae
<220> FEATURE:
<223> OTHER INFORMATION: tDIT1" <223> "tDIT1
<220> FEATURE:
<223> OTHER INFORMATION: tDIT1
<220> FEATURE:
<223> OTHER INFORMATION: tDIT1

<400> SEQUENCE: 123

```
taaagtaaga gcgctacatt ggtctaccit tttgttcttt tacttaaaca ttagttagtt    60
cgttttcttt ttctcatttt tttatgtttc cccccaaag ttctgatttt ataatatttt    120
atttcacaca attccattta acagaggggg aatagattct ttagcttaga aaattagtga   180
tcaatatata tttgccttc ttttcatctt ttcagtgata ttaatggttt cgagacactg    240
caatggccct agttgtctaa aggatagat gttactgtca aagatgatat tttgaatttc    300
```

```
<210> SEQ ID NO 124
<211> LENGTH: 300
<212> TYPE: DNA
<213> ORGANISM: Saccharomyces cerevisiae
<220> FEATURE:
<223> OTHER INFORMATION: tRPL3" <223> "tRPL3
<220> FEATURE:
<223> OTHER INFORMATION: tRPL3
<220> FEATURE:
<223> OTHER INFORMATION: tRPL3

<400> SEQUENCE: 124
```

```
gaagttttgt tagaaaataa atcattttt aattgagcat tcttattcct atttatttta   60
aatagtttta tgtattgtta gctacataca acagtttaaa tcaaattttc tttttcccaa   120
gtccaaaatg gaggtttatt ttgatgaccc gcatgcgatt atgttttgaa agtataagac   180
tacatacatg tacatatatt taaacatgta aacccgtcca ttatattgct tactttcttc   240
ttttttgccg ttttgacttg gacctctggt ttgctatttc cttacaatct ttgctacaat   300
```

```
<210> SEQ ID NO 125
<211> LENGTH: 300
<212> TYPE: DNA
<213> ORGANISM: Saccharomyces cerevisiae
<220> FEATURE:
<223> OTHER INFORMATION: tRPL41B" <223> "tRPL41B
<220> FEATURE:
<223> OTHER INFORMATION: tRPL41B
<220> FEATURE:
<223> OTHER INFORMATION: tRPL41B

<400> SEQUENCE: 125
```

```
gcggattgag agcaaatcgt taagttcagg tcaagtaaaa attgatttcg aaaactaatt   60
tctcttatac aatcctttga ttggaccgtc atcctttcga atataagatt ttgttaagaa   120
tattttagac agagatctac tttatattta atatctagat attacataat ttcctctcta   180
ataaaatatc attaataaaa taaaaatgaa gcgatttgat tttgtgttgt caacttagtt   240
tgccgctatg cctcttgggt aatgctatta ttgaatcgaa gggctttatt atattaccct   300
```

```
<210> SEQ ID NO 126
<211> LENGTH: 300
<212> TYPE: DNA
<213> ORGANISM: Saccharomyces cerevisiae
<220> FEATURE:
<223> OTHER INFORMATION: tRPL15A" <223> "tRPL15A
<220> FEATURE:
<223> OTHER INFORMATION: tRPL15A
<220> FEATURE:
<223> OTHER INFORMATION: tRPL15A

<400> SEQUENCE: 126
```

```
gctggttgat ggaaaatata attttattgg gcaaactttt gtttatctga tgtgttttat   60
actattatct ttttaattaa tgattctata tacaaacctg tatattttt ctttaaccaa   120 ttttttttt tatagaccta gagctgtact tttattctgc tatcaagcaa acccctaccc   180
```

```
cctcttctca atcctcccct caggcagaac ttatctacct gtatcaagga gcggacgagg    240
gagtcctaat tgttctacgt ataccaatgc tagcagctta cataggtggt ggcactacca    300
```

<210> SEQ ID NO 127
<211> LENGTH: 300
<212> TYPE: DNA
<213> ORGANISM: Saccharomyces cerevisiae
<220> FEATURE:
<223> OTHER INFORMATION: tIDP1" <223> "tIDP1
<220> FEATURE:
<223> OTHER INFORMATION: tIDP1
<220> FEATURE:
<223> OTHER INFORMATION: tIDP1

<400> SEQUENCE: 127

```
tcgaatttac gtagcccaat ctaccacttt tttttttcat tttttaaagt gttatactta     60
gttatgctct aggataatga actactttt tttttttttt tttactgtta tcataaatat    120
atataccttg ttgtttg caaccgtcgg ttaattcctt atcaaggttc cccaagttcg    180
gatcattacc atcaatttcc aacattttca tgagttcttc ttcttcatta ccgtgtttta    240
gggggctgtt cgcacttcta atagggctat caccaagctg ttctaattcg tccaaaagtt    300
```

<210> SEQ ID NO 128
<211> LENGTH: 1089
<212> TYPE: DNA
<213> ORGANISM: Kluveromyces lactis
<220> FEATURE:
<223> OTHER INFORMATION: Leu2" <223> "Leu2
<220> FEATURE:
<223> OTHER INFORMATION: Leu2
<220> FEATURE:
<223> OTHER INFORMATION: Leu2

<400> SEQUENCE: 128

```
atgtctaaga atatcgttgt cctaccgggt gatcacgtcg gtaaagaagt tactgacgaa     60
gctattaagg tcttgaatgc cattgctgaa gtccgtccag aaattaagtt caatttccaa    120
catcacttga tcggggtgc tgccatcgat gccactggca ctcctttacc agatgaagct    180
ctagaagcct ctaagaaagc cgatgctgtc ttactaggtg ctgttggtgg tccaaaatgg    240
ggtacgggcg cagttagacc agaacaaggt ctattgaaga tcagaaagga attgggtcta    300
tacgccaact tgagaccatg taactttgct tctgattctt tactagatct ttctcctttg    360
aagcctgaat atgcaaaggg taccgatttc gtcgtcgtta gagaattggt tggtggtatc    420
tactttggtg aaagaaaaga agatgaaggt gacggagttg cttgggactc tgagaaatac    480
agtgttcctg aagttcaaag aattacaaga atggctgctt tcttggcatt gcaacaaaac    540
ccaccattac caatctggtc tcttgacaag gctaacgtgc ttgcctcttc cagattgtgg    600
agaaagactg ttgaagaaac catcaagact gagttcccac aattaactgt tcagcaccaa    660
ttgatcgact ctgctgctat gattttggtt aaatcaccaa ctaagctaaa cggtgttgtt    720
attaccaaca acatgtttgg tgatattatc tccgatgaag cctctgttat tccaggttct    780
ttgggtttat accttctgc atctctagct tccctacctg acactaacaa ggcattcggt    840
ttgtacgaac catgtcatgg ttctgcccca gatttaccag caaacaaggt taacccaatt    900
gctaccatct tatctgcagc tatgatgttg aagttatcct tggatttggt tgaagaaggt    960
agggctcttg aagaagctgt tagaaatgtc ttggatgcag gtgtcagaac cggtgacctt   1020
ggtggttcta actctaccac tgaggttggc gatgctatcg ccaaggctgt caaggaaatc   1080
ttggcttaa                                                           1089
```

-continued

```
<210> SEQ ID NO 129
<211> LENGTH: 362
<212> TYPE: PRT
<213> ORGANISM: Kluveromyces lactis
<220> FEATURE:
<223> OTHER INFORMATION: Leu2 "
<223> Leu2
<220> FEATURE:
<223> OTHER INFORMATION: Leu2
<220> FEATURE:
<223> OTHER INFORMATION: Leu2

<400> SEQUENCE: 129
```

Met Ser Lys Asn Ile Val Val Leu Pro Gly Asp His Val Gly Lys Glu
1               5                   10                  15

Val Thr Asp Glu Ala Ile Lys Val Leu Asn Ala Ile Ala Glu Val Arg
            20                  25                  30

Pro Glu Ile Lys Phe Asn Phe Gln His His Leu Ile Gly Gly Ala Ala
        35                  40                  45

Ile Asp Ala Thr Gly Thr Pro Leu Pro Asp Glu Ala Leu Glu Ala Ser
    50                  55                  60

Lys Lys Ala Asp Ala Val Leu Leu Gly Ala Val Gly Gly Pro Lys Trp
65                  70                  75                  80

Gly Thr Gly Ala Val Arg Pro Glu Gln Gly Leu Leu Lys Ile Arg Lys
                85                  90                  95

Glu Leu Gly Leu Tyr Ala Asn Leu Arg Pro Cys Asn Phe Ala Ser Asp
            100                 105                 110

Ser Leu Leu Asp Leu Ser Pro Leu Lys Pro Glu Tyr Ala Lys Gly Thr
        115                 120                 125

Asp Phe Val Val Val Arg Glu Leu Val Gly Gly Ile Tyr Phe Gly Glu
    130                 135                 140

Arg Lys Glu Asp Glu Gly Asp Gly Val Ala Trp Asp Ser Glu Lys Tyr
145                 150                 155                 160

Ser Val Pro Glu Val Gln Arg Ile Thr Arg Met Ala Ala Phe Leu Ala
                165                 170                 175

Leu Gln Gln Asn Pro Pro Leu Pro Ile Trp Ser Leu Asp Lys Ala Asn
            180                 185                 190

Val Leu Ala Ser Ser Arg Leu Trp Arg Lys Thr Val Glu Glu Thr Ile
        195                 200                 205

Lys Thr Glu Phe Pro Gln Leu Thr Val Gln His Gln Leu Ile Asp Ser
    210                 215                 220

Ala Ala Met Ile Leu Val Lys Ser Pro Thr Lys Leu Asn Gly Val Val
225                 230                 235                 240

Ile Thr Asn Asn Met Phe Gly Asp Ile Ile Ser Asp Glu Ala Ser Val
                245                 250                 255

Ile Pro Gly Ser Leu Gly Leu Leu Pro Ser Ala Ser Leu Ala Ser Leu
            260                 265                 270

Pro Asp Thr Asn Lys Ala Phe Gly Leu Tyr Glu Pro Cys His Gly Ser
        275                 280                 285

Ala Pro Asp Leu Pro Ala Asn Lys Val Asn Pro Ile Ala Thr Ile Leu
    290                 295                 300

Ser Ala Ala Met Met Leu Lys Leu Ser Leu Asp Val Glu Glu Gly
305                 310                 315                 320

Arg Ala Leu Glu Glu Ala Val Arg Asn Val Leu Asp Ala Gly Val Arg
                325                 330                 335

Thr Gly Asp Leu Gly Gly Ser Asn Ser Thr Thr Glu Val Gly Asp Ala

```
            340                 345                 350
Ile Ala Lys Ala Val Lys Glu Ile Leu Ala
        355                 360

<210> SEQ ID NO 130
<211> LENGTH: 499
<212> TYPE: DNA
<213> ORGANISM: Saccharomyces cerevisiae
<220> FEATURE:
<223> OTHER INFORMATION: pNUP57
<220> FEATURE:
<223> OTHER INFORMATION: pNUP57

<400> SEQUENCE: 130
tcatctgcgc aatgactatc aagaccttct gcaagaattt caaatctcac tgaaaatctt      60
gaccgaaaag tgtcttgaaa acccatcaag cctgcaaaac ctatctttga cattagtctc     120
cattataaaa acggcatagt tgggagaaaa cttttcatac ttcaattgtg gactgatata     180
agtattttgg ttttgcccgc atgatcatcc cacatggcta cagcagttct ctcataggaa     240
atagtacaat agctacgtga tataatctaa ataattgttg ccaatgtgta attatatcat     300
tttgaacgtt cgcgaaatgg attattttca aaaattttgt ttcttgaaat gagtaaaagc     360
aaaagtccaa ctctccaagt cgatgtaaac aacttttgc caagggact gaaagactaa      420 atcgaggatt atcccgttca aactattcca gaaacgctcg ttagtaacaa aagacatacc     480
ttgttgacca attgatcac                                                  499

<210> SEQ ID NO 131
<211> LENGTH: 451
<212> TYPE: DNA
<213> ORGANISM: Saccharomyces cerevisiae
<220> FEATURE:
<223> OTHER INFORMATION: pGAP1
<220> FEATURE:
<223> OTHER INFORMATION: pGAP1

<400> SEQUENCE: 131
cactttcacc agatcccaaa tgtcccgccc ctattcccgt gttccatcac gtaccataac      60
ttaccatttc atcacgttct ctatggcaca ctggtactgc ttcgactgct ttgcttcatc     120
ttctctatgg gccaatgagc taatgagcac aatgtgctgc gaaataaagg gatatctaat     180
ttatattatt acattataat atgtactagt gtggttattg gtaattgtac ttaatttga     240 tatataaagg gtggatcttt ttcattttga atcagaattg gaattgcaac ttgtctcttg     300
tcactattac ttaatagtaa ttatatttct tattaacctt ttttttaagt caaaacacca     360
aggacaagaa ctactcttca aaggtatttc aagttatcat acgtctcaca cacgcttcac     420
agtttcaagt aaaaaaaaag aatattacac a                                    451

<210> SEQ ID NO 132
<211> LENGTH: 998
<212> TYPE: DNA
<213> ORGANISM: Saccharomyces cerevisiae
<220> FEATURE:
<223> OTHER INFORMATION: pJEN1
<220> FEATURE:
<223> OTHER INFORMATION: pJEN1

<400> SEQUENCE: 132
aatgtgttta taaattattt ttttttgctgg tagcaaaatc aactcattgt cttccattca      60
gagtctaatc gaacgttatc gcaatgcttg cacactttta aacaatacga tttagtttaa     120
```

```
gtggatggac ccccacgctt agtgttccac aggtttgtcc ccactgtttt tacattccac      180
tgtacatttt tgcaatagaa ggtcattgta tgctaccttg ggcggctaag aatacctgta      240
aaaatttgga gaaattagat tcgtaaagaa tgactcgcaa cgactccaat gatttcttct      300 tttcacccctt tgaacggccg atatccgcgc gggatcctga ccccgcaatt tactccacta     360
gaccggcgtg tttctctttt tccttttcct ggggttagag cccaagagct aatagccgac      420
aaacggactc caaaaaaaaa aggaggcaca ggacaaacgc agcacctgcg tcattcacgc      480
tgaagcggca gcaagcattt tcgatcagct ccaattaaat gaagactatt cgccgtaccg      540
ttcccagatg ggtgcgaaag tcagtgatcg aggaagttat tgagcgcgcg gcttgaaact      600
atttctccat ctcagagccg ccaagcctac cattattctc caccaggaag ttagtttgta      660
agcttctgca caccatccgg acgtccataa ttcttcactt aacggtcttt tgcccccccct     720 tctactataa tgcattagaa cgttacctgg tcatttggat ggagatctaa gtaacactta      780
ctatctccta tggtactatc ctttaccaaa aaaaaaaaa aaaaaaaaaa aaaaaatcag       840
caaagtgaag taccctcttg atgtataaat acattgcaca tcattgttga gaaatagttt      900
tggaagttgt ctagtccttc tcccttagat ctaaaaggaa gaagagtaac agtttcaaaa      960 gttttttcctc aaagagatta aatactgcta ctgaaaat                             998

<210> SEQ ID NO 133
<211> LENGTH: 450
<212> TYPE: DNA
<213> ORGANISM: Saccharomyces cerevisiae
<220> FEATURE:
<223> OTHER INFORMATION: pICL1
<220> FEATURE:
<223> OTHER INFORMATION: pICL1

<400> SEQUENCE: 133
ttttgctact cgtcatccga tgagaaaaac tgttcccttt tgccccaggt ttccattcat       60
ccgagcgatc acttatctga cttcgtcact ttttcatttc atccgaaaca atcaaaactg      120
aagccaatca ccacaaaatt aacactcaac gtcatctttc actacccttt acagaagaaa      180
atatccatag tccggactag catcccagta tgtgactcaa tattggtgca aaagagaaaa      240
gcataagtca gtccaaagtc cgcccttaac caggcacatc ggaattcaca aaacgtttct      300
ttattatata aaggagctgc ttcactggca aaattcttat tatttgtctt ggcttgctaa      360
tttcatctta tccttttttt cttttcacac ccaaatacct aacaattgag agaaaactct      420
tagcataaca taacaaaaag tcaacgaaaa                                       450

<210> SEQ ID NO 134
<211> LENGTH: 598
<212> TYPE: DNA
<213> ORGANISM: Saccharomyces cerevisiae
<220> FEATURE:
<223> OTHER INFORMATION: pADH2
<220> FEATURE:
<223> OTHER INFORMATION: pADH2

<400> SEQUENCE: 134
tatcttaact gatagtttga tcaaaggggc aaaacgtagg ggcaaacaaa cggaaaaatc       60
gtttctcaaa ttttctgatg ccaagaactc taaccagtct tatctaaaaa ttgccttatg     120
atccgtctct ccggttacag cctgtgtaac tgattaatcc tgcctttcta atcaccattc      180
taatgtttta attaagggat tttgtcttca ttaacgggct tcgctcataa aaatgttatg      240
acgttttgcc cgcaggcggg aaaccatcca cttcacgaga ctgatctcct ctgccggaac     300
```

```
accgggcatc tccaacttat aagttggaga aataagagaa tttcagattg agagaatgaa      360
aaaaaaaaaa aaaaaaggca gaggagagca tagaaatggg gttcactttt tggtaaagct      420
atagcatgcc tatcacatat aaatagagtg ccagtagcga cttttttcac actcgaaata      480
ctcttactac tgctctcttg ttgttttttat cacttcttgt ttcttcttgg taaatagaat     540
atcaagctac aaaaagcata caatcaacta tcaactatta actatatcgt aatacaca       598

<210> SEQ ID NO 135
<211> LENGTH: 793
<212> TYPE: DNA
<213> ORGANISM: Saccharomyces cerevisiae
<220> FEATURE:
<223> OTHER INFORMATION: pMLS1
<220> FEATURE:
<223> OTHER INFORMATION: pMLS1

<400> SEQUENCE: 135
tgtctaatgc gaaggtactt ttatttttt cagattcaaa gcaatattat ttagacaatt       60
gatactaagt gagcttaagg aggattaaac aactgtggaa tccttcacaa ggattcaata     120 tttgttttc ctggttattt tgccatcatt caactttcct cagacgtaaa attcgtgctt     180
agtgatgtct caatattccc gcagggtaat aaaattcaat aactatcact atatacgcaa     240
cagtattacc ctacattgct atcggctcaa tggaaatccc catatcatag cttccattgg     300
gccgatgaag ttagtcgacg gatagaagcg gttgtcccct ttcccggcga gccggcagtc     360
gggccgaggt tcggataaat tttgtattgt gttttgattc tgtcatgagt attacttatg     420
ttctctttag gtaaccccag gttaatcaat cacagtttca taccggctag tattcaaatt     480
atgacttttc ttctgcagtg tcagccttac gacgattatc tatgagcttt gaatatagtt     540
tgccgtgatt cgtatctta attggataat aaaatgcgaa ggatcgatga cccttattat     600
tatttttcta cactggctac cgatttaact catcttcttg aaagtatata agtaacagta     660
aaatataccg tacttctgct aatgttattt gtcccttatt tttcttttct tgtcttatgc     720
tatagtacct aagaataacg actattgttt tgaactaaac aaagtagtaa aagcacataa     780
aagaattaag aaa                                                        793
```